US012746254B2

(12) United States Patent
Plath et al.

(10) Patent No.: US 12,746,254 B2
(45) Date of Patent: Sep. 29, 2026

(54) METHODS FOR X CHROMOSOME REACTIVATION

(71) Applicant: THE REGENTS OF THE UNIVERSITY OF CALIFORNIA, Oakland, CA (US)

(72) Inventors: Kathrin Plath, Los Angeles, CA (US); Amy Pandya-Jones, Los Angeles, CA (US); Shawn Tan, Los Angeles, CA (US); Douglas Black, Los Angeles, CA (US); Giolanta Markaki, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 682 days.

(21) Appl. No.: 18/248,160

(22) PCT Filed: Oct. 6, 2021

(86) PCT No.: PCT/US2021/053733

§ 371 (c)(1),
(2) Date: Apr. 6, 2023

(87) PCT Pub. No.: WO2022/076529

PCT Pub. Date: Apr. 14, 2022

(65) Prior Publication Data

US 2023/0372385 A1 Nov. 23, 2023

Related U.S. Application Data

(60) Provisional application No. 63/117,226, filed on Nov. 23, 2020, provisional application No. 63/088,297, filed on Oct. 6, 2020, provisional application No. 63/088,265, filed on Oct. 6, 2020.

(51) Int. Cl.

| | |
|---|---|
| ***C12N 15/113*** | (2010.01) |
| ***A61K 31/706*** | (2006.01) |
| ***A61K 31/7072*** | (2006.01) |
| ***A61K 31/713*** | (2006.01) |
| ***A61K 45/06*** | (2006.01) |

(52) U.S. Cl.
CPC .......... *A61K 31/713* (2013.01); *A61K 31/706* (2013.01); *A61K 31/7072* (2013.01); *A61K 45/06* (2013.01); *C12N 15/113* (2013.01); *C12N 2310/11* (2013.01); *C12N 2310/14* (2013.01)

(58) Field of Classification Search
CPC ............................ C12N 15/113; A61K 31/706
See application file for complete search history.

(56) References Cited

U.S. PATENT DOCUMENTS

2016/0313304 A1 10/2016 Guttman et al.
2017/0044609 A1* 2/2017 Guttman ............ G01N 33/5023

FOREIGN PATENT DOCUMENTS

WO WO 2019/112975 6/2019
WO WO 2020/168241 8/2020

OTHER PUBLICATIONS

Légaré et al., Breast Cancer Research, 2017, vol. 19, Article No. 104.*
Smola et al., PNAS, 2016, vol. 113(37):10322-10327.*
Beard, C. et al., "Efficient method to generate single-copy transgenic mice by site- specific integration in embryonic stem cells", *Genesis,* 44, 23-28, 2006.
Cerase, A. et al., "Phase separation drives X-chromosome inactivation: a hypothesis", *Nature Structural and Molecular Biology,* 26(5), pp. 1-4, 2019.
International Search Report and Written Opinion issued in corresponding PCT Application No. PCT/US2021/053733, mailed Mar. 24, 2022.
Minkovsky, A. et al., "The Mbd1-Atf7ip-Setdb1 pathway contributes to the maintenance of X chromosome inactivation", *Epigenetics & Chromatin,* 7, 12, 2014.
Plath, K. et al., "Role of histone H3 lysine 27 methylation in X inactivation", *Science,* 300, 131-135, 2003.
Plath, K. et al., "Xist RNA and the mechanism of X chromosome inactivation". *Annual Review of Genetics,* 36, 233-278, 2002.
Quinodoz, S.A., et al., "RNA promotes the formation of spatial compartments in the nucleus", bioRxiv, 2020.2008.2025.267435; *Cell,* 184, 5775-5790, 2021.

* cited by examiner

*Primary Examiner* — Xiaozhen Xie
(74) *Attorney, Agent, or Firm* — Norton Rose Fulbright US LLP

(57) ABSTRACT

Aspects of the disclosure relate to a method for re-activating the X-chromosome in cells comprising administering a SPEN inhibitor to the cell. Further aspects relate to a method for re-activating the X-chromosome in a subject in need thereof, the method comprising administering a SPEN inhibitor to the subject. Yet further aspects relate to a method for treating Rett Syndrome in a subject in need thereof, the method comprising administering a SPEN inhibitor to the subject. Aspects of the disclosure relate to a method for re-activating the X-chromosome in cells comprising administering a PTBP1 inhibitor and a DNA demethylating agent to the cell. Further aspects relate to a method for re-activating the X-chromosome in a subject in need thereof, the method comprising administering a PTBP1 inhibitor and a DNA demethylating agent to the subject. Yet further aspects relate to a method for treating Rett syndrome in a subject in need thereof, the method comprising administering a PTBP1 inhibitor and a DNA demethylating agent to the subject.

10 Claims, 60 Drawing Sheets

Specification includes a Sequence Listing.

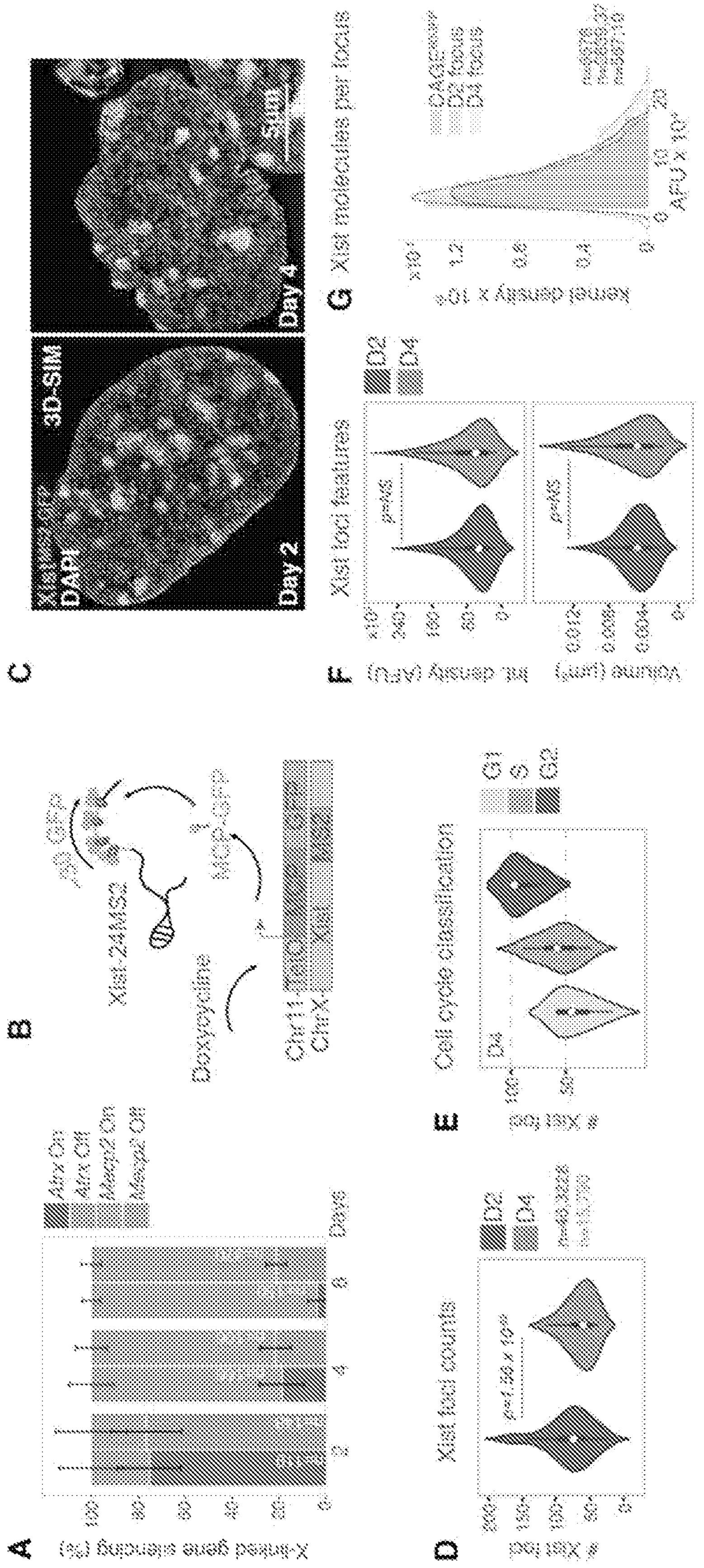
FIG. 1A-G

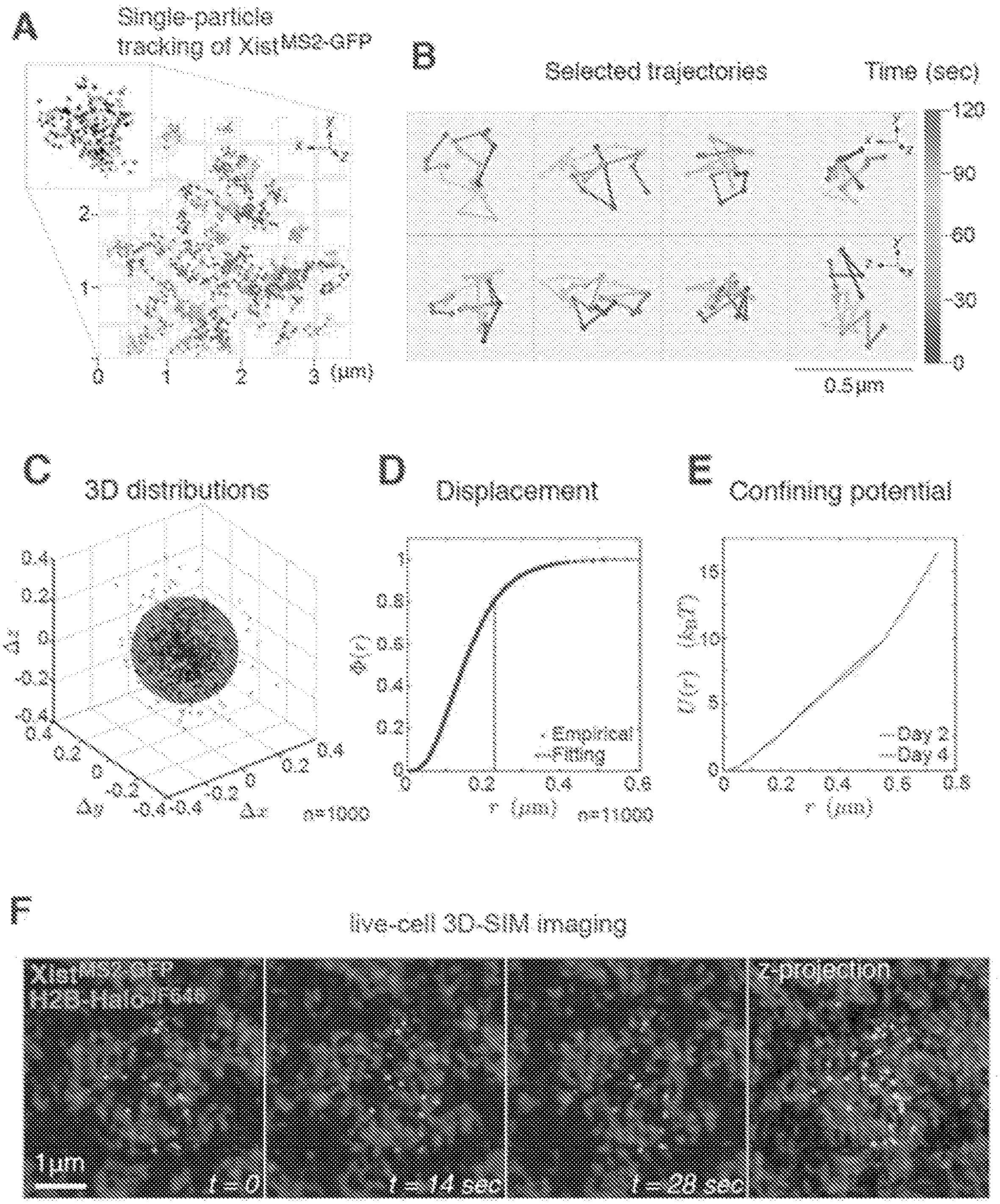
FIG. 2A-F

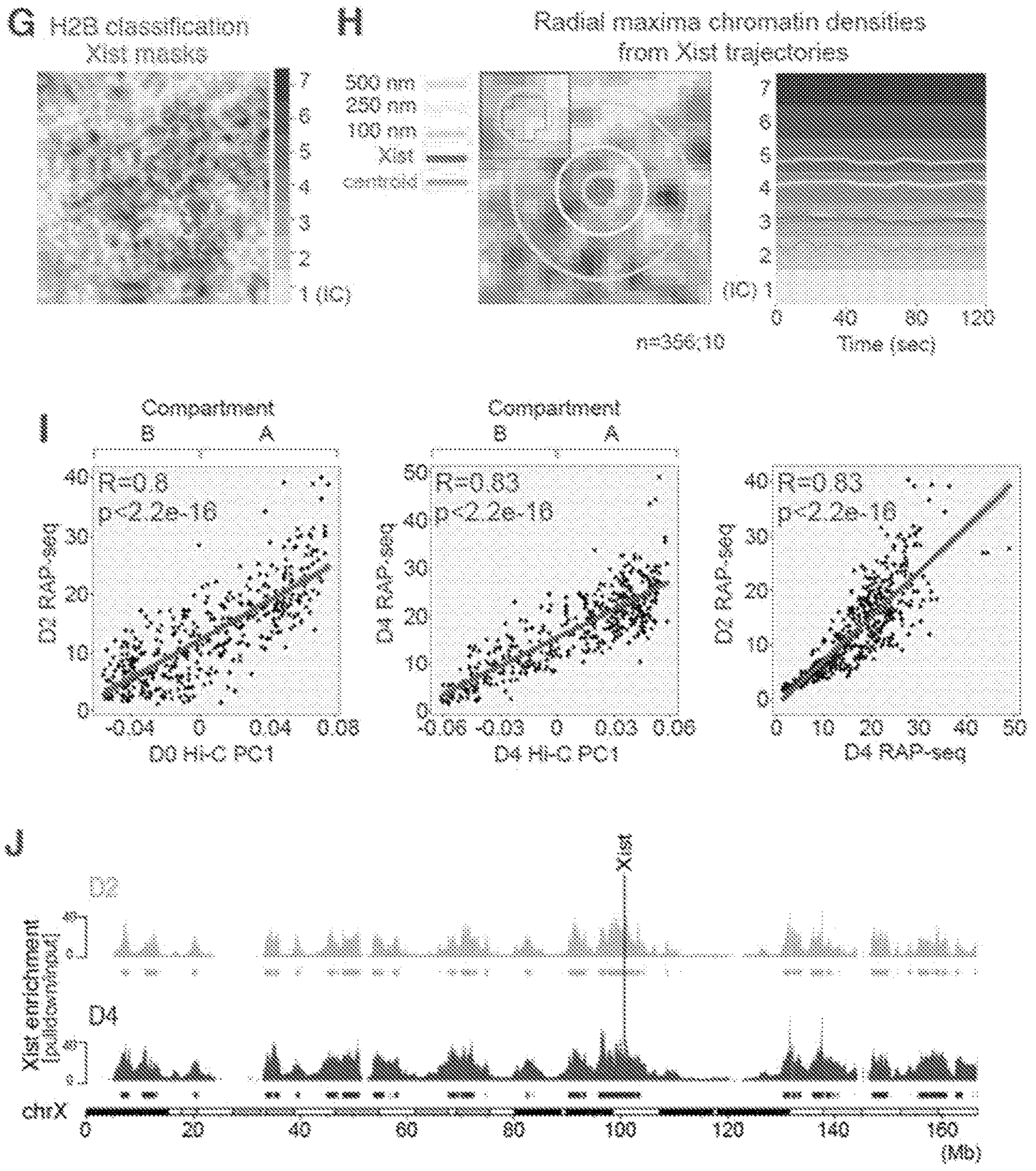
FIG. 2G-J

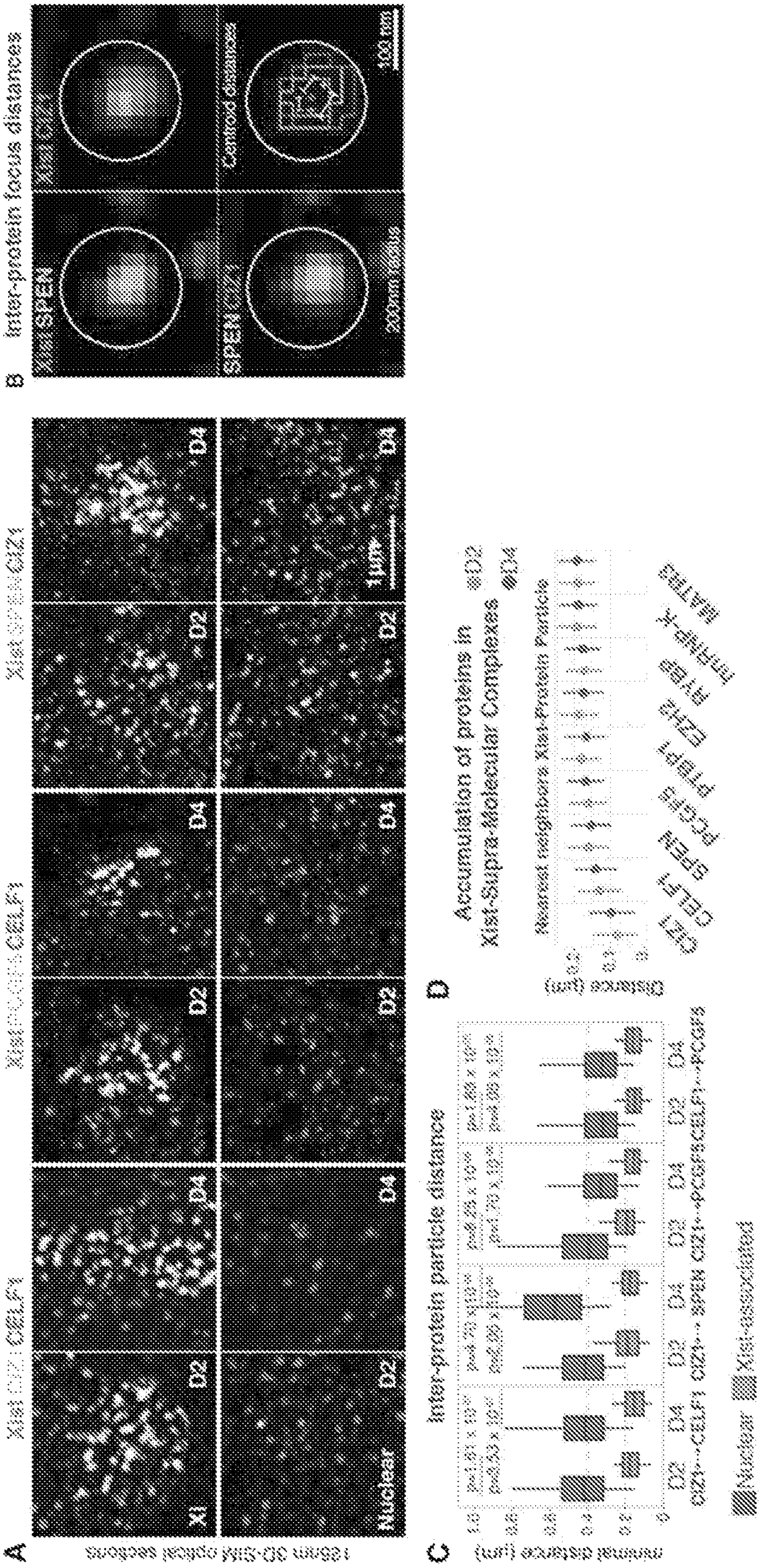
FIG. 3A-D

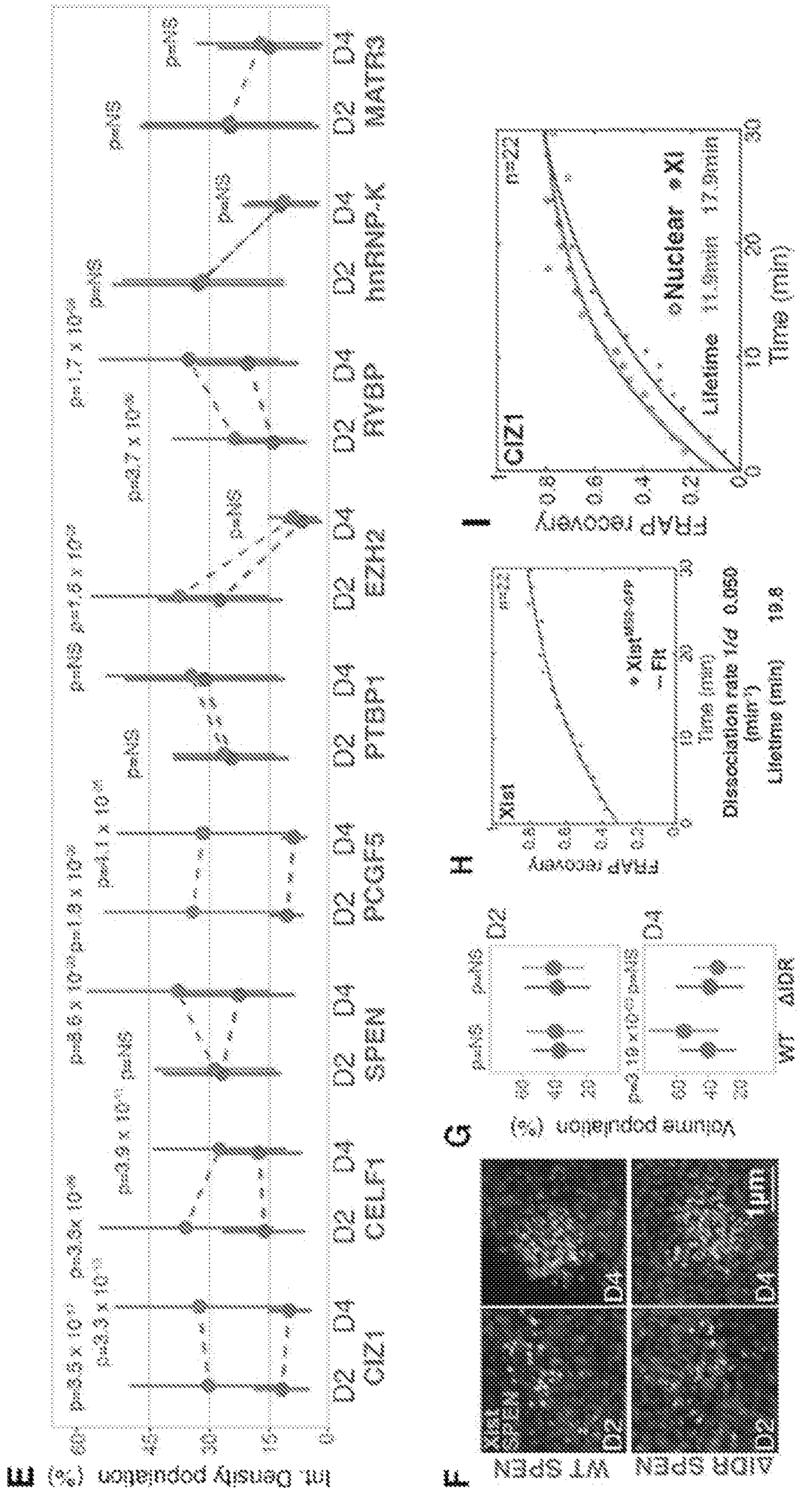
FIG. 3E-I

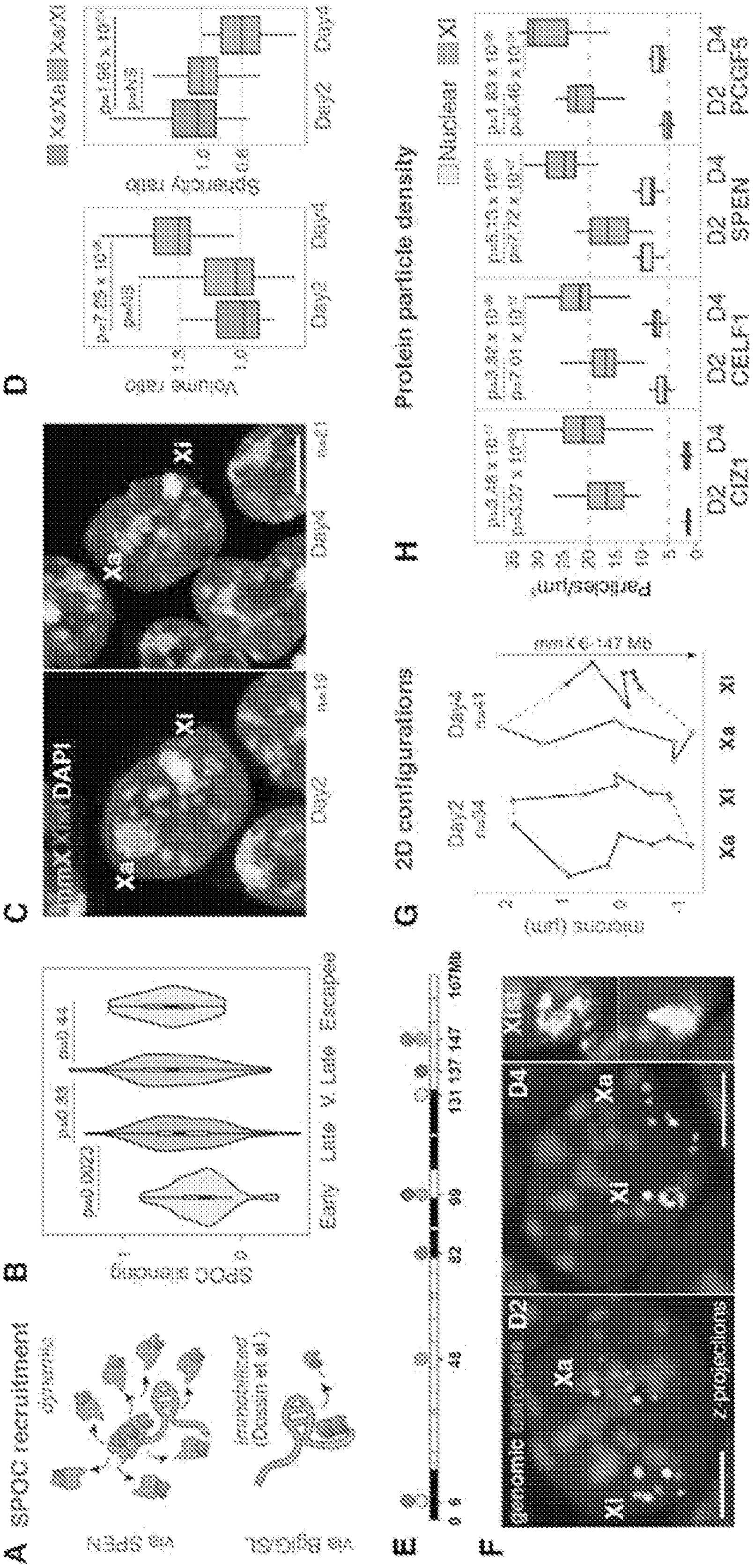
FIG. 4A-H

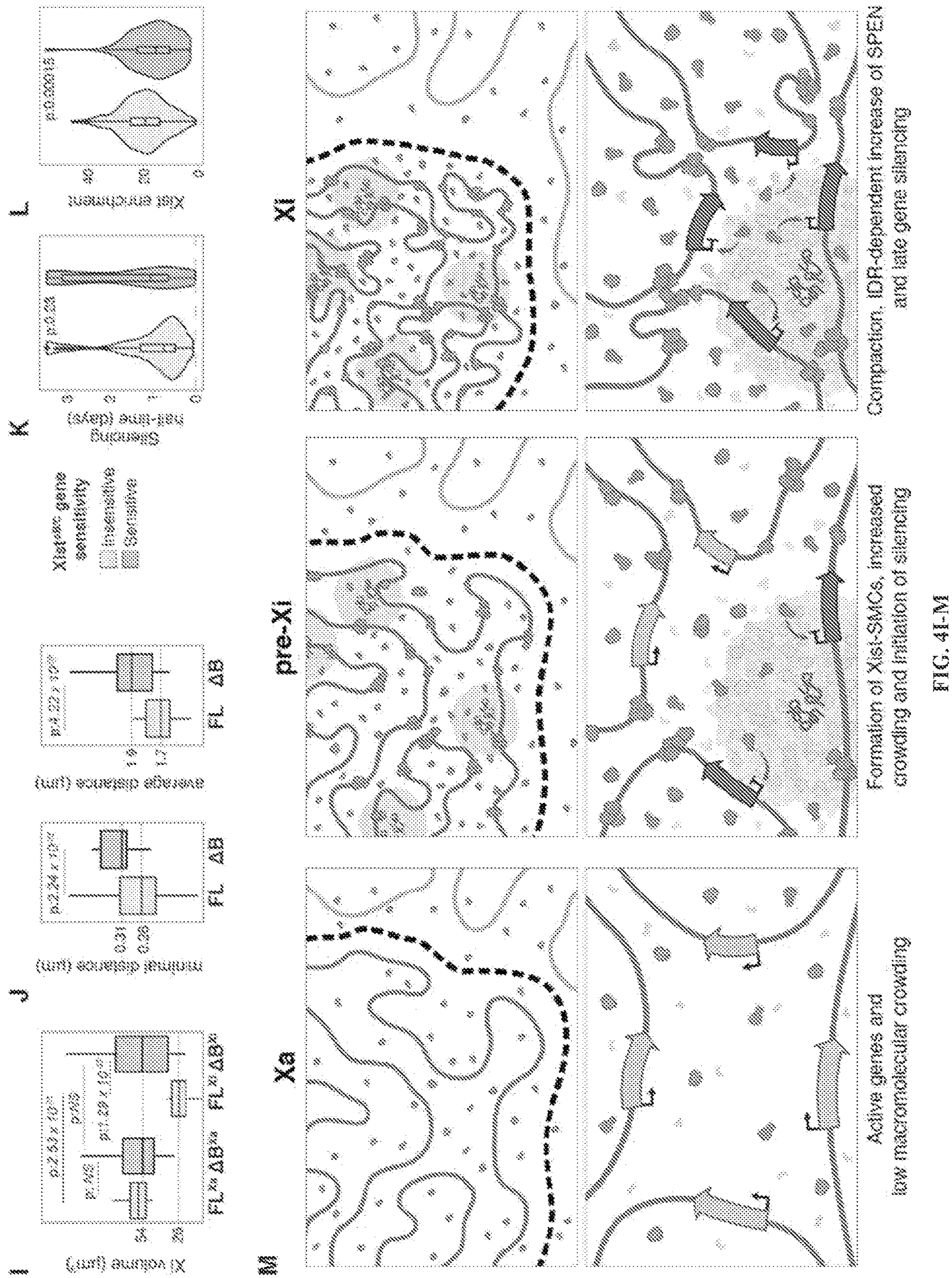
FIG. 4I-M

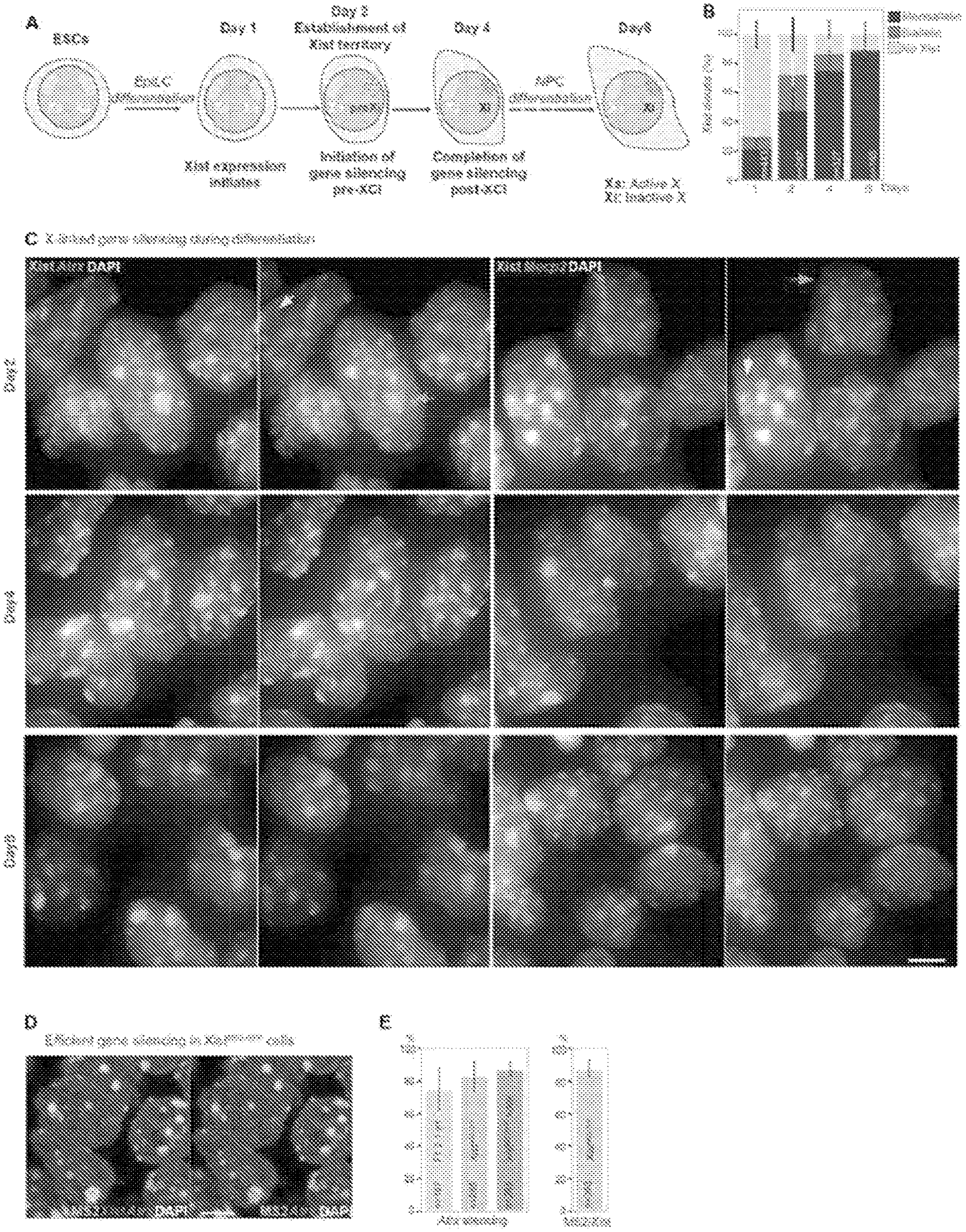
FIG. 5A-E

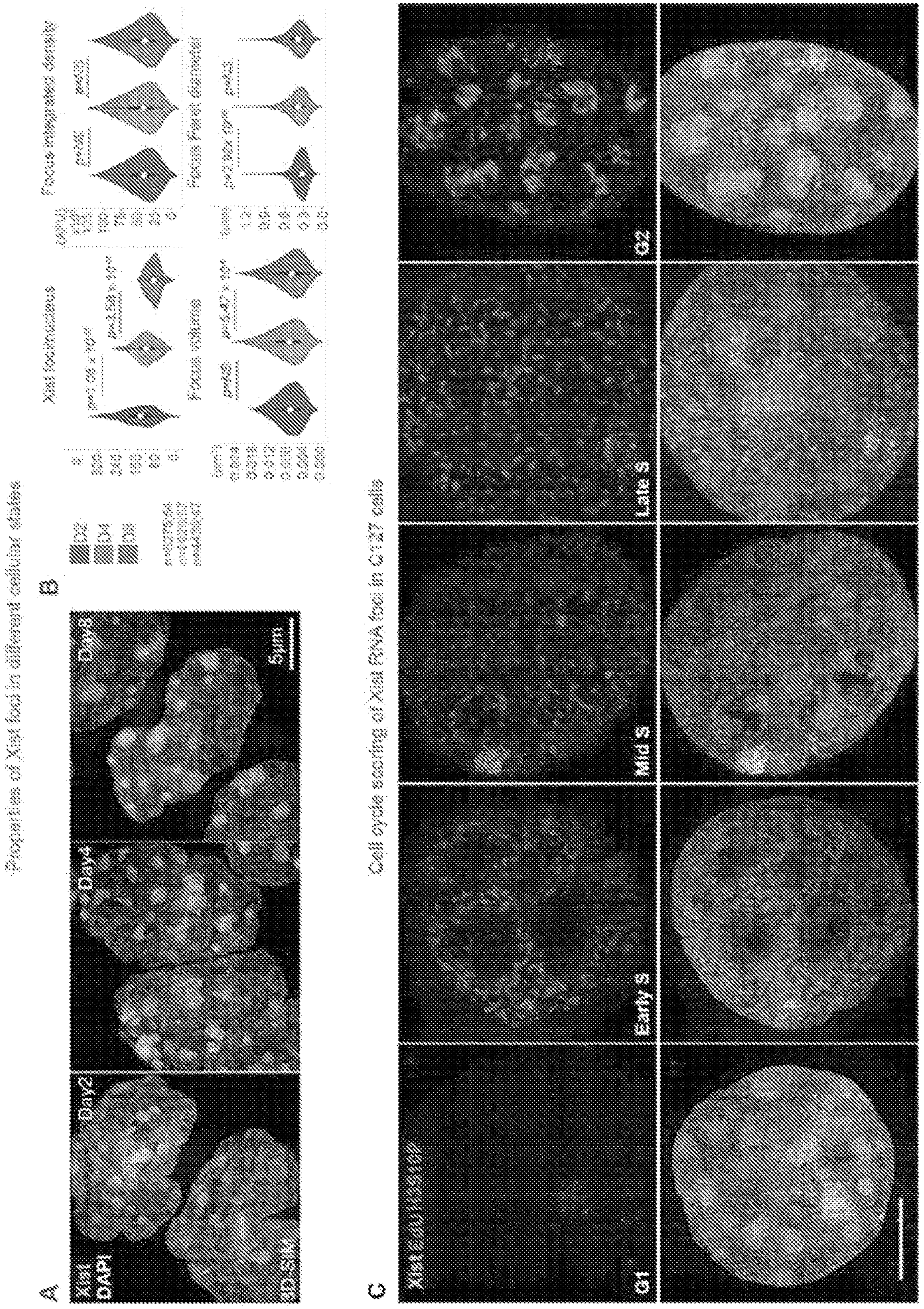
FIG. 6A-C

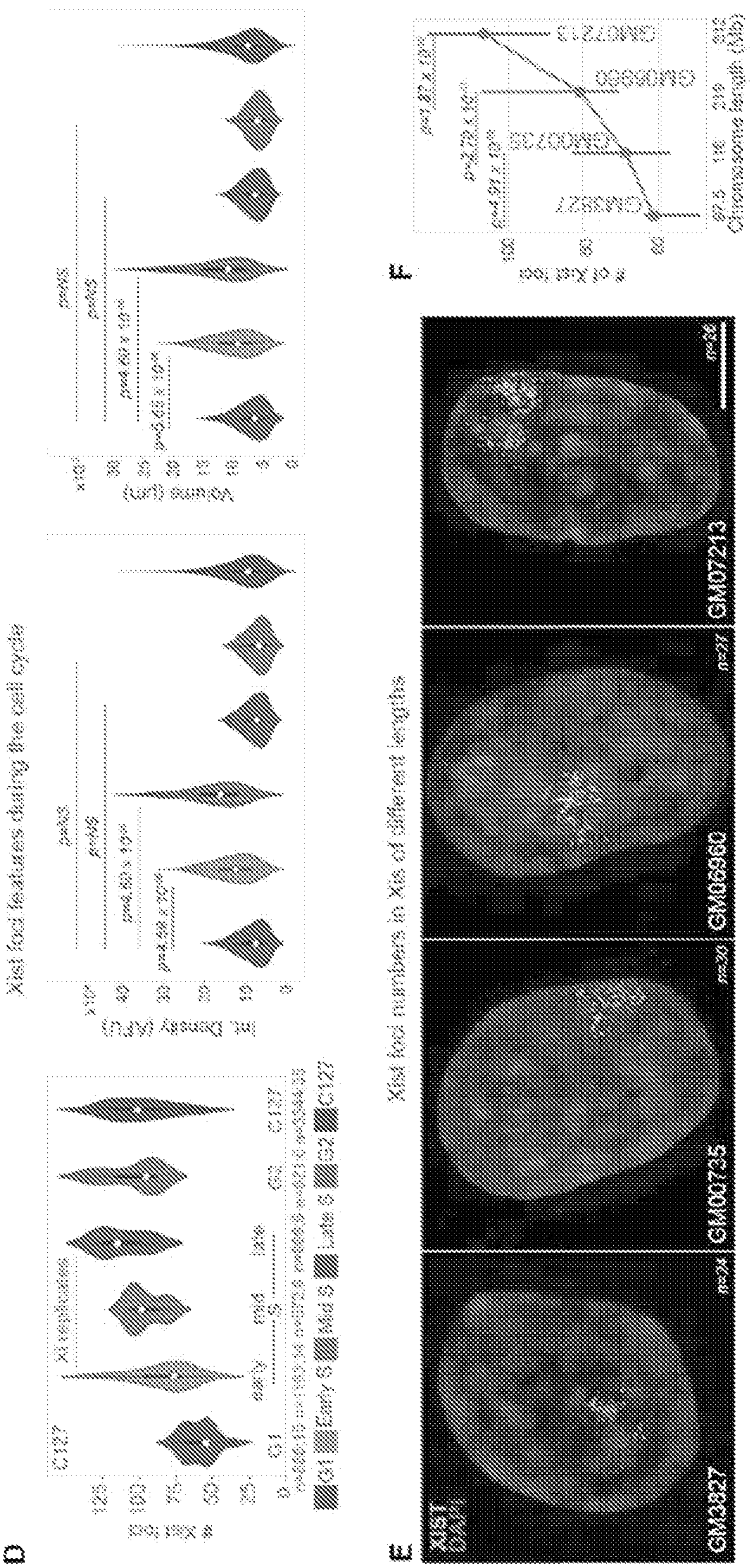
FIG. 6D-F

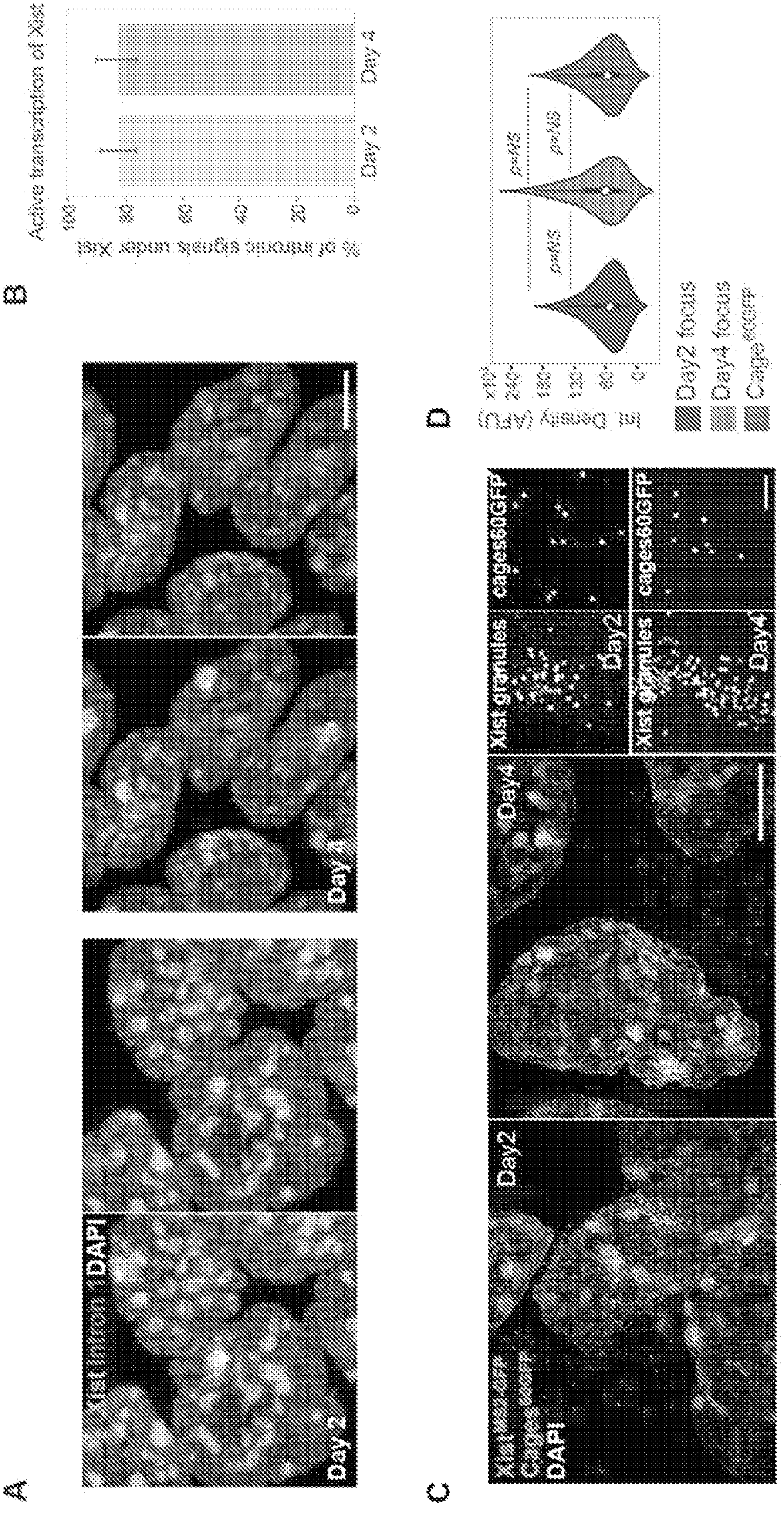
FIG. 7A-D

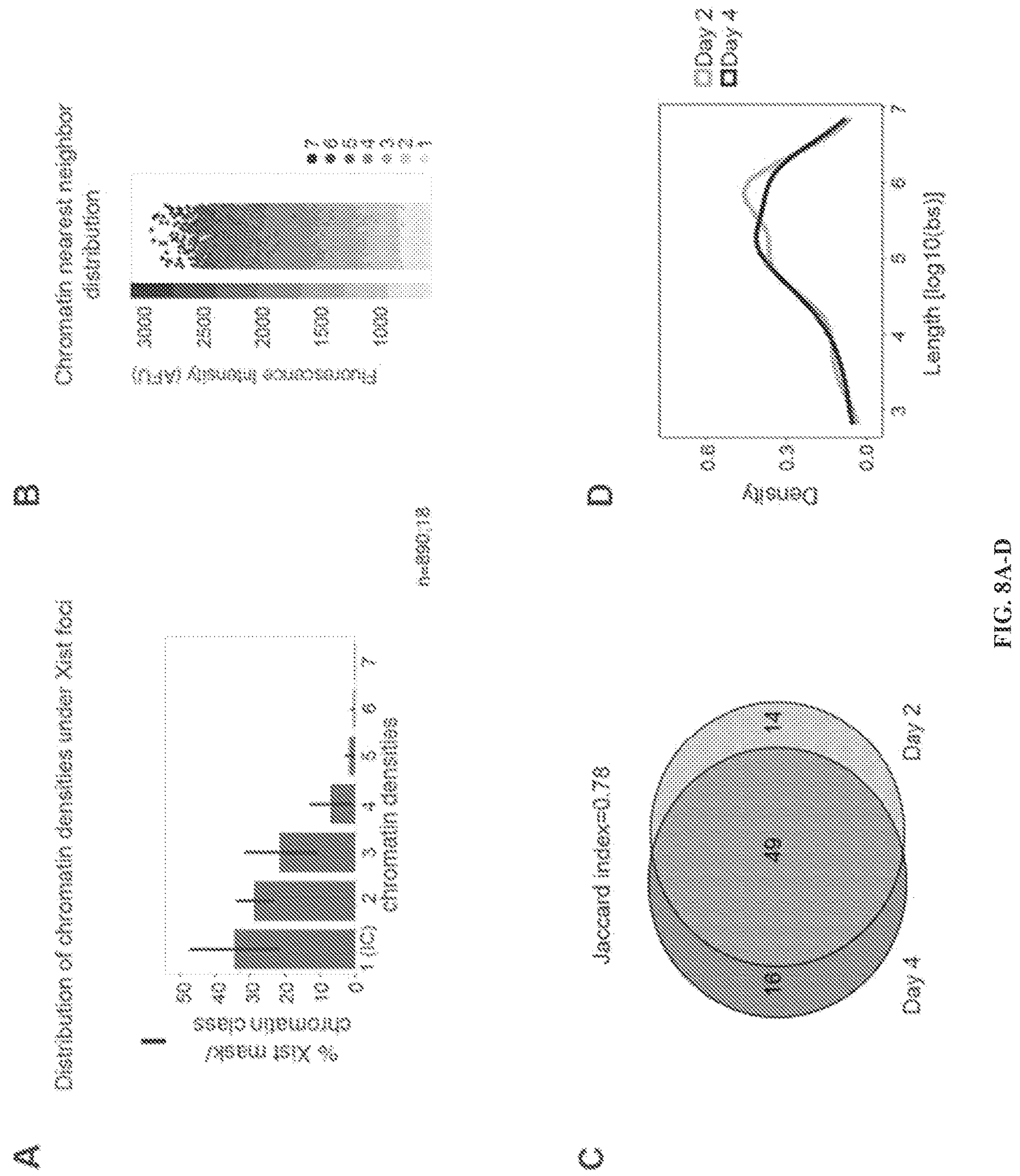
FIG. 8A-D

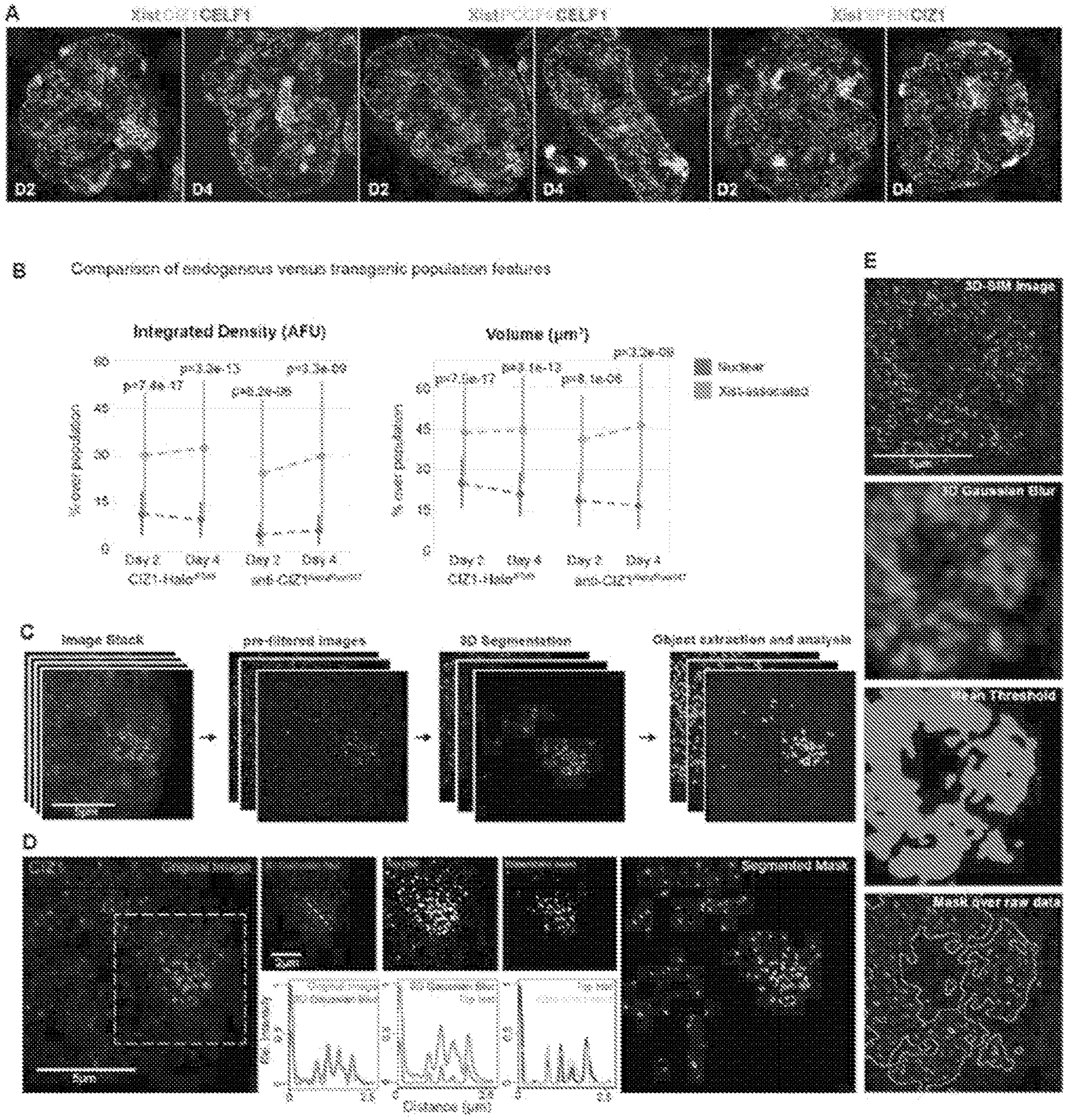
FIG. 9A-E

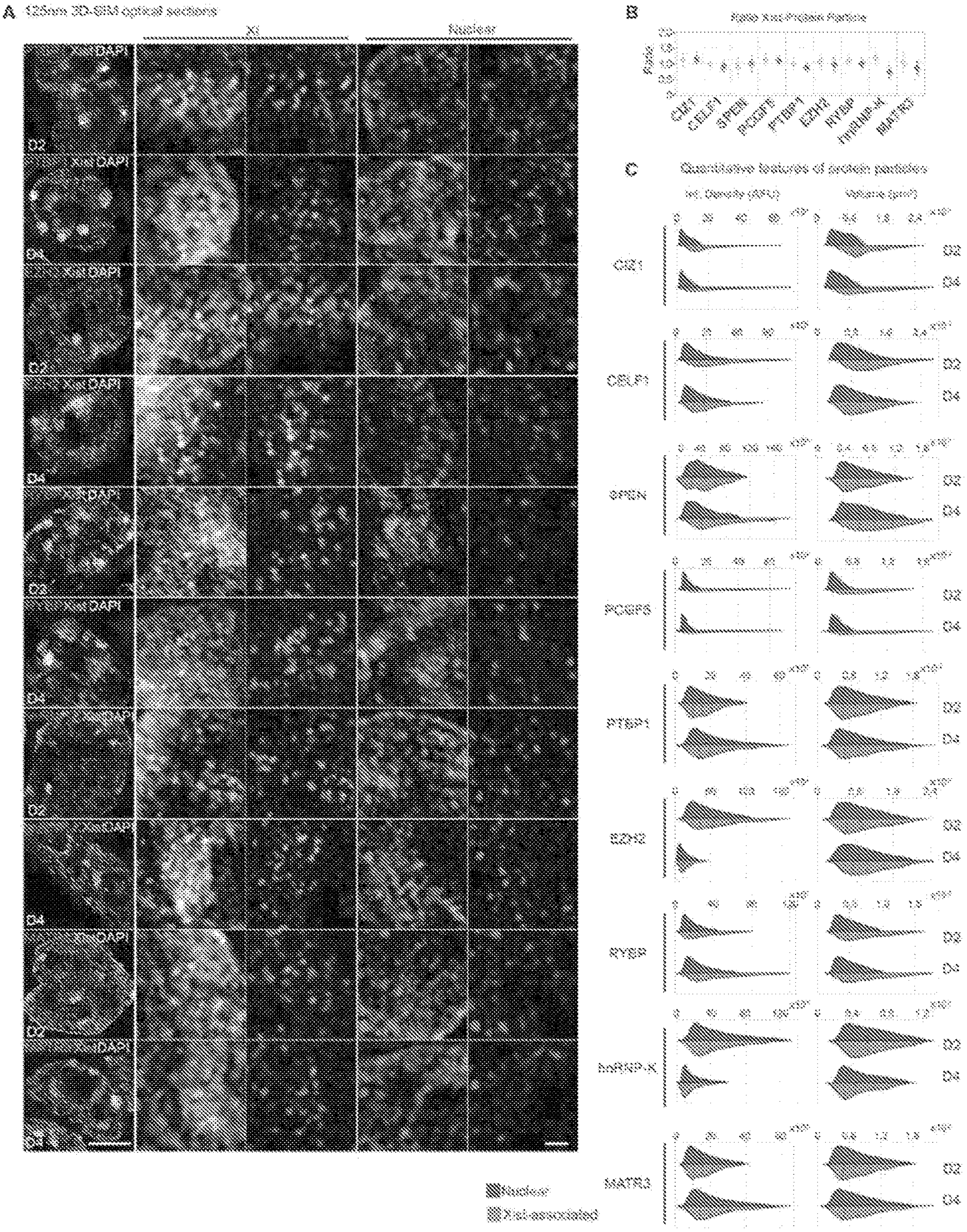
FIG. 10A-C

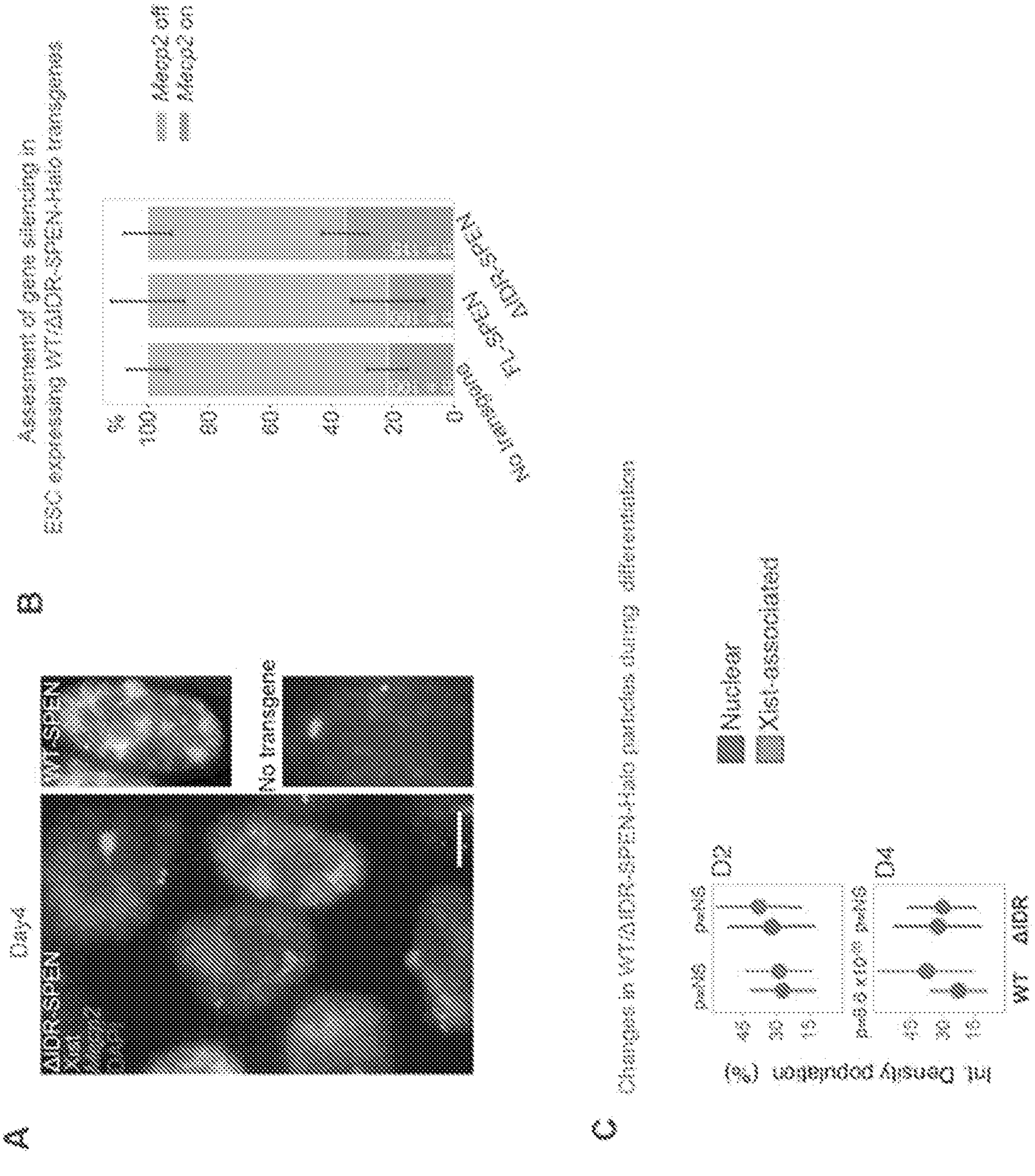
FIG. 11A-C

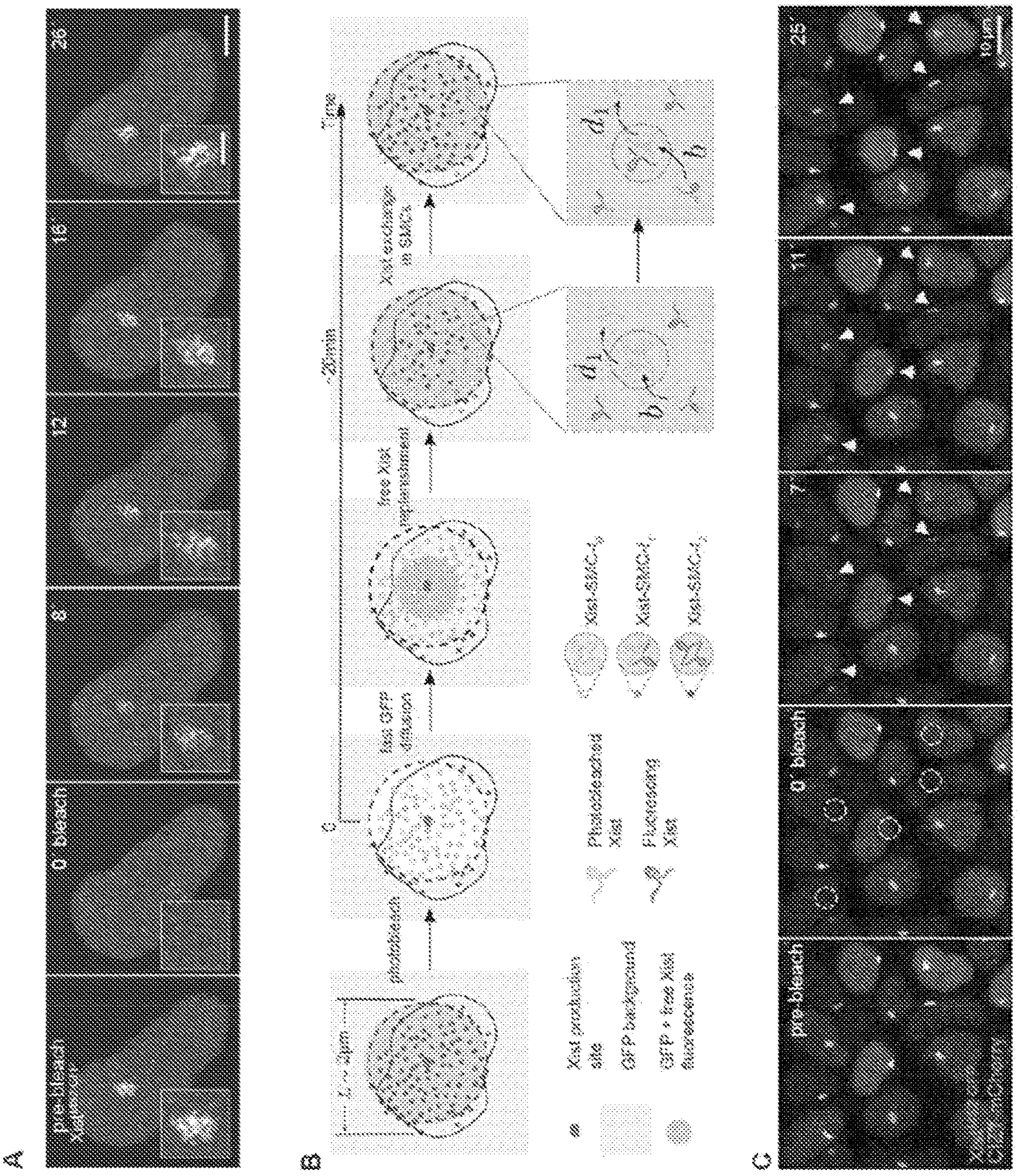
FIG. 12A-C

A
Fluorescence recovery after Photobleaching (FRAP) of Xist interactors in the nucleus and Xist territory
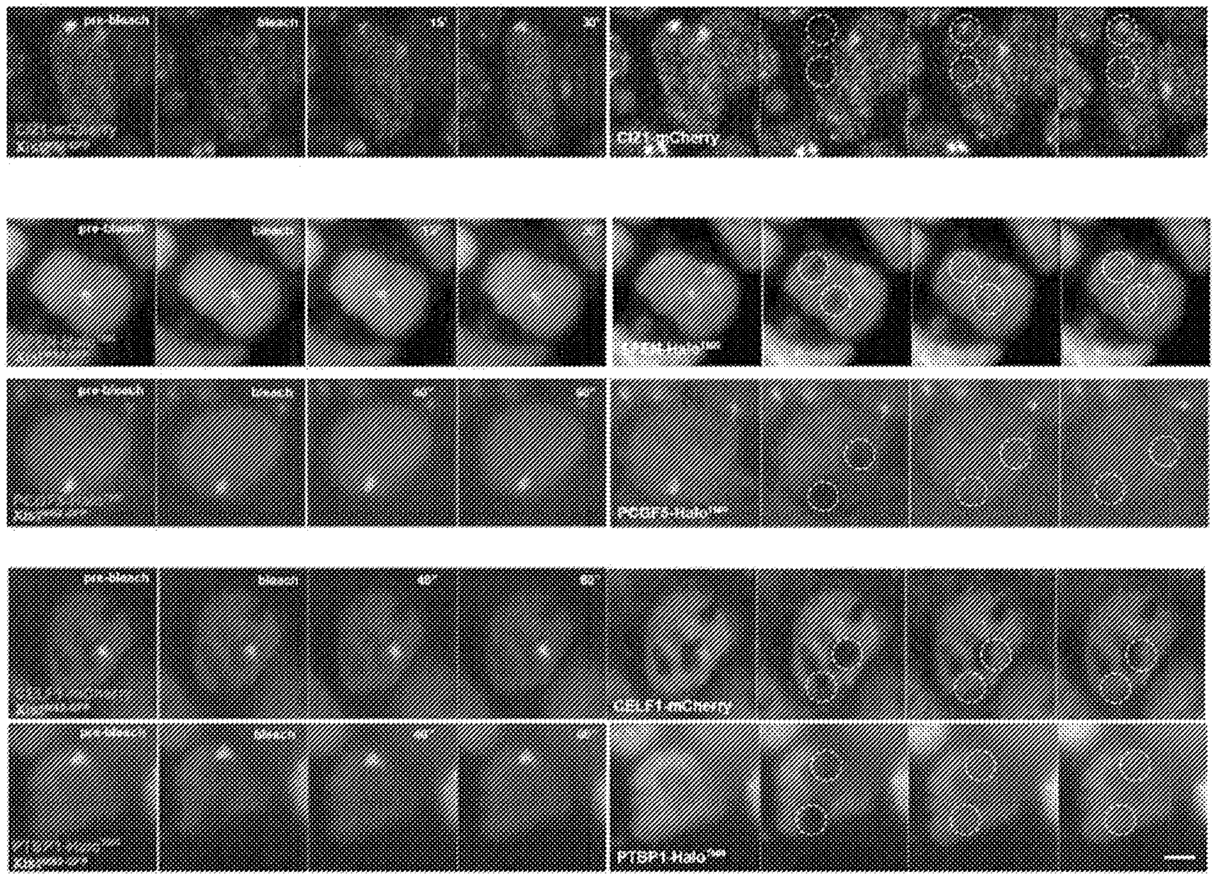
B
| | SPEN | | PCGF5 | | CELF1 | | PTBP1 | |
|---|---|---|---|---|---|---|---|---|
| | Nuclear | Xi | Nuclear | Xi | Nuclear | Xi | Nuclear | Xi |
| Fraction 1 ($f_1$) | 28 % | 23 % | 33 % | 22 % | 33 % | 18 % | 32 % | 30 % |
| Fraction 2 ($f_2$) | 10 % | 19 % | 29 % | 52 % | 31 % | 49 % | 44 % | 42 % |
FIG. 13A-B A
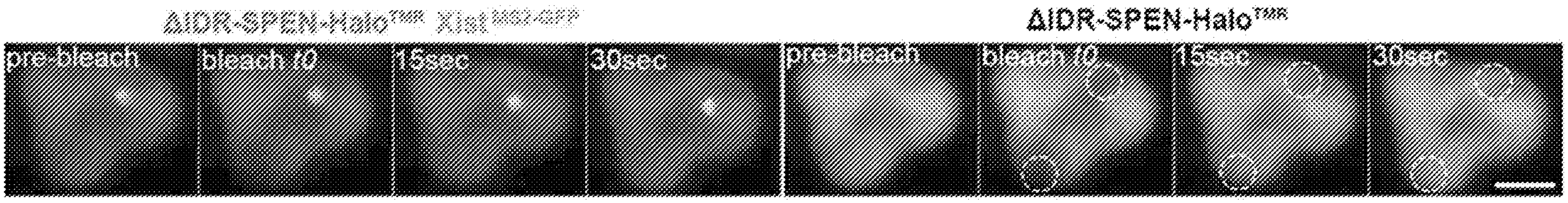
B
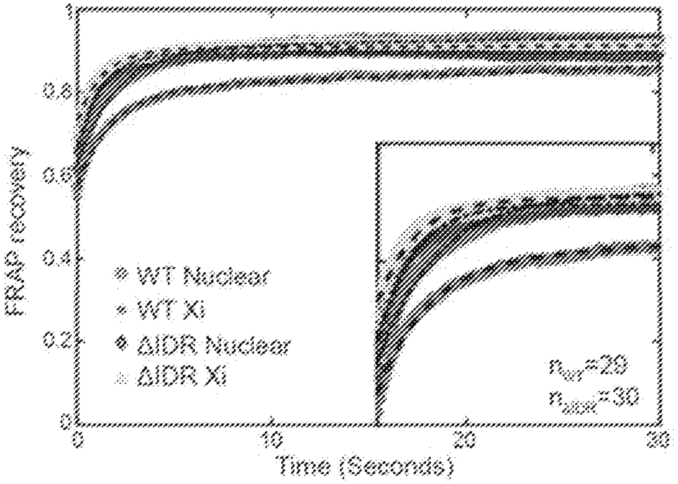
C
| ΔIDR | Lifetime | | Percentage | |
|---|---|---|---|---|
| | Nuclear | Xi | Nuclear | Xi |
| Fraction $f_1$ | 1.3sec | 1.3sec | 23% | 18% |
| Fraction $f_2$ | ∞ | 5.7min | 10% | 9% |
| WT | Lifetime | | Percentage | |
|---|---|---|---|---|
| | Nuclear | Xi | Nuclear | Xi |
| Fraction $f_1$ | 2sec | 1.9sec | 28% | 23% |
| Fraction $f_2$ | 80sec | 91.7sec | 10% | 19% |
FIG. 14A-C

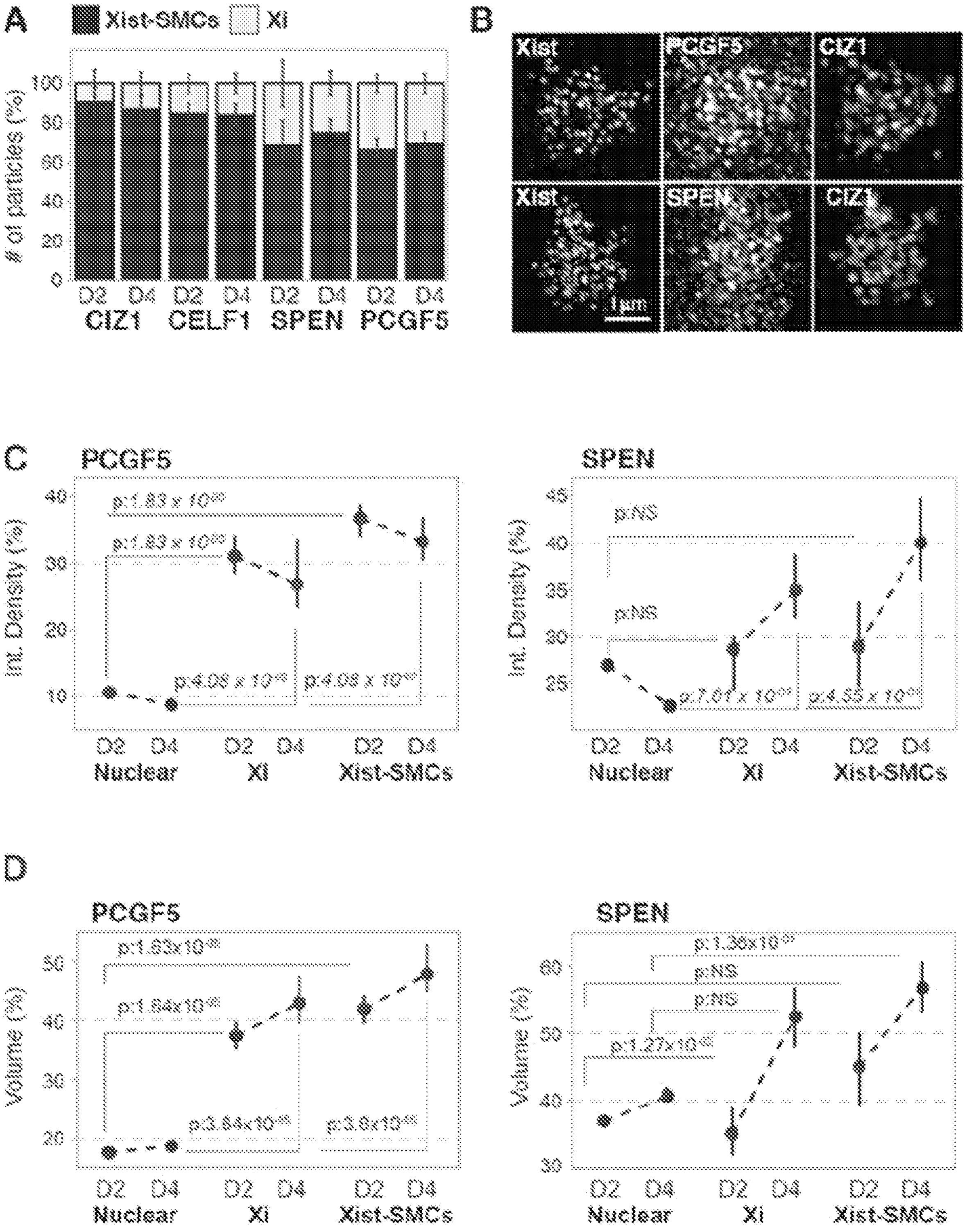
FIG. 15A-D

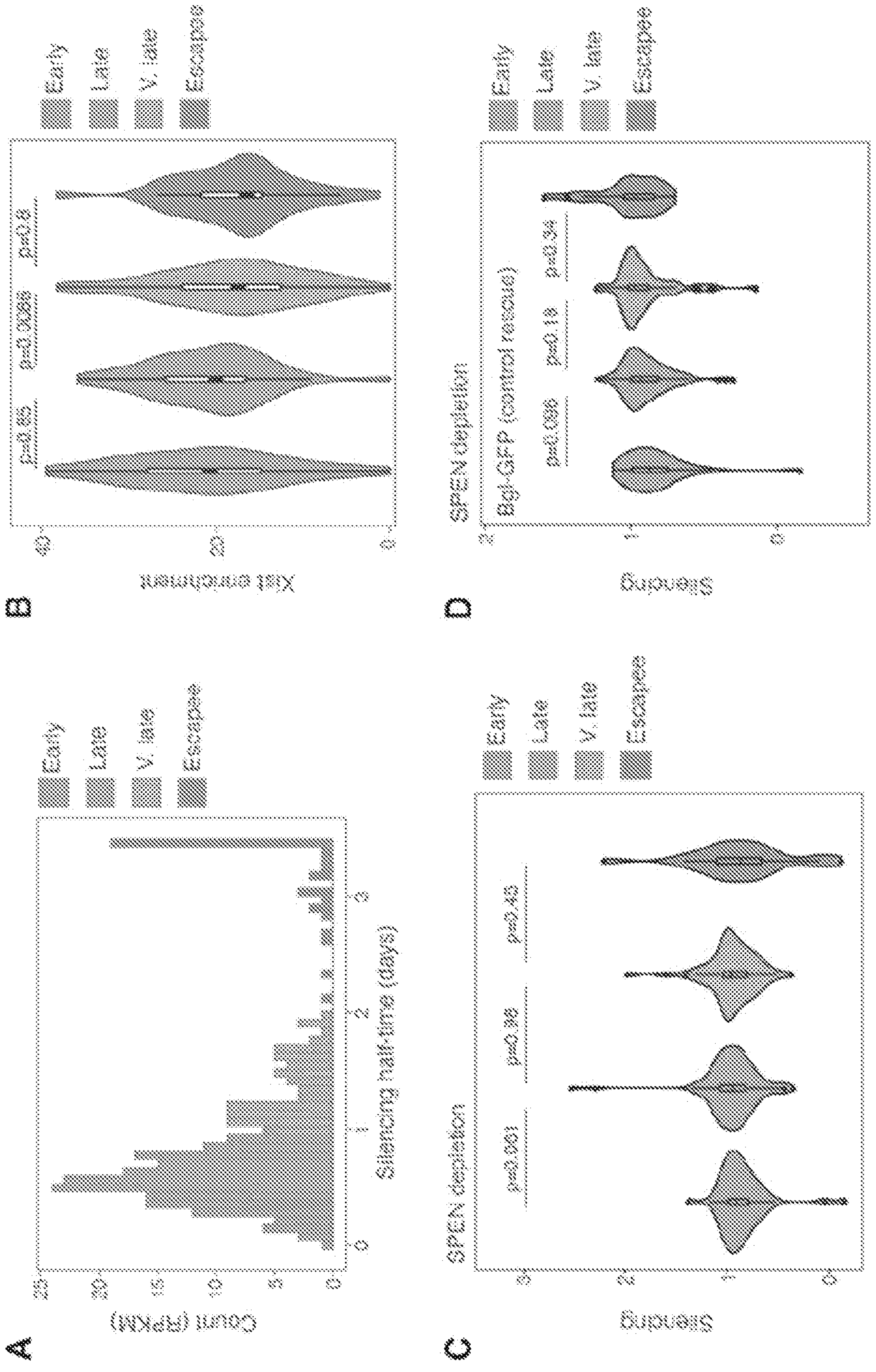
FIG. 16A-D

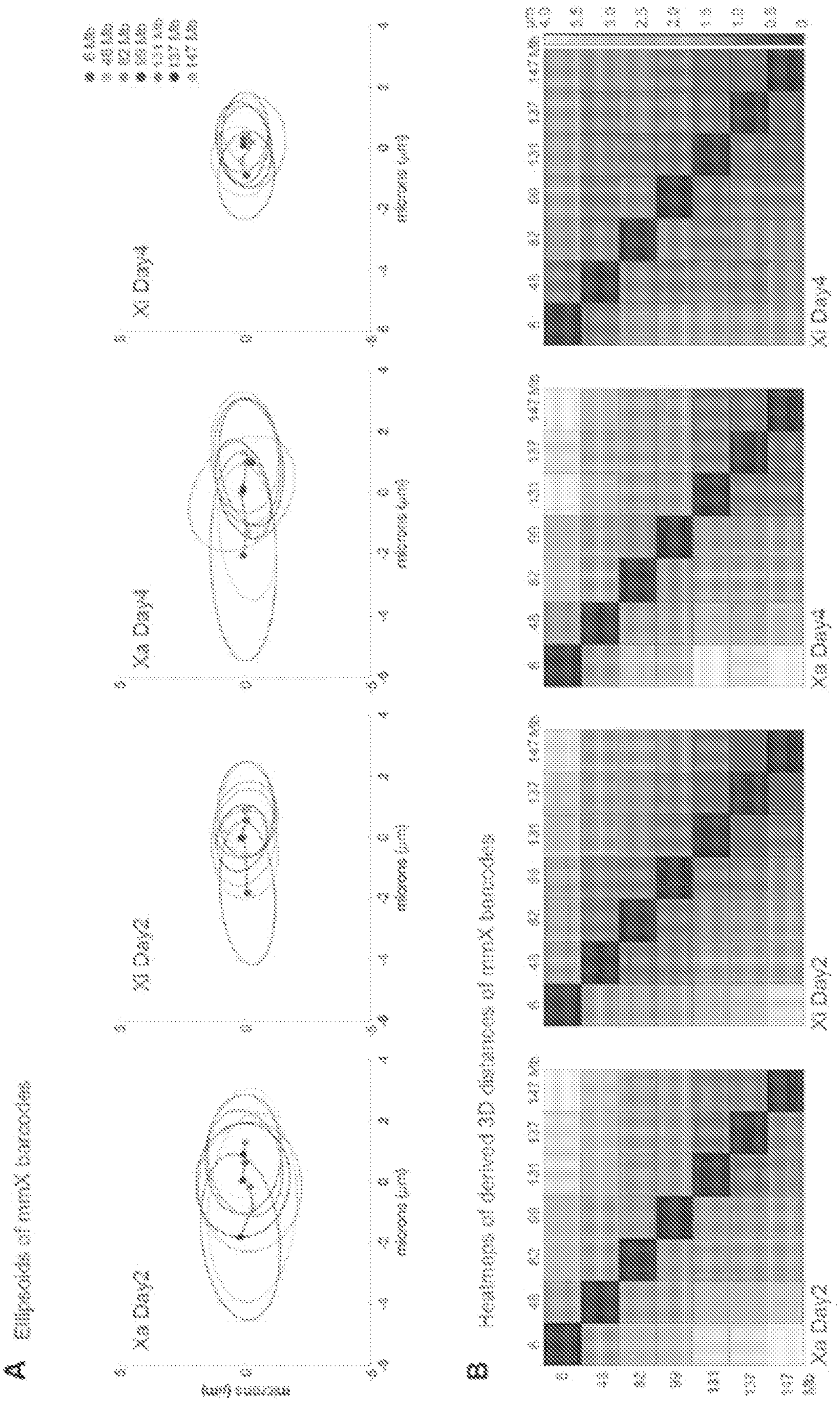
FIG. 17A-B

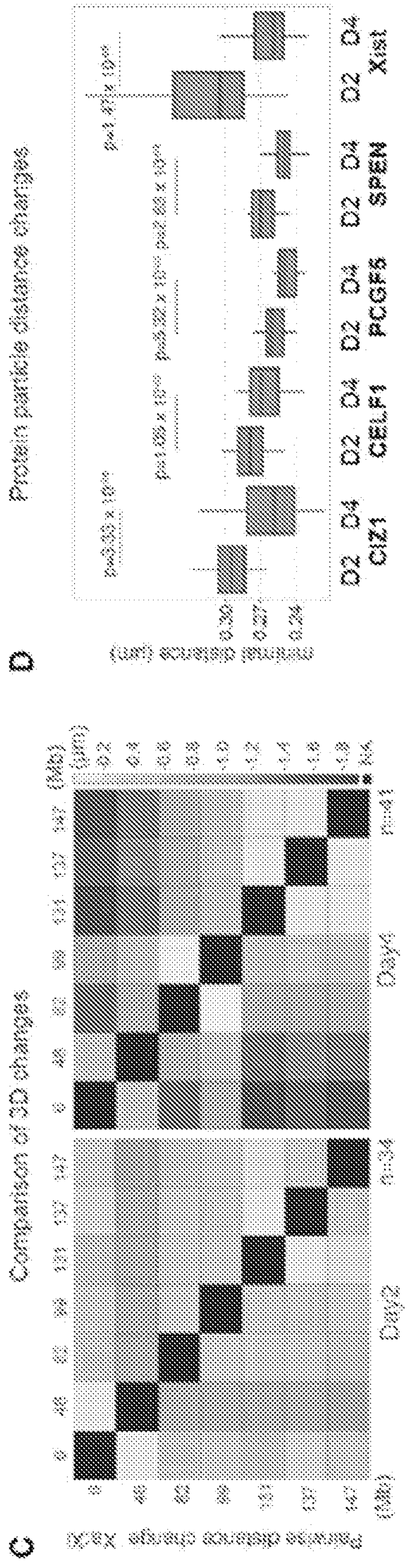
FIG. 17C-D

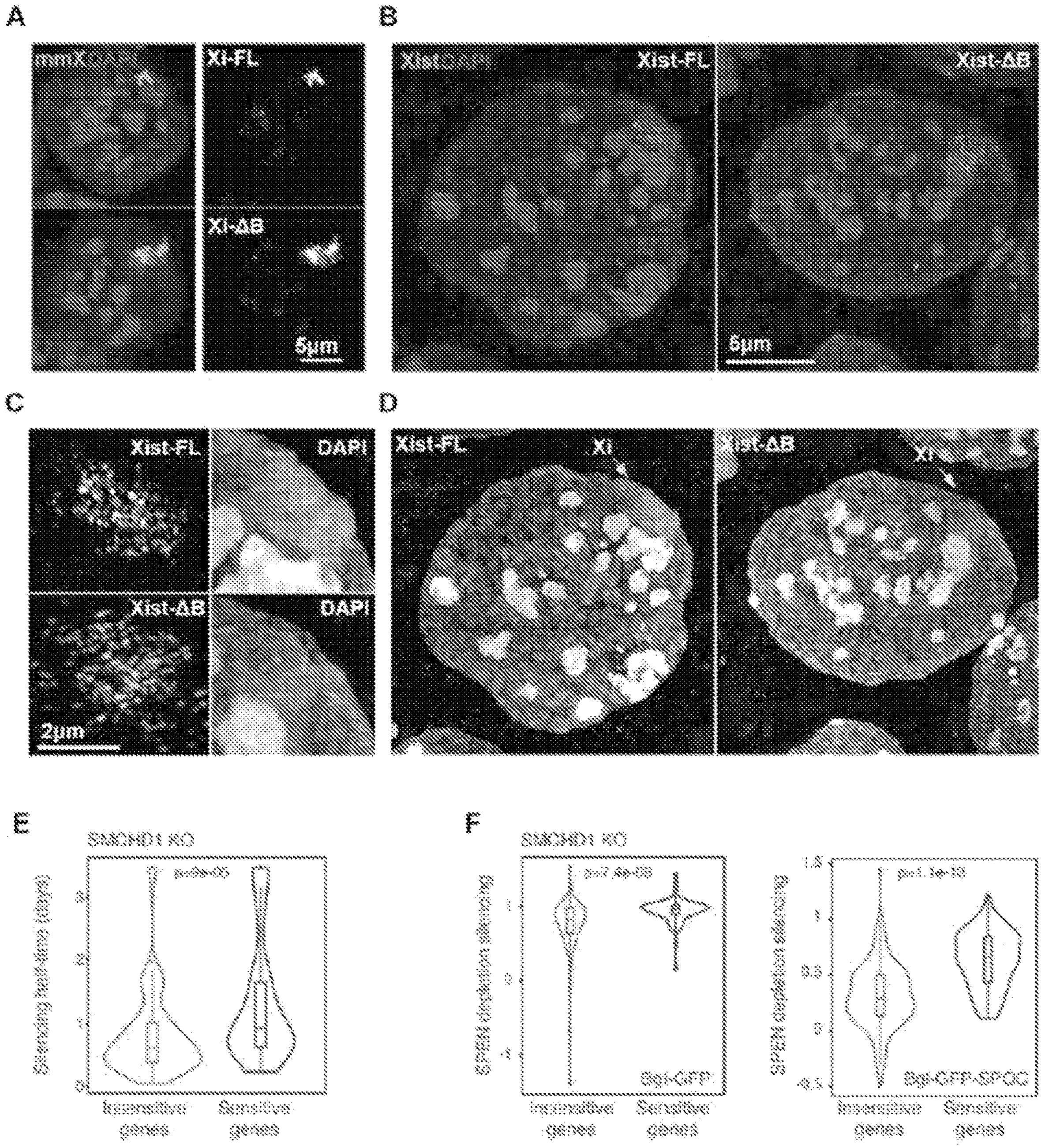
FIG. 18A-F

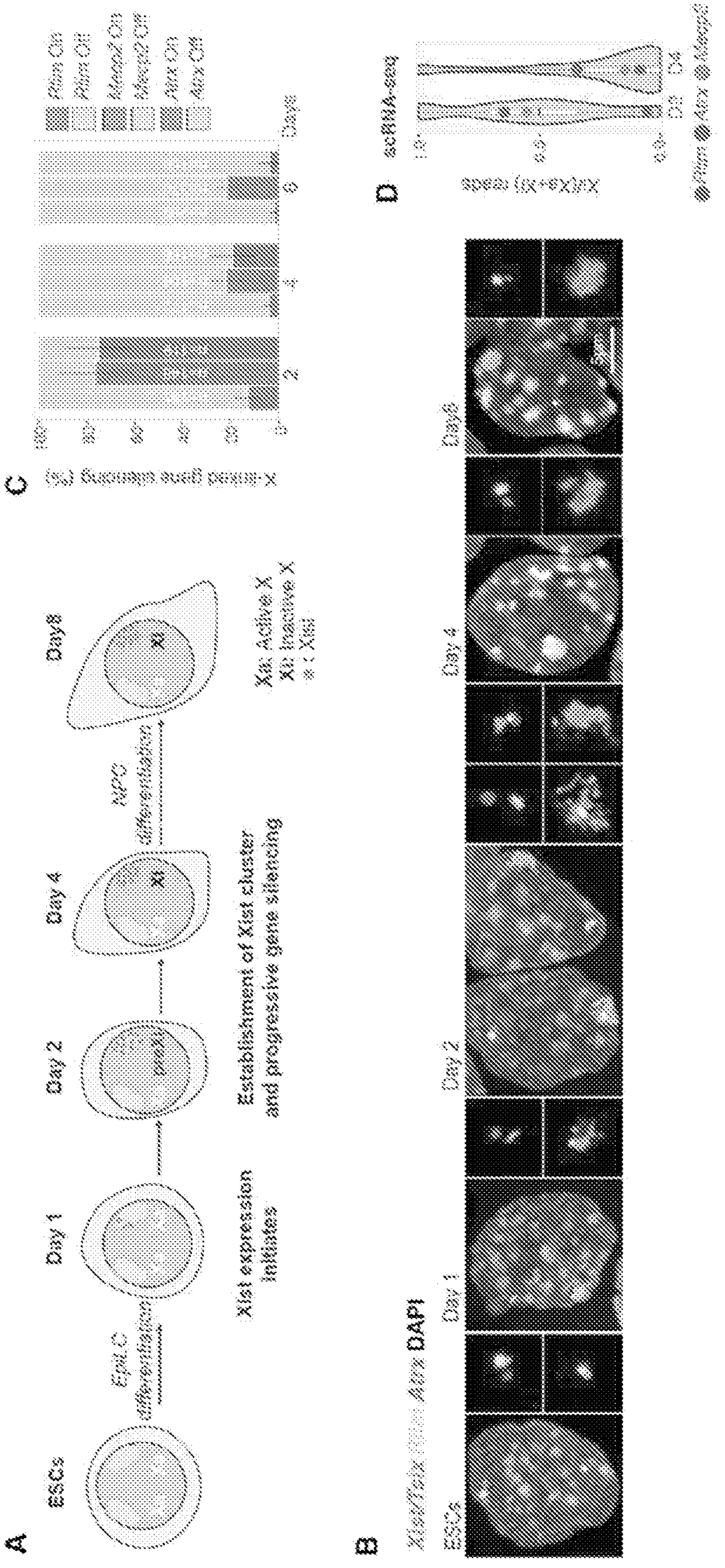
FIG. 19A-D

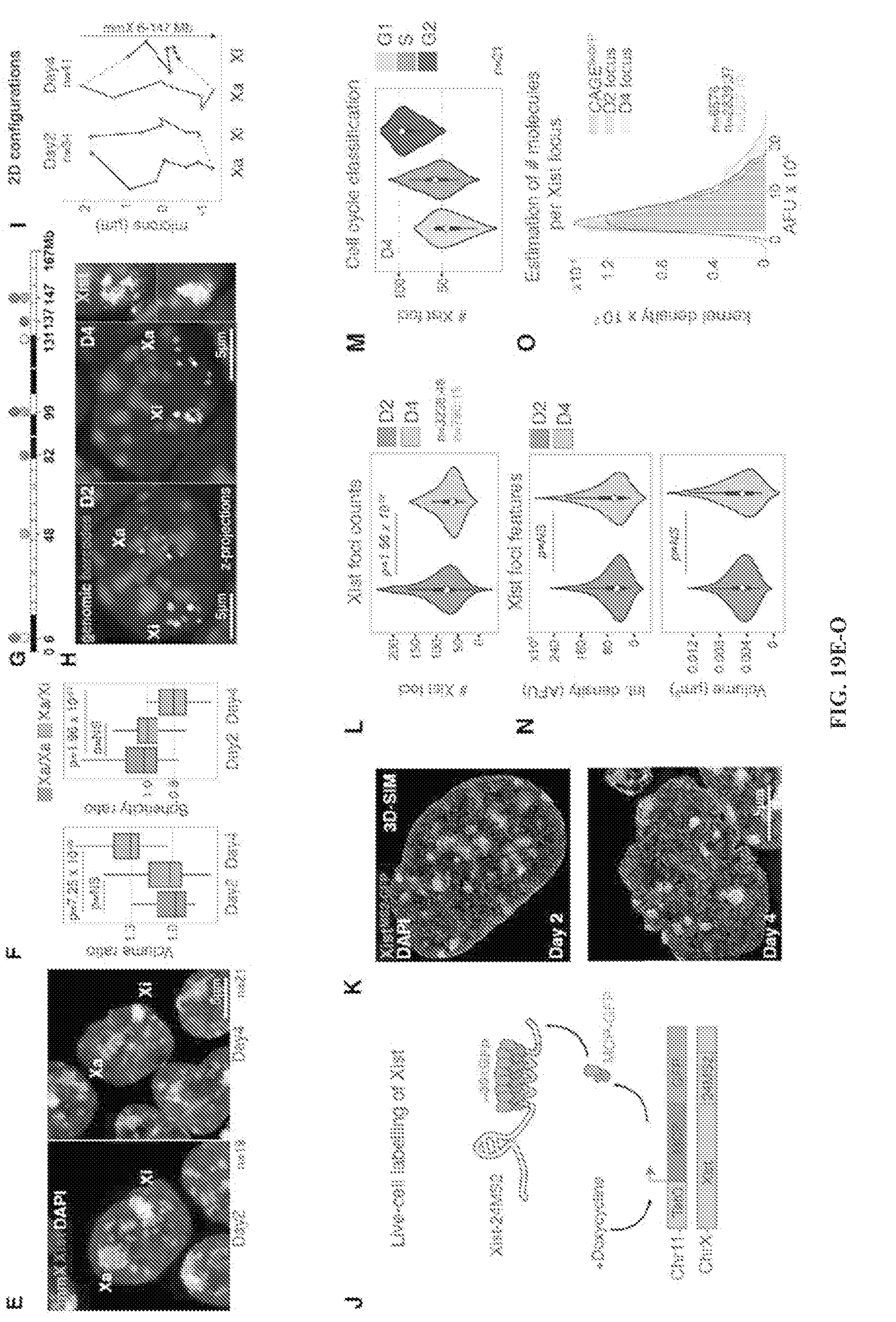
FIG. 19E-O

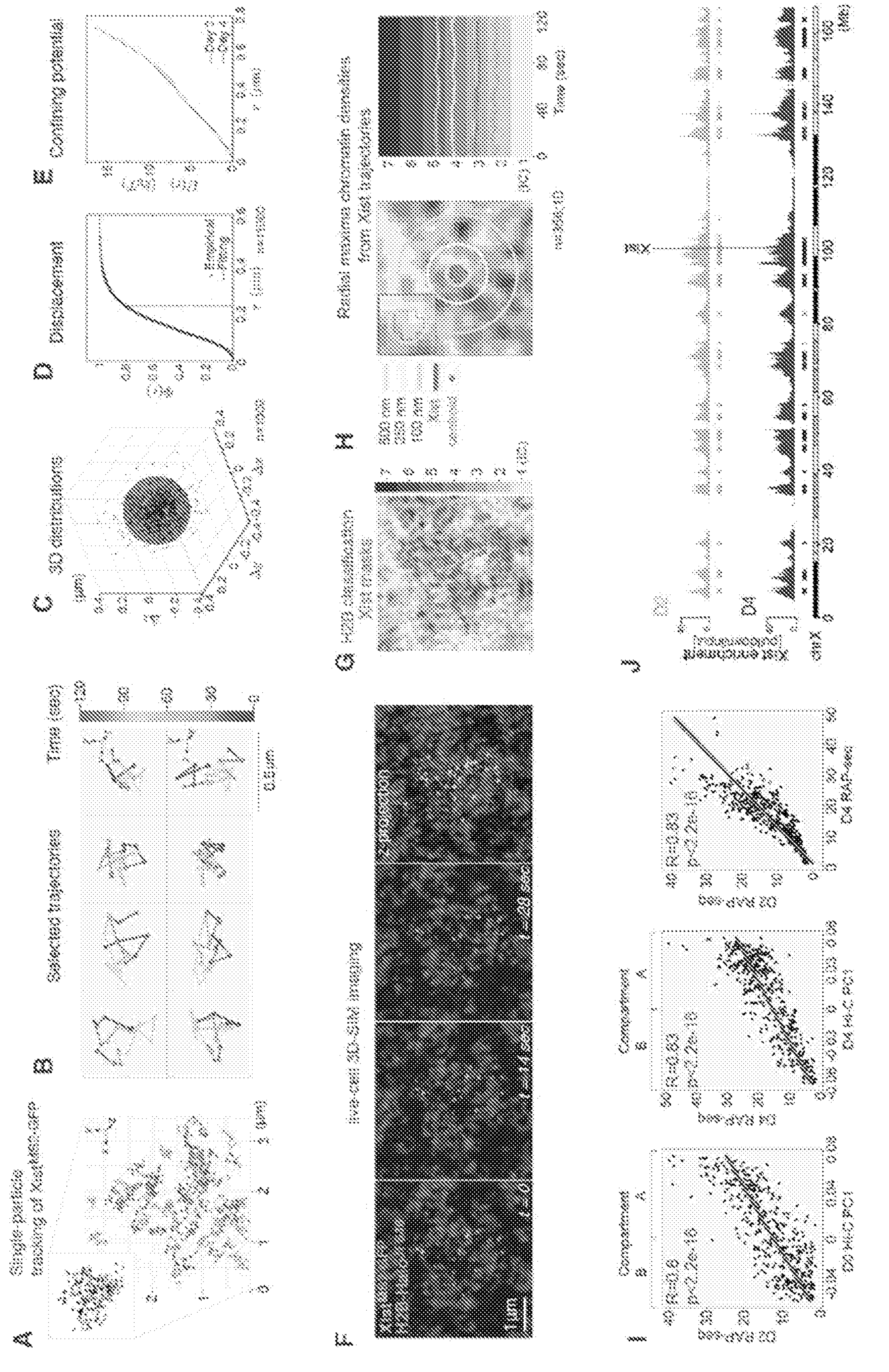
FIG. 20A-J

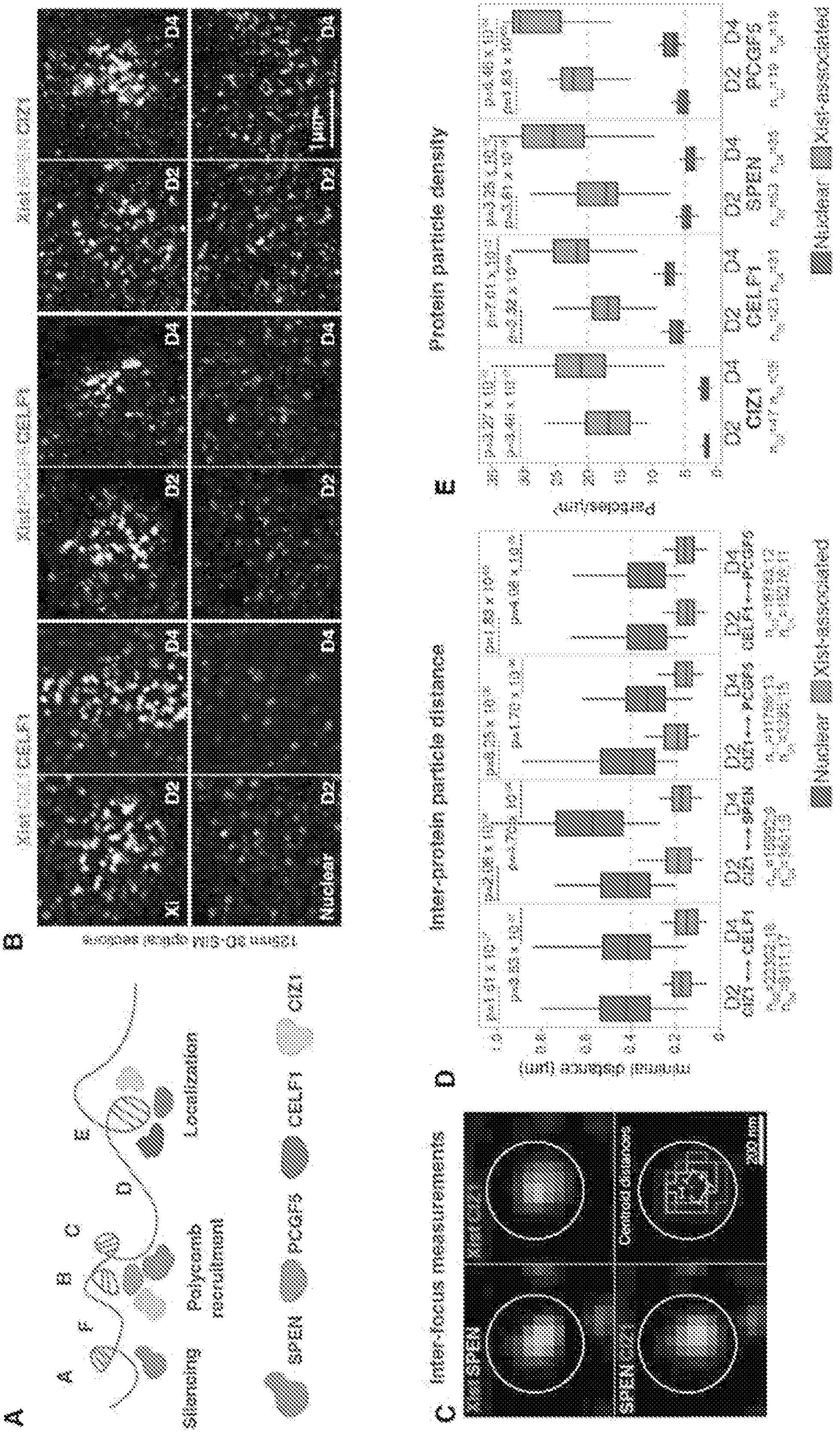
FIG. 21A-E

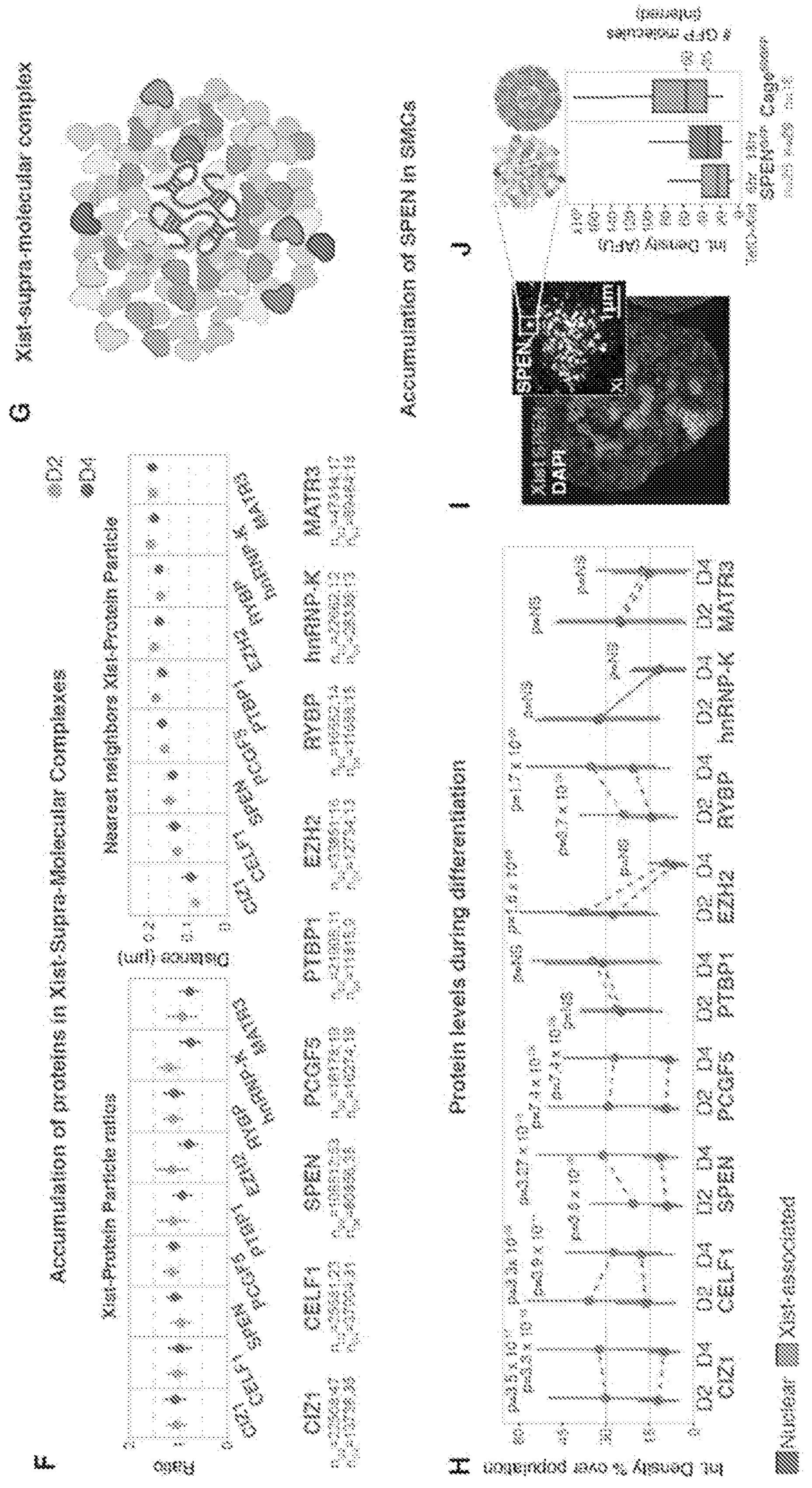
FIG. 21F-J

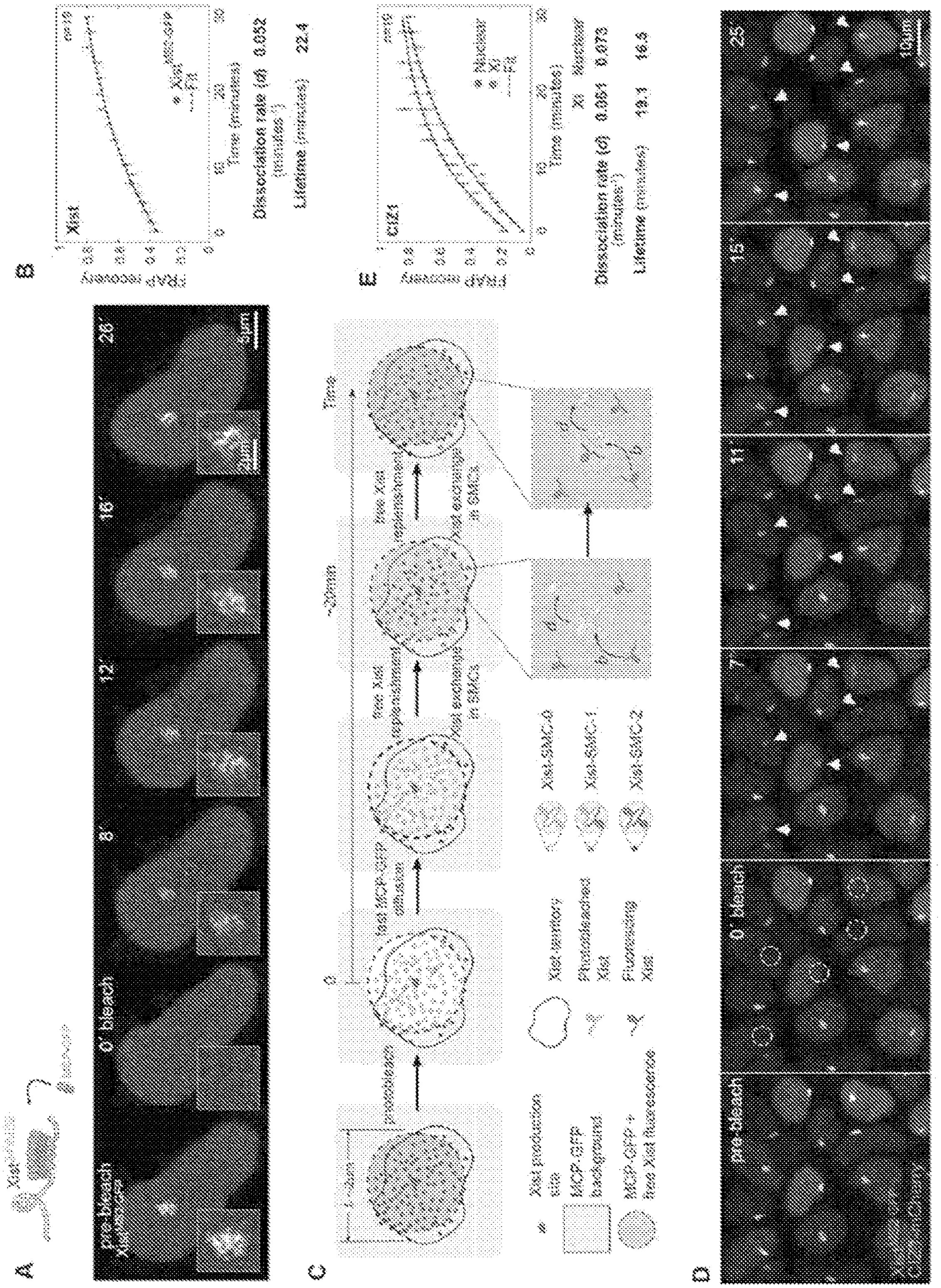
FIG. 22A-E

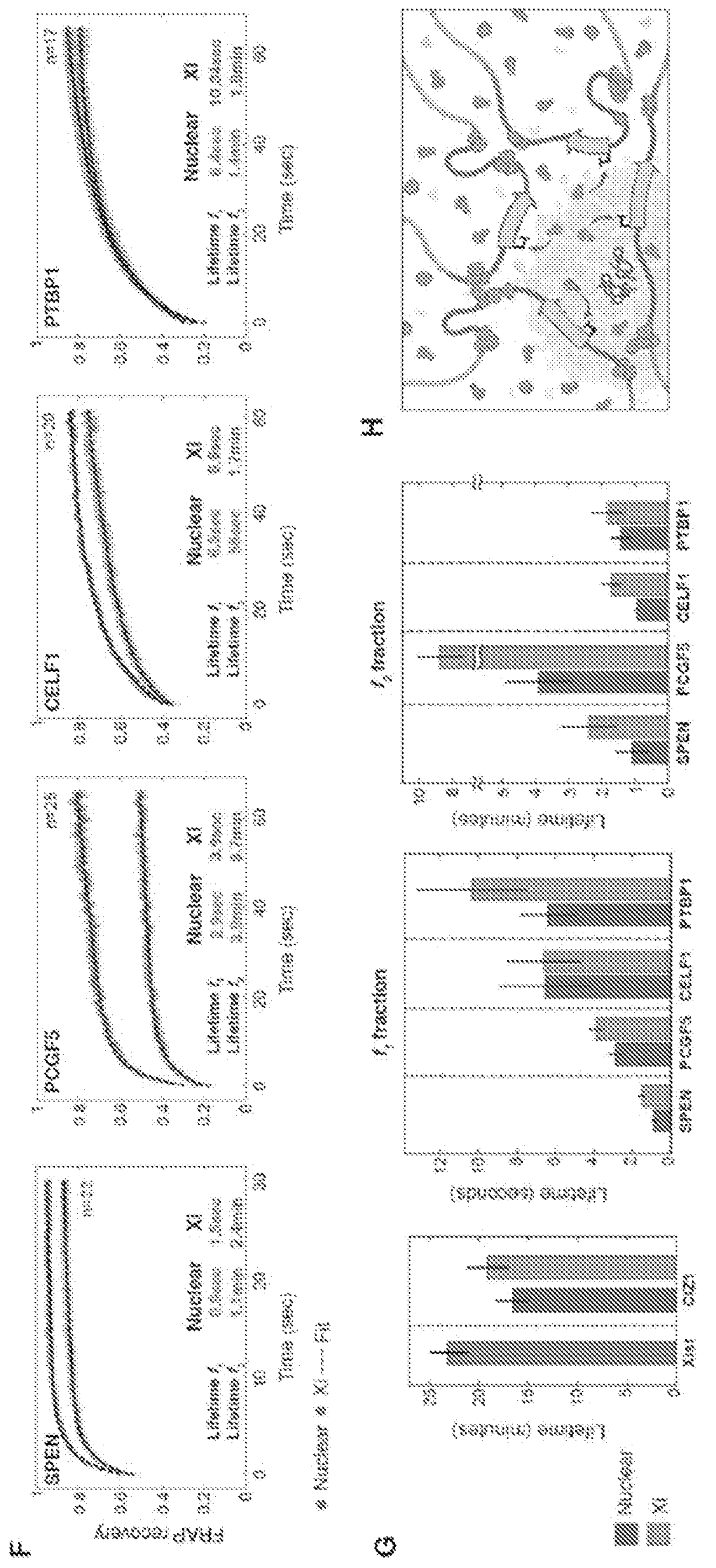
FIG. 22F-H

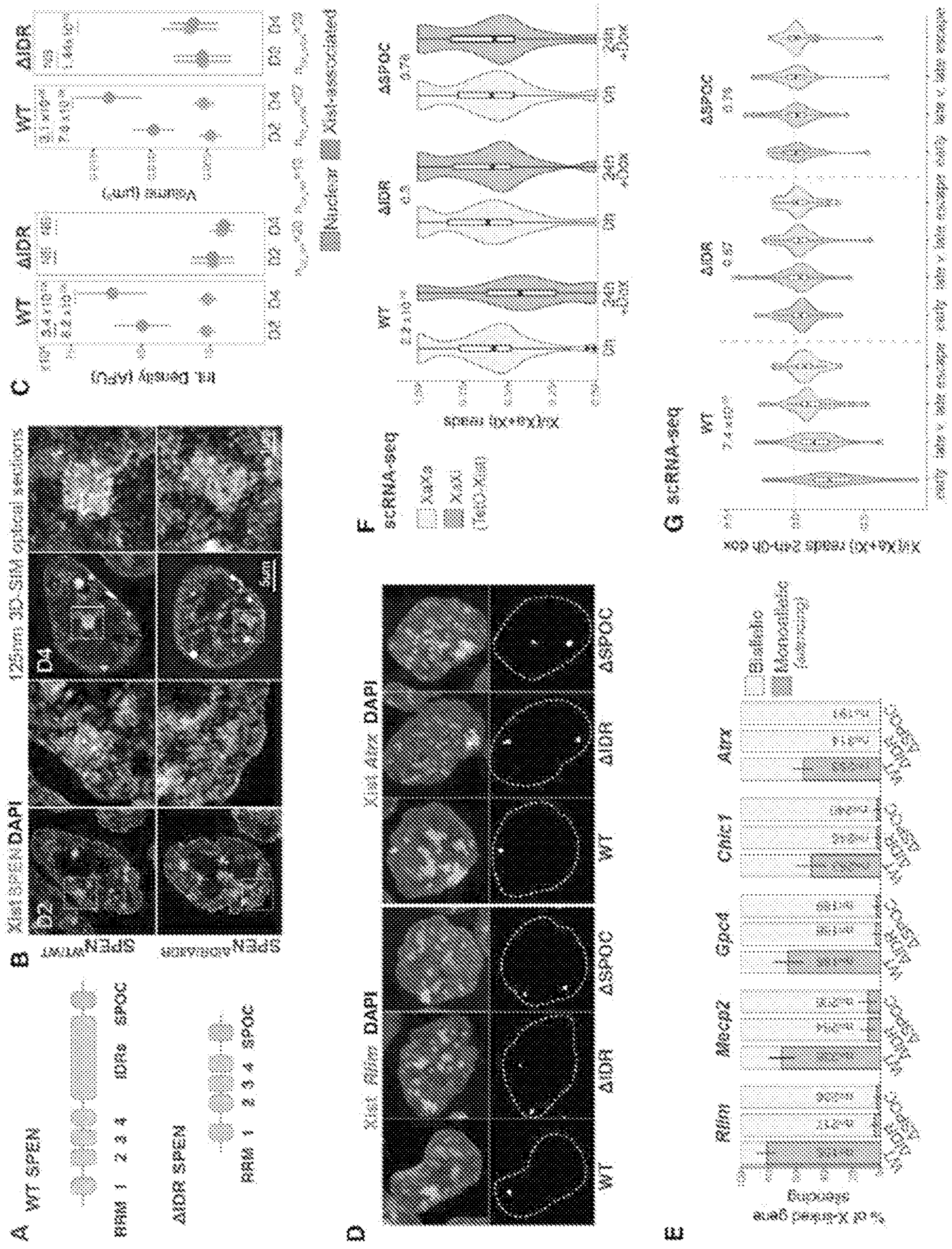
FIG. 23A-G

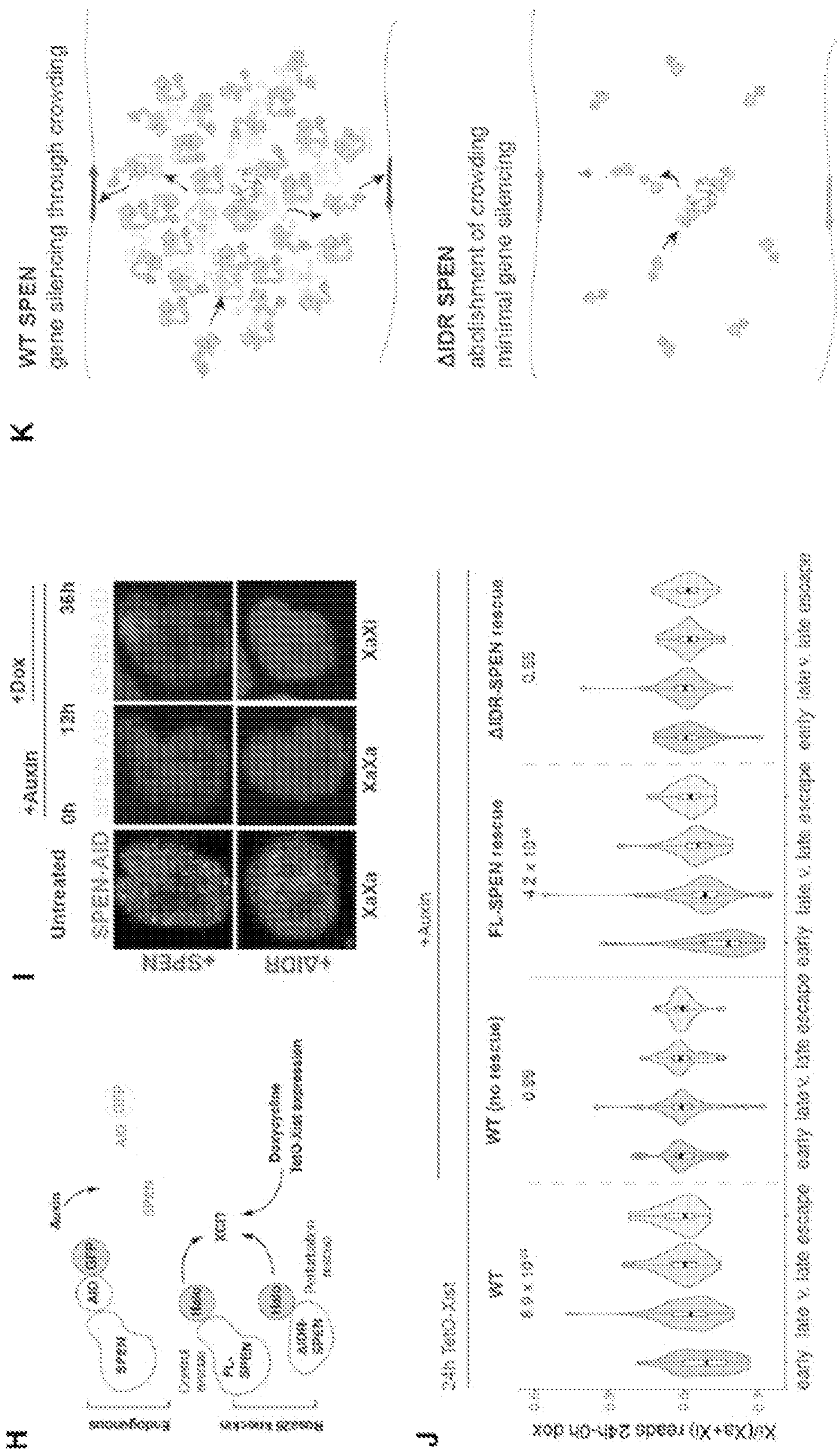
FIG. 23H-K

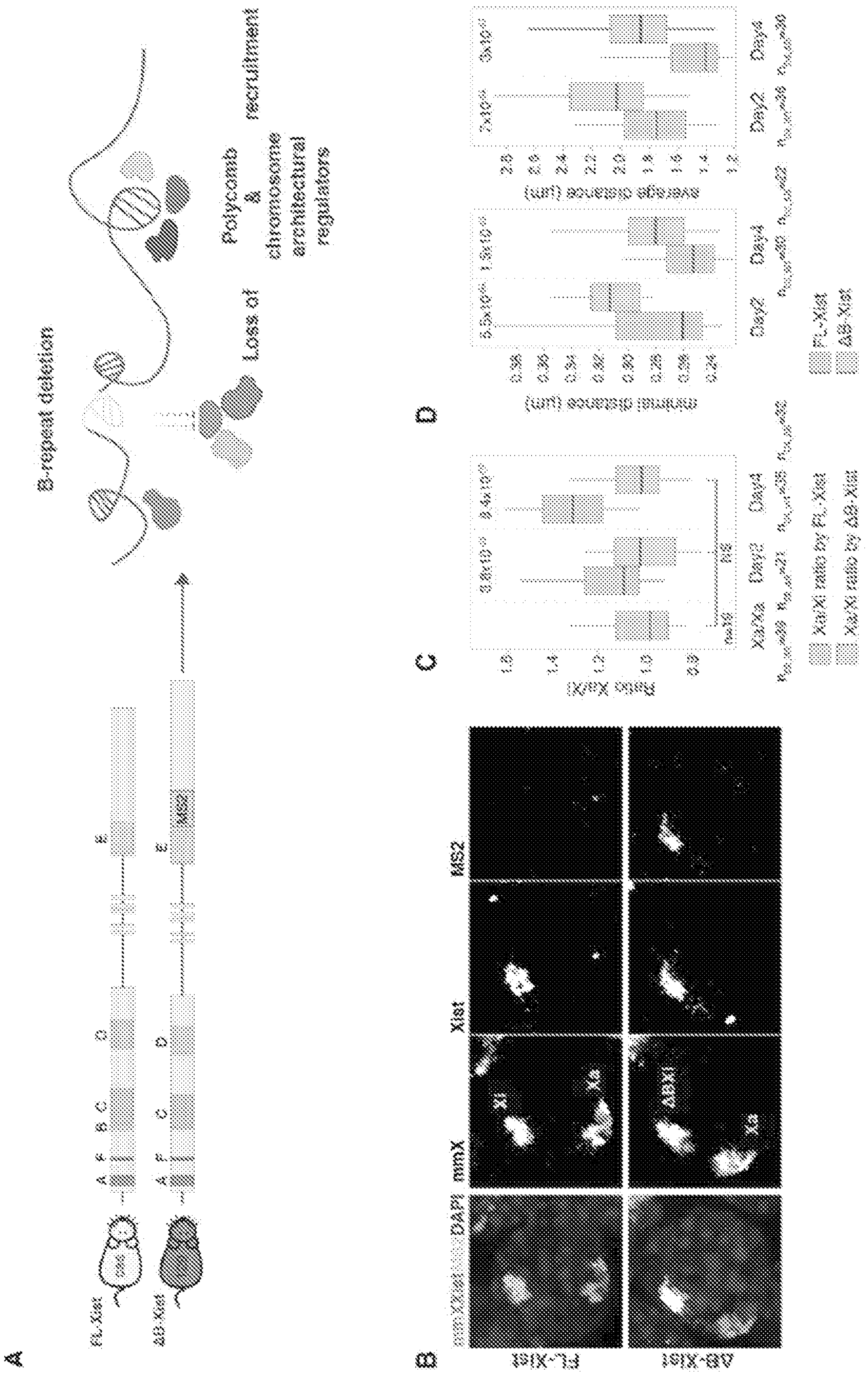
FIG. 24A-D

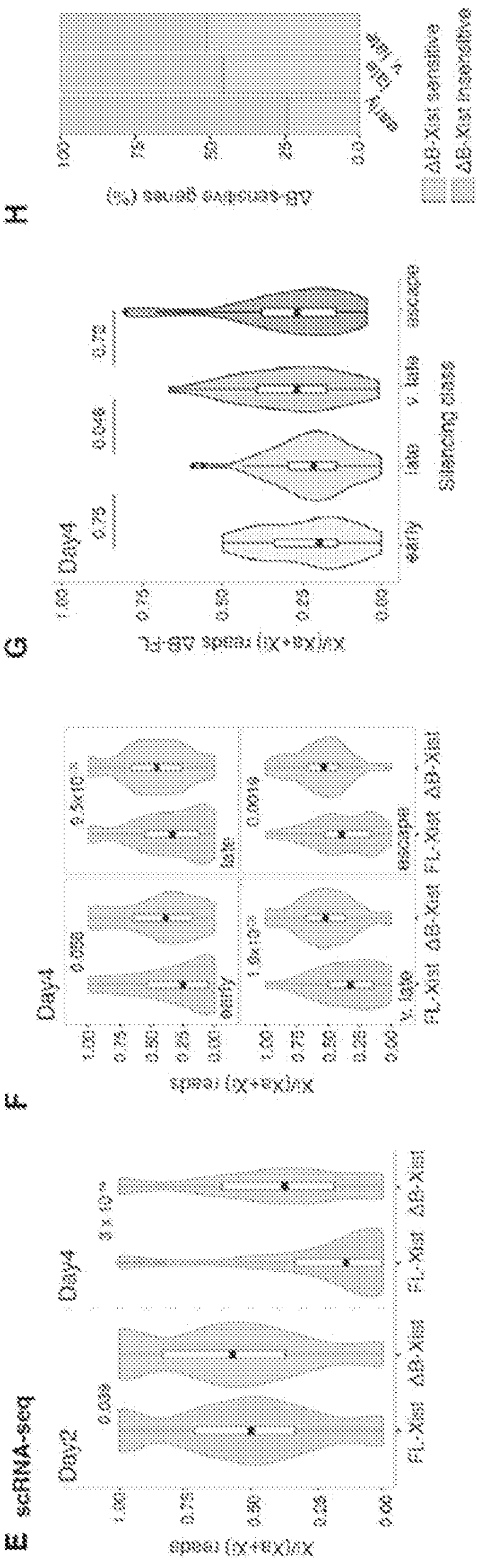
FIG. 24E-H

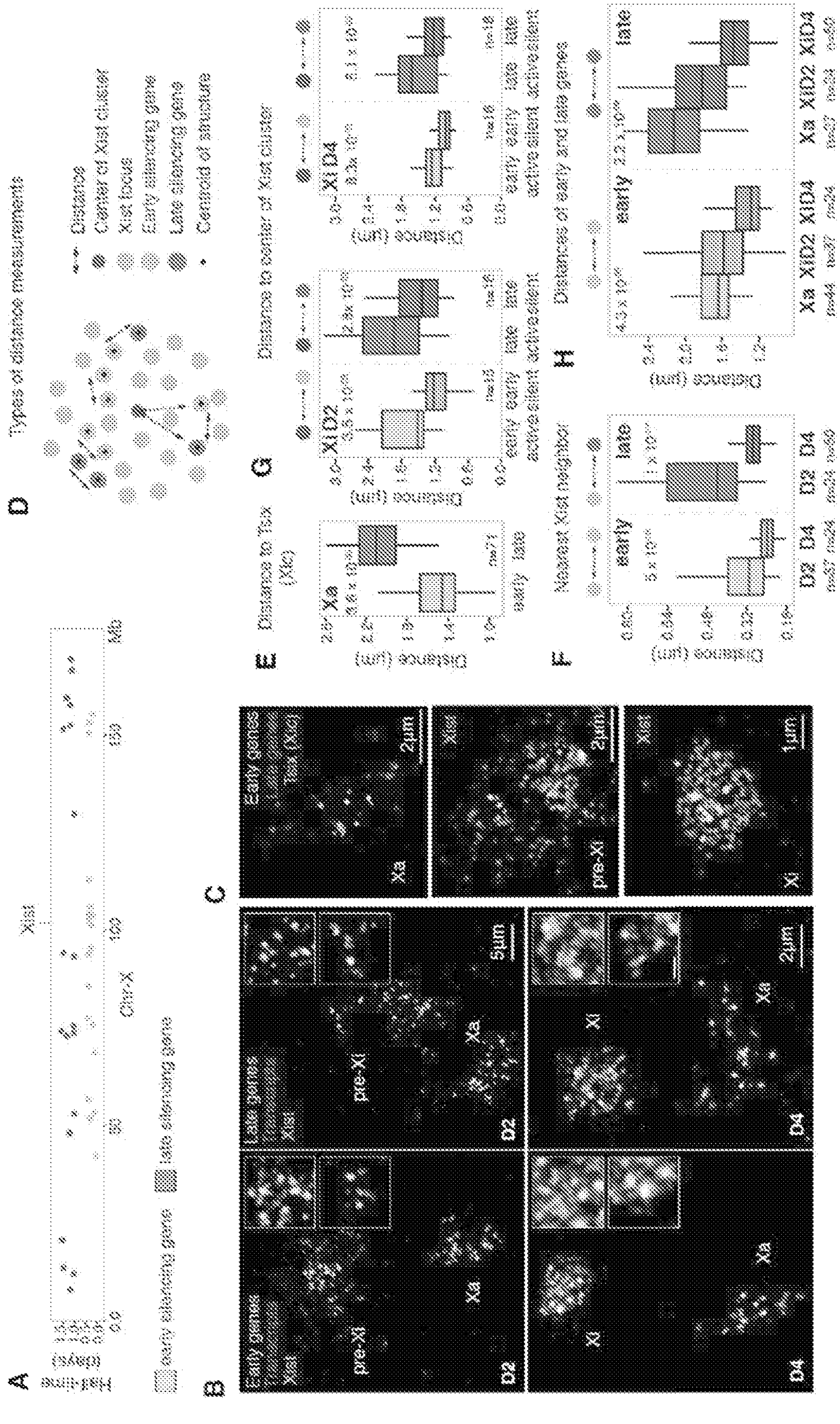
FIG. 25A-H

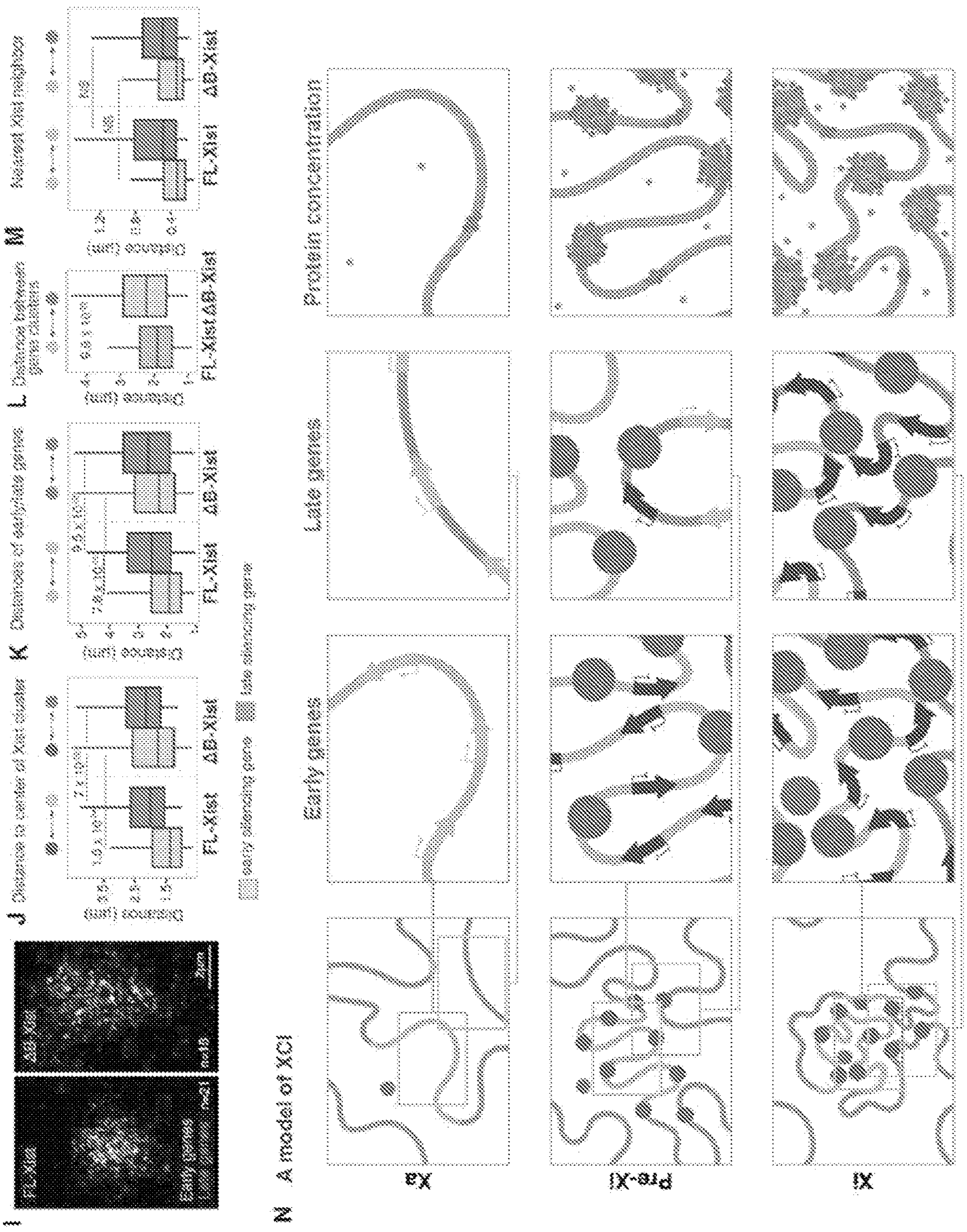
FIG. 25I-N

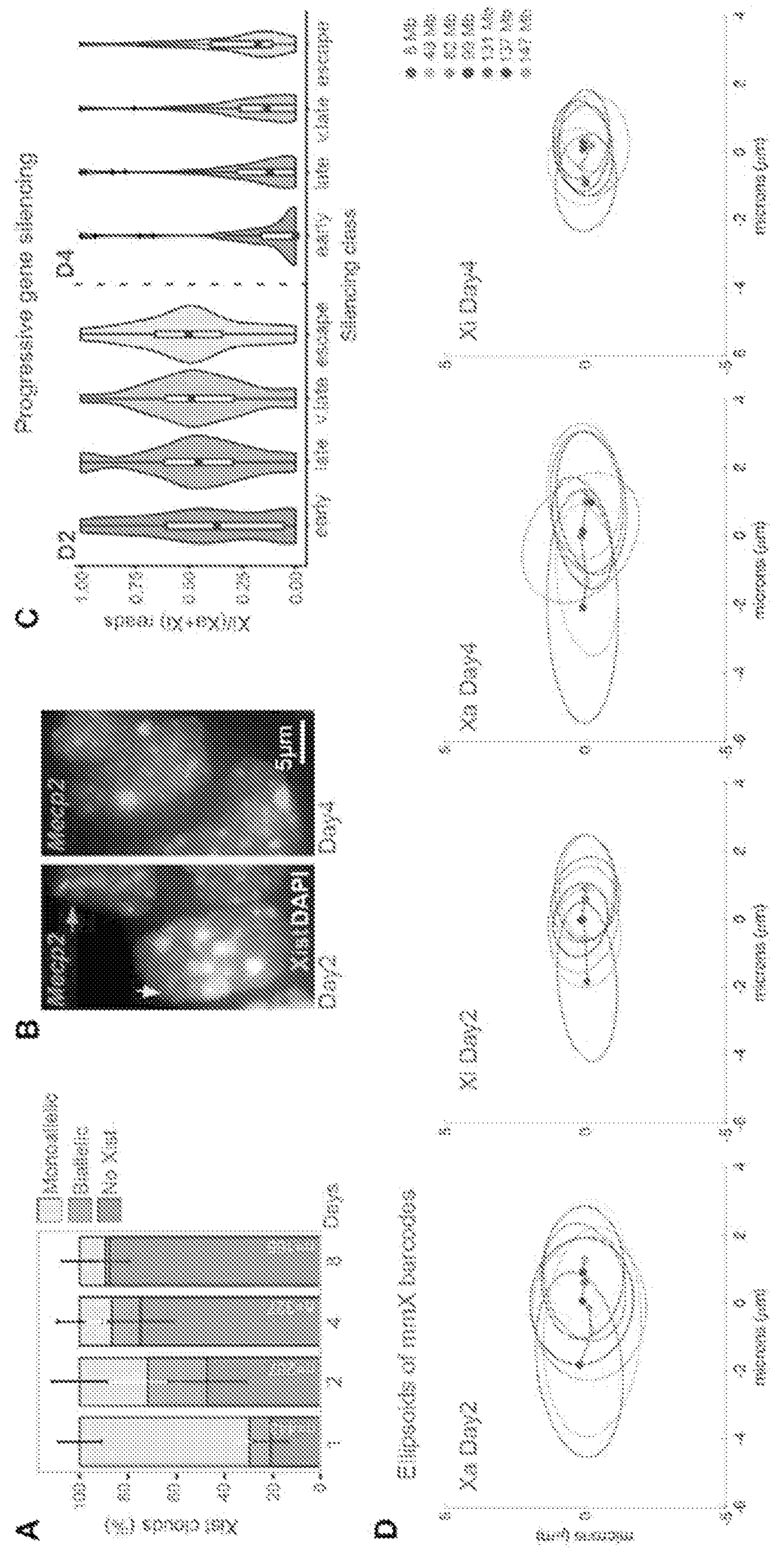
FIG. 26A-D

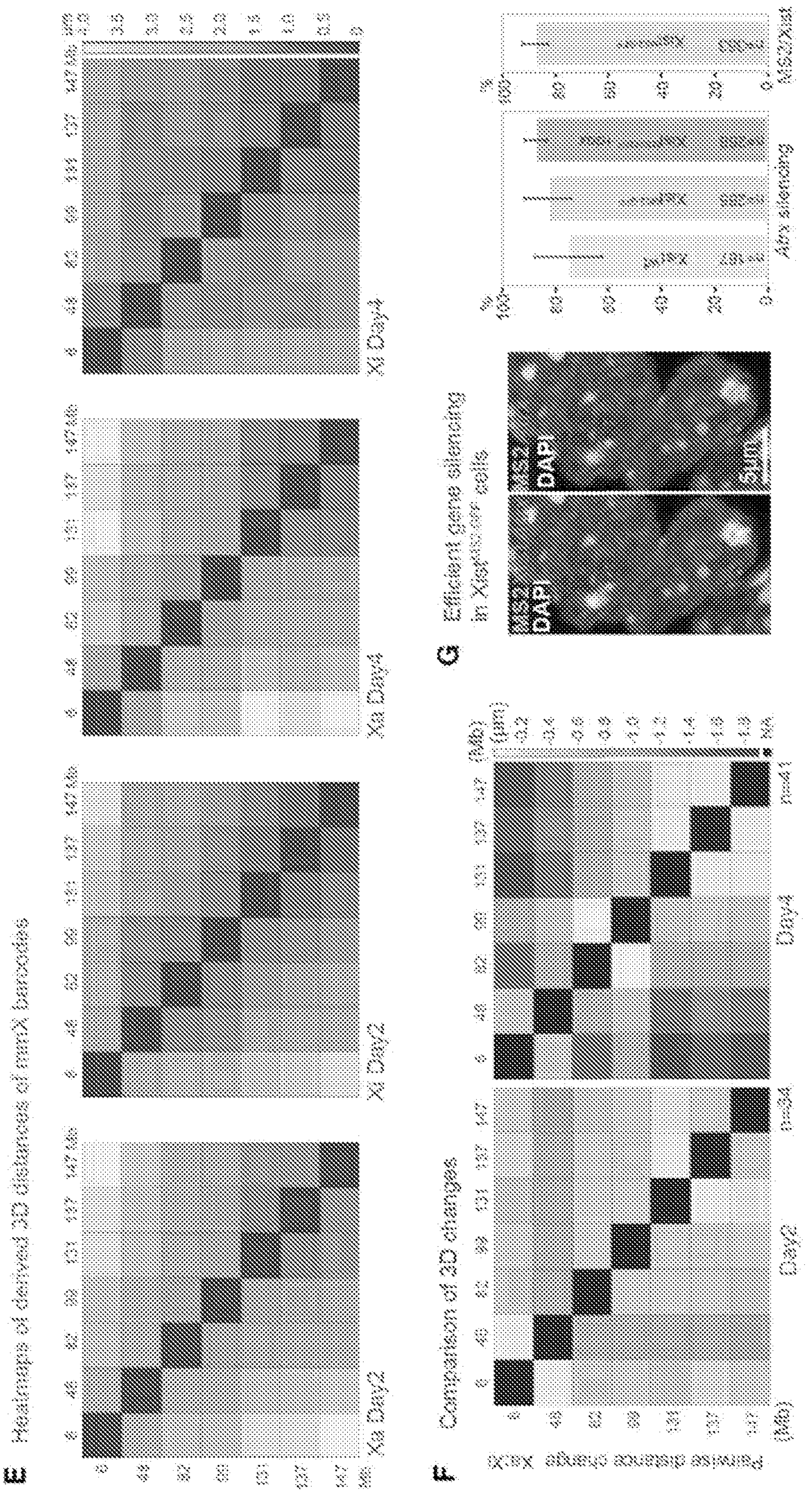
FIG. 26E-G

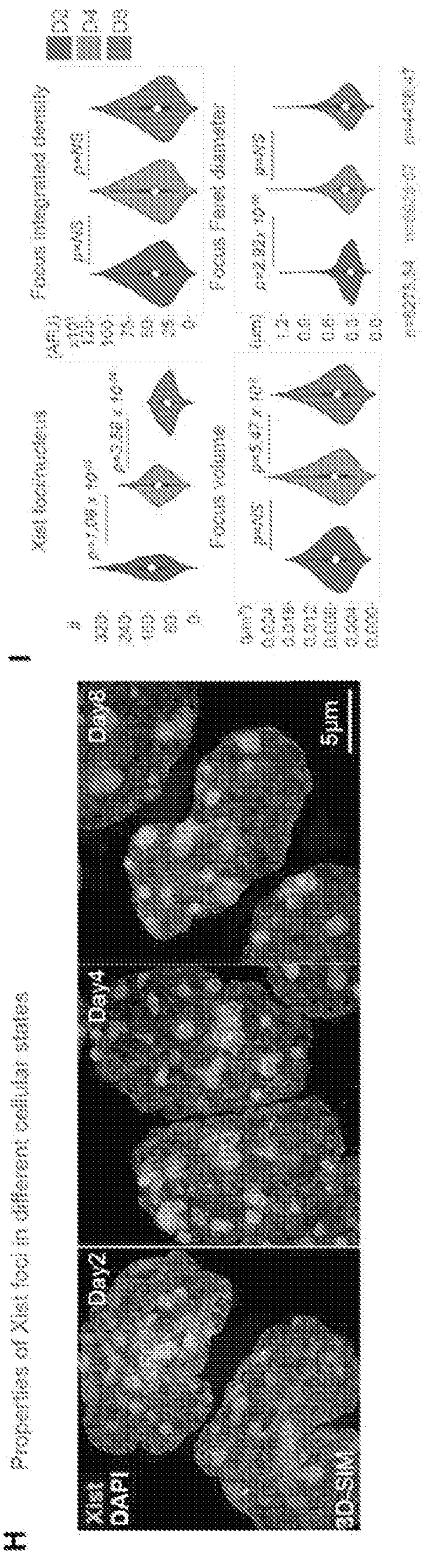
FIG. 26H-I

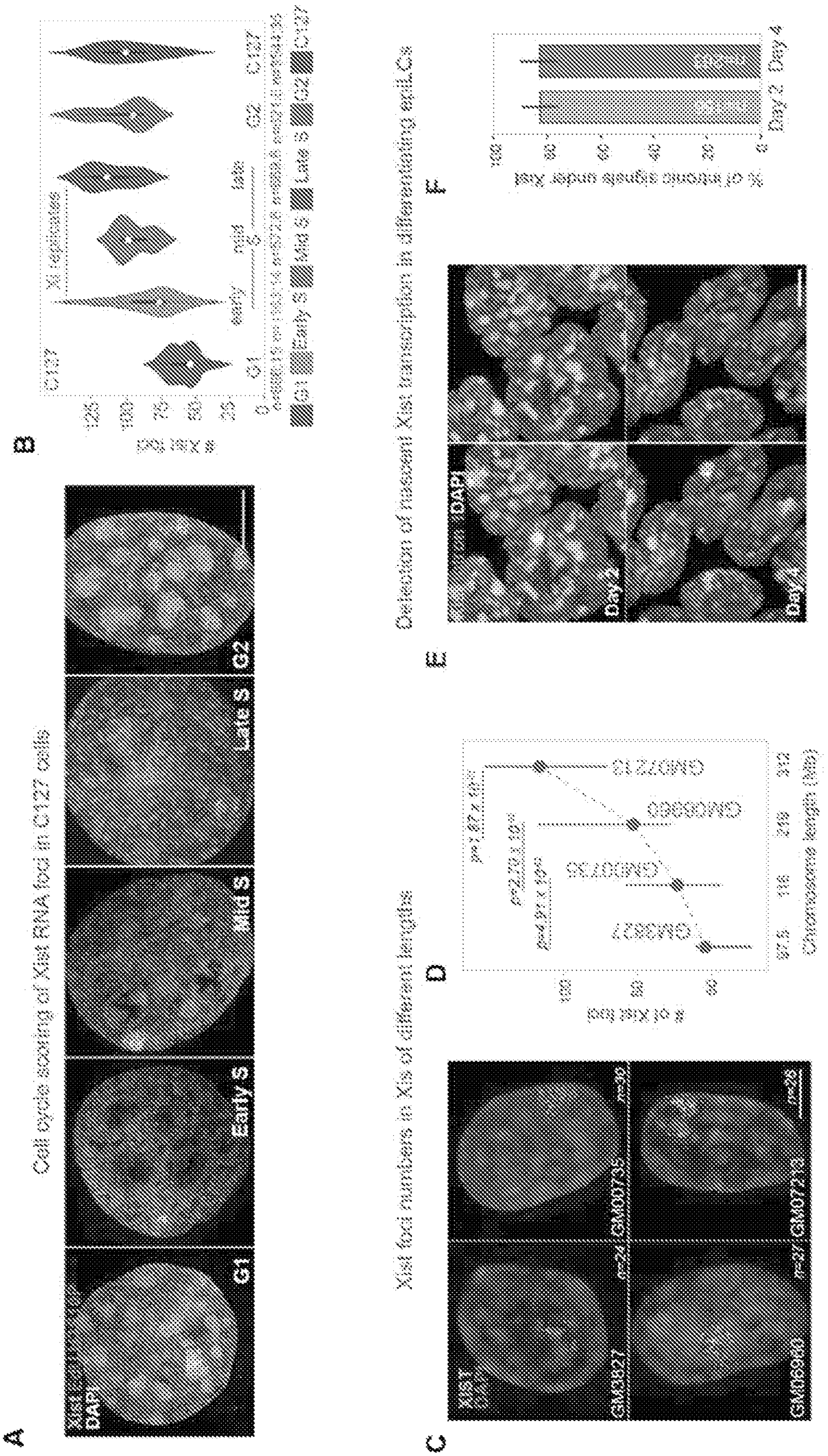
FIG. 27A-F

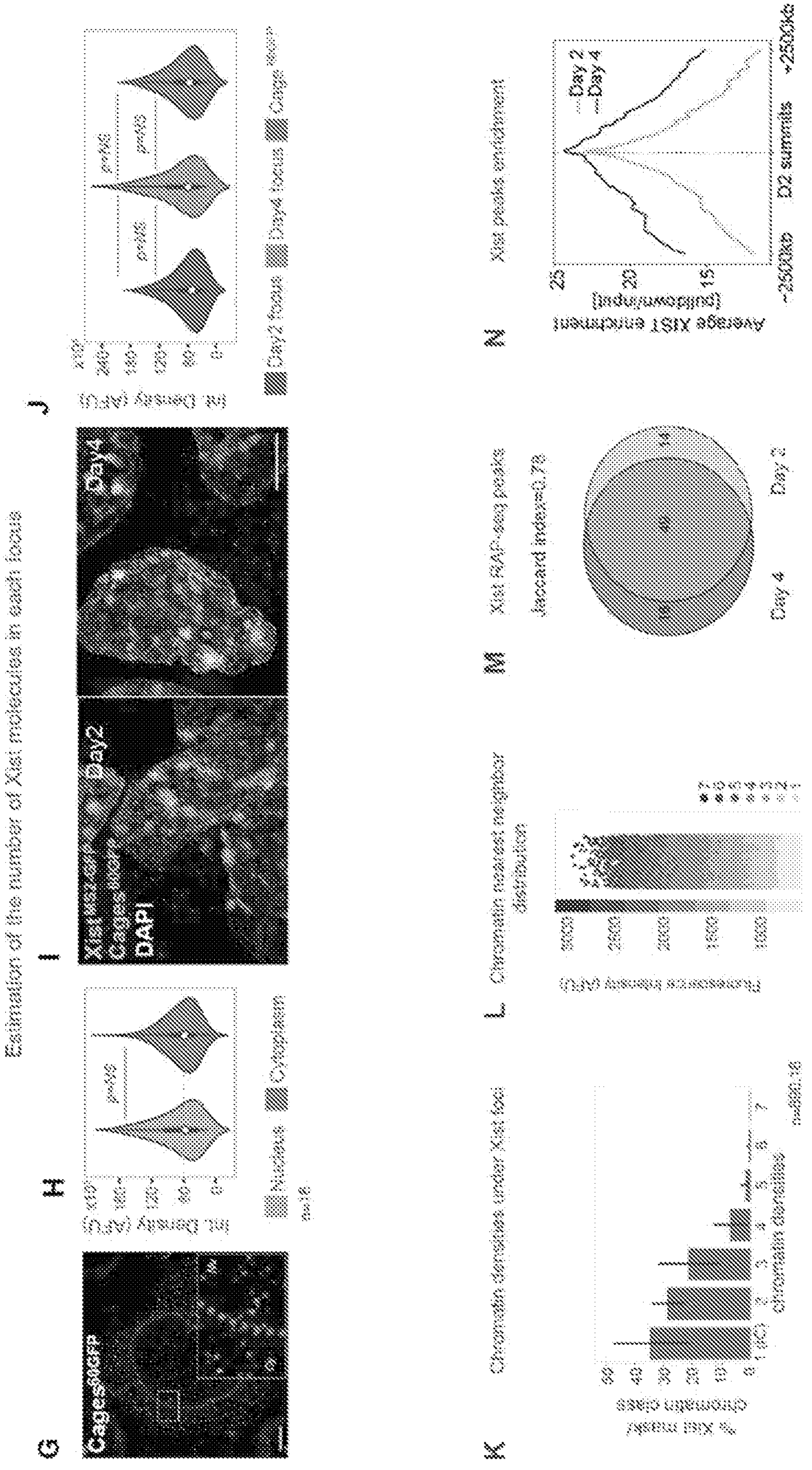
FIG. 27G-N

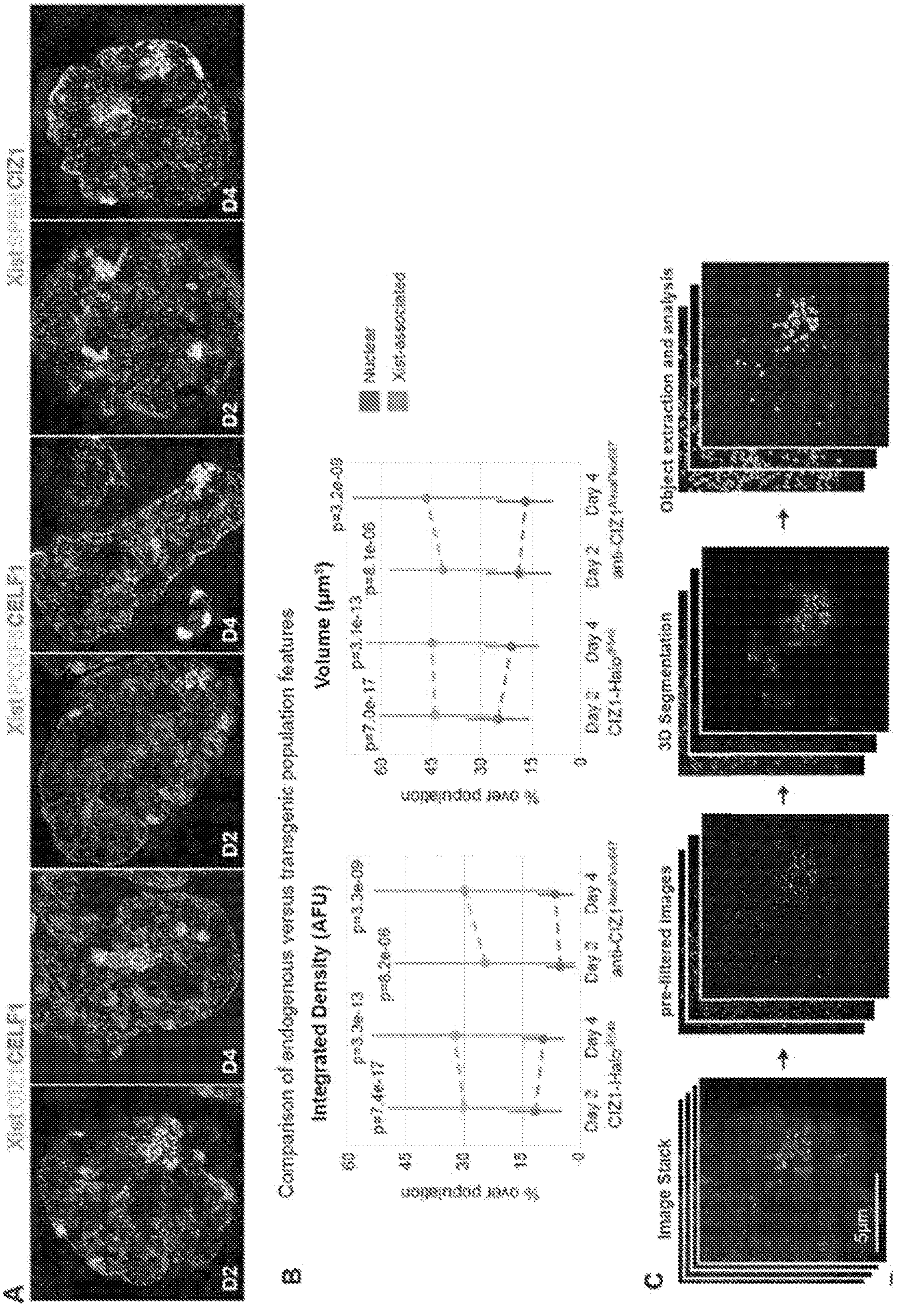
FIG. 28A-C

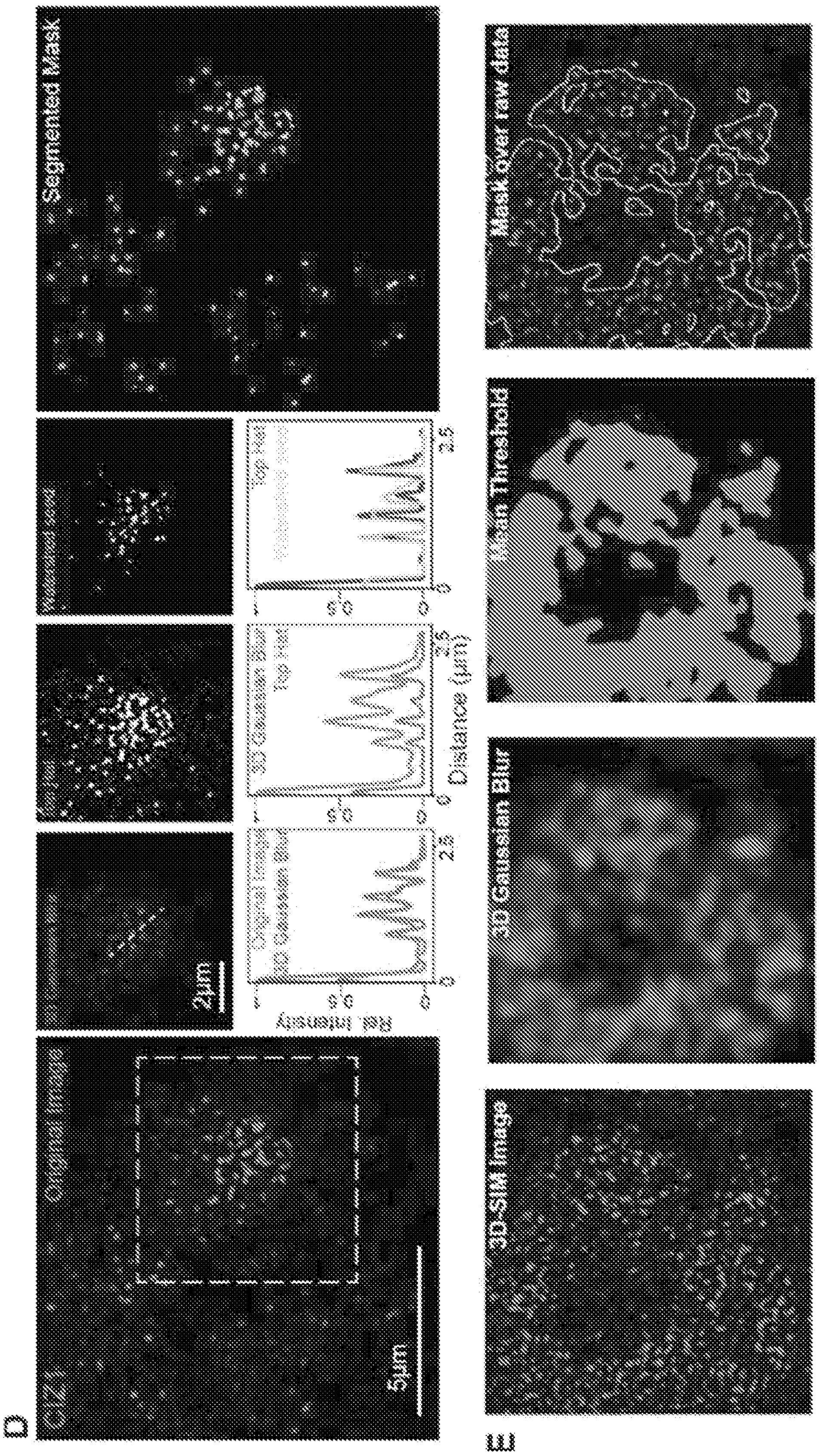
FIG. 28D-E

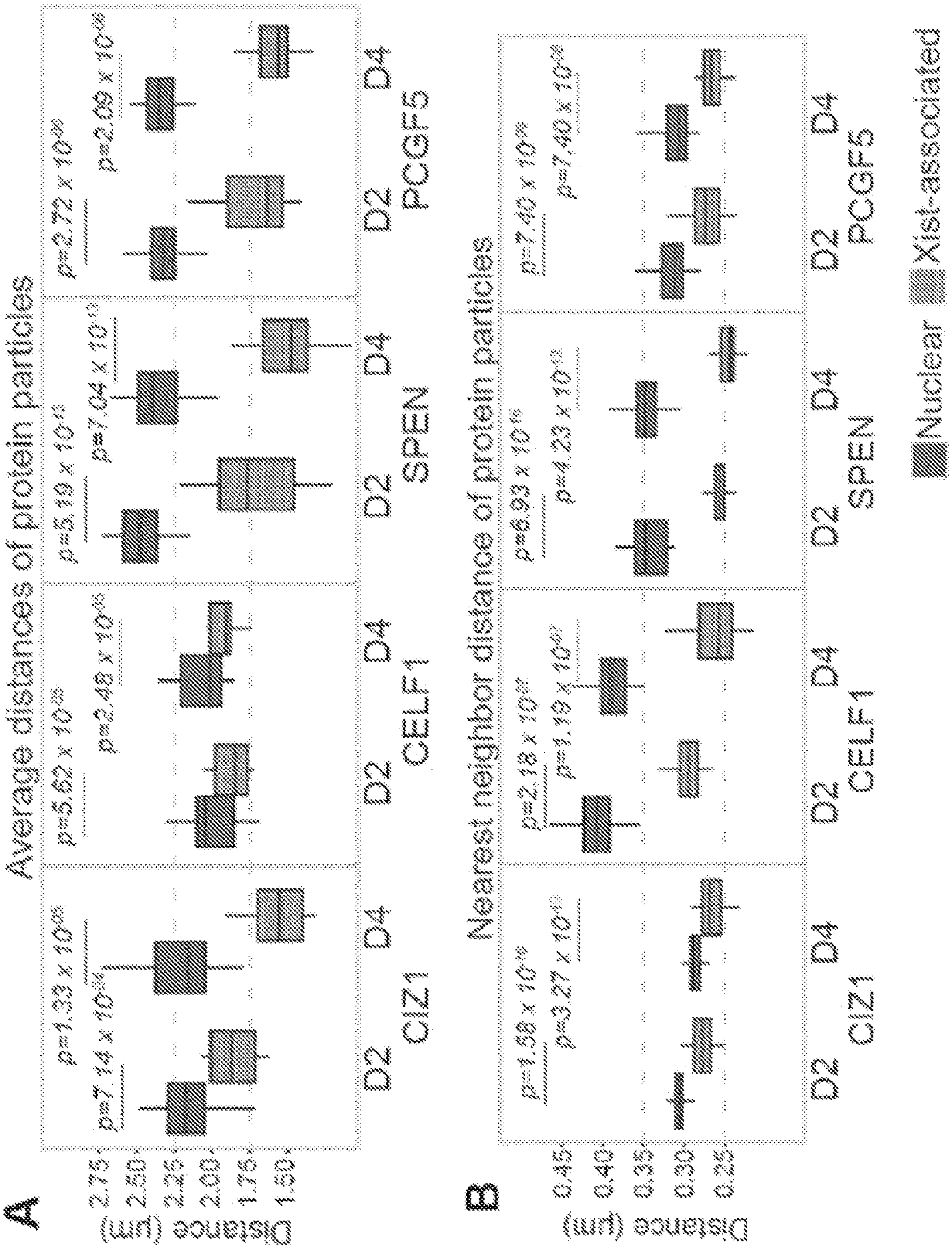
FIG. 29A-B

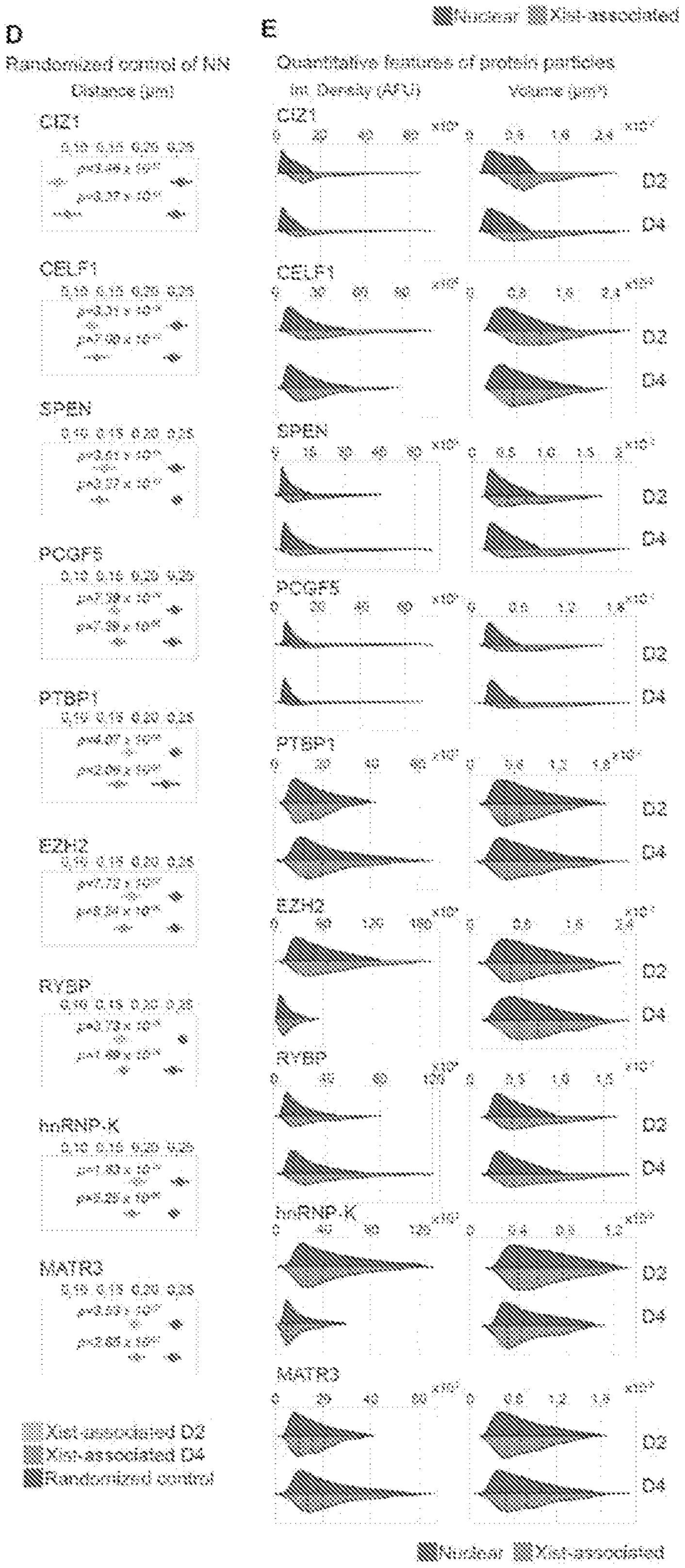
FIG. 29D-E

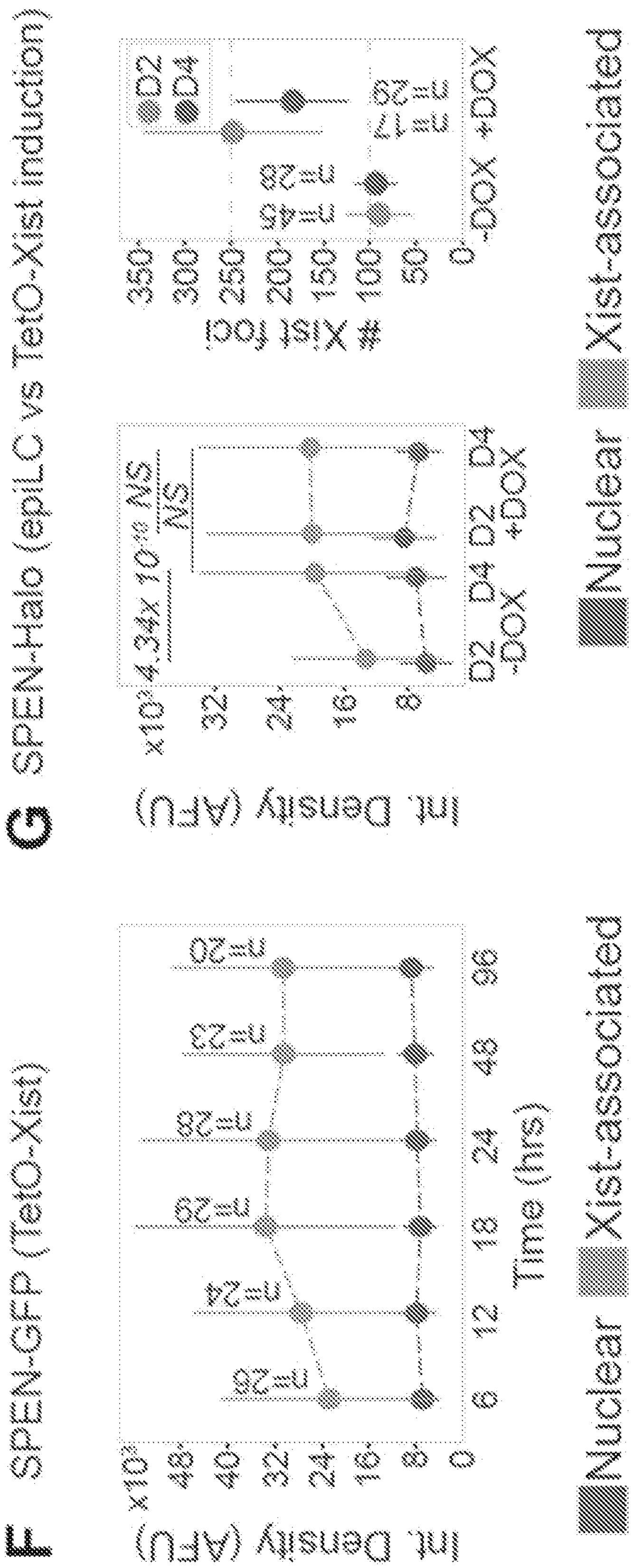
FIG. 29F-G

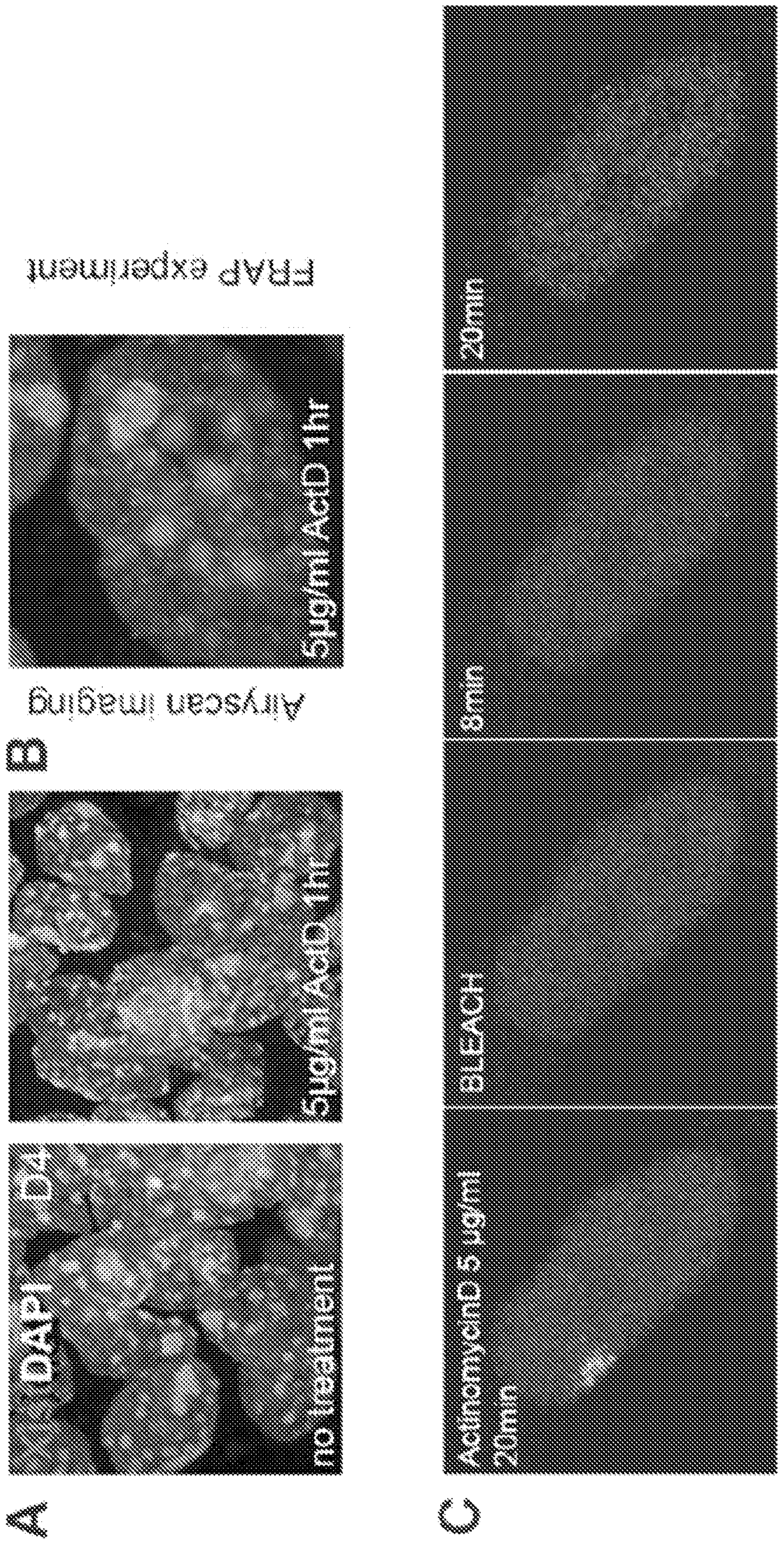
FIG. 30A-C

E
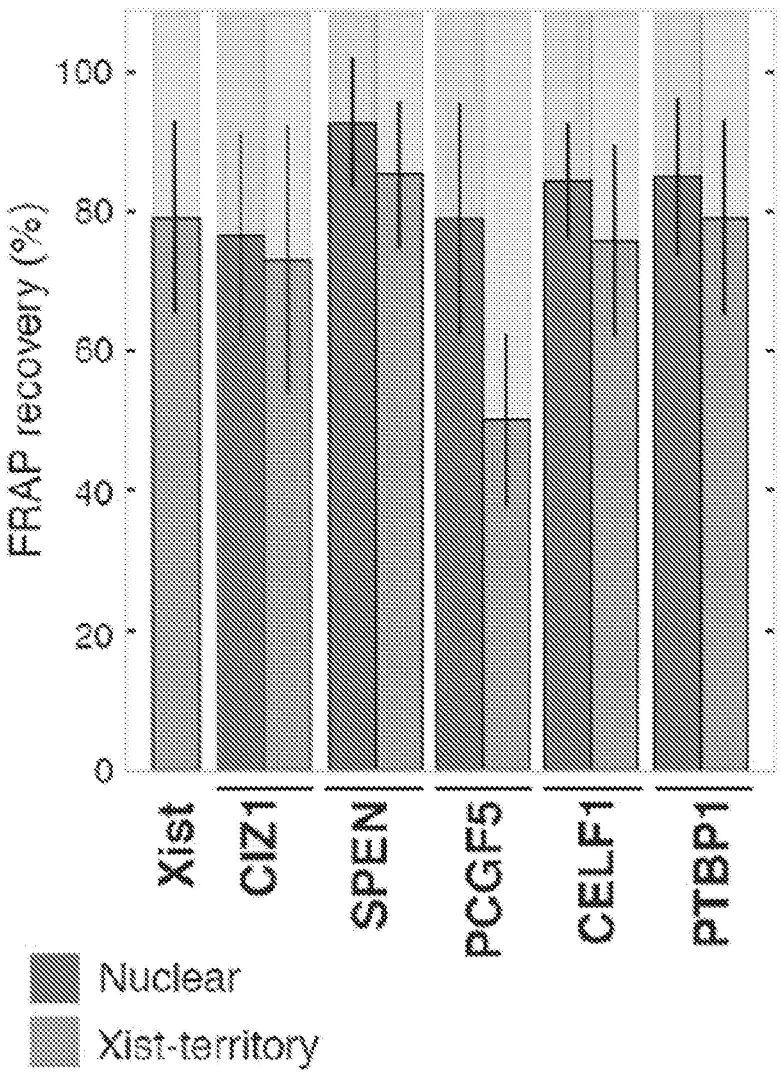
F
$$F(t) = \frac{C_{ss}^* + \sum_i \left(\frac{k_i^* C_i^{(0)}}{k_i^* + d_i}\right)(1 - e^{-d_i t})}{C_{ss}^* + \sum_i \left(\frac{k_i^* C_i^{(0)}}{k_i^* + d_i}\right)}$$
$$= 1 - \frac{\sum_i \tilde{C}_i^* e^{-d_i t}}{C_{ss}^* + \sum_j \tilde{C}_j^*}, \quad \tilde{C}_i^* \equiv \frac{k_i^* C_i^{(0)}}{k_i^* + d_i},$$
$$\equiv 1 - \sum_i f_i e^{-d_i t}$$
FIG. 30E-F G
| | SPEN | | PCGF5 | | CELF1 | | PTBP1 | |
|---|---|---|---|---|---|---|---|---|
| | Nuclear | Xi | Nuclear | Xi | Nuclear | Xi | Nuclear | Xi |
| Fraction 1 ($f_1$) | 18 % | 21 % | 30 % | 21 % | 20 % | 18 % | 27 % | 24 % |
| Fraction 2 ($f_2$) | 25 % | 24 % | 40 % | 59 % | 44 % | 50 % | 51 % | 49 % |
H
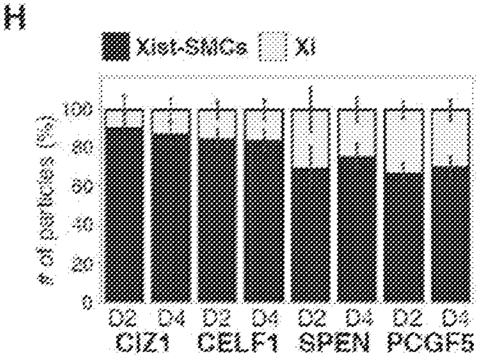
I
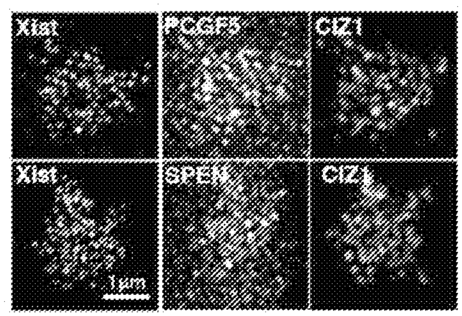
J
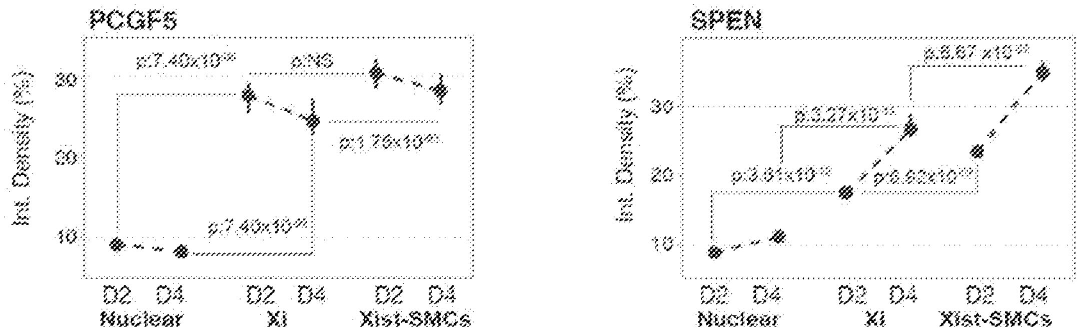
K
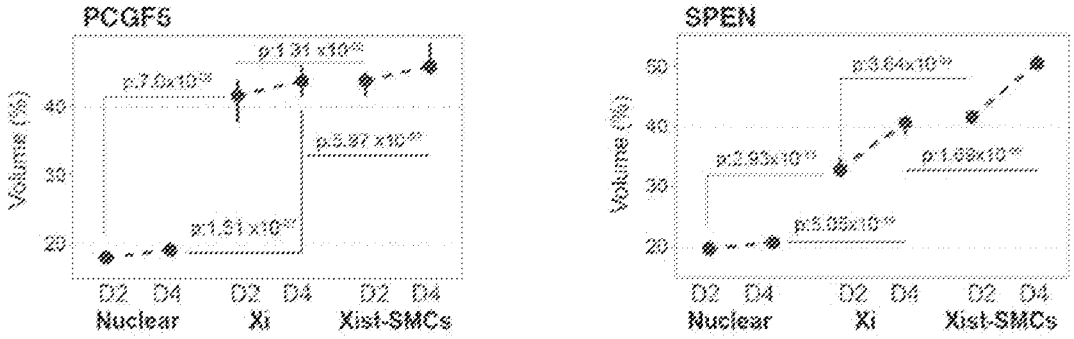
FIG. 30G-K

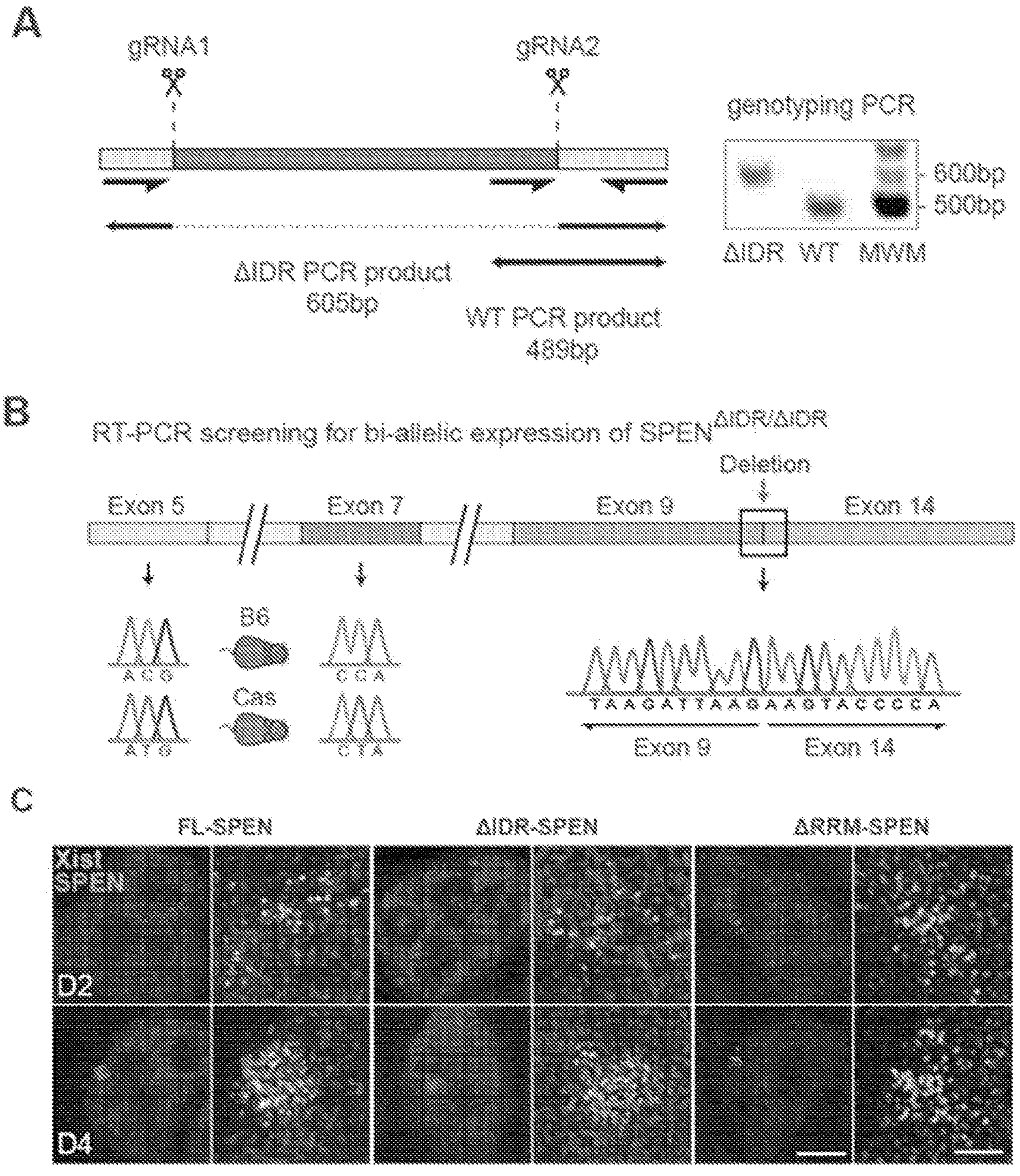
FIG. 31A-C

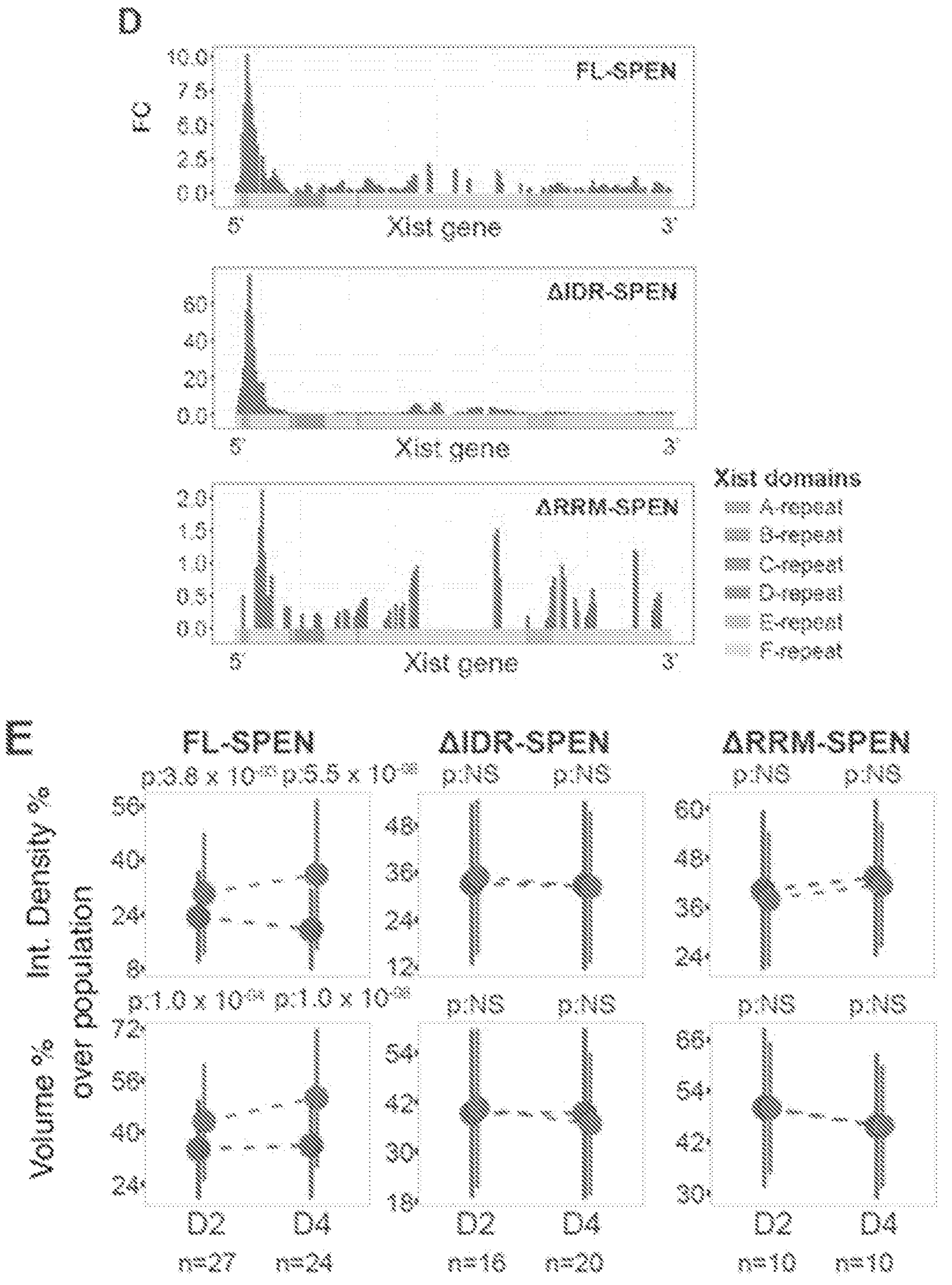
FIG. 31D-E

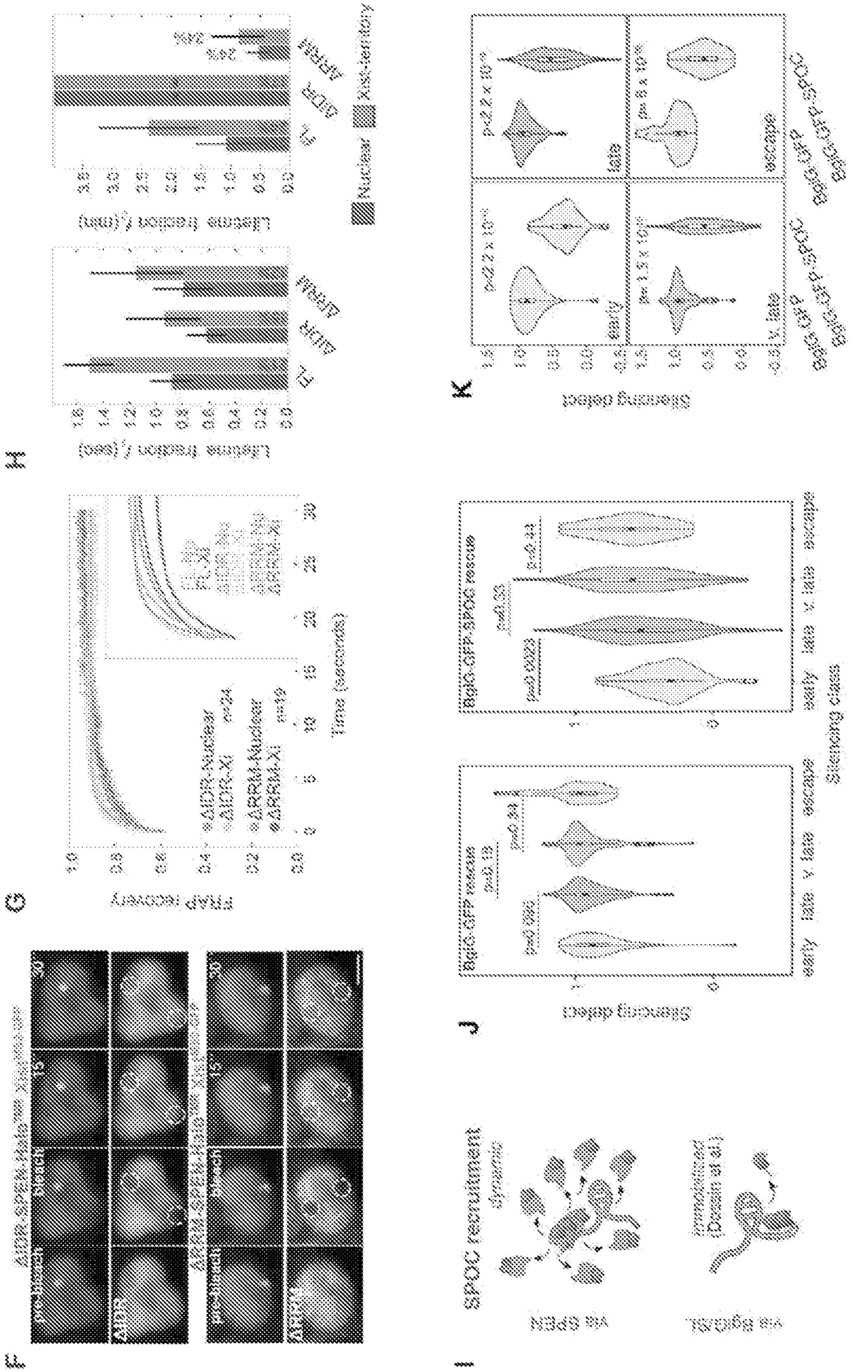
FIG. 31F-K

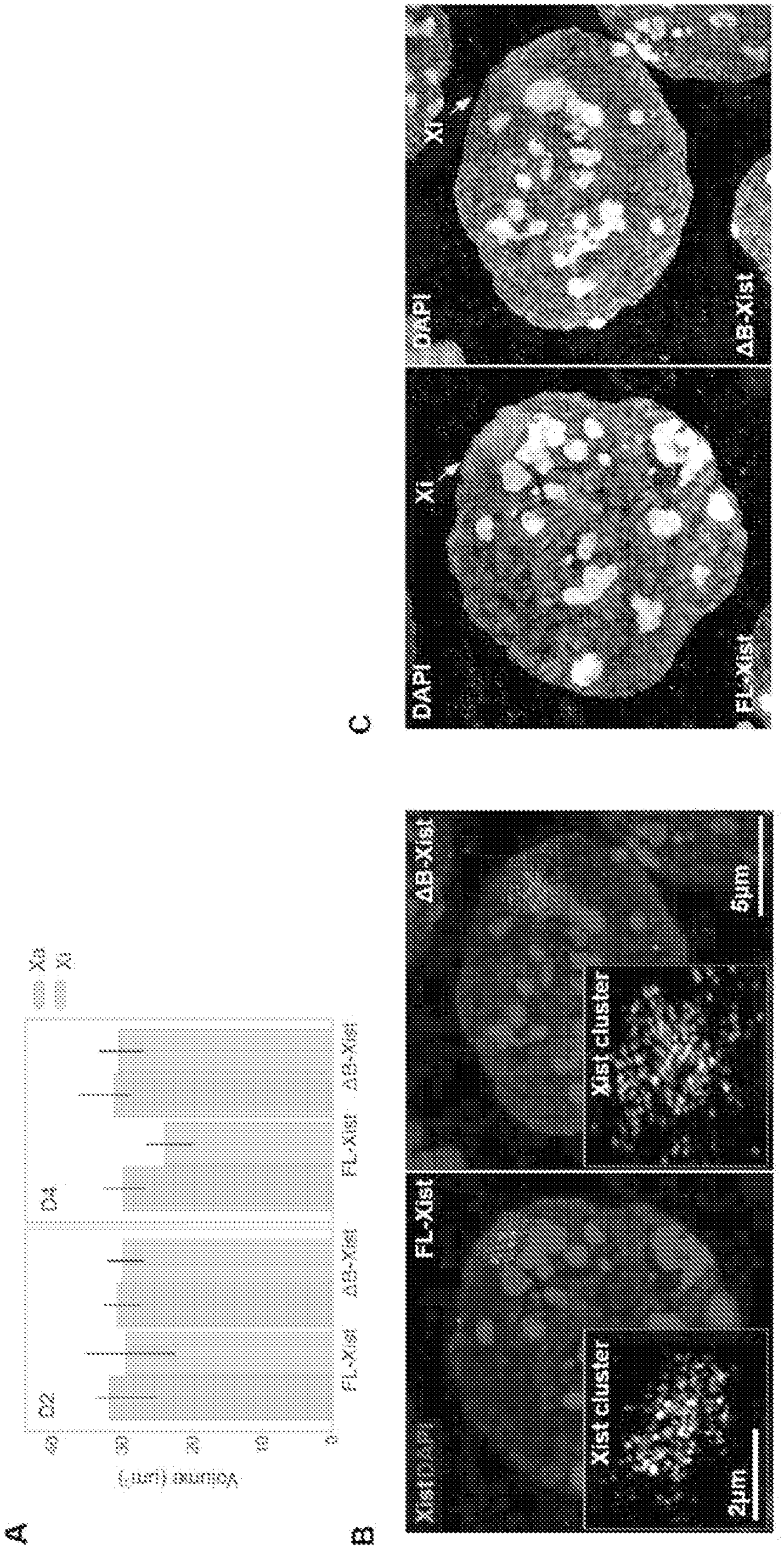
FIG. 32A-C

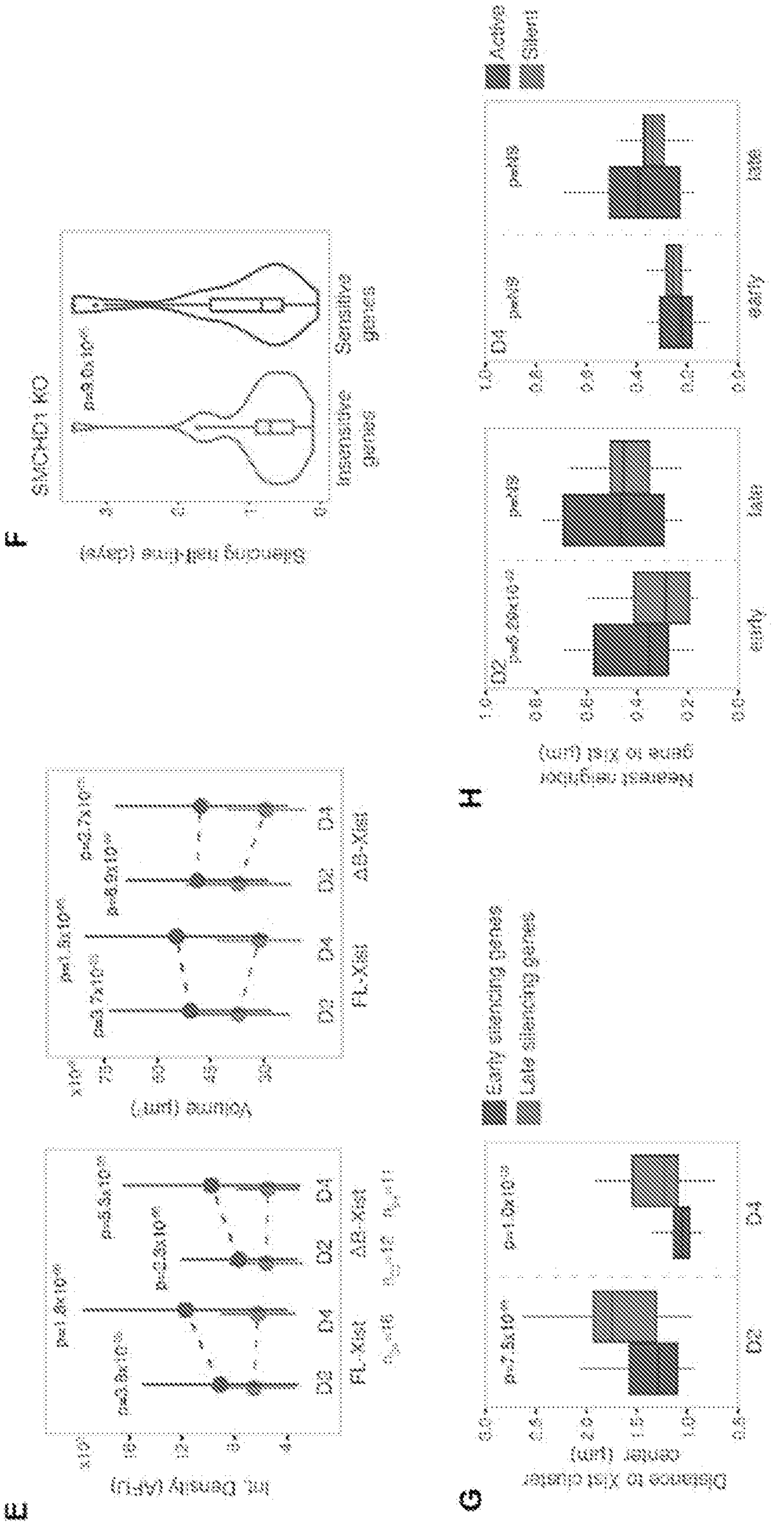
FIG. 32E-H

METHODS FOR X CHROMOSOME REACTIVATION

This application is a national phase application under 35 U.S.C. § 371 of International Application No. PCT/US2021/053733 filed Oct. 6, 2021, which claims the benefit of priority of U.S. Provisional Application No. 63/088,265, filed Oct. 6, 2020; U.S. Provisional Application No. 63/088,297, filed Oct. 6, 2020; and U.S. Provisional Application No. 63/117,226, filed Nov. 23, 2020. These applications are hereby incorporated by reference in their entirety.

This invention was made with government support under GM099134, HD094172, GM115233, and HD095086, awarded by the National Institutes of Health. The government has certain rights in the invention.

The application contains a Sequence Listing in compliance with ST.25 format and is hereby incorporated by reference in its entirety. Said Sequence Listing, created on Apr. 6, 2023 is named UCLA_P0098US_SL and is 1,009 bytes in size.

BACKGROUND

I. Field of the Invention

This invention relates to the field of molecular biology and medical treatments.

II. Background

X-inactivation is a process by which one of the copies of the X chromosome is inactivated in female mammals. The inactive X chromosome is silenced by it being packaged into a transcriptionally inactive structure called heterochromatin. As nearly all female mammals have two X chromosomes, X-inactivation prevents them from having twice as many X chromosome gene products as males, who only possess a single copy of the X chromosome.

Since males only have one copy of the X chromosome, all expressed X-chromosomal genes (or alleles, in the case of multiple variant forms for a given gene in the population) are located on that copy of the chromosome. Females, however, will primarily express the genes or alleles located on the X-chromosomal copy that remains active. In females that are heterozygous at disease causal genes, the inactivation of one copy of the chromosome over the other can have a direct impact on their phenotypic value. Because of this phenomenon, there is an observed increase in phenotypic variation in females that are heterozygous at the involved gene or genes than in females that are homozygous at that gene or those genes.

Rett syndrome is an X-linked disorder that is due to a genetic mutation in the MECP2 gene, on the X chromosome. It almost always occurs as a new mutation, with less than one percent of cases being inherited from a person's parents. Re-activation of the silenced copy of MECP2 may abrogate the disorder in affected females. Therefore, there is a need for therapeutic strategies for re-activating the silenced X chromosome.

SUMMARY

Aspects of the disclosure relate to a method for re-activating the X-chromosome in cells comprising administering a SPEN inhibitor to the cell. Further aspects relate to a method for re-activating the X-chromosome in a subject in need thereof, the method comprising administering a SPEN inhibitor to the subject. Yet further aspects relate to a method for treating Rett Syndrome in a subject in need thereof, the method comprising administering a SPEN inhibitor to the subject. Aspects of the disclosure relate to a method for re-activating the X-chromosome in cells comprising administering a PTBP1 inhibitor and a DNA demethylating agent to the cell. Further aspects relate to a method for re-activating the X-chromosome in a subject in need thereof, the method comprising administering a PTBP1 inhibitor and a DNA demethylating agent to the subject. Yet further aspects relate to a method for treating Rett syndrome in a subject in need thereof, the method comprising administering a PTBP1 inhibitor and a DNA demethylating agent to the subject. The disclosure also describes a method for treating an X-linked disorder in a subject, the method comprising administering a SPEN inhibitor to the subject. In further aspects, the method is for treating an X-linked disorder in a subject, the method comprising administering a PTBP1 inhibitor and a DNA demethylating agent to the subject.

The SPEN inhibitor may be one that inhibits SPEN self-association or association with other proteins. In some aspects, the SPEN inhibitor binds to the IDR and inhibits association with one or more proteins. SPEN refers to a protein that acts as a transcriptional repressor and is also known as Spen Family Transcriptional Repressor, SHARP, MINT, SMART/HDAC1-associated Repressor Protein, Msx2-Interacting Protein, KIAA0929, and RBM15C. SPEN self-association refers to the binding of one SPEN polypeptide to another SPEN polypeptide. In some aspects, the SPEN inhibitor bins to the intrinsically disordered domain (IDD) of SPEN and inhibits SPEN self-association. The inhibitor may be a peptide inhibitor, a nucleic acid inhibitor, or an antibody. Nucleic acid inhibitors may be one that hybridizes with a nucleic acid molecule encoding the SPEN gene. The nucleic acid inhibitor may be an siRNA, a double stranded RNA, a short hairpin RNA, or an antisense oligonucleotide. In some aspects, the inhibitor comprises a peptide or antibody that specifically binds to the IDD. In some aspects, the inhibitor comprises a blocking antibody. In some aspects, the inhibitor comprises an aptamer.

The term "re-activate" or "re-activating" refers to a de-repression of genes, such as a de-repression of at least 1, 2, 3, 4, 5, 6, 7, 8, 9, 10, 20, 40, 50, 60, 70, 80, 90, or 100 genes (or any derivable range therein) that leads to the expression of the at least 1, 2, 3, 4, 5, 6, 7, 8, 9, 10, 20, 40, 50, 60, 70, 80, 90, or 100 genes (or any derivable range therein).

In aspects of the disclosure, the methods may comprise or further comprise administration of a DNA demethylating agent to the subject. The DNA demethylating agent may be 5-Aza-2'-deoxycytidine (decitabine), 5-azacytidine (azacitidine), or combinations thereof.

In some aspects, the PTBP1 inhibitor is an isolated nucleic acid molecule that hybridizes with a nucleic acid molecule encoding PTBP1. In some aspects, the PTBP1 inhibitor is an siRNA, a double stranded RNA, a short hairpin RNA, or an antisense oligonucleotide. In some aspects, the PTBP1 inhibitor is an siRNA. In some aspects, the PTBP1 inhibitor is an antibody that binds to a PTBP1 protein and inhibits the activity of PTBP1 or the binding of PTBP1 to other proteins.

PTBP1 refers to Polypyrimidine Tract Binding Protein 1. The PTBP1 gene and protein sequence is known. The PTBP1 gene is located at chr19:797,075-812,327 (GRCh38/hg38).

The X-linked disorder may be Rett syndrome, Fragile X syndrome, ataxia syndrome, Duchenne muscular dystrophy, Becker muscular dystrophy, hypophosphatasia rickets, alport syndrome, ornithine transcarbamylase deficiency, fabry disease, or Emery-Dreifuss muscular dystrophy.

In aspects of the disclosure, the inhibitor may be administered intravenously, intramuscularly, intraperitoneally, intracerobrospinally, subcutaneously, intra-articularly, intrasynovially, intrathecally, orally, topically, through inhalation, or through a combination of two or more routes of administration.

The term "treatment" or "treating" means any treatment of a disease in a mammal, including: (i) preventing the disease, that is, causing the clinical symptoms of the disease not to develop by administration of a protective composition prior to the induction of the disease; (ii) suppressing the disease, that is, causing the clinical symptoms of the disease not to develop by administration of a protective composition after the inductive event but prior to the clinical appearance or reappearance of the disease; (iii) inhibiting the disease, that is, arresting the development of clinical symptoms by administration of a protective composition after their initial appearance; and/or (iv) relieving the disease, that is, causing the regression of clinical symptoms by administration of a protective composition after their initial appearance.

In aspects of the disclosure, the methods may comprise alleviating one or more symptoms of Rett's syndrome. The symptom may include slowed growth like in microcephaly, repetitive jerky movement of limbs, developmental regression, motor dysfunction, intellectual disability, respiratory disorder, blindness, hearing loss, delayed speech and loss of communication skills, agitation and irritability, seizures, irregular heartbeat and breathing, scoliosis, abnormal muscle stiffness, sleep disorders, and/or gastrointestinal problems such as constipation. In some aspects, the symptom excludes one or more of include slowed growth like in microcephaly, repetitive jerky movement of limbs, developmental regression, motor dysfunction, intellectual disability, respiratory disorder, blindness, hearing loss, delayed speech and loss of communication skills, agitation and irritability, seizures, irregular heartbeat and breathing, scoliosis, abnormal muscle stiffness, sleep disorders, and/or gastrointestinal problems such as constipation.

The subject or patient in aspects of the disclosure may be a mammal. In some aspects, the subject or patient comprises a laboratory test animal, such as a mouse, rat, rabbit, dog, cat, horse, or pig. In some aspects, the subject or patient is a human.

Throughout this application, the term "about" is used according to its plain and ordinary meaning in the area of cell and molecular biology to indicate that a value includes the standard deviation of error for the device or method being employed to determine the value.

The use of the word "a" or "an" when used in conjunction with the term "comprising" may mean "one," but it is also consistent with the meaning of "one or more," "at least one," and "one or more than one."

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment or aspect.

The words "comprising" (and any form of comprising, such as "comprise" and "comprises"), "having" (and any form of having, such as "have" and "has"), "including" (and any form of including, such as "includes" and "include"), "characterized by" (and any form of including, such as "characterized as"), or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments or aspects described in the context of the term "comprising" may also be implemented in the context of the term "consisting of" or "consisting essentially of."

It is specifically contemplated that any limitation discussed with respect to one embodiment or aspect of the invention may apply to any other embodiment or aspect of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-G. ~50 Xist foci are maintained during progression of gene silencing. A, Percentage of cells, from two RNA FISH experiments, with indicated nascent transcription patterns of Atrx and Mecp2 at the indicated day of differentiation. Error bars indicate standard deviation. n is the number of cells analyzed. B, Illustration of live-cell Xist labelling strategy. C, 3D-SIM projections showing $Xist^{MS2\text{-}GFP}$ signals and DAPI counterstaining at the indicated differentiation day. D, Violin plots of the 3D-SIM quantification of $Xist^{MS2\text{-}GFP}$ foci number at differentiation D2 and D4. Dots denote the median, thick black bars the interquartile range, thin bars show upper/lower values. n denotes the number of Xist foci measured (first number) and the number of cells analyzed (second number). Mann-Whitney-Wilcoxon (MWW) p-value is given. E, As in D at differentiation D4 after scoring for cell cycle stages. F, Violin plots of the 3D-SIM quantification of $Xist^{MS2\text{-}GFP}$ foci showing integrated density of fluorescence (AFU) and volume ($\mu m^3$) of Xist foci at D2 and D4. G, Histograms depicting integrated fluorescence of $Xist^{MS2\text{-}GFP}$ foci and cages of 60 GFP molecules ($cage^{60GFP}$) (AFU) per pixel kernel density, detected by 3D-SIM FIG. 2A-J. Xist foci are locally confined. A, Trajectories of Xist$^{MS2-GFP}$ foci imaged for 2 minutes (5 sec/frame). Inset: Projection of one frame from live-cell 3D-SIM experiment showing an Xist$^{MS2-GFP}$ cluster at D4. B, Selected trajectories from A showing the displacement of Xist foci over time (color-gradient) in top (xyz, top) and side (zyx, bottom) views. C, Coordinates of D4 Xist foci displacements derived from ~100 trajectories, each centered about their centers of mass. n denotes the number of foci analyzed. D, Cumulative distribution function $\Phi(r)$ of the number of displacement positions at D4 with distance from origin $<r$. The distance marked with the dashed line at r=0.22 μm corresponds to the radius of the shaded sphere in C where ~80% of all distances lie (see Text S3). n denotes the number of foci analyzed from ~800 trajectories. E, Effective spherically symmetric confining potential inferred from the spatial distribution of displacement distances of Xist foci at differentiation D2 and D4. We assume an equilibrium Boltzmann distribution over an effective potential energy well that is a function of r (see Text S3). F, Image sequence from t=0 to t=28 sec and z-projection (from t=0) of Xist$^{MS2-GFP}$ and H2B-Halo$^{JF646}$, based on live-cell 3D-SIM. Bar: 1 μm. G, Segmentation of H2B-Halo$^{JF646}$ from live-cell 3D-SIM images into seven density classes and overlay of Xist foci masks. H, Left: Schematic for the assessment of the chromatin landscape around one Xist focus. Mask of one Xist focus showing distances (circles) from its centroid. Inset: magnification showing the outline of the Xist mask. Right: Plot of Xist trajectories showing the average radial maxima of chromatin density reached at each timepoint, where Xist foci never surpass density class 3 and the Xist centroid remains within class 2. Light shaded areas show 95% confidence interval. n denotes the number of foci and cells analyzed. I, Correlation of Xist enrichment at D2 and D4 of differentiation, based on RAP-seq data, to the first principal component of Hi-C data (A-compartment=positive values, B-compartment=negative values). Far right panel shows the correlation between D2 and D4 Xist RAP-seq data. Pearson correlation r-coefficients and the associated p-values are given. J, Xist enrichment tracks along the entire X chromosome, defined based on RAP-seq data for Xist over the input, at differentiation D2 and D4, with peak calls below. The Xist locus is indicated.

FIG. 3A-J. Xist-seeds SMCs of interacting proteins and alters their kinetics. A, 125 nm 3D-SIM optical sections showing detection of indicated Halo protein-fusions labelled with JF549 and immunodected proteins in Xist$^{MS2-GFP}$ cells at D2 and D4 of differentiation. Chromatin counterstained with DAPI (grey). Top panels show the Xist-demarcated X-territory (Xi); bottom panels a nuclear region (Nuclear). Note the distinctive enrichment of all pairs of interactors around Xist foci. B, Overview of inter-protein particle distance measurements between proteins associated with one Xist focus, based on data in A. Overlay: Xist, SPEN and CIZ1. Bottom right panel shows mask outlines after image segmentation, depiction of protein and Xist foci centroids (crosses) and measurement of inter-particle distances as annotated in C and D are shown. Circle denotes a 200 nm radius. C, Boxplots showing the distribution of nearest-neighbor distances between the indicated pairs of protein particles in nuclear and Xist-associated fractions (obtained within 250 nm from Xist foci centroids) on differentiation D2 and D4. Boxes delineate the upper/lower quartiles, horizontal lines denote the median. n denotes the number of protein particles measured; the number of cells analyzed. Mann-Whitney-Wilcoxon (MWW) p-value for the comparison between the nuclear and Xist-associated fractions is given. D, Point-plots showing the median distance (dot) of the nearest protein particle centroids to Xist particle centroids on D2 and D4. The bars denote the standard deviation. E, Point-plots showing the integrated density of fluorescence of indicated protein particles in Xist-associated and nuclear fractions, on D2 and D4, from two experiments. Dots denote the median, bars the standard deviation. The medians at D2 and D4 are connected by dotted lines to visualize any changes. Data are normalized to the highest signal observed across the entire population. MWW p-values for the comparison between the nuclear and Xist-associated fractions are given. F, 3D-SIM projections of the Xist-territory in wild-type (WT) SPEN-Halo$^{JF646}$ and ΔIDR-SPEN-Halo$^{JF646}$ together with Xist$^{MS2-GFP}$ on D2 and D4. G, Particle volume measurements in Xist-associated and nuclear fractions, on D2 and D4, comparing ΔIDR-SPEN and WT-SPEN. H, Xist$^{MS2-GFP}$ FRAP curve and fitting at D4. Dissociation rate and lifetime inferred from fitting are indicated. I, FRAP recovery curve and fitting showing the nuclear and Xist-associated populations of CIZ1-mCherry at D4. Parameters from fitting with a single exponential are given. J, FRAP recovery curves and fitting (dashed black lines) showing the nuclear and Xist-associated populations of SPEN-Halo$^{TMR}$, PCGF5-Halo$^{TMR}$, CELF1-mCherry and PTBP1-HaloTMR at differentiation D4. Lifetimes for two subpopulations (f1, f2) extracted from bi-exponential fitting are indicated.

FIG. 4A-M. PRC1-mediated compaction is required for late gene silencing by SPEN. A, Schematic showing recruitment of the SPEN silencing domain SPOC to Xist under physiological conditions (via the full length SPEN protein) or aptamer tethering (via BglG/SL, Xist$^{SPOC}$). B, Violin plots showing the silencing of X-linked genes on Xist$^{SPOC}$ upon depletion of endogenous SPEN. X-linked genes are classified according to their silencing half-times during normal XCI. 0 indicates complete silencing by Xist$^{SPOC}$ and 1 complete lack of silencing. Wilcoxon p-values are given. C, Projections of confocal stacks of D2 and D4 of differentiation after DNA-RNA FISH using X-chromosome paints (mmX) and Xist probes (Xist). DAPI counterstaining shown in grey. Bar: 5 μm. D, Boxplots showing the ratio of volumes (left) and sphericity (right) for Xa/Xa at day 2 and Xa/Xi at D2 and D4. E, Schematic of the spectral barcoding strategy applied to X-chromosome mapping through sequential DNA FISH rounds in F. F, DNA FISH images of the spectrally barcoded genomic regions on days 2 and 4 of differentiation, as described in E. Overlay with Xist RNA FISH signals (far right) to score for the Xi. Bars: 5 μm. G, 2D configuration plots of average coordinates of genomic barcodes along the X-chromosome from F, extracted with 95% confidence. H, Boxplots showing the distribution of the density of indicated protein particles (per $\mu m^3$) in the Xi and in nuclear regions on D2 and D4. I, Boxplots showing the volume ($\mu m^3$) of the Xi territory after RNA-DNA FISH with X-chromosome paints and Xist probes in ESCs expressing tet-inducible full-length Xist (FL-Xist) or a deletion-mutant of the B-repeat (ΔB-Xist) after 18 hrs of doxycycline induction. J, Boxplots showing the minimal (left) and average (right) distance between Xist foci in FL- or ΔB-Xist expressing female cells at D4 of differentiation. K, Violin plots showing the silencing half-times (in days) of genes sensitive or insensitive to Xist B/C-repeat deletion. Wilcoxon p-value is given. L, Violin plots showing Xist RAP-seq enrichment (day 2) of B/C-repeat sensitive/insensitive genes. Wilcoxon p-value is given. M, Model of XCI. Top panels illustrate part of the X chromosome (chromatin) in active (Xa), early silencing (pre-Xi) and inactive (Xi) states and surrounding autosome (chromatin). Bottom panels show a zoom into the chromatin neighborhood where two Xist molecules nucleate one Xist-SMC. Left: Xa, active genes (light grey arrows). Middle: pre-Xi, macromolecular crowding of Xist-effector proteins around Xist 'cores' leads to the formation of SMCs and initiation of gene silencing (dark grey arrows) in their vicinity. The rapid binding kinetics of proteins creates a local concentration gradient across the entire X-territory and an early Polycomb deposition across the X. Right: Xi, Polycomb-mediated compaction increases the density of Xist-SMCs, promoting IDR-dependent crowding of SPEN within Xist-SMCs that leads to an increase in the occupancy of SPEN across the X-territory and completion of gene silencing.

FIG. 5A-E. Progressive gene silencing after Xist localization on the X chromosome. A, Schematic of ESC differentiation protocol used throughout this study. B, Quantification of the proportion of cells with Xist signals on one or both X-chromosomes at the indicated differentiation day, based on RNA FISH from two experiments. Error bars indicate standard deviation. n is the number of cells analyzed. C, Wide-field projections of RNA FISH experiments with Xist RNA and Atrx or Mecp2 probes at days 2, 4 and 8 of differentiation, with DAPI counterstaining in grey. The second column of images shows only the DAPI and X-linked transcript channels. Arrows indicate the presence or lack of gene expression, respectively. Bar: 5 μm. D, RNA FISH of $Xist^{MS2\text{-}GFP}$ cells at D4 of differentiation with Xist, MS2 and Atrx probes. Chromatin counterstaining by DAPI is shown in grey. The second image lacks the Xist FISH signal. Bar: 5 μm. E, Left: Demonstration of effective silencing of Atrx in differentiated unmodified (F1 2-1) cells and $Xist^{MS2\text{-}GFP}$ cells at D4 of differentiation, before and after induction of MCP-GFP expression with doxycycline. Right: Quantification of the proportion of $Xist^{MS2\text{-}GFP}$ cells with Xist-MS2 clouds. Error bars indicate the standard deviation FIG. 6A-F. FIG. 6. Features of Xist foci during differentiation, across cell types and X chromosome lengths. A, 3D-SIM projections showing Xist RNA FISH signals and DAPI counterstaining (grey) at the indicated differentiation day. Bar: 5 μm. B, Violin plots of the 3D-SIM quantification of Xist foci number (#), integrated density of fluorescence (AFU), volume ($\mu m^3$), and Feret diameter (μm) at differentiation days 2, 4, and 8 of 2 replicates. White dots denote the median, thick black bars the interquartile range, thin bars show upper/lower values. n denotes the number of Xist foci measured; the number of cells analyzed. Mann-Whitney-Wilcoxon (MWW) p-values are given by comparing populations indicated by horizontal black lines. NS, Not significant. C, 3D-SIM projections of immuno-RNA FISH experiments detecting Xist, EdU and H3 phospho-serine10 in C127 cells to score for the cell cycle stages G1, early S-phase (Early S), mid S-phase (Mid S), late S-phase (Late S) and G2. DAPI counterstaining in grey is additionally shown in the bottom panels. Stainings for EdU (to detect S-phase cells) and anti-H3 phospho-serine10 antibodies (to detect cells in G2) are detected in the same channel. Bar: 5 μm. D, Quantitative features of Xist RNA foci in different cell cycle stages from C. The C127-labelled violin plot depicts the data for the entire cell population. The p-value is derived from a MWW test comparing plots as indicated by black horizontal lines. NS, Not Significant. E, 3D-SIM projections of RNA FISH experiments in human cell lines harboring abnormal Xi-chromosomes. Bar: 5 μm. n denotes the number of cells used for quantification in F. F, Graph showing the average number of XIST granules in each human cell line from E (y axis), ordered by the length of the abnormal Xi-chromosome in Mb (x axis). Dots denote the median, bars the 95% confidence interval. p-values were derived from a MWW test FIG. 7A-D. Stable Xist levels during ESC differentiation. A, RNA FISH with Xist and intron 1 of Xist probes to detect nascent transcripts of Xist at differentiation D2 and D4. Chromatin is counterstained with DAPI (grey). The second images show intron 1 and DAPI signals. Bar: 5 μm. B, Bar graphs showing the percentages of cells exhibiting a signal for the nascent transcript of Xist under Xist signal-filled nuclear regions (i.e. the pre-Xi/Xi) from experiment in A. Error bars denote the standard deviation. C, 3D-SIM projections showing visualization of $Xist^{MS2\text{-}GFP}$ signals at D2 and D4 after addition of 1 μg/ml doxycycline for 2 hrs to induce MCP-GFP expression. Cells were transfected with plasmids expressing $cages^{60GFP}$ 24 hrs prior to fixation. Chromatin is counterstained with DAPI (grey). Bar: 5 μm. Bottom panels: magnifications of $Xist^{MS2\text{-}GFP}$ or $cages^{60GFP}$ signals. Bar: 1 μm. D, Comparison of integrated density of fluorescence of Xist granules at D2 and D4 and $cage^{60GFP}$ from C after image segmentation. The p-values from the MWW test were non-significant (NS).

FIG. 8A-D. Persistent localization of Xist in low chromatin density during XCI initiation. A, Quantification of the percentages of chromatin density classes under Xist masks. Error bars denote the standard deviation. n is the number of Xist foci analyzed; number of cells. B, Graph indicating the transition between chromatin densities. For each $H2B\text{-}Halo^{JF646}$ pixel, the intensity of all neighboring pixels was determined and plotted across the 7 density classes (y axis). The data show that the neighbors (placed in the bin of their associated chromatin density and color-coded by the chromatin class of the pixel of origin) will be found in the same or the directly incrementing density class to the pixel of origin. C, Overlap of Xist RAP-seq peaks across the X-chromosome at D2 and D4 of differentiation. D, Density plot of the length (log 10(number of bases (bs))) of Xist RAP-seq peaks on the X-chromosome at D2 and D4 of differentiation.

FIG. 9A-E. FIG. 9. Quantitative 3D-SIM analysis pipelines. A, 125 nm 3D-SIM optical sections showing detection of Halo protein-fusions labelled with JF549 and immunodected proteins in $Xist^{MS2\text{-}GFP}$ cells at day 2 (D2) and 4 (D4) of differentiation. Data are whole nucleus images of insets shown in FIG. 3A. B, Comparison of the $CIZ1\text{-}Halo^{JF549}$ pattern to the localization of the endogenous CIZ1 detected with anti-CIZ1 primary and AlexaFluor647-conjugated secondary antibodies showing the same trend in both endogenous and transgenic protein populations after 3D-SIM quantitative analyses. p-values are derived from a MWW test. C, Overview of image segmentation pipeline of 3D-SIM data for assignment of objects (particles) for downstream measurements of features. D, Outline of image segmentation pipeline with the example of CIZ1 signals, showing the output of pre- and post-filtering steps for assigning protein particles. 3D Gaussian and TopHat kernels are applied for contrast enhancement and a 3D-seeded watershed algorithm is used to obtain segmented particles. Histograms indicate the intensity profiles obtained under the dashed line during the processing steps, showing the increased resolving and separation of individual particle signals. E, Pipeline for the creation of masks to include all protein signals quantified in 3D-SIM particles analyses FIG. 10A-C. Quantitative features of proteins in nuclear and Xist-associated fractions A, Left panels: 3D-SIM 125 nm optical sections of cells at days 2 (D2) and 4 (D4) of differentiation showing $Xist^{MS2\text{-}GFP}$ signals and immunodetected or Halo-fused proteins labelled with primary and secondary CF568-conjugated antibodies or JF549 Halo ligands (see methods). DAPI counterstaining shown in grey. Right panels: magnifications of the Xi and nuclear regions with or without DAPI. Bar: 5 μm; Magnifications: 1 μm. B, Point-plots showing the average ratio of the number of segmented protein particles to Xist foci within 250 nm. C, Violin plots of integrated densities and volumes of nuclear and Xist-associated protein particles from experiment shown in FIGS. 10A and 3E, at days 2 and 4 of differentiation. Long-dashed black lines denote the median, short-dashed lines denote the upper/lower quartiles FIG. 11A-C. Assessment of gene silencing and protein levels in differentiated cells expressing the WT or ΔIDR-SPEN transgene. A, Left: RNA FISH experiment with Xist probes, and Mecp2 probes on $Xist^{MS2-GFP}$ cells expressing the ΔIDR-SPEN-Halo transgene at day 4 of differentiation ΔIDR-SPEN-Halo signals are detected with JF549 ligand (grey) and chromatin is counterstained with DAPI. Right: Same RNA FISH experiment for $Xist^{MS2-GFP}$ cells expressing the WT-SPEN-Halo transgene (top) and lacking a transgene (no transgene, bottom). Bar: 5 μm. B, Demonstration of effective X-linked gene silencing capacity of $Xist^{MS2-GFP}$ cells expressing ΔIDR-SPEN-Halo or WT-SPEN-Halo transgenes or cells without transgene expression. C, Particle integrated density measurements, comparing data for ΔIDR-SPEN and WT-SPEN at D4 of differentiation.

FIG. 12A-C. Xist and CIZ1 exhibit similar kinetics. A, Image sequence from FRAP experiment of $Xist^{MS2-GFP}$ at differentiation day 4, showing Airyscan optical sections. Insets show magnifications of the Xist territory. Bar: 5 μm; inset: 2 μm. B, Schematic of the model for the Xist FRAP process. The expression and replenishment of Xist from its expression site, and of proteins from other chromosomes the nuclear fraction is assumed to be fast (free MCP-GFP replenishment is even faster; we assume is almost instantaneous just after t=0). The exchange of photobleached Xist with fluorescing Xist is fast in the Xi-territory outside of Xist-SMCs (free pool) and slow within Xist-SMCs. Xist-SMCs with zero, one, and two fluorescing Xist molecules are denoted Xist-SMC-0, -1, and -2, respectively. Binding of Xist to sites in the SMCs occurs at rate b, while dissociation occurs at rate d1, which sets the timescale for FRAP recovery. The FRAP curves for Xist were fit with a single exponential. Besides the dissociation rates d, the percentage of fluorescence coming from freely diffusing and SMC-associated compartments, 1-f1 and f1, were also inferred. See Text S4 for modeling details. C, Image sequence showing projections from FRAP experiment of $Xist^{MS2-GFP}$ cells expressing CIZ1-mCherry at D4. Dashed circles indicate bleached Xist-territories and arrows monitor recoveries of bleached regions. Bar: 10 μm.

FIG. 13A-B. FRAP experiments of Xist interactors in nuclear and Xi-regions. A, Time series from FRAP experiments showing bleaching (dashed circles) of nuclear or the Xi regions demarcated by $Xist^{MS2-GFP}$ signals, for CIZ1-mCherry, CELF1-mCherry, SPEN-Halo, PCGF5-Halo and PTBP1-Halo transgenes at day 4 of differentiation. Bar: 5 μm. B, FRAP parameters extracted from fitting for indicated proteins in the nucleus and the Xi, respectively, showing the percentage of slow (f1) and fast (f2) detaching fractions inferred for each protein.

FIG. 14A-C. Abolishment of Xi-immobility and increased detachment rates upon deletion of the IDR domain of SPEN. A, Time-sequence from FRAP experiment of $Xist^{MS2-GFP}$ cells expressing the ΔIDR-SPEN-Halo transgene at D4 of differentiation. Bar: 5 μm. B, FRAP recovery curves comparing WT and ΔIDR-SPEN-Halo recoveries in nuclear and Xist territories. The first 12 seconds of this graph are shown as a magnified inset. C, FRAP parameters extracted from fitting for indicated proteins in the nucleus and the Xi, respectively, showing the lifetime and percentage of slow (f1) and fast (f2) detaching fractions inferred for each protein. Top panel are parameters inferred for ΔIDR and bottom panel for WT SPEN for comparison. Note, that the data for WT SPEN are the same shown in FIG. 3 and FIG. 13, for comparison purposes.

FIG. 15A-D. Influx of proteins from Xist-SMCs regulates protein levels in the X chromosome. A, Bar graphs showing the percentage of protein particles detected in the pre-Xi/Xi outside Xist-SMCs (labelled as Xi) or in Xist-SMCs, at D2 and D4. Error bars indicate standard deviation. B, 3D-SIM projections showing magnifications of the Xi region for Xist, PCGF5 and CIZ1 (top) and Xist, SPEN and CIZ1 (bottom). Note the extended population of PCGF5 and SPEN in the Xi compared to Xist and CIZ1. C, Point-plots showing the integrated densities of protein particles for PCGF5 (left) and SPEN (right) within the nuclear fraction, the Xi (outside Xist-SMCs) or in Xist-SMCs, at D2 and D4. Dots denote the median, bars the 95% confidence interval. The medians at days 2 and 4 are connected by dotted lines to visualize any changes. Data are normalized to the highest signal observed across the entire population. MWW p-values for the comparison between the nucleus and the Xi or Xist-SMCs at day 2 or 4 are given. D, Same as C expect showing volume measurements.

FIG. 16A-D. SPEN-dependence of X-linked gene silencing and Xist enrichment for genes with differing silencing kinetics. A, Distribution of silencing half-times of X-linked genes as determined in (29) and classification in early, late, and very late (v. late) silenced genes as well as XCI escapees. B, Violin plots showing Xist enrichment (D2) for gene groups described in A. Wilcoxon p-value is given. C, Violin plots showing silencing profiles of the gene groups defined in A in SPEN depleted cells. 0 indicates complete silencing and 1 complete lack of silencing. Wilcoxon p-value is given. D, Violin plots showing the effect on gene silencing upon SPEN depletion and GFP is recruited to Xist via the BglG/SL tethering. X-linked genes are classified according to their silencing half-times during normal XCI as given in A. 0 indicates complete silencing and 1 complete lack of silencing by $Xist^{GFP}$ (Bgl-GFP). Wilcoxon p-value is given. This figure serves as control for the $Xist^{SPOC}$ (Bgl-GFP-SPOC) experiment in FIG. 4B.

FIG. 17A-D. Progressive compaction of the Xi and concentration of Xist-SMCs during differentiation. A, Ellipsoids of 2D coordinates of X-chromosome (mmX) barcodes on the Xa and Xi at D2 and D4 of differentiation, showing a radius of 95% confidence in the allocated positions. The position along the X-chromosome for each probed location is given in megabases (Mb). B, Heatmaps showing the average 3D spatial distances of genomic barcodes across the X chromosome on the Xa and Xi at D2 and D4 of differentiation. C, Heatmaps as in B, showing changes in distances between probes on the Xa and Xi on D2 and D4. D, Nearest neighbor Xist foci and protein particle distances in the Xi at D2 and D4

FIG. 18A-F. Gene silencing originates at SMCs and proceeds via PRC1-mediated chromosome compaction. A, Projection of DNA FISH with X-chromosome paints (mmX) in ESCs expressing tet-inducible full-length Xist (FL-Xist) or a deletion-mutant of the B-repeat (ΔB-Xist) after 18 hrs of doxycycline induction. B, 3D-SIM projections of RNA FISH with Xist probes in WT (FL-Xist) or a deletion-mutant of the B-repeat (ΔB-Xist) in female cells at D4 of differentiation. C, Magnified insets from B showing Xist or DAPI signals. Note the characteristic compaction of the Xi territory evident in WT cells, which is not present in ΔB-Xist cells. D, As in C showing only the DAPI channel. The Xi regions are indicated by arrows. E, Violin plots showing the silencing half-times (in days) of SCMHD1-sensitive and insensitive X-linked genes. Wilcoxon p-value is given. F, Violin plots showing the effect on gene silencing when WT-SPEN is depleted and GFP or the SPOC-domain of SPEN is recruited to Xist via the Bgl tethering, for X-linked genes sensitive and insensitive to SCMHD1 deletion, respectively. 0 indicates complete silencing and 1 complete lack of silencing by $Xist^{GFP}$ or $Xist^{SPOC}$. Wilcoxon p-value is given.

FIG. 19A-O: ~50 Xist foci initiate XCI. A) Schematic of the ESC differentiation protocol. B) RNA FISH for Xist/Tsix RNA, Rlim and Atrx during differentiation. DAPI staining is shown in grey. Small images show magnifications of the Tsix signal on the Xa or the Xist signal on the Xi and nascent transcription states of the genes. C) Percentage of cells with given nascent transcription patterns of Rlim, Atrx and Mecp2 under Xist clouds during differentiation from two replicates. Error bars denote standard deviation; n is the number of cells analyzed. D) Violin plots of the Xi expression ratios of X-linked genes averaged across single cells expressing Xist from the 129 allele at D2 and D4. The ratios of Rlim, Atrx and Mecp2 are highlighted. E) DNA/RNA FISH with X-chromosome paints (mmX) and Xist probes of cells at D2 and D4. DAPI is shown in grey. n is the number of cells analyzed in F. F) Boxplots showing the ratio of volumes and sphericity for Xa/Xa in cells not expressing Xist at D2 and Xa/Xi in cell with an Xist cloud at D2 and D4. Mann-Whitney-Wilcoxon (MWW) p-values are given. G) Schematic of the spectral barcoding strategy applied to map X chromosome conformation. H) DNA FISH of the spectrally barcoded genomic regions described in G. Overlay with Xist RNA FISH signals (far right) was used to score for the Xi at D2 (top) and D4 (bottom). I) 2D configuration plots of average coordinates of genomic barcodes from H, extracted with 95% confidence. n is the number of cells analyzed from three experiments. J) Illustration of live-cell Xist labelling strategy. K) 3D-SIM projections showing $Xist^{MS2\text{-}GFP}$ signals and DAPI staining (grey) at the indicated differentiation day. L) Violin plots of the 3D-SIM quantification of $Xist^{MS2\text{-}GFP}$ foci number at D2 and D4. n denotes the number of Xist foci measured, followed by the number of cells analyzed from two replicates. MWW p-value is given. M) As in L at D4 after scoring for cell cycle stages. N) As in L, except for showing integrated density (AFU) and volume ($\mu m^3$) of $Xist^{MS2\text{-}GFP}$ foci at D2 and D4 for the same sets of foci. 0) Histograms depicting integrated fluorescence (AFU) of $Xist^{MS2\text{-}GFP}$ foci (~30 GFP molecules per Xist) and GFP nanocages ($cage^{60GFP}$) per pixel kernel density, detected by 3D-SIM. n denotes the number of foci measured followed by the number of cells analyzed from two replicates.

FIG. 20A-J. Xist foci are locally confined at open chromatin regions. A) Trajectories of $Xist^{MS2\text{-}GFP}$ foci from live-cell 3D-SIM imaging for 2 minutes (5 sec/frame) at D4. Inset: Projection of one frame showing an $Xist^{MS2\text{-}GFP}$ cluster. B) Selected trajectories from A showing the displacement of Xist foci over time (color-gradient) in top (xyz, top) and side (zyx, bottom) views. C) D4 Xist foci displacements derived from ~100 trajectories, each centered about their centers of mass. n denotes the number of foci analyzed from four experiments. D) Cumulative distribution function Φ(r) of the number of displacement positions at D4 with distance from origin <r. The distance marked with the dashed line at r=0.22 μm corresponds to the radius of the shaded sphere in C where ~80% of all distances lie (Methods S1 file). n denotes the number of foci analyzed from ~800 trajectories from four experiments. E) Effective spherically symmetric confining potential inferred from the spatial distribution of displacement distances of Xist foci at D2 and D4. We assume an equilibrium Boltzmann distribution over an effective potential energy well that is a function of r. F) Image sequence from t=0 to t=28 sec and z-projection (from t=0) of $Xist^{MS2\text{-}GFP}$ and $H2B\text{-}Halo^{JF646}$ based on live-cell 3D-SIM. Bar: 1 μm. G) Segmentation of $H2B\text{-}Halo^{JF646}$ from live-cell 3D-SIM data into seven density classes and overlay of Xist foci masks. H) Left: Schematic for the assessment of the chromatin landscape around one Xist focus. Mask of one Xist focus showing distances (circles) from its centroid. Inset: magnification showing the outline of the Xist mask. Right: Plot of trajectories of features explained in the left, showing the average radial maxima of chromatin density reached at indicated timepoints. Light shaded areas show 95% confidence interval. n denotes the number of foci and cells analyzed from three experiments. I) Correlation of Xist enrichment determined by RAP-seq at D2 and D4 to the first principal component of ESC (DO) and D4 Hi-C data (A-compartment=positive values, B-compartment=negative values). Far right panel shows the correlation between D2 and D4 Xist RAP-seq data. Pearson correlation r-coefficients and associated p-values are given. J) Xist enrichment along the X chromosome, defined based on RAP-seq data for Xist over the input, at D2 and D4, with peak calls below. The Xist locus is indicated.

FIG. 21A-J. Xist nucleates supra-molecular complexes. A) Schematic of Xist RNA with its repeat sequences A-F, different repeat-binding proteins, and repeat functions. Proteins examined in B are indicated. B) 125 nm 3D-SIM optical sections showing detection of indicated Halo protein-fusions labelled with JF549 and immunodected proteins in $Xist^{MS2\text{-}GFP}$ cells at D2 and D4. Top panels show the Xist-demarcated X-territory (pre-Xi/Xi); bottom panels a nuclear region (Nuclear). Note the distinctive enrichment of all pairs of interactors around Xist foci. C) Overview of inter-protein particle distance measurements for protein foci associated with one Xist focus, based on data in B (STAR methods). Overlay: Xist, SPEN and CIZ1. Bottom right panel shows mask outlines after image segmentation, depiction of protein and Xist foci centroids (crosses) and measurement of inter-particle distances performed in D. Circle denotes a 200 nm radius. D) Boxplots from data in B showing the nearest-neighbor distances between the indicated pairs of protein particles in nuclear and Xist-associated fractions obtained as shown in C for D2 and D4. n denotes the number of protein particles followed by the number of cells analyzed. MWW p-values are given. E) Boxplots of the distribution of the density of indicated protein particles (number of particles per $\mu m^3$) in the Xi and in nuclear regions on D2 and D4. n denotes the number of cells analyzed. MWW p-values are given. F) Point-plots showing the average ratio of the number of indicated protein particles per Xist particle within 250 nm radial search (left) and their nearest distance (right) on D2 and D4. The bars denote the standard deviation and n the number of particles followed by number of cells analyzed. G) Schematic of a Xist-supra-molecular complex. H) Point-plots from data in F showing the integrated density of fluorescence of indicated protein particles in Xist-associated and nuclear fractions, on D2 and D4 from two experiments. Dots denote the median, bars the standard deviation. Dotted lines are included to visualize changes. Data are normalized to the highest signal observed across the entire population of each protein. Absolute values are shown in FIG. 28E. MWW p-values are given. I) Projection of a nucleus imaged with 3D-SIM expressing SPEN-GFP from the endogenous locus and Xist-Bgl-mCherry at 18 hrs post tetO-Xist induction. Inset shows SPEN signals in the Xi. J) Boxplots showing integrated densities of cages$^{60GFP}$, Xist-associated SPEN at 6 or 18 hrs after tetO-Xist induction. n denotes the number of cells analyzed from two replicates.

FIG. 22A-H. Binding to Xist alters the kinetic behavior of interacting proteins. A) Top: Schematic of Xist live-cell labeling. Bottom: Image sequence from an Airyscan FRAP experiment of Xist$^{MS2\text{-}GFP}$ at D4. Insets show the Xist territory. B) Xist$^{MS2\text{-}GFP}$ FRAP recovery at D4 and fitting. Error bars indicate the standard error. Dissociation rate and lifetime inferred from fitting are given. n denotes the number of cells analyzed from four experiments. C) Model for the Xist FRAP process. The expression and replenishment of Xist from its expression site is assumed to be fast and free MCP-GFP replenishment is assumed almost instantaneous after t=0. The exchange of photobleached with fluorescing Xist is assumed fast in the Xi-territory outside Xist-SMCs (free pool) and slow within Xist-SMCs. Xist-SMCs with zero, one, and two fluorescing Xist molecules are denoted Xist-SMC-0, -1, and -2. Binding of Xist to sites in SMCs occurs at rate b and dissociation at rate d, which sets the timescale for FRAP recovery. The FRAP curves for Xist were fit with a single exponential. D) Image sequence showing a FRAP experiment of Xist$^{MS2\text{-}GFP}$ and CIZ1-mCherry at D4. Dashed circles indicate bleached Xist-territories and arrows monitor recovery. E) FRAP recovery and fitting (dashed black lines) of the nuclear and Xist-associated populations of CIZ1-mCherry. Error bars denote the standard error. Parameters from fitting with a single exponential are given. n denotes the number of cells analyzed from four experiments. F) FRAP recovery and fitting (dashed black lines) of the nuclear and Xist-associated populations of SPEN-Halo$^{TMR}$, PCGF5-Halo$^{TMR}$, CELF1-mCherry and PTBP1-Halo$^{TMR}$ at D4. Error bars denote the standard error. Every fifth timepoint is shown. Lifetimes for the slow ($f_1$) and fast ($f_2$) detaching fractions inferred for each protein from bi-exponential fitting are indicated. n denotes the number of cells analyzed from two experiments. G) Bargraphs showing the lifetimes for Xist and CIZ1 (left) and for the two subpopulations ($f_1$, $f_2$) of bi-exponentially fitted proteins (right). Error bars denote the standard error. H) Schematic showing an Xist-SMC and its dynamic regulatory compartment. The increased accumulation of proteins surrounding Xist and their rapid cycling results in gradients over broad chromosomal regions in the vicinity to the SMC.

FIG. 23A-K. IDR-mediated crowding of SPEN in SMCs is required for gene silencing. A) Schematic of the domains of WT and ΔIDR SPEN. B) 3D-SIM optical sections of immuno-RNA-FISH with Xist probes and GFP antibodies at D2 and D4 in cells homozygously expressing GFP-tagged WT- or ΔIDR-SPEN. Second columns show the Xi. Staining by DAPI is shown in grey. C) Point-plots of integrated density and volume measurements for WT- and ΔIDR-SPEN particles that are Xist-associated or in the nuclear fraction, on D2 and D4 from B. n denotes the number of cells analyzed from two experiments. MWW p-values are given. D) RNA FISH of Xist and nascent transcripts of Rlim or Atrx at 24 hrs after doxycycline induction of tetO-Xist expression in female Xist$^{wt/tetO}$ cells homozygously expressing WT-, ΔIDR- and ΔSPOC-SPEN. Chromatin is stained with DAPI (grey). Second row images show Rlim or Atrx signals and nuclei masks (dashed lines). E) Quantification of experiment in D showing percentage of Xist clouds with a nascent transcript spot (monoallelic) versus no transcripts (grey, biallelic). n denotes the number of cells analyzed from two replicates. F) Violin plots of Xi expression ratios of X-linked genes averaged across single Xist$^{wt/tetO}$ cells homozygously expressing WT-, ΔIDR- or ΔSPOC-SPEN without and with 24 hours of doxycycline addition. MWW p-values are given. G) Violin plots of the change in Xi expression ratio for data in F, grouped according to gene silencing dynamics in normal cells. Kruskal-Wallis p-values are given. H) Schematic of rescue assay used in I and J. SPEN-AID-GFP encoded from the endogenous locus is depleted with addition of auxin for 12 hrs and FL- or ΔIDR-SPEN-Halo are constitutively expressed from the R26 locus. Xist expression and XCI are induced by addition of doxycycline for 24 hrs in the presence of auxin. I) Images of SPEN-AID-GFP with transgenic FL-SPEN (top) and ΔIDR-SPEN (bottom) rescue proteins. Columns from left to right: untreated; 12 hrs auxin treated; and 24 hrs doxycycline and 36 hrs auxin treated cells. This strategy was used in J to explore rescue of XCI by transgenically encoded SPEN proteins after depletion of endogenously encoded SPEN and induction of tetO-Xist. J) Violin plots of the change in Xi expression ratios of X-linked genes over 24 hrs of doxycycline-induced Xist expression, grouped according to gene silencing dynamics in normal cells, for conditions described in H. The Xi ratio was averaged across 3 replicates. Kruskal-Wallis p-values are given. K) Model of the augmented and dynamic distribution of WT-SPEN (top) in a Xist-SMC compared to ΔIDR-SPEN (bottom). Xist and SPEN domains are annotated as in A. Silent and active X-linked genes are indicated with black and grey arrows.

FIG. 24A-H. Lack of compaction on the ΔB-Xi predominantly affects late gene silencing. A) Schematic of the heterozygous deletion of the B-repeat of Xist and insertion of a MS2 tag on the 129 X chromosome in female mouse 129/cas ESCs (Xist$^{\Delta B+MS2/WT}$ ESCs). The consequences of the B-repeat deletion are indicated. B) RNA/DNA FISH of Xist$^{\Delta B+MS2/WT}$ cells at D4 using X-chromosome paints (mmX), Xist and MS2 probes. Greyscale images show individual channels as indicated. C) Boxplots showing the ratio of Xa/Xa at D2 in cells not expressing Xist and of Xa/Xi in FL-Xist or ΔB-Xist (grey) expressing Xist$^{\Delta B+MS2/WT}$ cells at D2 and D4. n is the number of cells analyzed from two replicates. D) Boxplots showing the minimal (left) and average (right) distance between Xist foci in FL- or ΔB-Xist expressing Xist$^{\Delta B+MS2/WT}$ cells at D2 and D4. n is the number of cells analyzed from three experiments. E) Violin plots of Xi ratios of X-linked gene expression at D2 and D4 in Xist$^{\Delta B+MS2/WT}$ cells or parent WT (Xist$^{WT\text{-}MS2/WT}$) cells silencing the WT- or ΔB-Xist 129 X chromosome. Mean Xi ratio per gene was averaged across single cells based on scRNA-seq data. MWW p-values are given. F) As in E, except that genes are grouped by gene silencing dynamics. MWW p-values are given. G) Violin plots of the difference in Xi ratio between the ΔB- and WT-Xist expressing Xi shown in F. MWW p-values are given. H) Bargraphs showing the proportion of ΔB-sensitive or insensitive genes from F. Genes were considered ΔB-sensitive based on a one-sided Welch t-test comparing ΔB and WT $Xi^{129}$ ratios, p-value <0.05.

FIG. 25A-N. Xist-SMCs progressively re-configure and silence the Xi. A) Annotation of the position of early and late genes on the X chromosome simultaneously detected with oligo probes in RNA/DNA FISH experiments and their silencing half-time in normal cells. B) 3D-SIM projections of nuclei after RNA/DNA FISH, showing indicated gene sets, their corresponding transcripts, and Xist signals at D2 and D4. Xa, pre-Xi and Xi are indicated. Insets show magnifications of pre-Xi or Xi areas with high (top) and low (bottom) Xist density. Images are smoothed with a 3×3 px for clarity. C) 3D-SIM projections of Xa, pre-Xi or Xi regions after RNA/DNA FISH for Xist, early and late genes at D2 and D4. The Xist probe labels Tsix RNA on the Xa and therefore detects the X-inactivation center (Xic). D) Schematic of different types of distance measurements performed in this figure. E) Boxplots of distances of early or late genes relative to Tsix signals on the Xa. n denotes the number of cells analyzed from three experiments. MWW p-value is given. F) Boxplots of the nearest distance of Xist foci to early or late genes at D2 and D4. n denotes the number of cells analyzed from three experiments. MWW p-values are given. G) Boxplots of distances of early or late genes to the center of the Xist cluster at D2 and D4, divided into silent or active based on nascent transcripts detection. n is the number of cells analyzed from three experiments. MWW p-values are given. H) Intra-genic distances of early or late genes on the Xa, pre-Xi, or Xi at D2 and D4. n denotes the number of cells analyzed from three experiments. Kruskal-Wallis p-values are given. I) 3D-SIM projections of the Xi after RNA/DNA FISH for Xist, early and late genes in male FL- or ΔB-Xist expressing ESCs after 18 hrs doxycycline induction of tetO-Xist. n denotes the number of cells analyzed in J to M from two experiments. MWW p-values are given. J) Boxplots of distances of early or late genes to the center of the Xist cluster in FL- or ΔB-Xist expressing cells described in I. K) As in J, except for intra-genic distances of early or late genes. L) As in J, except for the distances of early to late silencing genes. M) As in J, except for nearest neighbor distance of early or late genes to Xist foci. N) SMC-based model of XCI. Left column shows the changes in the higher-order chromatin organization between the Xa (top), pre-Xi (middle) and Xi (bottom). Arrows indicate active and silent genes. Fourth column shows the increase in protein concentration upon establishment of Xist-SMCs. Dots indicate Polycomb-group proteins and SPEN. Free protein dots indicate increased concentrations in the Xi due to the presence of SMCs. Architectural protein-mediated chromosomal compaction is depicted by islets on the DNA fiber.

FIG. 26A-I. Related to FIG. 19. Progressive compaction of the X through a conserved Xist cluster. (A) Quantification of the proportion of cells with Xist signals on one or both X chromosomes at the indicated differentiation day, based on RNA FISH from two experiments. Error bars indicate standard deviation and n the number of cells analyzed. (B) Wide-field projections of RNA FISH experiments with Xist RNA and Mecp2 probes at D2 and D4, with DAPI counterstaining in grey. (C) Violin plots of the Xi expression ratios of X-linked genes previously classified as early, late, very late silencing and escaping from XCI (Barros de Andrade et al., 2019), averaged across single cells expressing Xist from the 129 or cas allele in female WT cells at D2 and D4. (D) Ellipsoids of two-dimensional (2D) coordinates of X chromosome (mmX) barcodes on the Xa and Xi at D2 and D4, showing a radius of 95% confidence in the allocated positions. The position along the X chromosome for each probe location is given in megabases (Mb). (E) Heatmaps showing the average three-dimensional (3D) spatial distances of genomic barcodes across the X chromosome on the Xa and Xi at D2 and D4 of differentiation. (F) Heatmaps as in E, showing changes in distances between probes on the Xa and Xi on D2 and D4. (G) Demonstration of effective silencing of Atrx in differentiating unmodified cells (Xist$^{wt}$) and Xist$^{MS2\text{-}GFP}$ cells at D4. For Xist$^{MS2\text{-}GFP}$ cells, silencing was assessed before and after induction of MCP-GFP expression with doxycycline. Representative image of Atrx silencing in an Xist$^{MS2\text{-}GFP}$ cell shown. Additionally, the proportion of Xist$^{MS2\text{-}GFP}$ cells with Xist-MS2 clouds was quantified. Error bars indicate the standard deviation. n is the number of cells analyzed from three experiments. (H) 3D-SIM projections showing Xist RNA FISH signals and DAPI counterstaining (grey) at the indicated differentiation day. Bar: 5 μm. (I) Violin plots of the 3D-SIM quantification of Xist foci number (#), integrated density of fluorescence (AFU), volume (μm$^3$), and Feret diameter (μm) at indicated differentiation days of 2 replicates. White dots denote the median, thick black bars the interquartile range, thin bars show upper/lower values. n denotes the number of Xist foci measured followed by the number of cells analyzed from three experiments. MWW p-values are given for comparisons indicated by horizontal black lines. NS, Not Significant.

FIG. 27A-N. Related to FIGS. 19 and 20. Features of Xist foci across cell types and X chromosome lengths. (A) 3D-SIM projections of immuno-RNA FISH experiments detecting Xist, EdU and H3 phospho-serine10 in C127 cells to score for the cell cycle stages (G1, early S-phase (Early S), mid S-phase (Mid S), late S-phase (Late S) and G2). DAPI counterstaining is shown in grey. Stainings for EdU (to detect S-phase cells) and anti-H3 phospho-serine10 antibodies (to detect cells in G2) were detected in the same channel. Bar: 5 μm. (B) Violin plots showing the number of Xist RNA foci in different cell cycle stages from A. Dots denote the median, thick black bars the interquartile range, thin bars show upper/lower values. n denotes the number of Xist foci measured. 47 cells were analyzed from two replicates and the number (n) of cells scored for each cell cycle stage is indicated. A separate experiment of 35 cells from two replicates without scoring for cell cycle is shown for comparison (C127). The Xi is known to replicate around mid-S. (C) 3D-SIM projections of RNA FISH experiments in human cell lines harboring abnormal Xi-chromosomes. Bar: 5 μm. n denotes the number of cells used for quantification in D from two replicates. (D) Graph showing the average number of XIST foci in each human cell line from C (y axis), ordered by the length of the abnormal Xi-chromosome in Mb (x axis). Dots denote the median, bars the 95% confidence interval. p-values were derived from a MWW test. (E) RNA FISH with Xist and intron 1 of Xist probes to detect nascent transcripts of Xist at D2 and D4. Chromatin is counterstained with DAPI (grey). The second images show intron 1 and DAPI signals. Bar: 5 μm. (F) Bar graphs showing the percentages of cells exhibiting a signal for the nascent transcript of Xist under Xist signal-filled nuclear regions (i.e. the pre-Xi/Xi) from the experiment in E. Error bars denote the standard deviation. n denotes the number of cells analyzed from two replicates. (G) 3D-SIM projections showing visualization of cages$^{60GFP}$ (grey) expressed in the cytosol and nucleus (demarcated by a dashed line) at D2. Cells were transfected with plasmids expressing cages$^{60GFP}$ 24 hrs prior to fixation. Inset shows a magnification of the framed region including cytosolic (Cy) and nuclear (Nu) cages$^{60GFP}$. (H) Violin plots showing comparison of the integrated density of fluorescence (AFU) of nuclear versus cytoplasmic cages from G. Dots denote the median, thick black bars the interquartile range, thin bars show upper/lower values. n denotes the number of cells analyzed from two replicates. MWW p-value is given. NS:

Figure 3J:
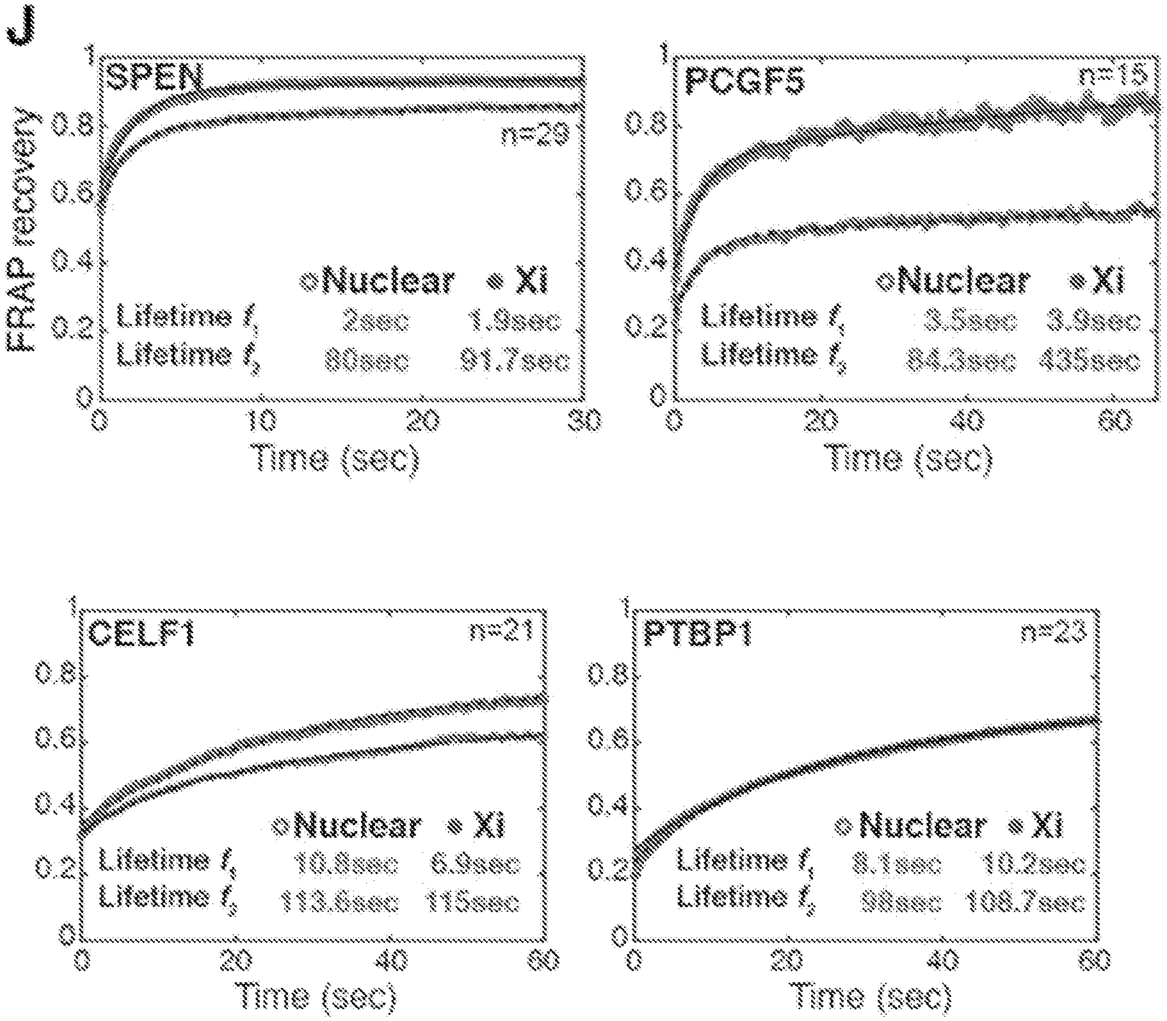
Figure 28F:
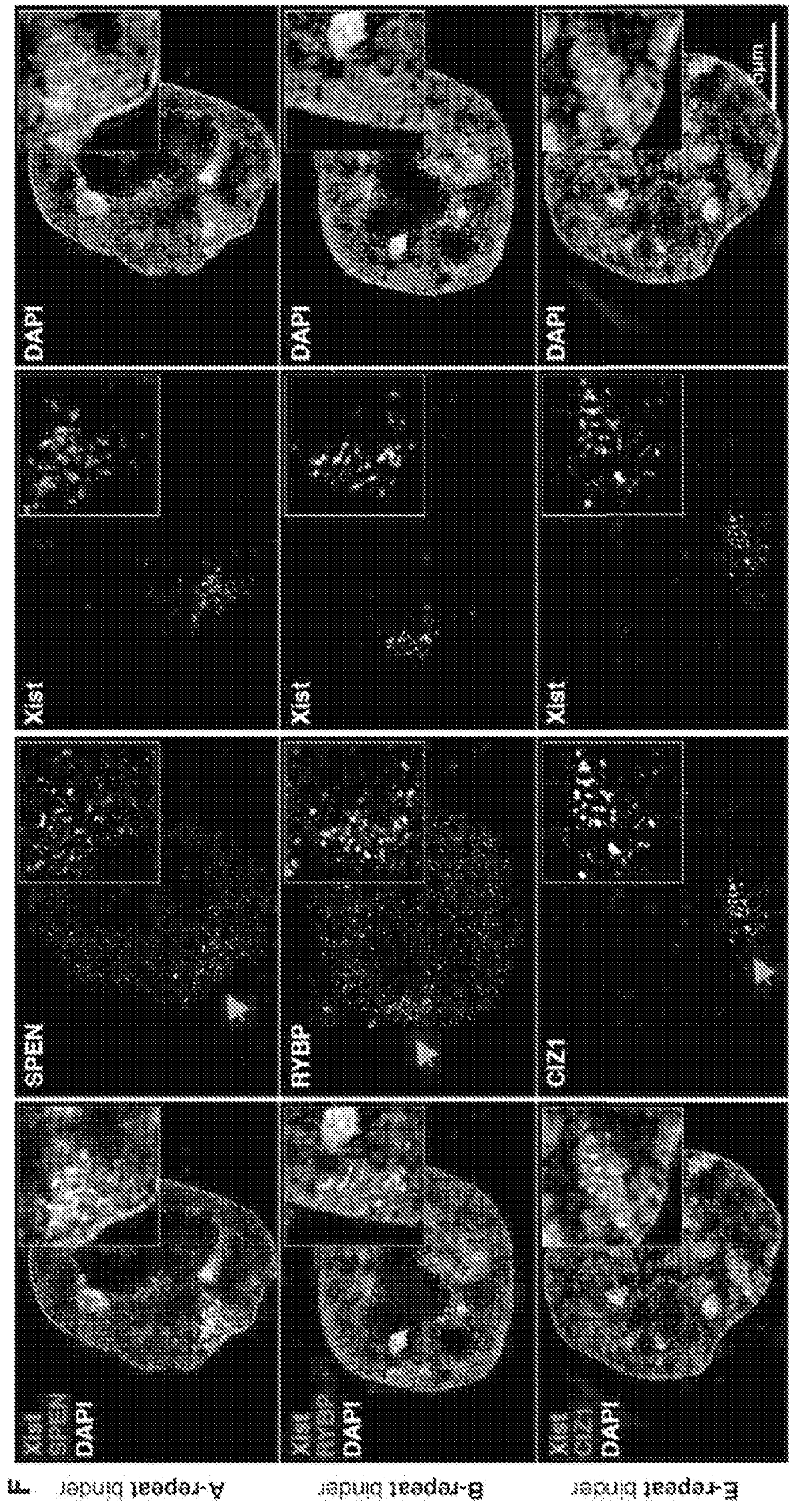

Non-Significant. (I) 3D-SIM projections showing visualization of Xist$^{MS2-GFP}$ signals at D2 and D4 after addition of 1 µg/ml doxycycline for 2 hrs to induce MCP-GFP expression. Cells were transfected with plasmids expressing cages$^{60GFP}$ 24 hrs prior to fixation. Chromatin is counterstained with DAPI (grey). Bar: 5 µm. (J) Comparison of integrated density of fluorescence of Xist foci at D2 and D4 and cage$^{60GFP}$ from I after image segmentation. Dots denote the median, thick black bars the interquartile range, thin bars show upper/lower values. Data are also shown in histogram in FIG. 19O. The calculated integrated density of cages was 64577±14467, Xist at D2: 59413±19555, Xist at D4: 74174±9933 AFU. The p-values from the MWW test were non-significant (NS). (K) Quantification of the percentages of chromatin density classes under Xist masks. Error bars denote the standard deviation. n is the number of Xist foci analyzed followed by the number of cells from three experiments. (L) Graph indicating the transition between chromatin densities. For each H2B-Halo$^{JF646}$ pixel, the intensity of all neighboring pixels was determined and plotted across the 7 density classes (y axis). The data show that the neighbors (placed in the bin of their associated chromatin density and color-coded by the chromatin class of the pixel of origin) is found in the same or the directly incrementing density class to the pixel of origin. (M) Overlap of Xist RAP-seq peaks on the X-chromosome at D2 and D4. (N) Metaplot of the Xist enrichment at D2 and D4 at the genomic locations of D2 Xist peak summits. Similar results were obtained for different cutoffs for peak calling.

FIG. 28A-F. Related to FIG. 21. Identification of Xist-SMCs. (A) 125 nm 3D-SIM optical sections showing detection of Halo protein-fusions labelled with JF549 and immunodetected proteins in Xist$^{MS2-GFP}$ cells at D2 and D4. Data are whole nucleus images of insets shown in FIG. 21B. (B) Comparison of the CIZ1-Halo$^{JF549}$ pattern to the localization of the endogenous CIZ1 detected with anti-CIZ1 primary and AlexaFluor647-conjugated secondary antibodies from data in FIG. 21B, showing the same trend in both endogenous and transgenic protein populations after 3D-SIM quantitative analyses. MWW p-values are given. Thus, endogenous proteins detected by antibody staining or Halo-fused transgenes displayed similar distributions. (C) Overview of image segmentation pipeline of 3D-SIM data for assignment of objects (particles) for downstream measurements of features. (D) Outline of image segmentation pipeline on the example of CIZ1 signals, showing the output of pre- and post-filtering steps for assigning protein particles. 3D Gaussian and TopHat kernels are applied for contrast enhancement and a 3D-seeded watershed algorithm is used to obtain segmented particles. Histograms indicate the intensity profiles obtained under the dashed line during the processing steps, showing the increased resolving and separation of individual particle signals. (E) Pipeline for the creation of masks to include all protein signals quantified in 3D-SIM particles analyses. (F) 3D-SIM optical sections of immuno-RNA FISH in a male ESC line carrying an autosomal tetO-Xist transgene (on chromosome 11) showing the distribution of Xist and representative Xist-repeat binding proteins. Greyscale images show individual channels as indicated. Arrows show the enrichment of SPEN, RYBP and CIZ1 in the Xist-coated Xi-territory. DAPI counterstaining is shown in grey. Insets show two-times magnifications of the Xist-demarcated regions.

FIG. 29A-G. Related to FIG. 21. Macromolecular crowding of Xist-associated proteins in SMCs. (A) Boxplots showing nuclear and Xist-associated segmented average intra-particle distances of XCI proteins at D2 and D4 from data in FIG. 21E. (B) Same as in A showing the nearest neighbor distances. (C) Left column: 3D-SIM 125 nm optical sections of D2 and D4 cells showing Xist$^{MS2-GFP}$ signals and immunodetected or Halo-fused proteins labelled with primary and secondary CF568-conjugated antibodies or JF549 Halo ligands (see methods). DAPI counterstaining shown in grey. Three right columns: magnifications of the Xi and nuclear regions with or without DAPI. Bar: 5 µm; Magnifications: 1 µm. (D) Point-plots showing the nearest neighbor distances of Xist-associated protein particles to Xist foci (same data as shown in FIG. 21F) and the nearest neighbor distances of the same number of randomized protein positions to Xist foci, at D2 and D4. MWW p-values are given. (E) Violin plots of integrated densities and volumes of nuclear and Xist-associated protein particles from experiment shown in FIG. 27H, at D2 and D4. Long-dashed black lines denote the median, short-dashed lines denote the upper/lower quartiles. (F) Point-plots showing the integrated density of fluorescence of Xist-associated and nuclear SPEN-GFP levels across a time course of Xist induction. Here, doxycycline was added at t=0 hrs to induce Xist expression from the tetO-Xist allele in B6$^{tetOXist-Bgl-mCherry}$Cas$^{WTXist}$ ESCs expressing GFP-tagged SPEN from the endogenous Spen locus. n denotes the number of nuclei analyzed for each timepoint from two replicates. (G) Left: Point-plots comparing the integrated density of nuclear and Xist-associated SPEN-Halo at D2 and D4 of differentiation of B6$^{tetOXist-Bgl-mCherry}$Cas$^{WTXist}$ ESCs expressing Halo-tagged SPEN from the endogenous Spen locus. Xist expression was induced from the tetO-Xist allele by addition of doxycycline (+dox) or differentiation-induced (−dox). The differentiation-induced Xist-SMCs display the increase of SPEN levels from D2 to D4, whereas SPEN levels have already plateaued in doxycycline induced Xist SMCs, likely due to faster Xist induction in the latter case. Right: Comparison of the number of Xist foci in both conditions at D2 and D4. n denotes the number of cells analyzed from two experiments. MWW p-values are given.

FIG. 30A-K. Related to FIG. 22. FRAP of Xist interactors identifies diverse protein behaviors in the Xi. (A) Projections of confocal optical stacks from RNA-FISH experiment with Xist probes at D4 with or without treatment with the transcriptional inhibitor actinomycinD. DAPI counterstaining is shown in grey. (B) As in A showing one nucleus after actinomycinD treatment with high-resolution Airyscan imaging. (C) FRAP experiment of Xist$^{MS2-GFP}$ at D4 after actinomycinD treatment for 20 min showing no recovery of Xist$^{MS2-GFP}$ signals. (D) Time series from FRAP experiments showing bleaching (dashed circles) of nuclear regions and the Xi demarcated by Xist$^{MS2-GFP}$ signals, for CIZ1-mCherry, CELF1-mCherry, SPEN-Halo, PCGF5-Halo and PTBP1-Halo transgenes at D4. Bar: 5 µm. (E) Bar graphs showing percentages of mobile (high opacity) and immobile (low opacity) protein fractions during the time course of each FRAP experiment in FIG. 22. Black bars denote the standard deviation. (F) Equation used to infer parameters and kinetic modeling of FRAP data (see STAR methods). (G) Parameters extracted from fitting the FRAP data for indicated proteins in the nucleus and the Xi, respectively, showing the percentage of the slow ($f_1$) and fast ($f_2$) detaching fractions inferred for each protein. (H) Bar graphs showing the percentage of protein particles detected in the pre-Xi/Xi outside Xist-SMCs (labelled as Xi) or in Xist-SMCs, at D2 and D4. Error bars indicate standard deviation. (I) 3D-SIM projections showing magnifications of the Xi region for Xist, PCGF5 and CIZ1 (top) and Xist, SPEN and CIZ1 (bottom). Note the extended population of PCGF5 and SPEN in the Xi compared to Xist and CIZ1. (J) Point-plots showing the integrated densities of protein particles for PCGF5 (left) and SPEN (right) within the nuclear fraction, the Xi (outside Xist-SMCs) or in Xist-SMCs at D2 and D4 from data in FIG. 21H. Dots denote the median, bars the 95% confidence interval. The medians at days 2 and 4 are connected by dotted lines to visualize any changes. Data are normalized to the highest signal observed across the entire population. MWW p-values for the comparison between the nucleus and the Xi or Xist-SMCs at D2 and D4 4 are given. (K) Same as J, except showing volume measurements.

FIG. 31A-K. Related to FIG. 23. Regulation of late gene silencing by SPEN is mediated by IDR-aggregation. (A) Schematic of the CRISPR genome editing strategy used to delete the IDRs of SPEN with two gRNAs (gRNA1, gRNA2) and annotation of the genotyping primers (black single-headed arrowed lines) and PCR amplicons (black double headed arrowed lines/dashed lines) in female B16/Cas $Xist^{tetO/wt}$ ESCs (left). PCR products after genotyping of $SPEN^{WT/WT}$ and $SPEN^{\Delta IDR/\Delta IDR}$ cells showing the expected band sizes (right). (B) Illustration of $SPEN^{\Delta IDR/\Delta IDR}$ locus after genome editing described in A, with indicated exons, introns and deletion site. Below, histograms of reads obtained by Sanger sequencing for cDNA from RT-PCR reactions with oligodT-primers from RNA derived from $SPEN^{\Delta IDR/\Delta IDR}$ cells confirm the presence of deleted transcripts for the B6 and Cas alleles. (C) 3D-SIM projections of nuclei of female cells stably expressing $FL\text{-}SPEN\text{-}Halo^{JF646}$, $\Delta IDR\text{-}SPEN\text{-}Halo^{JF646}$ or $\Delta RRM\text{-}SPEN\text{-}Halo^{JF646}$ together with $Xist^{MS2\text{-}GFP}$ on D2 and D4. Second columns show magnifications of the Xist-territory. Bars: 5 μm; insets: 1 μm. (D) Halo-tagged SPEN CLAP-seq with cells described in C. Shown is the fold change of IP/input RPKMs in 100 bp bins smoothed over 300 bp across the Xist genomic locus. The Xist RNA repeat elements are labeled. Data are averaged from two replicates of FL- and ΔIDR-, and from one replicate for ΔRRM-SPEN. Note the different y-axis labels, which indicates the lack of Xist A-repeat binding specifically for ΔRRM-SPEN. Together, these data demonstrate that ΔIDR SPEN binds to the A-repeat region of Xist similar to FL SPEN, whereas ΔRRM SPEN does not interact significantly. (E) Point-plots of particle integrated density of fluorescence and volume measurements in Xist-associated and nuclear fractions on D2 and D4, comparing FL-, ΔIDR- and ΔRRM-SPEN levels in cells described in C. Dots denote the median, bars the standard deviation. The medians at D2 and D4 are connected by dotted lines to visualize any changes. Data are normalized to the highest signal observed across the entire population. n is the number of cells from two replicates. MWW p-values for the comparison between the nucleus and the Xi at D2 or D4 are given. (F) Time-sequence from FRAP experiments of $Xist^{MS2\text{-}GFP}$ cells stably expressing the ΔIDR- or ΔRRM-SPEN-Halo at D4 of differentiation. Bar: 5 μm. (G) FRAP recovery curves comparing ΔIDR- to ΔRRM-SPEN-Halo in the nucleus and Xist-territory from data in F. Error bars denote the standard error. Every fifth timepoint is shown for clarity. The fitted curves for the first 10 seconds of this graph are shown in a magnified inset in comparison to FL-SPEN-Halo. n is the number of cells analyzed from two experiments. (H) Bar graphs showing parameters extracted from the fitting of FRAP data shown in G for ΔIDR- and ΔRRM-SPEN in the nucleus and the Xi, respectively, showing the lifetimes of slow ($f_1$) and fast ($f_2$) detaching fractions in comparison to FL-SPEN. Note that ΔIDR-SPEN exhibits very long lifetimes for the $f_2$ fraction denoted as ∞. Error bars denote the standard error. Percentages indicate the proportion of each population. (I) Schematic showing recruitment of the SPEN silencing domain SPOC to Xist under physiological conditions (via the full length SPEN protein) or by aptamer tethering (via BglG/SL, $Xist^{SPOC}$) as described in (Dossin et al., 2020). (J) Violin plots of the silencing defects of X-linked genes upon loss of endogenously encoded SPEN-AID (upon auxin addition) and rescue with GFP or Xist-tethered SPOC (re-analyzing published data (Dossin et al., 2020)). Genes are grouped by published silencing dynamics. A silencing defect of 0 indicates no difference in silencing efficacy between WT and the rescue construct, whereas 1 indicates a complete loss of silencing in the rescue compared to the WT. MWW p-values given. (K) Same as in J, but directly showing genes in each silencing group side-by-side.

FIG. 32A-H. Related to FIGS. 24 and 25. Progressive X-chromosome compaction links PRC1/SMCHD1 function to late gene silencing. (A) Volume measurements of chromosome territories by X-chromosome painting shown in FIG. 24B. Error bars denote the standard deviation. (B) 3D-SIM projections of RNA FISH with Xist probes for the Xi formed by FL-Xist or the Xi formed by ΔB-Xist in $Xist^{\Delta B/wt}$ cells at D4. Magnified insets showing Xist signals (Xist cluster, grey). (C) As in B showing only the DAPI channel. The Xi regions are indicated by arrows. Note the characteristic compaction of the Xi territory evident in WT cells, which is not present in ΔB-Xist cells. (D) 3D-SIM optical sections of RNA FISH with Xist probes in Xist-$FL^{cas}Xist\text{-}\Delta B^{129}$ female ESCs stably expressing SPEN-Halo detected with JF549 ligand at D2 and D4. DAPI counterstaining is shown in grey. Second columns show magnifications of the Xi regions. Far right columns show z-projections at D4 and magnifications of the Xi region without Xist signals. (E) Point-plots for data in D showing the integrated density of fluorescence of SPEN particles in Xist-associated and nuclear fractions, on D2 and D4, from two experiments. Dots denote the median, bars the standard deviation. The medians at D2 and D4 are connected by dotted lines to visualize any changes. Data are normalized to the highest signal observed across the entire population. MWW p-values for the comparison between the nuclear and Xist-associated fractions are given. n denotes the number of cells analyzed from two experiments. (F) Violin plots showing the silencing half-times (in days) of SMCHD1-sensitive and insensitive X-linked genes (based on a reanalysis of published data (Wang et al., 2018)). Genes that lose silencing under Smchd1 knockout (KO) are later silencing than genes that continue to silence. MWW p-value is given. (G) Boxplots showing the median distances of early and late genes from data in FIG. 25G to the center of the Xist cluster at D2 and D4, without dividing the genes according to expression status. MWW p-values are given. (H) Boxplots showing the nearest neighbor distances of active and silent early and late genes to Xist foci from data in FIG. 25G. MWW p-values are given.

Figure 33:
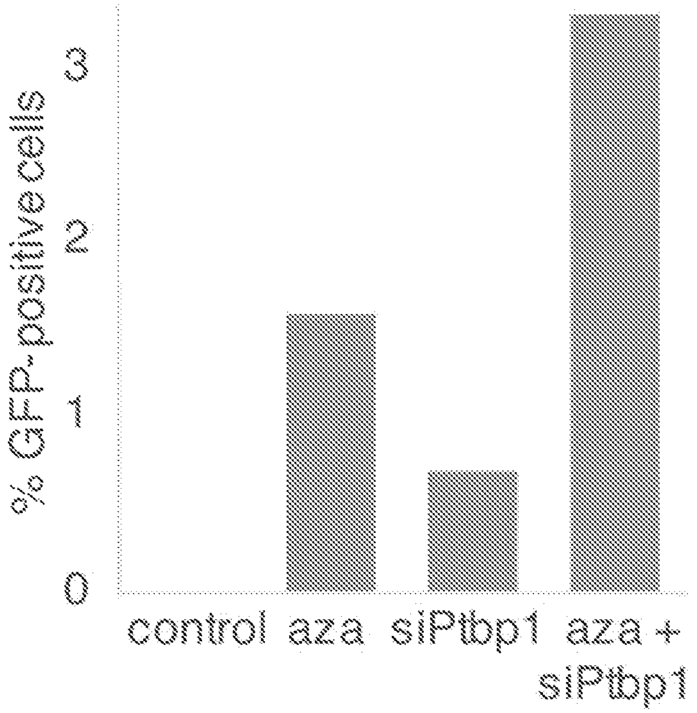

FIG. 33 shows Xi reactivation by the combined inhibition of Ptbp1 and DNA methylation. Aza is used at 0.2 uM in this experiment to induce some DNA demethylation, which on its own does not lead to Xi reactivation.

DETAILED DESCRIPTION OF THE INVENTION

I. SPEN and PTBP1 Inhibitors

A SPEN inhibitor or PTBP1 inhibitor may refer to any member of the class of compound or agents having an IC50 of 100 μM or lower concentration for a SPEN activity, for example, at least or at most or about 200, 100, 80, 50, 40, 20, 10, 5, 1 μM, 100, 10, 1 nM or lower concentration (or any range or value derivable therefrom) or any compound or agent that inhibits the expression of the protein.

A. Inhibitory Nucleic Acids

Inhibitory nucleic acids or any ways of inhibiting gene expression of proteins such as SPEN or PTBP1 are known in the art are contemplated in certain aspects. Examples of an inhibitory nucleic acid include but are not limited to siRNA (small interfering RNA), short hairpin RNA (shRNA), double-stranded RNA, an antisense oligonucleotide, a ribozyme and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain aspects from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 or any range derivable therefrom.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

Inhibitory nucleic acids are well known in the art. For example, siRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Particularly, an inhibitory nucleic acid may be capable of decreasing the expression of SPEN by at least 10%, 20%, 30%, or 40%, more particularly by at least 50%, 60%, or 70%, and most particularly by at least 75%, 80%, 90%, 95% or more or any range or value in between the foregoing.

In further aspects, there are synthetic nucleic acids that are SPEN inhibitors. An inhibitor may be between 17 to 25 nucleotides in length and comprises a 5' to 3' sequence that is at least 90% complementary to the 5' to 3' sequence of a mature SPEN mRNA. In certain aspects, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature SPEN mRNA, particularly a mature, naturally occurring mRNA. One of skill in the art could use a portion of the probe sequence that is complementary to the sequence of a mature mRNA as the sequence for an mRNA inhibitor. Moreover, that portion of the probe sequence can be altered so that it is still 90% complementary to the sequence of a mature mRNA.

B. Aptamers

Aptamers may be used to inhibit PTBP1 or SPEN in the methods of the disclosure. Aptamers are single stranded nucleic acids which selectively bind a molecular target, such as a protein. Aptamers may comprise DNA, RNA, and/or modified nucleotides, although in certain aspects it may be desirable to use DNA aptamers or aptamers comprising modified nucleotides which resist enzymatic degradation in order to increase half-life when administered to a subject in vivo.

The idea of using single stranded nucleic acids (aptamers) as affinity molecules for proteins has shown modest progress. See Tuerk and Gold, (1990); Ellington and Szostak (1990); and Ellington and Szostak (1992). The concept is based on the ability of short oligomer (20-80 mer) sequences to fold, in the presence of a target, into unique 3-dimensional structures that bind the target with high affinity and specificity. Aptamers are generated by a process that combines combinatorial chemistry with in vitro evolution, commonly known as SELEX (Systematic Evolution of Ligands by Exponential Enrichment). Following the incubation of a protein with a library of DNA or RNA sequences (typically about 1014 molecules in complexity) protein-DNA complexes are isolated, the DNA is amplified, and the process is repeated until the sample is enriched with sequences that display high affinity for the protein of interest. Since the selection pressure is high affinity for the target, aptamers with low nanomolar affinities may be obtained. Aptamers offer advantages over protein-based affinity reagents because nucleic acids possess increased stability, ease of regeneration (PCR or oligonucleotide synthesis), and simple modification for detection and immobilization. High-throughput methods for aptamer production which utilize robotics may also be used with the present invention (Cox et al., 2002).

Several variations in aptamer production protocols (e.g., varying target partitioning) may be used with the present invention. Unbound DNA molecules may be removed from target proteins via: 1) filtration on a membrane (Ellington and Szostak, 1992); 2) column chromatography, in which the targets are bound to a matrix, such as sepharose, using a covalent linkage or an affinity tag (Ylera et al., 2002); and 3) binding of the protein to the wells of a microtiter plate (Drolet et al., 1999). Methods for aptamer production which may be used with the present invention are also described, e.g., in U.S. Pat. Nos. 6,423,493; 6,515,120; 6,180,348; 5,756,291, and 7,329,742.

C. Inhibitory Antibodies

In certain aspects, an antibody or a fragment thereof that binds to at least a portion of SPEN protein and inhibits SPEN self-association is contemplated in aspects. In aspects of the disclosure, an antibody or a fragment thereof that binds to at least a portion of PTBP1 protein. The antibody may interfere with one or more activities of the protein and/or block the association of the protein with other proteins.

In some aspects, the antibody is a monoclonal antibody or a polyclonal antibody. In some aspects, the antibody is a chimeric antibody, an affinity matured antibody, a humanized antibody, or a human antibody. In some aspects, the antibody is an antibody fragment. In some aspects, the antibody is a Fab, Fab', Fab'-SH, F(ab')2, or scFv. In one aspect, the antibody is a chimeric antibody, for example, an antibody comprising antigen binding sequences from a non-human donor grafted to a heterologous non-human, human or humanized sequence (e.g., framework and/or constant domain sequences). In one aspect, the non-human donor is a mouse. In one aspect, an antigen binding sequence is synthetic, e.g., obtained by mutagenesis (e.g., phage display screening, etc.). In one aspect, a chimeric antibody has murine V regions and human C region. In one aspect, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

A monoclonal antibody is a single species of antibody wherein every antibody molecule recognizes the same epitope because all antibody producing cells are derived from a single B-lymphocyte cell line. Hybridoma technology involves the fusion of a single B lymphocyte from a mouse previously immunized with a SPEN antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced. However, in therapeutic applications a goal of hybridoma technology is to reduce the immune reaction in humans that may result from administration of monoclonal antibodies generated by the non-human (e.g. mouse) hybridoma cell line.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules which retain the antigen or epitope specificity of the original antibody, i.e., the molecule has a binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513, and 6,881,557, which are incorporated herein by this reference.

By known means as described herein, polyclonal or monoclonal antibodies, binding fragments and binding domains and CDRs (including engineered forms of any of the foregoing), may be created that are specific to SPEN protein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Particularly, the antibodies may be ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by this reference. These techniques are further described in: Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art. Methods for producing these antibodies are also well known. For example, the following U.S. patents and patent publications provide enabling descriptions of such methods and are herein incorporated by reference: U.S. Patent publication Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent publications, and other publications cited herein and therein are hereby incorporated by reference in the present application.

It is fully expected that antibodies to SPEN will have the ability to neutralize or counteract the effects of the SPEN regardless of the animal species, monoclonal cell line or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into binding fragments having the binding domain or CDR. Removal of the Fc portion reduces the likelihood that the antigen binding fragment will elicit an undesirable immunological response and, thus, antibodies without Fc may be particularly useful for prophylactic or therapeutic treatments. As described above, antibodies may also be constructed so as to be chimeric, partially or fully human, so as to reduce or eliminate the adverse immunological consequences resulting from administering to an animal an antibody that has been produced in, or has sequences from, other species.

D. SPEN or PTBP1-Targeting Peptides

A SPEN-targeting or PTBP1-targeting protein or peptide may be used to inhibit the activities of the proteins. For example, a library of peptides may be screened, e.g., using phage display in cells in vitro, to identify peptides or proteins which can bind SPEN or PTBP2 and inhibit it's function or binding or self-assembly. Various methods may be used for this purpose including, e.g., those described in Mintz P J et al. Nat Biotechnol 2003 21(1) 57-63; Kim Y et al. Biochemistry 45(31) 9434-44; Jakobsen C G et al. Cancer Res 2007 67(19) 9507-17; and Gonzalez-Gronow M et al. Cancer Res 2006 66(23) 11424-31, which are incorporated by reference herein. As used herein, a protein or peptide generally refers, but is not limited to, a protein of greater than about 200 amino acids up to a full length sequence translated from a gene; a polypeptide of about 100 to 200 amino acids; and/or a peptide of from about 3 to about 100 amino acids. For convenience, the terms "protein," "polypeptide" and "peptide are used interchangeably herein.

In certain aspects the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain aspects, the residues of the protein or peptide are sequential, without any non-amino acid interrupting the sequence of amino acid residues. In other aspects, the sequence may comprise one or more non-amino acid moieties. In particular aspects, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown in the Table below.

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

1. Peptide Mimetics

Another aspect for the preparation of polypeptides according to the invention is the use of peptide mimetics. Mimetics are peptide-containing molecules that mimic elements of protein secondary structure. See, for example, Johnson et al., (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

2. Fusion Proteins

Other aspects of the present invention concern fusion proteins. These molecules generally have all or a substantial portion of a targeting peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred aspects, the fusion proteins of the instant invention comprise a targeting peptide linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually and protein or peptide could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

3. Synthetic Peptides

Because of their relatively small size, the inhibitory peptides of the disclosure can be synthesized in solution or on a solid support in accordance with conventional techniques. Various automatic synthesizers are commercially available and can be used in accordance with known protocols. See, for example, Stewart and Young, 1984; Tam et al., 1983; Merrifield, 1986; and Barany and Merrifield, 1979, each incorporated herein by reference. Short peptide sequences, usually from about 6 up to about 35 to 50 amino acids, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

II. Nucleic Acid Modifications

The nucleic acid inhibitors of the disclosure may comprise modified oligonucleotides that increase the stability of the nucleic acid. In some aspects, the nucleic acid inhibitor or aptamer is an oligonucleotide analogs. The term "oligonucleotide analog" refers to compounds which function like oligonucleotides but which have non-naturally occurring portions. Oligonucleotide analogs can have altered sugar moieties, altered base moieties or altered inter-sugar linkages. The term "oligomers" is intended to encompass oligonucleotides, oligonucleotide analogs or oligonucleosides. Thus, in speaking of "oligomers" reference is made to a series of nucleosides or nucleoside analogs that are joined via either natural phosphodiester bonds or other linkages, including the four atom linkers. Although the linkage generally is from the 3' carbon of one nucleoside to the 5' carbon of a second nucleoside, the term "oligomer" can also include other linkages such as 2'-5' linkages.

Oligonucleotide analogs also can include other modifications, particularly modifications that increase nuclease resistance, improve binding affinity, and/or improve binding specificity. For example, when the sugar portion of a nucleoside or nucleotide is replaced by a carbocyclic moiety, it is no longer a sugar. Moreover, when other substitutions, such a substitution for the inter-sugar phosphodiester linkage are made, the resulting material is no longer a true nucleic acid species. All such compounds are considered to be analogs. Throughout this specification, reference to the sugar portion of a nucleic acid species shall be understood to refer to either a true sugar or to a species taking the structural place of the sugar of wild type nucleic acids. Moreover, reference to inter-sugar linkages shall be taken to include moieties serving to join the sugar or sugar analog portions in the fashion of wild type nucleic acids.

The present disclosure concerns modified oligonucleotides, i.e., oligonucleotide analogs or oligonucleosides, and methods for effecting the modifications. These modified oligonucleotides and oligonucleotide analogs may exhibit increased chemical and/or enzymatic stability relative to their naturally occurring counterparts. Extracellular and intracellular nucleases generally do not recognize and therefore do not bind to the backbone-modified compounds. When present as the protonated acid form, the lack of a negatively charged backbone may facilitate cellular penetration.

The modified internucleoside linkages are intended to replace naturally-occurring phosphodiester-5'-methylene linkages with four atom linking groups to confer nuclease resistance and enhanced cellular uptake to the resulting compound. Preferred linkages have structure CH2-RA-NR1 CH2, CH2-NR1-RA-CH2, RA-NR1-CH2-CH2, CH2-CH2-NR1-RA, CH2-CH2-RA-NR1, or NR1-RA-CH2-CH2 where RA is O or NR2.

Modifications may be achieved using solid supports which may be manually manipulated or used in conjunction with a DNA synthesizer using methodology commonly known to those skilled in DNA synthesizer art. Generally, the procedure involves functionalizing the sugar moieties of two nucleosides which will be adjacent to one another in the selected sequence. In a 5' to 3' sense, an "upstream" synthon is modified at its terminal 3' site, while a "downstream" synthon is modified at its terminal 5' site.

Oligonucleosides linked by hydrazines, hydroxylamines, and other linking groups can be protected by a dimethoxytrityl group at the 5'-hydroxyl and activated for coupling at the 3'-hydroxyl with cyanoethyldiisopropyl-phosphite moieties. These compounds can be inserted into any desired sequence by standard, solid phase, automated DNA synthesis techniques. One of the most popular processes is the phosphoramidite technique. Oligonucleotides containing a uniform backbone linkage can be synthesized by use of CPG-solid support and standard nucleic acid synthesizing machines such as Applied Biosystems Inc. 380B and 394 and Milligen/Biosearch 7500 and 8800s. The initial nucleotide (number 1 at the 3'-terminus) is attached to a solid support such as controlled pore glass. In sequence specific order, each new nucleotide is attached either by manual manipulation or by the automated synthesizer system.

Free amino groups can be alkylated with, for example, acetone and sodium cyanoboro hydride in acetic acid. The alkylation step can be used to introduce other, useful, functional molecules on the macromolecule. Such useful functional molecules include but are not limited to reporter molecules, RNA cleaving groups, groups for improving the pharmacokinetic properties of an oligonucleotide, and groups for improving the pharmacodynamic properties of an oligonucleotide. Such molecules can be attached to or conjugated to the macromolecule via attachment to the nitrogen atom in the backbone linkage. Alternatively, such molecules can be attached to pendent groups extending from a hydroxyl group of the sugar moiety of one or more of the nucleotides. Examples of such other useful functional groups are provided by WO1993007883, which is herein incorporated by reference, and in other of the above-referenced patent applications.

Solid supports may include any of those known in the art for polynucleotide synthesis, including controlled pore glass (CPG), oxalyl controlled pore glass [53], TentaGel Support—an aminopolyethyleneglycol derivatized support [54] or Poros—a copolymer of polystyrene/divinylbenzene. Attachment and cleavage of nucleotides and oligonucleotides can be effected via standard procedures [55]. As used herein, the term solid support further includes any linkers (e.g., long chain alkyl amines and succinyl residues) used to bind a growing oligonucleoside to a stationary phase such as CPG.

A. Locked Nucleotides

In some aspects, the nucleic acid of the disclosure, such as the nucleic acid inhibitor, molecule comprises a locked nucleic acid. A locked nucleic acid (LNA or Ln), also referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired and hybridize with DNA or RNA according to Watson-Crick base-pairing rules. Such oligomers are synthesized chemically and are commercially available. The locked ribose conformation enhances base stacking and backbone pre-organization. This significantly increases the hybridization properties (melting temperature) of oligonucleotides.

B. Ethylene Bridged Nucleotides

In some aspects, the nucleic acid of the disclosure, such as the nucleic acid inhibitor, molecule comprises one or more ethylene bridged nucleotides. Ethylene-bridged nucleic acids (ENA or En) are modified nucleotides with a 2'-O, 4'C ethylene linkage. Like locked nucleotides, these nucleotides also restrict the sugar puckering to the N-conformation of RNA.

C. Peptide Nucleic Acids

In some aspects, the nucleic acid of the disclosure, such as the nucleic acid inhibitor, molecule comprises one or more peptide nucleic acids. Peptide nucleic acids (PNA or Pn) mimic the behavior of DNA and binds complementary nucleic acid strands. The term, "peptide," when used herein may also refer to a peptide nucleic acid. PNA is an artificially synthesized polymer similar to DNA or RNA. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by a methylene bridge (—CH2-) and a carbonyl group (—(C═O)—). PNAs are depicted like peptides, with the N-terminus at the first (left) position and the C-terminus at the last (right) position.

Since the backbone of PNAs contains no charged phosphate groups, the binding between PNA/DNA strands is stronger than between DNA/DNA strands due to the lack of electrostatic repulsion. PNAs are not easily recognized by either nucleases or proteases, making them resistant to degradation by enzymes. PNAs are also stable over a wide pH range. In some aspects, the PNAs described herein have improved cytosolic delivery over other PNAs.

5'(E)-Vinyl-Phosphonate (VP) Modification

In some aspects, the nucleic acid of the disclosure, such as the RNA targeting molecule comprises one or more 5'(E)-vinyl-phosphonate (VP) modifications. 5'-Vinyl-phosphonate modifications (metabolically stable phosphate mimics) have been reported to enhance the metabolic stability and the potency of oligonucleotides.

D. Morpholinos

In some aspects, the nucleic acid of the disclosure, such as the nucleic acid inhibitor, molecule comprises a morpholino. Morpholinos are synthetic molecules that are the product of a redesign of natural nucleic acid structure. Usually 25 bases in length, they bind to complementary sequences of RNA or single-stranded DNA by standard nucleic acid base-pairing. In terms of structure, the difference between Morpholinos and DNA is that, while Morpholinos have standard nucleic acid bases, those bases are bound to methylenemorpholine rings linked through phosphorodiamidate groups instead of phosphates. The figure compares the structures of the two strands depicted there, one of RNA and the other of a Morpholino. Replacement of anionic phosphates with the uncharged phosphorodiamidate groups eliminates ionization in the usual physiological pH range, so Morpholinos in organisms or cells are uncharged molecules. The entire backbone of a Morpholino is made from these modified subunits.

III. Administration of Therapeutic Compositions

The therapy provided herein may comprise administration of a combination of therapeutic agents, such as a first therapy and a second therapy. The therapies may be administered in any suitable manner known in the art. For example, the first and second treatment may be administered sequentially (at different times) or concurrently (at the same time). In some aspects, the first and second treatments are administered in a separate composition. In some aspects, the first and second treatments are in the same composition.

Aspects of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some aspects, the therapy is administered intravenously, intramuscularly, subcutaneously, topically, orally, transdermally, intraperitoneally, intraorbitally, by implantation, by inhalation, intrathecally, intraventricularly, or intranasally. In some aspects, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some aspects, a unit dose comprises a single administrable dose.

The quantity to be administered, both according to number of treatments and unit dose, depends on the treatment effect desired. An effective dose is understood to refer to an amount necessary to achieve a particular effect. In the practice in certain aspects, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 μg/kg, mg/kg, μg/day, or mg/day or any range derivable therein. Furthermore, such doses can be administered at multiple times during a day, and/or on multiple days, weeks, or months.

In certain aspects, the effective dose of the pharmaceutical composition is one which can provide a blood level of about 1 μM to 150 μM. In another aspect, the effective dose provides a blood level of about 4 μM to 100 μM; or about 1 μM to 100 μM; or about 1 μM to 50 μM; or about 1 μM to 40 μM; or about 1 μM to 30 μM; or about 1 μM to 20 μM; or about 1 μM to 10 μM; or about 10 μM to 150 μM; or about 10 μM to 100 μM; or about 10 μM to 50 μM; or about 25 μM to 150 μM; or about 25 μM to 100 μM; or about 25 μM to 50 μM; or about 50 μM to 150 μM; or about 50 μM to 100 μM (or any range derivable therein). In other aspects, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μM or any range derivable therein. In certain aspects, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of μg/kg or mg/kg of body weight can be converted and expressed in comparable concentration units of μg/ml or mM (blood levels), such as 4 μM to 100 μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Xist-Seeded Nucleation Sites Form Local Concentration Gradients of Silencing Proteins to Inactivate the X-Chromosome

A. Introduction and Results

The long non-coding RNA Xist exploits numerous effector proteins to progressively induce gene silencing across the X chromosome and form the inactive X (Xi)-compartment. The mechanism underlying formation of the chromosome-wide Xi-compartment is poorly understood. Here, we find that formation of the Xi-compartment is induced by ~50 locally confined granules, where two Xist RNA molecules nucleate supra-molecular complexes (SMCs) of interacting proteins. Xist-SMCs are transient structures that concentrate rapidly recycling proteins in the X by increasing protein binding affinity. We find that gene silencing originates at Xist-SMCs and propagates across the entire chromosome over time, achieved by Polycomb-mediated coalescence of chromatin regions and aggregation, via its intrinsically disordered domains, of the critical silencing factor SPEN. Our results suggest a new model for X chromosome inactivation, in which Xist RNA induces macromolecular crowding of heterochromatinizing proteins near distinct sites which ultimately increases their density throughout the chromosome. This mechanism enables deterministic gene silencing without the need for Xist ribonucleoprotein complex-chromatin interactions at each target gene.

Non-coding RNAs are known to seed membraneless bodies in the cytosol and nucleus such as stress granules, the histone locus body, P-bodies, splicing speckles, paraspeckles or Cajal bodies (1-3). Their function relies on the recruitment of effector proteins and often on interactions between low-complexity domains that support Liquid-Liquid Phase Separation (LLPS) (2, 4-10) A subset of nuclear RNAs, including the long non-coding RNAs (lncRNAs) Xist, Kcnq1ot1, Rox1/2 and Airn, act by regulating chromatin structure and function through the formation of nuclear compartments (10-21). The mechanisms underlying compartment formation by this class of RNAs and how they exploit effector proteins to regulate gene expression and chromatin states within the compartment are still poorly understood. Here, we utilize Xist RNA as a model to interrogate these mechanisms. Our work reveals a spatial organization mechanism by which few RNA molecules can regulate a broad nuclear compartment through the recruitment and local concentration of dynamic effector proteins and provides a quantitative framework for studying such compartments.

Xist is transcribed from, coats and silences one of the two X chromosomes during the development of female mammals in a process referred to as X chromosome inactivation (XCI) (13, 14, 16-18, 21-26). Xist localization across the X progressively induces changes in gene expression and alters the three-dimensional chromatin structure (27-29) through the recruitment of silencing proteins (30-32) and the buildup of epigenetic modifications on the chromosome (33-39). The prevailing view is that Xist recruits effector proteins to form ribonucleoprotein complexes that spread across the X and silence genes in a stoichiometric manner (34, 35, 40-42). However, super-resolution microscopy has revealed that Xist distributes in few diffraction-limited foci on the inactive X chromosome (Xi) (43, 44). How a small number of Xist foci recruit interacting proteins to deterministically silence genes across an entire chromosome remains unexplored. Here, we analyzed the distribution and dynamics of Xist and its interacting proteins through quantitative and live-cell super-resolution microscopy, and functionally tested key relationships, to derive fundamental insights into this problem. We performed these analyses during the initiation of XCI in female embryonic stem cells (ESCs), at an early time point when Xist RNA has initially established its territory over the X and silencing initiates at first genes, and at a later timepoint when silencing of most genes has been completed. This critical comparison allowed us to observe changes in Xist and/or protein distributions, mediated by few Xist foci, that lead to robust gene silencing over time.

To explore how Xist RNA orchestrates the progressive formation of the Xi-compartment we first examined when Xist coats the X relative to gene silencing in our ESC to epiblast-like cell differentiation system (45, 46) (FIG. 5A). RNA FISH showed that Xist demarcated the X-chromosome and formed a large 'Xist cloud' by day 2 (D2) whereas silencing of Atrx and Mecp2, two X-linked genes known to be silenced late during XCI initiation, occurred by day 4 (D4) (FIG. 1A and FIGS. 5B and 5C). Thus, consistent with prior data (47), silencing progresses after Xist initially coats the X chromosome. We therefore chose to examine the X at D2 and D4 of differentiation to understand the mechanisms leading to progressive Xi-compartment formation. We refer to the X state at D2 as the "pre-XCI" state with the "pre-Xi", and at D4 as the "post-XCI" state with the "Xi".

To determine if the transition from the initial localization of Xist on D2 to the completion of silencing on D4 can be explained by a change in Xist foci number, we used super-resolution three-dimensional Structured Illumination Microscopy (3D-SIM). Previous reports have shown that about 50-200 Xist foci are present in the Xi of female somatic cells (41, 43), but whether this number changes during XCI initiation is unknown. To assess Xist foci, we labelled the RNA in living cells by exploiting the MS2 hairpin-MS2 Coat Protein (MCP) interaction (48). Briefly, we tagged the endogenous Xist RNA of one of the two X-chromosomes in female mouse ESCs with 24 MS2-repeats and co-expressed MCP-GFP (FIG. 1B). MCP-GFP was recruited to Xist ($Xist^{MS2-GFP}$) and the X-linked gene Atrx was efficiently silenced (FIGS. 5D and 5E), demonstrating the functionality of the $Xist^{MS2-GFP}$ allele. Quantitative 3D-SIM analysis of $Xist^{MS2-GFP}$ shows that the Xist territory consists, on average, of 74 diffraction-limited foci on the pre-Xi and 60 foci on the Xi (FIGS. 1C and 1D). These distributions were confirmed by RNA FISH with Xist probes (FIGS. 6A and 6B). We found that the doubling of the X chromosome with DNA replication in S-phase is accompanied by the doubling of the number of Xist foci, from ~50 foci in G1 to ~100 in G2, which was confirmed in somatic cells that maintain the Xi (FIG. 1E and FIGS. 6C and 6D). Thus, the range of Xist foci number in the cell population is largely due to cell cycle differences. Moreover, these findings show that the number of Xist foci is correlated with the length of the X-chromosome. We confirmed this correlation using cell lines that have abnormal X is of different length (49) (FIGS. 6E and 6F). Taken together, these data show that transition from the pre-Xi to the Xi is induced by a set number of ~50 Xist foci.

We next investigated whether the amount of Xist RNA in each focus changes during the transition from pre- to post-XCI. We found that Xist foci are stable assemblies that maintain their integrated fluorescence density and volume during differentiation (FIG. 1F and FIG. 6B). Consistent with this finding, the Xist locus is constitutively transcribed during differentiation (FIGS. 7A and 7B). To estimate the number of Xist molecules in each focus, we utilized a novel fluorescence quantification standard together with quantitative 3D-SIM. Specifically, we transiently expressed nanocages consisting of 60 GFP molecules ($cage^{60GFP}$) (50) as internal fluorescence standard in $Xist^{MS2-GFP}$ cells. Integrated density measurements showed that the amount of fluorescence within one $Xist^{MS2-GFP}$ focus on the pre-Xi and the Xi, respectively, corresponds to that of one $cage^{60GFP}$ (FIG. 1G, FIGS. 7C and 7D). Fluorescence fluctuation spectroscopy measurements have shown that ~30 MCP-GFP molecules are bound to 24 copies of the MS2-repeat at a given time (51). This number denote that, throughout XCI initiation, each focus contains two molecules of Xist. Thus, only ~100 Xist molecules orchestrate the initiation of gene silencing across the entire X-chromosome.

The X chromosome contains ~1000 genes that are subject to silencing (52), therefore, the limited number of Xist foci suggests that they should be highly diffusive if they are to directly regulate target genes across the entire chromosome. We therefore investigated the mobility of Xist foci in the pre- and post-XCI states by performing live-cell 3D-SIM of $Xist^{MS2-GFP}$, followed by single-particle tracking of individual foci. This experiment allows for near single-molecule tracking, as each focus contains two Xist transcripts. Unexpectedly, we found that Xist foci exhibited restricted motion and did not undergo fission or fusion (FIGS. 2A and 2B). In 90% of cases, the displacement of Xist foci over time was less than 200 nm and their movement was characterized as diffusion in a local confining potential (FIG. 2C-E). The confined motion of Xist foci is highly correlated with the motion of chromatin (53-57) both on the pre-Xi and the Xi (FIG. 2E). We conclude that Xist foci are tethered to chromosomal locations with high affinity, which constrains each of them locally and limits their movement to that of the Brownian motion of the bound chromatin. Thus, progression of XCI is mediated through ~50 sites where two Xist molecules are locally confined.

To investigate whether the 'wiggling' of Xist foci around their centers is confined within a specific chromatin environment, we introduced a histone H2B-Halo transgene into $Xist^{MS2-GFP}$ ESCs and performed live-cell 3D-SIM (FIG. 2F). H2B signals were segmented into seven intensity levels that correspond to chromatin density classes, where class 1 represents DNA-free space (interchromatin channels, IC) and classes 2 to 7 increasing chromatin densities (43) (FIG. 2G). Xist foci covered predominantly classes 1 to 3 (FIG. 8A). Over time, the chromatin densities underlying each focus footprint never surpassed class 3, and the centers of mass (centroids) of Xist foci remained within chromatin class 2 (FIG. 2H). These data are consistent with our finding that chromatin density increases in linear increments (FIG. 8B). We infer that Xist foci are spatially confined to the periphery of dense chromatin domains, facing the interchromatin channels, and stably maintain their positions relative to chromatin over time. In agreement with these observations, RNA antisense purification (RAP) of Xist from pre- and post-XCI stages followed by DNA sequencing of the associated chromatin (40) showed that Xist localizes to gene-rich, open chromatin regions of the A-compartment (28, 40, 58) (FIG. 2I). The Xist localization patterns are very similar between the pre-Xi and Xi (Pearson's correlation r=0.83) (FIG. 2I). We identified 65 and 63 highly correlated peaks of Xist enrichment on the pre-Xi and Xi, respectively (FIG. 2J and FIGS. 8C and 8D), similar to the number of Xist foci detected by 3D-SIM. Taken together these findings confirm that the localization of Xist relative to chromatin persists as gene silencing proceeds.

The discovery of only two Xist molecules in ~50 confined locations indicates that Xist and effector proteins cannot distribute across the entire chromosome space to induce XCI in a stoichiometric manner with gene targets. We reasoned that to effect gene silencing over the entire chromosome, hundreds of Xist-recruited proteins form diffuse clouds localized about Xist foci. These overlapping diffuse clouds can span the entire X and thereby more frequently interact with silencing sites. We addressed this hypothesis by first examining how Xist-interacting proteins accumulate relative to Xist foci, during the initiation of XCI.

We focused on SPEN, PCGF5, CELF1 and CIZ1, four proteins that bind to distinct repeat sequences of Xist RNA and differ in their function in XCI (59, 60). SPEN binds the A-repeat sequence of Xist and is the key transcriptional repressor of XCI that activates HDAC3 to induce histone deacetylation and gene silencing (30, 31, 42, 61-63). PCGF5 is recruited to the Xi via binding of hnRNP-K to the Xist B/C-repeat sequences (64), and is a component of the polycomb complex PRC1 that contributes to the silencing of X-linked genes (35, 63-67) and has a critical role in chromatin compaction genome-wide (68-71). CELF1 and CIZ1 both bind to the E-repeat sequence of Xist and are critical for restricting the localization of Xist in the X-territory (72-75).

We imaged antibody-stained and stably expressed Halo-fusion proteins together with $Xist^{MS2-GFP}$ by 3D-SIM to simultaneously detect Xist and two effector proteins at differentiation D2 and D4 (FIG. 9A). Endogenous proteins detected by antibody staining or Halo-fused transgenes displayed similar distributions (FIG. 9B). We found that the interrogated proteins formed distinctive assemblies in proximity to Xist foci on the pre-Xi as well as the Xi (FIG. 3A). Moreover, protein assemblies appeared larger in the pre-Xi and Xi-territory than in other nuclear accumulations, indicating that Xist induces the de novo formation of unique protein complexes. To quantitatively define the protein aggregates induced by Xist, we extracted the spatial coordinates of thousands of diffraction-limited segmented protein foci throughout nuclei (FIGS. 9C-E and Table S1). We measured the nearest-neighbor distances between pairs of different Xist interactors that were either associated with Xist foci or found in the remainder or the nucleus, which includes the active X-chromosome (Xa) (FIG. 3B). All investigated pairs of SPEN, CELF1, PCGF5 and CIZ1 foci were, on average, within ~150-200 nm of each other when associated with Xist foci but separated by >350 nm in the nucleus both pre- and post-XCI (FIG. 3C). Therefore, upon distributing across the pre-Xi, foci comprising two Xist molecules immediately recruit arrays of XCI-effector proteins and bring them closer to each other than elsewhere in the nucleus. Hence, large multi-protein assemblies, that are not typically found outside the Xi, form around Xist foci. We refer to these Xist-nucleated proteinaceous nanostructures as Xist-associated supra-molecular complexes (Xist-SMCs).

To explore whether protein integration into Xist-SMCs is the main mechanism of protein recruitment in the Xi, we probed the distribution of additional XCI effectors (FIG. 10A), including the PRC1 component RYBP (76); EZH2 (37, 39, 41, 77) belonging to the Polycomb repressive complex PRC2; hnRNP-K which binds the B/C-repeats of Xist to recruit PCGF5 (64) (reviewed in (59)); PTBP1 and MATR3, which function with CELF1 in the maintenance of silencing and Xist localization (74). Nearest-neighbor measurements showed a diffraction-limited particle for each of these proteins in a near 1:1 ratio within 200 nm from the center of Xist foci (FIG. 3D and FIG. 10B). These results corroborate the de novo assembly of a multi-protein cloud around Xist foci at the onset of XCI and identify the macromolecular crowding of many direct and indirect Xist interactors in Xist-SMCs, likely involving 100s to 1000s of protein molecules. Notably, our results revealed little differences between Xist-SMCs in the pre-Xi and Xi. Thus, SMCs around Xist foci contain all interrogated proteins before gene silencing completes.

We next investigated whether the pre-Xi to Xi transition is associated with changes in the concentration of proteins within Xist-SMCs compared to the nucleus (FIG. 3E and FIG. 10C, Tables S2 and S3). Integrated density and volume particle measurements showed that the levels of CIZ1, CELF1, PCGF5, EZH2 and RYBP are significantly higher in Xist-SMCs than in nuclear foci. For CIZ1, CELF1, PCGF5 levels are stable from D2 to D4, whereas EZH2 and RYBP levels in Xist-SMCs change along with nuclear changes. Conversely, the concentrations of MATR3, PTBP1 and hnRNP-K are similar in Xist-SMCs and nuclear assemblies throughout differentiation, suggesting that they can fulfill their function in XCI at baseline concentration. Overall, these results show that the intense protein accumulations in Xist-SMCs are relatively stable throughout progression of XCI initiation. However, we found that SPEN levels within Xist-SMCs increase from the pre-Xi to the Xi, reaching higher levels than in nuclear assemblies only in the Xi. Thus, the completion of gene silencing is linked to the presence of more SPEN molecules in Xist-SMCs.

We next explored the mechanism that leads to the increased concentration of SPEN in Xist-SMCs with the pre- to post-XCI transition. SPEN contains intrinsically disordered regions (IDRs), which often mediate weak, multivalent interactions (2, 44, 78-80). We thus investigated whether the IDRs are required for the progressive accumulation of SPEN. We stably expressed SPEN-Halo with an IDR deletion (ΔIDR SPEN) in $Xist^{MS2-GFP}$ cells and confirmed that it does not interfere with gene silencing (FIG. 3F and FIGS. 11A and 11B). We found that ΔIDR SPEN and wild type (WT) SPEN accumulated similarly in SMCs on the pre-Xi but, unlike WT SPEN, ΔIDR SPEN levels did not increase on SMCs in the Xi (FIGS. 3F and 3G, FIG. 11C). These results show that the time-dependent increase of SPEN in Xist-SMCs is driven by IDRs and suggest that increased protein aggregation is associated with the completion of gene silencing on the Xi.

Our analyses show that Xist nucleates SMCs, leading to macromolecular crowding of proteins at topologically confined locations. We next explored the kinetic behavior of protein components of Xist-SMCs. We reasoned that the accumulation of proteins in Xist-SMCs should reveal both long-lived binding events, allowing for a topological retention in the SMC, as well as rapidly exchanging constituents, facilitating their access and deposition across the X chromosome. In such a model, transient Xist-SMCs structures would allow SPEN to regulate genes across the entire X chromosome.

To investigate kinetic behavior of protein exchange in the Xi, we stably expressed Halo or mCherry SPEN, PCGF5, CIZ1, CELF1 or PTBP1 fusions, and performed Fluorescence Recovery After Photobleaching (FRAP) over the $Xist^{MS2-GFP}$ territory or other nuclear regions of the same size. We also examined Xist dynamics for comparison. We observed a slow exchange of photobleached $Xist^{MS2-GFP}$ (FIG. 12A), comparable to previous findings of ectopically expressed Xist (81). By fitting measured FRAP curves to a kinetic model with a single-exponential, we inferred a slow dissociation rate (0.05/min) resulting in an average Xist lifetime of ~20 min, consistent with a single dominant type of high-affinity interaction between Xist and chromatin (FIG. 3H, FIG. 12B). We found that CIZ1 exhibits a ~18 min recovery time in the Xi, similar to Xist and much longer than that of the other interacting proteins. The lifetime of CIZ1 in the Xi is longer than in other nuclear regions, suggesting that Xist recruitment reinforces CIZ1 binding to chromatin (FIG. 3I and FIG. 12C). The tight kinetic and spatial (FIG. 3D) relationship between Xist and CIZ1 suggests that CIZ1 and Xist molecules form a stable core of Xist-SMCs.

Kinetic modelling of the SPEN, PCGF5, CELF1 and PTBP1 FRAP curves yielded rapid exchange rates compared to CIZ1 and Xist and two types of binding sites (FIG. 3J and FIG. 13). Using two-exponential fits we inferred parameters for short-lived (f1) and long-lived (f2) bound fractions within and outside of the Xi. For all four proteins rapid binding occurred within seconds and the more stable interactions lasted several minutes (FIG. 3J). SPEN is the most dynamic protein, with kinetic rates characteristic of transcription factors (82, 83). It is likely that the more dynamic fraction of SPEN (f1), which has similar characteristics inside and outside the Xi (~2 s), represents fast-exchanging chromatin-engaging molecules that act to control gene expression. Conversely, the longer-lived fraction (f2) may represent SPEN molecules associated with Xist-SMCs. In line with this hypothesis, FRAP experiments showed a >50% reduction of ΔIDR SPEN of the long-lived Xi binding fraction compared to WT SPEN and a more rapidly dissociating fast population (FIG. 14). Notably, recruitment to the Xi extends the long-lived binding rates and/or increases the fraction of long-lived binding events for the interrogated proteins indicating that the Xi forms a unique nuclear compartment where proteins exhibit distinct kinetic behaviors (FIG. 3J and FIG. 13B). These data are also consistent with their increased accumulation in the Xist territory.

The kinetic assays revealed that proteins with short residence times aggregate around a slowly exchanging Xist-CIZ1 core. These findings denote that Xist-SMCs are rapidly exchanging 'transient complexes' that form local, high affinity concentration platforms, thereby increasing the typical residence times of proteins within the Xi. The accumulation in Xist-SMCs primes an increased amount of protein in the Xi, while the rapid binding and dissociation on Xist-SMCs allows proteins, particularly SPEN, to probe and spatially modulate targets further than the locations where two Xist molecules are confined. The presence of a large number of protein molecules in the Xi, without an interaction with Xist, may allow distinct protein species (such as SPEN or PRC1) to explore unique targets and with individual binding rates, which is reflected by the distinct residence time of each tested protein. Such a mechanism is likely thermodynamically favorable and critical for deterministic silencing.

To validate that the formation of Xist-SMCs yields an influx of proteins in the Xi, we next examined the protein population in the Xi but outside Xist-SMCs (referred to as Xi-fraction). We focused on the main two heterochromatinizing proteins SPEN and PCGF5. Using quantitative 3D-SIM, we detected protein assemblies formed in the X-territory, outside Xist-SMCs, which exhibit lower protein concentration than Xist-SMCs but a higher concentration than nuclear assemblies, as assessed by measurements of their integrated fluorescent density and volume (FIG. 15). PCGF5 levels in the Xi fraction are significantly higher than within nuclear assemblies on both the pre-Xi and Xi, whereas the level of SPEN in the Xi-fraction increases gradually during this transition. These data suggest that accumulation at Xist-SMCs leads to enrichment of constituent proteins across local neighborhoods in the X, through dynamic feeding from Xist-SMCs.

We next explored the relationship between gradual gene silencing and Xist-SMCs. It is well established that a subset of genes silences soon after Xist coating, whereas other genes, including Atrx and Mecp2, become silenced later (29, 34), yet the mechanism underlying these distinct silencing kinetics is unknown. We examined whether the formation of Xist-SMCs primes early gene silencing events. To test this idea, we investigated whether gene silencing originates at locations proximal to Xist-SMCs by measuring Xist enrichment over gene silencing half-times (29). Genes silencing with faster kinetics display more Xist binding on the pre-Xi compared to genes that become silenced later (FIGS. 16A and 16B). These results suggest that rapid silencing kinetics are favorable in proximity to Xist-SMCs. Despite these differences, both fast and slow silencing genes are dependent on SPEN for gene silencing (30, 31, 42, 61-63) (FIG. 16C). Therefore, we next interrogated whether the ablation of the dynamic association of SPEN with Xist-SMCs interferes with the progression of silencing.

To this end, we exploited an approach (42), in which the SPOC domain of SPEN, which is required for transcriptional repression, was tethered to Xist through the BglG/Bgl stem loop (SL) interactions and the endogenous copies of SPEN were depleted (42, 84). BglG-BglSL tethering of the SPOC domain to Xist ($Xist^{SPOC}$) is expected to prevent the rapid exchange from SMCs, normally observed for SPEN, and immobilize it primarily at the core of SMCs, where Xist is localized (FIG. 4A). If SPEN dynamics control gene inactivation kinetics, then $Xist^{SPOC}$ should result in more efficient silencing of genes that are typically silenced early in XCI than later silencing genes. Indeed, we found that genes normally silenced early during XCI are silenced more effectively by $Xist^{SPOC}$ than genes that are normally silenced late during XCI (FIG. 4B and FIG. 16D). This result suggests that SPEN-mediated silencing originates at regions that are proximal to Xist-SMCs and expansion of silencing to other target genes occurs progressively and requires the rapid kinetic behavior of the WT SPEN protein. We next addressed the mechanism underlying this expansion.

Gradual gene silencing occurs without major changes in Xist-SMC protein levels except for the IDR-dependent increase in SPEN. IDRs are known to adopt more protein-protein interactions upon changes in the local environment (85-88), such as an increase in chromatin density that promotes macromolecular crowding (89, 90). These observations suggest that the progression of gene silencing beyond targets in the spatial vicinity of Xist-SMCs, as well as the IDR-dependent concentration increase of SPEN, may be mechanistically linked to a conformational change in the X-territory. We therefore investigated whether higher-order chromatin changes occur during the pre- to post-XCI transition.

Measuring the volume and sphericity of the X chromosome upon X-chromosome painting, we found that the conformation of the pre-Xi is similar to that of the active X-chromosome (Xa) (FIGS. 4C and 4D). At D4, the Xi reached the distinct compact and spherical organization known for the silent X in somatic cells (91) (FIGS. 4C and 4D). We extended this result by assessing the conformation of seven unique genomic loci across the X through DNA FISH. We observed a moderate change in the higher-order chromosome configuration of the pre-Xi and a dramatic difference of the Xi compared to the Xa (FIGS. 4E-4G and FIG. 17-17C). These changes in chromosomal structure increase the concentration of Xist-SMCs within the X space (FIG. 4H, Table S4). Accordingly, minimal distances of Xist foci or protein assemblies in Xist-SMCs are significantly reduced on the Xi compared to the pre-Xi (FIG. 17D). Thus, increased chromosome compaction allows more genes to come in closer proximity to the Xist-SMC neighborhood, primes the IDR-dependent SPEN increase in the Xi, and the extension of silencing to more genes over time. However, the mechanisms controlling chromatin compaction on the Xi are not known.

PCGF5 exhibited the highest particle density in the X-territory among all interrogated proteins (FIG. 4H and FIG. 17D), suggesting that PCGF5-containing Polycomb complexes are significantly more concentrated on the pre-Xi than the other proteins, in agreement with its early occupancy over the chromosome upon induction of Xist (34, 35). Given the importance of PRC1 in controlling chromatin compaction and long-range chromatin contacts to regulate gene expression during development (68-71), we interrogated whether the extensive concentration of PRC1 on the pre-Xi is critical for inducing the transition of the pre-Xi to a compact Xi.

To test this hypothesis, we functionally perturbed PRC1 recruitment to the X-chromosome by deleting the B-repeat of Xist (ΔB-Xist) in ESCs (63, 65-67, 92). Chromosome territory measurements (by X-paints) showed that the volumetric occupancy of an Xi formed by ΔB-Xist is smaller than that formed by the full-length RNA (FL-Xist) and similar to the Xa (FIG. 4I and FIG. 18A). Consistent with this result, 3D-SIM measurements revealed that the distribution of Xist foci was significantly impaired on a ΔB-Xist Xi compared to a FL-Xist Xi, with larger focus-to-focus distances and an expansion of the Xist-territory, as well as a lack of the characteristic DAPI density of the Xi (FIG. 4J and FIG. 18B-18D). Moreover, the distribution of ΔB-Xist foci on the Xi is similar to that observed on the FL-Xist-coated pre-Xi (FIG. 17D). These results uncover a role of the B-repeat, and in turn PRC1, in driving the compaction of the X and the concentration of Xist-SMCs. Consistent with this result, we found that genes that are affected in their silencing by the absence of PRC1, through deletion of the B and C-repeats of the RNA (65), are normally more likely to be silenced late during XCI initiation and exhibit lower Xist enrichment (FIGS. 4K and 4L). These results extend to the architectural protein structural-maintenance of chromosomes hinge domain containing 1 (SMCHD1) that depends on PRC1 for its recruitment to the Xi and controls the compartmentalization of the Xi (93, 94) (FIGS. 18E and 18F). We found that genes with high Xist binding, i.e. close to SMCs, and silenced by $Xist^{SPOC}$ domain are more likely to be SCMHD1-independent, whereas genes controlled by SCMHD1 tend to be inaccessible for silencing by Xist SPOC. Thus, SPEN-mediated silencing originates at regions that are proximal to Xist-SMCs and progressive expansion of silencing to other target genes requires the compaction of the X by PRC1 and SCMHD1. Thus, in the absence of PRC1 recruitment to the X, SPEN can still initiate silencing of genes that are exposed to higher SPEN concentrations due to proximity to ~50 Xist-SMCs, explaining the differential effect on silencing upon SPEN and PRC1 ablation. We conclude that macromolecular crowding, chromatin compaction and silencing by SPEN are interdependent mechanisms of heterochromatin formation.

Taken together, our work reveals a fundamentally new model for how Xist establishes a repressive compartment and orchestrates deterministic transcriptional silencing along the entire X-chromosome (FIG. 4M). Our model arises from the key observation that XCI is mediated by a limited number of locally-confined Xist clusters. Through expression, diffusion, sequestration, and degradation (see Text S6), Xist becomes localized and tightly bound to chromatin at 50 sites across the X-territory where it strongly interacts with CIZ1 to form the stable core of protein concentration hubs. These Xist/CIZ1 hubs induce macromolecular crowding of multiple XCI effector proteins in their vicinity, prior to chromosome-wide gene silencing and heterochromatinization of the X. In this way, Xist nucleates the formation of SMCs where silencing initiates (FIG. 4M, pre-Xi). The high Xist-seeded concentration of PRC1 progressively induces chromatin compaction, altering the local environment of Xist-SMCs and enhancing IDR-dependent protein-protein interactions. Through this process the concentration of SPEN across the Xi also progressively increases, genes move closer to Xist-SMCs and silencing expands across the entire X (FIG. 4M, Xi).

The dense seeding of Xist-SMCs across the X-territory and the local binding and unbinding due to transient interactions enriches proteins, and not Xist-ribonucleoprotein complexes, over the X and allows them to spatially probe genomic targets. Consequently, XCI results from locally-confined Xist-mediated macromolecular crowding and supra-molecular aggregation of a large number of protein molecules. Through this process a relatively small number of confined Xist molecules can induce the robust and precise silencing of a much larger number of genes. The dramatic increase in macromolecular concentrations across the X-territory and the sharp change in protein particle density at the boundary of the Xi-territory define the membrane-free chromosome-wide condensate known as the Xi-compartment. The inhomogeneous distribution of Xist-SMCs and altered kinetics of proteins in the Xi, may suggest that Xist induces Polymer-Polymer Phase Separation (PPPS) rather than LLPS in the Xi (95, 96).

Finally, our model of how few Xist molecules can establish a chromosome-wide repressive compartment has implications for the regulation of gene expression by other lncRNAs. LncRNAs are typically expressed at low numbers, raising the question of how they can effectively regulate genes. The spatial organization of the X chromosome by few Xist molecules and IDR-based aggregation of protein effectors likely represents a general mechanism through which lncRNAs establish gene-regulatory nuclear compartments. Other lncRNAs have also been found to nucleate spreading of Polycomb complexes (20), suggesting that Polycomb-mediated compaction is a common mechanism in the organization of an efficient repressive nuclear compartment.

B. Materials and Methods

Plasmid construction for engineered cell lines. Plasmids containing the 24×MS2 repeats (#31865) and MS2-Coat-Protein-GFP (MCP-GFP) coding sequence (#27121) were obtained from Addgene. The pBglII5k plasmid was used for targeting the 24×MS2 repeats into Xist (described in (97)) and contains homology arms for insertion into exon 7 of Xist, downstream of the E-repeat sequence, and a floxed neomycin resistance cassette. The 24×MS2 repeats were excised from plasmid #31865 by restriction digest with BglII and BamHI and cloned into the pBglII5k plasmid by infusion cloning yielding the pBglII5k-24×MS2 plasmid (which replaces the 16×MS2 repeat array originally contained in the pBglII5k plasmid). The coding region for MCP-GFP was amplified by PCR and introduced under control of a tetracycline-inducible promoter (tetO) into the pBS31 plasmid (pgkATGfrt) (98) by infusion cloning yielding pBS31-MCP-GFP. A reverse tetracycline TransActivator (rtTA3) cassette containing the PGK promoter and a BGH polyA element was amplified by PCR from the MXS_PGK::rtTA3-bGHpA plasmid (#62446, Addgene) and introduced into the unique AscI site of pBS31-MCP-GFP, downstream of the tetO-MCP-GFP-polyA insert, by infusion cloning, resulting in the pBS31-MCP-GFP-rtTA3 plasmid. For deletion of the B-repeat of Xist the plasmid was constructed from PCR-amplified 5' and 3' homology regions and a loxP-flanked hygroTK cassette that replaces the B-repeat sequence (chrX: 103480156-103480430).

Genetic engineering strategy for integrating MS2 repeats into the Xist locus in ESCs. The pBglII5k-24×MS2 plasmid was electroporated into the polymorphic *Mus musculus/Mus castaneus* F1 2-1 ES cell line (99) after linearization with XhoI. The cell culture was exposed to neomycin selection 36 hours post-electroporation. Colonies were picked and expanded for screening by genotyping PCR and RNA FISH with Xist and MS2 probes. The loxP-flanked neomycin resistance cassette was removed from targeted clones by transient expression of the Cre-recombinase. Subsequently, a FRT-recombination site-containing landing pad was targeted into the Col1A locus (on chromosome 11) in F1 2-124×MS2-Xist ESCs as described in (98). MCP-GFP-rtTA3 expression cassette was then inserted into the FRT site by electroporation of a FlpO-recombinase-encoding plasmid and the pBS31-MCP-GFP-rtTA3 plasmid. The resulting ESC line was denoted as $Xist^{MS2\text{-}GFP}$.

Genetic engineering strategy for deletion of the B-repeat of Xist. F1 2-1 ES cell line (99) or male ESCs expressing Xist under a TetO promoter (40) were electroporated with linearized plasmid harboring homology arms for targeting into the B-repeat region or XIST and replacing it with a loxP-flanked hygroTK cassette for antibiotic selection. The loxP-flanked hygroTK resistance cassette was removed from targeted clones by transient expression of the Cre-recombinase. Genotyping and confirmation of deletion of the B-repeat on the 129 allele in F1 2-1 ESCs were performed by Southern blotting (not shown).

Establishment of transgenic ESC lines. For the integration of transgenes expressing various mCherry or Halo protein fusions under the control of the endogenous Rosa26 promoter of $Xist^{MS2\text{-}GFP}$ ESCs, we employed a parent plasmid harboring homology arms for targeting into the Rosa26 locus and a loxP-flanked puromycin cassette for antibiotic selection (R26 plasmid). A splice-acceptor (SA) and splice-donor (SD) coding sequence synthesized by Genewiz was inserted into the R26 plasmid after MluI/MfeI restriction digest by infusion reaction. The resulting R26-SA/SD plasmid was used as the parent plasmid for insertion of all protein fusions in three-piece infusion reactions. Coding sequence for CIZ1 was amplified from a donor plasmid described in (74). Coding sequences for histone H2B and mCherry were amplified from a H2B-mCherry plasmid (Addgene, #20972) and the Halo cDNA was obtained from plasmid Halo-EasyFusion (Addgene, #112852). The coding sequences for the PTBP1, PCGF5, CELF1 were synthesized (Genewiz). To generate the Spen-ΔIDR-Halo plasmid the full-length Spen Entry Clone (Sp22) was modified using Polymerase Incomplete Primer Extension-based mutagenesis with primers designed to delete amino acids 639-3460. Sp22 and the Spen-ΔIDR entry clone, respectively, were inserted into the PyPP-CAG-Halo-V5-IRES-Puro destination vector using Gateway LR Recombination, generating PyPP-CAG-Halo-full-length-Spen-V5 and PyPP-CAG-Halo-Spen-ΔIDR-V5, respectively, both also containing an IRES-puromycin resistance cassette. These plasmids enable constitutive expression of Spen variants with an N-terminal Halo tag and a C-terminal V5 tag and contain a polyoma episomal origin of replication for efficient propagation in mammalian cell culture. All plasmids were verified by restriction digests and sequencing.

Targeting of ESC lines. ESC lines were grown on DR4 feeders. All targetings were performed by electroporation using the GenePulserII (Biorad). Approximately $2\times10^7$ cells and 50 μg of DNA were resuspended in 400 μl PBS in 4 mm diameter cuvettes and pulsed twice for 0.2 msec at 800V. Antibiotics were added to the growth media 24-36 hours after electroporation. Puromycin was used at 1.5 μg/ml, hygromycin at 130 μg/ml and G418 at 400 μg/ml. The culture medium containing the respective antibiotics was exchanged every 2 to 3 days. Once adequate colony growth was observed (1-2 weeks), 100-200 colonies were picked under a stereoscope, dissociated by trypsinization and seeded in 96-well plate replicates. One replicate plate was used for genomic DNA extraction and subsequent genotyping PCR. All positive clones used in this study were screened to ensure gene silencing by Xist and normal Xist distribution across the X-territory upon induction of differentiation (FIGS. 5D and 5E). Additionally, we confirmed that the 24×MS2-repeat unit was introduced into the 129 allele (FIG. 5E).

Creation and delivery of the $cage^{60GFP}$ expression plasmid. The gene encoding ct-60 ($cage^{60GFP}$) (50) was amplified by PCR. The fragment was introduced under control of the CACGS promoter into the pBS32 plasmid by infusion reaction yielding pBS32-$cage^{60GFP}$ and positive clones were confirmed by restriction digests and sequencing. The pBS32 plasmid was derived from the pBS31 plasmid upon replacement of the tetO promoter with a CAGGS promoter. To visualize both $Xist^{MS2\text{-}GFP}$ and $cage^{60GFP}$, $Xist^{MS2\text{-}GFP}$ ESCs were differentiated into EpiLCs to induce Xist expression and doxycycline was added to induce MCP-GFP expression. Expression of the $cage^{60GFP}$ was achieved by transient transfection of the pBS32-$cage^{60GFP}$ plasmid into differentiating cells by Lipofectamine3000 (Thermo Fisher) 24 hours prior to imaging, according to the manufacturer's instructions.

Cell culture. Female mouse F1 2-1 ESCs and its engineered derivatives were grown on 0.5% gelatin-coated flasks seeded with irradiated DR4 feeders (obtained from day 14.5 embryos with appropriate animal protocols in place). Cultures were maintained in mouse ESC medium containing knockout medium DMEM (Life Technologies), 15% FBS (Omega), 2 mM L-glutamine (Life Technologies), 1×NEAA (Life Technologies), 0.1 mM β-Mercaptoethanol (Sigma), 1× Penicillin/Streptomycin (Life Technologies), and 1000 U/mL mouse LIF (homemade) in 5% CO2, 37° C. incubators.

For all differentiation experiments, cells were adjusted for 3 passages to feeder-free conditions in the presence of LIF and two inhibitors, CHIR99021 (3 μM) and PD0325901 (0.4 μM) (2i+LIF). Epiblast-like (EpiLC) differentiation was performed as described in (46). Briefly, cells were maintained for 3 passages in serum-free 2i+LIF N2B27 media containing 1×N2 supplement and 1×B27 supplement (Thermo Fischer), 2 mM L-glutamine (Life Technologies), 1×NEAA (Life Technologies), 0.1 mM β-Mercaptoethanol (Sigma), 0.5× Penicillin/Streptomycin (Life Technologies) prior to EpiLC differentiation. To induce differentiation, cells were dissociated and seeded at a density of $2\times10^5$ cells/ml in N2B27 media containing 20 ng/ml Activin A (Peprotech) and 12 ng/ml bFGF (Peprotech).

For experiments extending beyond day 4 of differentiation, we applied a protocol previously described in (100). Briefly, at day 4 of differentiation, EpiLCs were dissociated with accutase (Life Technologies) and seeded on geltrex-coated coverslips at a density of $5\times10^5$ cells/$cm^2$. Cells were then grown in N2B27 media supplemented with EGF and FGF (10 ng/ml each), on geltrex-coated coverslips for 4 more days (d8 of differentiation). At this developmental stage, cells have lost Tsix expression as observed in FIG. 5C. Media was exchanged daily.

C127 cells were purchased from ATCC and human fibroblasts containing abnormal X-chromosomes (GM3827, GM00735, GM06960, GM07213) were obtained from Coriell. These cell lines were cultured in DMEM (Life Technologies), 15% FBS (Omega), 2 mM L-glutamine (Life Technologies) and 1× Penicillin/Streptomycin (Life Technologies).

FISH Probe synthesis. Probes for DNA and RNA FISH experiments and X chromosome paints were labelled by home-made Nick Translation and fluorescent dUTPs as described in (101). DNA from flow sorted mouse X-chromosomes was a gift from Irina Solovei. To create mouse Xist probes, we used a full-length mouse Xist cDNA plasmid (p15A-31-17.9 kb Xist). Human XIST probes were created from a full-length XIST cDNA construct. For assessing X-linked gene silencing, Atrx probes were synthesized using BAC RP23-265D6 and Mecp2 probes using fosmid WI-894A5. For the chromosome barcoding experiment, we used BACs RP23-53H15, RP23-83J1, RP23-451D5, RP24-81K23, RP24-374B8, RP23-401G5, RP23-104K18. To create an intronic probe against the first intron of Xist, the corresponding region was amplified from the Xist-encoding BAC RP23-223G18 and was labelled by Nick Translation. RNA or DNA FISH probes were used at a concentration of 0.1 μm/cm$^2$. For multispectral chromosome barcoding experiments, individual BACs were labelled separately, pooled in a 1:1 ratio and used at a concentration of 0.2 μm/cm$^2$. Nick Translation products were labelled with Atto488-dUTP, Alexa Fluor 568-dUTP, Cy3-dUTP, Cy5-dUTP, Texas Red-dUTP and chromosome paints were labelled with Atto448-dUTPs or Cy3-dUTPs. A summary of the probes used in each experiment can be found in Table S5. All BACs and fosmids used in this study were purchased from CHORI-BACPAC.

Halo labelling. For FRAP experiments of Halo-fused proteins, 5 μM of TMR Halo ligand (Promega) was added to the culture medium for 30 min following a 30 min incubation in media without added ligand to wash-off unbound ligand. For fixed and live-cell 3D-SIM imaging, 1 μM JF549 or JF646 Halo ligands (Promega) were introduced to the media for 15 min, washed-off twice with PBS and exchanged with fresh medium which was incubated for another 15 min. Live-cell imaging or fixation was done as described in the corresponding sections.

Immunofluorescence staining. Immunodetection was performed as described in (102). For combined Halo ligand and antibody detection, cells were labelled with the Halo ligands and fixed followed by immunofluorescence staining. For the 4-color 3D-SIM imaging where we detect combinations of proteins together with Xist$^{MS2-GFP}$ (FIG. 3A and FIG. 9A) we used CIZ1-Halo and CELF1 antibody staining, SPEN-Halo and CIZ1 antibody staining, PCGF5-Halo and CIZ1/CELF1 antibody staining. Halo transgenes were detected with the Halo ligand JF549 and primary antibodies with secondary antibodies conjugated to AlexaFluor647. In FIGS. 3D and 3E we used Halo transgenes for detection of CIZ1, WT-/ΔIDR-SPEN, PCGF5, and PTBP1 the Halo ligand JF549 and antibody stainings for RYBP, EZH2, hnRNP-K with secondary antibodies conjugated to CF568 dye. We compared the localization of the CIZ1-Halo fusion protein and the endogenous (antibody-stained) CIZ1 protein and show the same trend (FB).

RNA/DNA FISH. RNA and DNA FISH experiments were conducted as previously described (103). For sequential RNA and DNA FISH experiments with X chromosome paints (mmX paints) and Xist probes, RNA FISH preceded DNA FISH.

For the detection of genomic regions across the X chromosome with spectral barcoding, cells were seeded in ibidi chambers with a gridded bottom and DNA FISH was performed first. 5-color optical z-stacks of 0.35 μm were acquired on a confocal Zeiss LSM880 system. Spatial coordinates of the acquired positions were recorded on the ZEN software and saved. Following samples were equilibrated with 50% formamide in 2×SSC pH 7.2 solution for 3 hours at 37° C. followed by RNA FISH with Cy3-labelled Xist probes. Specimens were returned to the microscope stage and saved spatial coordinates were revisited to acquire the Xist RNA signal and discriminate between the Xi and Xa. Z-stacks from sequential rounds were superimposed using ImageJ/Fiji and alignment of the two sequential rounds was performed with the affine transformation of the StackReg plugin based on the DAPI channel. Although hybridization of RNA usually precedes DNA FISH, we have found that Xist RNA is remarkably stable during the sequential process. Since the sequential hybridization for this experiment was only necessary for the scoring of the Xi, without the need for harsh probe strip-off steps, RNA FISH was performed last.

Cell cycle analysis of Xist foci. To discriminate between different cell cycle stages, we used a combination of EdU pulse labelling, to detect S-phase cells, and anti-histone H3-phospho-Serine10 (Active Motif, #39253), to detect G2/M phase cells, while G1 cells remained marker-free. A 10 mM EdU stock solution was diluted 1:1000 in growth media and cells were pulsed for 20 minutes prior to fixation. RNA FISH with Xist RNA probes and detection of EdU by click-iT reaction with CF dye Azide 568 (Biotium, #92082) were combined with immunodetection of phospho-histone H3 Serine 10 as described in (103). For the assessment of Xist foci features and number throughout the cell cycle in EpiLCs (at day 4 of differentiation), we used the Xist$^{MS2-GFP}$ cell line and detected Xist$^{MS2-GFP}$ signals after addition of doxycycline.

Super-resolution microscopy. 3D-Structured Illumination Microscopy (3D-SIM) was performed on a DeltaVision OMX-SR system (Cytiva, Marlborough, MA, USA) equipped with a 60×/1.42 NA Plan Apo oil immersion objective (Olympus, Tokyo, Japan), sCMOS cameras (PCO, Kelheim, Germany) and 405, 488, 642 nm diode lasers and a 568 nm DPSS laser. Image stacks were acquired on the OMX AcquireSR software package 4.4.9934 with a z-steps of 125 nm and with 15 raw images per plane (five phases, three angles). Raw data were computationally reconstructed with the soft-WoRx 7.0.0 software package (Cytiva, Marlborough, MA, USA) using a Wiener filter set at 0.001 to 0.002 (up to 0.006 for DAPI) and optical transfer functions (OTFs) measured specifically for each channel using immersion oil with different refractive indices (RIs) as described in (102, 104). Images from different channels were registered using alignment parameters obtained from a calibration slide of 100 nm gold grid holes and a second calibration for axial alignment using 100 nm diameter Tetraspeck beads (Invitrogen) as described in (104).

Live-cell imaging. Wide-field and confocal scanning microscopy (for FRAP experiments) or 3D-SIM live-cell imaging (4D-SIM) were performed at 37° C. (for 3D-SIM in conjunction with an objective heater), with 5% CO2, controlled humidity and 10% O2, having equilibrated the system and immersion oils for at least five hours prior to acquisitions. This equilibration was particularly important for obtaining artifact-free 3D-SIM datasets and minimize stage drift. Cells were differentiated in geltrex-coated chambers fitted with a high precision glass (ibidi) with daily exchange of media.

To induce MCP-GFP expression, doxycycline was added to the cells two hours prior to acquisitions at a concentration of 1 μm/ml. Imaging was performed in media containing no phenol red and supplemented with ProlongLive Antifade reagent (Thermo Fisher). For live-cell 3D-SIM imaging, typically 1 μm to 2 μm stacks of 125 nm z-sections were acquired in 1- or 2-color 3D-SIM imaging to obtain 240-500 raw images per frame in 5-8 second intervals depending on exposure times and z-depth. Photobleaching over time was corrected by using histogram matching on the BleachCorrection plugin in ImageJ/Fiji.

Quantitative 3D-SIM analyses. For image segmentation, 32-bit raw datasets were imported into ImageJ/Fiji (102) and converted to 16-bit tiff composite stacks. The segmentation of Xist and protein foci was performed as previously described in (102) using the TANGO suite (105). Image segmentation pipelines, adjustment of thresholds and creation of seeds were performed in high-throughput batch-processing and without manual intervention. Specifically, raw datasets without filtering or subtraction of signals were imported into the segmentation pipeline. Resulting masks of segmented particles were inspected by overlays over the raw data to ensure that the majority of signals was contained in the area to be analyzed. Nuclear masks were created using the DAPI channel as the segmentation volume. For each channel, a duplicate was generated and filtered with a 3D Gaussian filter with standard deviation of 1 ($\sigma$=1) and a Tophat filter with a radius of two pixels in xy and a one-pixel radius in z. The filtered image was segmented using the 3D Suite's Watershed method. Seed threshold and image threshold for watershed were calculated by equations Mean+StdDev*2*seed multiplier and (Mean+StdDev*2*seed multiplier)/image multiplier (Signal-to-Noise Ratio, SNR) respectively, where seed multiplier and image multiplier were determined and inspected manually to ensure the inclusion of all the regions of interest (ROIs) and the removal of background noise. Object features and distance measurements were performed using the 3D ImageJ Suite's "Measure 3D", "Quantif 3D" and "Distance" option plugins for ImageJ/Fiji.

For the assessment of the cage$^{60GFP}$ versus Xist signals, cells expressing the cage$^{60GFP}$ plasmid were typically imaged in the same Field of View (FOV) as cells with the Xist$^{MS2\text{-}GFP}$ signal, allowing us to obtain data that could be directly compared. When cells expressed both entities, since the cages are located in the cytosol, nuclear masks from the DAPI channel were created and Xist$^{MS2\text{-}GFP}$ signals were measured inside the masked regions, whereas the signal from the GFP-expressing cages was measured outside the nuclear masks.

To extract global nuclear protein particle features (in and outside the Xi), masks of the protein signals of interest were created by filtering raw data with a 3D Gaussian blur followed by automatic thresholding to include all signals and exclude nucleoli. ROIs within a 4 μm radius of Xist centroids were selected for features extraction to limit computation time to ~1 hour per nucleus. Nearest neighbor centroid distances and all distances between ROIs within each channel and across different channels were extracted using the 3D ImageJ Suite for minimal distance and average distance analysis, respectively. Distance averaging was performed in Python. Assignment of Xist-associated signals was based on a proximity threshold to Xist centroids with a radius of 250 nm. Signals 500 nm away from Xist centroids, resulting in a 'rim' around the Xi due to the scattering of many Xist foci throughout the Xi, were defined as the nuclear fraction. To assign the Xi territory coordinates of protein signals within a 250 nm radius of a Xist foci were selected, overlapping (double-called) pixels were removed and multiplied by voxel dimensions. The comparison of protein features, such as integrated density of fluorescence and volume, was performed by measurements acquired in the same laser line (568 nm) for all proteins detected either with the Halo ligand JF549 or primary and secondary antibodies conjugated to CF568 dye. For each experiment, ROIs with integrated density and volume values below the 10th percentile or above the 90th percentile of the dataset were removed as outliers.

Creation of X-chromosome masks and measurements of X-territory volume and sphericity. Confocal optical stacks were imported to ImageJ/Fiji and converted to 16-bit tiffs. Using the Yen method, an automatic threshold was set to create 3D masks for the X chromosome territories. Assignment of the Xi was based on RNA FISH signals from the Xist channel. Masks were imported into 3D Suite and the volume and sphericity measurements of the X chromosomes (Xa and Xi) were extracted. Sphericity is defined as the length of the object over its width, with a maximum value of one. For the creation of mmX masks from 3D-SIM stacks to allocate Xist foci inside and outside the X-territory, a 3D Gaussian blur with standard deviation of 5 ($\sigma$=5) was used to filter the channel with the mmX paint followed by automatic threshold by the Yen method. After creating X-chromosome masks, Xist foci inside the masked region or in the remaining nucleus were analyzed as described in the 'Quantitative 3D-SIM analyses' section.

Analysis of X chromosome conformation from genomic barcoding. Confocal optical stacks were imported into Fiji/ImageJ and smoothed with a 3D Gaussian blur with a standard deviation of 1 ($\sigma$=1) and background removal using the "Subtract Background" plugin with a rolling ball radius of 10 pixels. Xa and Xi (scored by the presence of Xist RNA) were identified and saved as separate stacks. Subsequently, each probe signal centroid was extracted using the "3D Object Counter" plugin. The 3D Object Counter generated a list of coordinates of probe signals for each channel. To assign signals to multi-spectral barcodes consisting of two labels, a nearest neighbor search between the two corresponding channels was applied based on all spatial coordinates in each channel. Once pairs of signals were assigned to the multi-spectral barcodes the coordinates obtained in the shortest wavelength were used. In cases were two adjacent signals were detected per probe, potentially due to the presence of transcripts or DNA replication, only one of the signals was used. The coordinates of individual barcodes for the Xa and Xi at days 2 and 4 of EpiLC differentiation were reoriented in 3D space to compute spatial statistics across all cells. To obtain configurations of chromosomal backbones, for each set of probe coordinates, principal component analysis (PCA) was performed in the x and y axes. The z axis was unused as the segmentation resolution in that axis is significantly lower, contributing to large variations in the z coordinate (106) and confounding the reorientation method used which is highly sensitive to anisotropic error. The principle component is assumed to be the "backbone" of the chromosome: the expected orientation of a chromosome if initially stretched out along that component's direction before entropically relaxing into an equilibrium configuration. Each set of probes are rotated in order to align its corresponding principle components with the y-axis and translated such that the probes' centroid is aligned with the coordinate origin. Probes of the same loci were then statistically compared to locate their local spatial centroid and 95% confidence interval for Xa day 2, Xi day 2, Xa day 4, and Xi day 4 separately. Ellipsoids encompassing the 95% confidence interval were plotted around each loci centroid. In order to quantify the relative compaction between Xa and Xi from day 2 to day 4, the pairwise distances of 3D coordinates (x,y,z) between each barcode location were measured and averaged over all cells. Averages of Xa distances were subtracted from those of Xi at day 2 and the same was done for day 4 in order to measure the absolute change between chromosomes. A heatmap of this change was plotted where large negative numbers indicate a higher compaction.

Single-Particle Tracking (SPT) and extraction of trajectories. Individual Xist particles from live-cell 3D-SIM data were extracted by using TrackMate (107) an ImageJ plugin. DoG Detector with a 0.2 μm diameter was used to define the particles and the Simple LAP Tracker with 0.25 max linking distance, 0.3 gap-closing max distance and 2 gap-closing max frame gap were used to track the particles. Trajectories that were not possible to track for over 10 consecutive frames were not used. Over 850 trajectories from 30 cells were analyzed and approximately 50% of all Xist granules without manual intervention were possible to track per nucleus for an average of two minutes. Data extracted from the software were fed into downstream confinement analyses (see Text S3).

Live-cell 3D-SIM image registration: subtracting background developmental motion. Two types of motion are captured simultaneously in live-cell 3D-SIM microscopy: a) the developmental motion of the cell and the nucleus, and b) the individual motion of Xist granules within the nucleus. To specifically extract (b) from live-cell 3D-SIM images, a custom Python/Jupyter tool was created that implemented the following algorithm: 1) A set of Xist granules were tracked using TrackMate. 2) For each timestep t, the individual displacement vectors xi,t of each Xist granule were calculated. 3) For each time-step, individual displacement vectors were averaged to obtain Xt, an approximation of the developmental motion in that time-step. 4) This developmental motion was then subtracted from each Xist granule's displacement vector to arrive at an approximation to granule i's motion, xi,t−Xt.

Segmentation of H2B density classes and assignment of the maximal radial distances of chromatin. density classes to Xist granules Histone H2B-Halo$^{JF646}$ intensities were extracted on ImageJ/Fiji plugin using the "getValue" macro command, that iterates over every pixel in the image to get the intensity value of each pixel, generating a list of all the pixel intensities and their corresponding coordinates. The list of intensities was imported to Python. Then, seven intensity/density classes of equal variance were determined. The 3D Suite was used to create Xist masks, while Xist trajectories were extracted from TrackMate to obtain spatial coordinates (centroids) from each time point. The matrices were paired within the radius of one pixel and chromatin density classes were measured under the masks. Radial distances were measured at all pixels within the respective 100, 250, 500 nm radius of the Xist centroid and the maximal intensity value within that range was defined. Averaged values were then plotted in a line graph as a function of time. To extract the nearest neighbors in chromatin density maps, neighboring intensities for each H2B pixel were determined as the average intensity of all adjacent pixels and stored in an array. A strip plot was used to plot the averaged intensity values where each value was assigned to one of the 7 classes based on the class of the origin pixel.

Statistical analyses of imaging data and visualization. Data analysis and visualization were performed using Python. All violin plots, boxplots, bar plots and point-plots were generated using Seaborn and Matplotlib. NumPy and SciPy were used for mathematical computation and Pandas for data manipulation and analysis. Unless stated otherwise, all graphs show the median as the central point or the central line, and bars on point plots represent the standard deviation. Point plots of protein integrated intensity and volume in FIGS. 3, 11, and 15 show the percentage of the maximum absolute value in each group. Statistical differences were analyzed by the two-sided Wilcoxon's or Mann-Whitney rank-sum test.

FRAP experiments. FRAP experiments with z-sectioning for Xist$^{MS2-GFP}$ and CIZ1-mCherry were performed on an LSM880 equipped with an Airyscan on a Plan-Apochromat 63×1.4NA oil immersion objective, an image size of 67.5 μm×67.5 μm with a pixel size of 0.085 μm. Z-optical stacks of 0.5 μm were obtained through a 15 μm z-depth. Bleaching was performed in ROIs demarcating the Xist territory or corresponding nuclear (control) regions at full laser power and 4 iterations with a pixel dwell time of 4.04 μsec. The first post-bleach frame was acquired immediately after bleaching. Time series were acquired every 1.3 minutes up to 10 frames and every 2 minutes thereafter for a total of 30 minutes with an Argon ion 488 nm laser or a DPSS 561 nm laser set to 1% laser power. Single-plane FRAP experiments for all other proteins were performed on the OMX-SR platform in widefield mode and an image size of 512×512 pixels with a pixel size of 0.08 μm. In these experiments we employed transgenic cells lines carrying mCherry-tagged CIZ1 and CELF1 and carrying Halo-tagged SPEN, PCGF5 and PTBP1, respectively (FIGS. 12 and 13). Images were acquired for Xist$^{MS2-GFP}$ in the 488 nm channel (95 MHz—6% amplitude, 20 msec) and for all mCherry- or Halo-fused-TMR proteins in the 568 nm channel (272 MHz, 6% amplitude, 50-100 ms exposure). Bleaching in ROIs demarcating the Xist territory or a corresponding nuclear (control) regions was performed by using the 568 nm laser line in the Ring-TIRF/PK photokinetics module with a bleach spot of 1 μm for one iteration for 0.1 seconds. FRAP time series from z-stacking were projected and all FRAP data were analyzed as described (108). In brief, ~2 μm user-defined ROIs identified the bleached region and data intensities were measured through time after normalization for fluorescence decay. To correct for drift, images were registered using the Correct3DDrift plugin. For compiling figures, FRAP time series were bleach-corrected using the BleachCorrect ImageJ/Fiji plugin. FRAP curves for Xist and all proteins were fit to single or double exponential models derived from mass-action kinetics. Squared errors were minimized to obtain best-fit detachment rates, binding site densities, and freely diffusing fractions. Details are given in Text S4.

RNA-Antisense purification (RAP-seq). F1 2-1 female mouse ESCs were seeded on geltrex-coated plates and differentiated for 2 or 4 days. 5×106 cells were collected per conditions after dissociation by accutase and RAP-seq was performed as previously described (40). In brief, reads were trimmed using trim_galore (v0.4.1) with default parameters to remove the standard Illumina adaptor sequence. Bowtie2 (v2.2.9) was used to align reads to the mouse genome (mm9) with the default parameters. Reads with mapping quality less than 30 were removed using samtools (v1.2). Picard MarkDuplicates (v2.1.0) was used to remove PCR duplicates. Bedtools intersect (v2.26.0) was used to count reads in sliding windows (100 Kb every 25 Kb) along the X chromosome. Xist localization across the X-chromosome was defined by calculating the Xist enrichment scores (pull-down/input) in the sliding windows. Unmappable regions were masked.

Hi-C compartments. To compare Hi-C compartmentalization and Xist enrichment, Hi-C PC1 values for the inactive X were downloaded from GSE99991(28). PC1 values at day 0 were correlated with Xist enrichment at day 2 and PC1 values at day 4 with Xist enrichment at day 4. In addition, Xist enrichment at day 2 and day 4 were correlated. Datasets were intersected with plyranges (v1.4.4) (109). Pearson's correlation coefficients and p-values (t-test, r≠=/=0) were calculated in R (v3.6.0), and plots were made with ggplot2 (v3.3.2) and ggpubr (v0.4.0).

Xist-tethered SPOC silencing. To identify genes that were repressed by SPOC tethered to Xist in the absence of SPEN, we used allele-specific RNA-seq count data from (42). SPOC silencing values for each gene were calculated as described in (42). Briefly, we filtered out genes that were skewed or not silenced under control conditions. We then calculated a silencing index under normal conditions ($silencing\_index_{DOX}=1-(allelic\_ratio_{DOX}/allelic\_ratio_{control})$) and after degrading SPEN and expressing SPOC tethered to Xist ($silencing\_index_{SPOC}=1-(allelic\_ratio_{SPOC}/allelic\_ratio_{control})$). To quantify the silencing defect in cells expressing only $Xist^{SPOC}$, we calculated the SPOC_[silencing_index (SPOC_[silencing_index=1−(silencing_index$_{SPOC}$+aux/silencing_index$_{DOX}$). To determine whether SPOC was more effective at repressing early or late silencing genes, we downloaded the proseq-estimated silencing half-times from (29) and categorized genes with a half-time range of (0-0.4] days as early silencing genes, (0.4-1 days] as late silencing genes (1-2] days as very late silencing genes, and >2 as escapee genes. Wilcoxon p-values were calculated in R. SPEN dependence index and Bgl-GFP [silencing] indices were calculated in the same way.

SMCHD1 sensitivity. To identify genes with a silencing defect as a result of SMCHD1 KO, we downloaded RNA-seq allelic counts from GSE99991 and classified genes as SMCHD1 sensitive or insensitive following the method in (Wang et al). Briefly, % Xi was determined by finding the percentage of reads from the Xi out of the total allele specific reads in each gene. We only included active genes with >13 allele specific reads in all samples, that are normally silenced during X inactivation. SMCHD1 sensitive genes were defined as having % Xi in SMCHD1−/−3-fold greater than % Xi in WT.

Xist BC-repeat deletion. To identify genes sensitive to Xist BC repeat, we downloaded RNA-seq count data from GSE123743(65). We found the log 2 fold change of genes with and without dox-induced Xist expression for 2 days using ΔESeq2 (110), for both full length and ΔBC Xist. We then found the difference between the log 2 fold changes (Dfc) for full length and ΔBC Xist. We considered genes to be ΔBC sensitive if Δfc was greater than 0.5.

$$\Delta fc=\log 2(\text{Dox 2 days/No dox})_{\Delta BC}-\log 2(\text{Dox 2 days/No dox})_{\text{Full length}}$$

We compared the silencing rate of ΔBC sensitive and insensitive genes by intersecting with proseq-identified silencing half-times. We compared the Xist enrichment of ΔBC sensitive and insensitive genes by intersecting with RAP-seq day 2 Xist enrichment using plyranges (109). Xist was excluded from these comparisons. Wilcoxon p-values were calculated in R.

Antibodies and dilutions. Endogenous CELF1 was detected with monoclonal rabbit anti-CUG-BP1 antibody ab129115 (1/800; Abcam); hnRNP-K with polyclonal rabbit antibody A300-678A (1/800); SPEN (Sharp) with polyclonal rabbit antibody A301-119A (1/1000); MATR3 with polyclonal rabbit antibody IHC-00081(1/200, all from Bethyl); RYBP (DEDAF) with polyclonal rabbit antibody AB3637 (1/1000; Sigma); Ezh2 with monoclonal rabbit antibody #5246 (1/500; Cell Signaling Technology); CIZ1 with a polyclonal rabbit antibody NB100-74624 (1/800; Novus Biologicals), and histone H3 phospho-Serine 10 with the polyclonal rabbit anti-histone H3-phospho-Serine10 #39253 (1/1000; Active Motif). Two secondary antibodies were used, including high cross-absorbed donkey anti-rabbit IgG CF568 antibody SAB4600076 (1/400; Sigma) and high cross-absorbed goat anti-rabbit IgG Alexa Fluor 647 antibody A21245 (1/400; Life Technologies).

C. Tables

TABLE S1

A list of the number of cells and protein particles analyzed in FIG. 3C is given.

| Protein pairs | number of cells | number of particles |
|---|---|---|
| CIZ1-CELF1, D2 | 18 | 22392 |
| CIZ1-CELF1, D4 | 17 | 8111 |
| CIZ1-SPEN, D2 | 9 | 15992 |
| CIZ1-SPEN, D4 | 8 | 3601 |
| CIZ1-PCGF5, D2 | 13 | 11756 |
| CIZ1-PCGF5, D4 | 15 | 3285 |
| CELF1-PCGF5, D2 | 12 | 16783 |
| CELF1-PCGF5, D4 | 11 | 15276 |

TABLE S2

A list of the number of cells and protein particles analyzed in FIGS. 3D-E and 4H is given.

| Protein | number of cells | number of particles |
|---|---|---|
| CIZ1, D2 | 47 | 22508 |
| CIZ1, D4 | 35 | 13736 |
| CELF1, D2 | 23 | 25581 |
| CELF1, D4 | 31 | 37904 |
| SPEN, D2 | 16 | 19788 |
| SPEN, D4 | 10 | 8741 |
| PCGF5, D2 | 12 | 12902 |
| PCGF5, D4 | 11 | 22580 |
| PTBP1, D2 | 11 | 21905 |
| PTBP1, D4 | 9 | 11815 |
| EZH2, D2 | 16 | 33851 |
| EZH2, D4 | 13 | 12734 |
| RYBP, D2 | 14 | 16552 |
| RYBP, D4 | 15 | 11688 |
| hnRNP-K, D2 | 12 | 22662 |
| hnRNP-K, D4 | 13 | 11688 |
| MTR3, D2 | 17 | 47314 |
| MTR3, D4 | 18 | 89464 |
| ΔIDR SPEN, D2 | 16 | 49283 |
| ΔIDR SPEN, D4 | 20 | 57429 |

TABLE S3

A list of the p-values derived from a Mann-Whitney Wilcoxon (MWW) test comparing the integrated density and volume of Xist-associated or nuclear fractions of Xist interactors in days 2 and 4 of differentiation is given.

| Protein | Location | Feature | D2/D4 p-value |
|---|---|---|---|
| CIZ1 | Nuclear | Adjusted_IntDen | 5.98e-07 |
| CIZ1 | Xist_Associated | Adjusted_IntDen | 1.56e-01 |
| CIZ1 | Nuclear | Adjusted_Volume | 5.50e-08 |
| CIZ1 | Xist_Associated | Adjusted_Volume | 3.00e-01 |
| CELF1 | Nuclear | Adjusted_IntDen | 6.18e-03 |
| CELF1 | Xist_Associated | Adjusted_IntDen | 1.94e-06 |
| CELF1 | Nuclear | Adjusted_Volume | 1.64e-01 |
| CELF1 | Xist_Associated | Adjusted_Volume | 4.01e-06 |
| SPEN | Nuclear | Adjusted_IntDen | 9.83e-02 |
| SPEN | Xist_Associated | Adjusted_IntDen | 2.12e-02 |
| SPEN | Nuclear | Adjusted_Volume | 1.11e-01 |
| SPEN | Xist_Associated | Adjusted_Volume | 3.05e-03 |
| PCGF5 | Nuclear | Adjusted_IntDen | 2.77e-05 |
| PCGF5 | Xist_Associated | Adjusted_IntDen | 1.70e-01 |
| PCGF5 | Nuclear | Adjusted_Volume | 2.98e-02 |
| PCGF5 | Xist_Associated | Adjusted_Volume | 4.38e-03 |
| PTBP1 | Nuclear | Adjusted_IntDen | 3.12e-03 |
| PTBP1 | Xist_Associated | Adjusted_IntDen | 7.53e-03 |
| PTBP1 | Nuclear | Adjusted_Volume | 3.80e-01 |
| PTBP1 | Xist_Associated | Adjusted_Volume | 2.47e-01 |
| EZH2 | Nuclear | Adjusted_IntDen | 2.83e-06 |
| EZH2 | Xist_Associated | Adjusted_IntDen | 2.83e-06 |
| EZH2 | Nuclear | Adjusted_Volume | 8.18e-02 |
| EZH2 | Xist_Associated | Adjusted_Volume | 1.10e-01 |
| RYBP | Nuclear | Adjusted_IntDen | 2.55e-06 |
| RYBP | Xist_Associated | Adjusted_IntDen | 3.13e-06 |
| RYBP | Nuclear | Adjusted_Volume | 5.51e-02 |
| RYBP | Xist_Associated | Adjusted_Volume | 1.06e-01 |
| hnRNP-K | Nuclear | Adjusted_IntDen | 1.25e-05 |
| hnRNP-K | Xist_Associated | Adjusted_IntDen | 1.25e-05 |
| hnRNP-K | Nuclear | Adjusted_Volume | 1.16e-05 |
| hnRNP-K | Xist_Associated | Adjusted_Volume | 1.52e-05 |
| MTR3 | Nuclear | Adjusted_IntDen | 3.40e-07 |
| MTR3 | Xist_Associated | Adjusted_IntDen | 3.49e-05 |
| MTR3 | Nuclear | Adjusted_Volume | 3.79e-02 |
| MTR3 | Xist_Associated | Adjusted_Volume | 1.20e-01 |

TABLE S4

A list of the p-values derived from a Mann-Whitney Wilcoxon (MWW) test comparing the change in density of Xi or nuclear fractions in days 2 and 4 of differentiation is given.

| Protein | Location | MWW p-value |
|---|---|---|
| CELF1 | Nuclear | 6.84e-04 |
| CELF1 | Xi | 6.84e-04 |
| CIZ1 | Nuclear | 2.19e-02 |
| CIZ1 | Xi | 3.45e-04 |
| PCGF5 | Nuclear | 5.32e-03 |
| PCGF5 | Xi | 1.96e-02 |
| SPEN | Nuclear | 2.85e-01 |
| SPEN | Xi | 2.52e-04 |

D. References

The following references, to the extent that they provide exemplary procedural or other details supplementary to those set forth herein, are specifically incorporated herein by reference.

1. M. Dundr, T. Misteli, Biogenesis of nuclear bodies. Cold Spring Harb Perspect Biol 2, a000711 (2010).
2. S. F. Banani, H. O. Lee, A. A. Hyman, M. K. Rosen, Biomolecular condensates: organizers of cellular biochemistry. Nat Rev Mol Cell Biol 18, 285-298 (2017).
3. S. P. Shevtsov, M. Dundr, Nucleation of nuclear bodies by RNA. Nat Cell Biol 13, 167-173 (2011).
4. X. Li, X. D. Fu, Chromatin-associated RNAs as facilitators of functional genomic interactions. Nat Rev Genet 20, 503-519 (2019).
5. S. Jain et al., ATPase-Modulated Stress Granules Contain a Diverse Proteome and Substructure. Cell 164, 487-498 (2016).
6. T. Yamazaki et al., Functional Domains of NEAT1 Architectural lncRNA Induce Paraspeckle Assembly through Phase Separation. Mol Cell 70, 1038-1053 e1037 (2018).
7. T. Hirose et al., NEAT1 long noncoding RNA regulates transcription via protein sequestration within subnuclear bodies. Mol Biol Cell 25, 169-183 (2014).
8. A. Hubstenberger et al., P-Body Purification Reveals the Condensation of Repressed mRNA Regulons. Mol Cell 68, 144-157 e145 (2017).
9. D. C. Tatomer et al., Concentrating pre-mRNA processing factors in the histone locus body facilitates efficient histone mRNA biogenesis. J Cell Biol 213, 557-570 (2016).
10. C. I. K. Valsecchi et al., RNA nucleation by MSL2 induces selective X chromosome compartmentalization. Nature, (2020).
11. R. W. Yao, Y. Wang, L. L. Chen, Cellular functions of long noncoding RNAs. Nat Cell Biol 21, 542-551 (2019).
12. J. M. Engreitz, N. Ollikainen, M. Guttman, Long noncoding RNAs: spatial amplifiers that control nuclear structure and gene expression. Nat Rev Mol Cell Biol 17, 756-770 (2016).
13. A. Wutz, Gene silencing in X-chromosome inactivation: advances in understanding facultative heterochromatin formation. Nat Rev Genet 12, 542-553 (2011).
14. R. Galupa, E. Heard, X-Chromosome Inactivation: A Crossroads Between Chromosome Architecture and Gene Regulation. Annu Rev Genet 52, 535-566 (2018).
15. A. V. Gendrel, E. Heard, Noncoding RNAs and epigenetic mechanisms during X-chromosome inactivation. Annu Rev Cell Dev Biol 30, 561-580 (2014).
16. A. Cerase, G. Pintacuda, A. Tattermusch, P. Avner, Xist localization and function: new insights from multiple levels. Genome Biol 16, 166 (2015).
17. N. Brockdorff, J. S. Bowness, G. Wei, Progress toward understanding chromosome silencing by Xist RNA. Genes & development 34, 733-744 (2020).
18. K. Plath, S. Mlynarczyk-Evans, D. A. Nusinow, B. Panning, Xist RNA and the mechanism of X chromosome inactivation. Annu Rev Genet 36, 233-278 (2002).
19. C. Kanduri, Kcnq1ot1: a chromatin regulatory RNA. Semin Cell Dev Biol 22, 343-350 (2011).
20. M. D. Schertzer et al., lncRNA-Induced Spread of Polycomb Controlled by Genome Architecture, RNA Abundance, and CpG Island DNA. Mol Cell 75, 523-537 e510 (2019).
21. T. Jegu, E. Aeby, J. T. Lee, The X chromosome in space. Nat Rev Genet 18, 377-389 (2017).
22. N. Brockdorff et al., The product of the mouse Xist gene is a 15 kb inactive X-specific transcript containing no conserved ORF and located in the nucleus. Cell 71, 515-526 (1992).
23. C. J. Brown et al., The human XIST gene: analysis of a 17 kb inactive X-specific RNA that contains conserved repeats and is highly localized within the nucleus. Cell 71, 527-542 (1992).
24. G. D. Penny, G. F. Kay, S. A. Sheardown, S. Rastan, N. Brockdorff, Requirement for Xist in X chromosome inactivation. Nature 379, 131-137 (1996).

25. Y. Marahrens, J. Loring, R. Jaenisch, Role of the Xist gene in X chromosome choosing. Cell 92, 657-664 (1998).
26. A. Wutz, R. Jaenisch, A shift from reversible to irreversible X inactivation is triggered during ES cell differentiation. Mol Cell 5, 695-705 (2000).
27. L. Giorgetti et al., Structural organization of the inactive X chromosome in the mouse. Nature 535, 575-579 (2016).
28. C. Y. Wang, T. Jegu, H. P. Chu, H. J. Oh, J. T. Lee, SMCHD1 Merges Chromosome Compartments and Assists Formation of Super-Structures on the Inactive X. Cell 174, 406-421 e425 (2018).
29. E. S. L. Barros de Andrade et al., Kinetics of Xist-induced gene silencing can be predicted from combinations of epigenetic and genomic features. Genome Res 29, 1087-1099 (2019).
30. C. Chu et al., Systematic discovery of Xist RNA binding proteins. Cell 161, 404-416 (2015).
31. C. A. McHugh et al., The Xist lncRNA interacts directly with SHARP to silence transcription through HDAC3. Nature 521, 232-236 (2015).
32. A. Minajigi et al., Chromosomes. A comprehensive Xist interactome reveals cohesin repulsion and an RNA-directed chromosome conformation. Science 349, (2015).
33. M. Escamilla-Del-Arenal, S. T. da Rocha, E. Heard, Evolutionary diversity and developmental regulation of X-chromosome inactivation. Hum Genet 130, 307-327 (2011).
34. J. J. Zylicz et al., The Implication of Early Chromatin Changes in X Chromosome Inactivation. Cell 176, 182-197 e123 (2019).
35. M. Almeida et al., PCGF3/5-PRC1 initiates Polycomb recruitment in X chromosome inactivation. Science 356, 1081-1084 (2017).
36. A. V. Gendrel et al., Smchd1-dependent and -independent pathways determine developmental dynamics of CpG island methylation on the inactive X chromosome. Dev Cell 23, 265-279 (2012).
37. K. Plath et al., Role of histone H3 lysine 27 methylation in X inactivation. Science 300, 131-135 (2003).
38. C. Costanzi, J. R. Pehrson, Histone macroH2A1 is concentrated in the inactive X chromosome of female mammals. Nature 393, 599-601 (1998).
39. J. Silva et al., Establishment of histone h3 methylation on the inactive X chromosome requires transient recruitment of Eed-Enx1 polycomb group complexes. Dev Cell 4, 481-495 (2003).
40. J. M. Engreitz et al., The Xist lncRNA exploits three-dimensional genome architecture to spread across the X chromosome. Science 341, 1237973 (2013).
41. H. Sunwoo, J. Y. Wu, J. T. Lee, The Xist RNA-PRC2 complex at 20-nm resolution reveals a low Xist stoichiometry and suggests a hit-and-run mechanism in mouse cells. Proc Natl Acad Sci USA 112, E4216-4225 (2015).
42. F. Dossin et al., SPEN integrates transcriptional and epigenetic control of X-inactivation. Nature 578, 455-460 (2020).
43. D. Smeets et al., Three-dimensional super-resolution microscopy of the inactive X chromosome territory reveals a collapse of its active nuclear compartment harboring distinct Xist RNA foci. Epigenetics Chromatin 7, 8 (2014).
44. A. Cerase et al., Phase separation drives X-chromosome inactivation: a hypothesis. Nat Struct Mol Biol 26, 331-334 (2019).
45. E. G. Schulz et al., The two active X chromosomes in female ESCs block exit from the pluripotent state by modulating the ESC signaling network. Cell Stem Cell 14, 203-216 (2014).
46. K. Hayashi, M. Saitou, Generation of eggs from mouse embryonic stem cells and induced pluripotent stem cells. Nat Protoc 8, 1513-1524 (2013).
47. J. Chaumeil, P. Le Baccon, A. Wutz, E. Heard, A novel role for Xist RNA in the formation of a repressive nuclear compartment into which genes are recruited when silenced. Genes Dev 20, 2223-2237 (2006).
48. E. Bertrand et al., Localization of ASH1 mRNA particles in living yeast. Mol Cell 2, 437-445 (1998).
49. B. P. Chadwick, Characterization of chromatin at structurally abnormal inactive X chromosomes reveals potential evidence of a rare hybrid active and inactive isodicentric X chromosome. Chromosome Res 28, 155-169 (2020).
50. Y. Hsia et al., Design of a hyperstable 60-subunit protein dodecahedron. [corrected]. Nature 535, 136-139 (2016).
51. B. Wu, J. A. Chao, R. H. Singer, Fluorescence fluctuation spectroscopy enables quantitative imaging of single mRNAs in living cells. Biophys J 102, 2936-2944 (2012).
52. T. Tukiainen et al., Landscape of X chromosome inactivation across human tissues. Nature 550, 244-248 (2017).
53. T. Nozaki et al., Dynamic Organization of Chromatin Domains Revealed by Super-Resolution Live-Cell Imaging. Mol Cell 67, 282-293 e287 (2017).
54. B. Chen et al., Dynamic imaging of genomic loci in living human cells by an optimized CRISPR/Cas system. Cell 155, 1479-1491 (2013).
55. V. Levi, Q. Ruan, M. Plutz, A. S. Belmont, E. Gratton, Chromatin dynamics in interphase cells revealed by tracking in a two-photon excitation microscope. Biophys J 89, 4275-4285 (2005).
56. J. R. Chubb, S. Boyle, P. Perry, W. A. Bickmore, Chromatin motion is constrained by association with nuclear compartments in human cells. Curr Biol 12, 439-445 (2002).
57. T. Germier et al., Real-Time Imaging of a Single Gene Reveals Transcription-Initiated Local Confinement. Biophys J 113, 1383-1394 (2017).
58. E. Lieberman-Aiden et al., Comprehensive mapping of long-range interactions reveals folding principles of the human genome. Science 326, 289-293 (2009).
59. A. Loda, E. Heard, Xist RNA in action: Past, present, and future. PLoS Genet 15, e1008333 (2019).
60. A. Wutz, T. P. Rasmussen, R. Jaenisch, Chromosomal silencing and localization are mediated by different domains of Xist RNA. Nat Genet 30, 167-174 (2002).
61. B. Moindrot et al., A Pooled shRNA Screen Identifies Rbm15, Spen, and Wtap as Factors Required for Xist RNA-Mediated Silencing. Cell Rep 12, 562-572 (2015).
62. A. Monfort et al., Identification of Spen as a Crucial Factor for Xist Function through Forward Genetic Screening in Haploid Embryonic Stem Cells. Cell Rep 12, 554-561 (2015).
63. T. B. Nesterova et al., Systematic allelic analysis defines the interplay of key pathways in X chromosome inactivation. Nat Commun 10, 3129 (2019).
64. G. Pintacuda et al., hnRNPK Recruits PCGF3/5-PRC1 to the Xist RNA B-Repeat to Establish Polycomb-Mediated Chromosomal Silencing. Mol Cell 68, 955-969 e910 (2017).

65. A. Bousard et al., The role of Xist-mediated Polycomb recruitment in the initiation of X-chromosome inactivation. EMBO Rep 20, e48019 (2019).
66. S. T. da Rocha et al., Jarid2 Is Implicated in the Initial Xist-Induced Targeting of PRC2 to the Inactive X Chromosome. Mol Cell 53, 301-316 (2014).
67. D. Colognori, H. Sunwoo, A. J. Kriz, C. Y. Wang, J. T. Lee, Xist Deletional Analysis Reveals an Interdependency between Xist RNA and Polycomb Complexes for Spreading along the Inactive X. Mol Cell 74, 101-117 e110 (2019).
68. D. J. Grau et al., Compaction of chromatin by diverse Polycomb group proteins requires localized regions of high charge. Genes Dev 25, 2210-2221 (2011).
69. N. J. Francis, R. E. Kingston, C. L. Woodcock, Chromatin compaction by a polycomb group protein complex. Science 306, 1574-1577 (2004).
70. S. Boyle et al., A central role for canonical PRC1 in shaping the 3D nuclear landscape. Genes Dev 34, 931-949 (2020).
71. R. S. Illingworth, Chromatin folding and nuclear architecture: PRC1 function in 3D. Curr Opin Genet Dev 55, 82-90 (2019).
72. R. Ridings-Figueroa et al., The nuclear matrix protein CIZ1 facilitates localization of Xist RNA to the inactive X-chromosome territory. Genes Dev 31, 876-888 (2017).
73. H. Sunwoo, D. Colognori, J. E. Froberg, Y. Jeon, J. T. Lee, Repeat E anchors Xist RNA to the inactive X chromosomal compartment through CDKN1A-interacting protein (CIZ1). Proc Natl Acad Sci USA 114, 10654-10659 (2017).
74. A. Pandya-Jones et al., A protein assembly mediates Xist localization and gene silencing. Nature, (2020).
75. M. Yue et al., Xist RNA repeat E is essential for ASH2L recruitment to the inactive X and regulates histone modifications and escape gene expression. PLoS Genet 13, e1006890 (2017).
76. L. Tavares et al., RYBP-PRC1 complexes mediate H2A ubiquitylation at polycomb target sites independently of PRC2 and H3K27me3. Cell 148, 664-678 (2012).
77. J. Zhao, B. K. Sun, J. A. Erwin, J. J. Song, J. T. Lee, Polycomb proteins targeted by a short repeat RNA to the mouse X chromosome. Science 322, 750-756 (2008).
78. T. Mittag, J. D. Forman-Kay, Atomic-level characterization of disordered protein ensembles. Curr Opin Struct Biol 17, 3-14 (2007).
79. K. K. Turoverov et al., Stochasticity of Biological Soft Matter: Emerging Concepts in Intrinsically Disordered Proteins and Biological Phase Separation. Trends Biochem Sci 44, 716-728 (2019).
80. V. N. Uversky, The multifaceted roles of intrinsic disorder in protein complexes. FEBS Lett 589, 2498-2506 (2015).
81. K. Ng et al., A system for imaging the regulatory noncoding Xist RNA in living mouse embryonic stem cells. Mol Biol Cell 22, 2634-2645 (2011).
82. Z. Liu, R. Tjian, Visualizing transcription factor dynamics in living cells. J Cell Biol 217, 1181-1191 (2018).
83. D. Mazza, A. Abernathy, N. Golob, T. Morisaki, J. G. McNally, A benchmark for chromatin binding measurements in live cells. Nucleic Acids Res 40, el 19 (2012).
84. J. Chen et al., High efficiency of HIV-1 genomic RNA packaging and heterozygote formation revealed by single virion analysis. Proc Natl Acad Sci USA 106, 13535-13540 (2009).
85. A. P. Minton, Implications of macromolecular crowding for protein assembly. Curr Opin Struct Biol 10, 34-39 (2000).
86. C. Tan, S. Saurabh, M. P. Bruchez, R. Schwartz, P. Leduc, Molecular crowding shapes gene expression in synthetic cellular nanosystems. Nat Nanotechnol 8, 602-608 (2013).
87. M. Kato et al., Cell-free formation of RNA granules: low complexity sequence domains form dynamic fibers within hydrogels. Cell 149, 753-767 (2012).
88. S. K. Maji et al., Functional amyloids as natural storage of peptide hormones in pituitary secretory granules. Science 325, 328-332 (2009).
89. K. Richter, M. Nessling, P. Lichter, Experimental evidence for the influence of molecular crowding on nuclear architecture. J Cell Sci 120, 1673-1680 (2007).
90. A. Bancaud et al., Molecular crowding affects diffusion and binding of nuclear proteins in heterochromatin and reveals the fractal organization of chromatin. EMBO J 28, 3785-3798 (2009).
91. K. Teller et al., A top-down analysis of Xa- and Xi-territories reveals differences of higher order structure at >1=20 Mb genomic length scales. Nucleus 2, 465-477 (2011).
92. N. Brockdorff, Polycomb complexes in X chromosome inactivation. Philos Trans R Soc Lond B Biol Sci 372, (2017).
93. C. Y. Wang, D. Colognori, H. Sunwoo, D. Wang, J. T. Lee, PRC1 collaborates with SMCHD1 to fold the X-chromosome and spread Xist RNA between chromosome compartments. Nat Commun 10, 2950 (2019).
94. N. Jansz et al., Smchd1 Targeting to the Inactive X Is Dependent on the Xist-HnrnpK-PRC1 Pathway. Cell Rep 25, 1912-1923 e1919 (2018).
95. L. Frank, K. Rippe, Repetitive RNAs as Regulators of Chromatin-Associated Subcompartment Formation by Phase Separation. J Mol Biol 432, 4270-4286 (2020).
96. F. Erdel et al., Mouse Heterochromatin Adopts Digital Compaction States without Showing Hallmarks of HP1-Driven Liquid-Liquid Phase Separation. Mol Cell 78, 236-249 e237 (2020).
97. I. Jonkers et al., Xist RNA is confined to the nuclear territory of the silenced X chromosome throughout the cell cycle. Mol Cell Biol 28, 5583-5594 (2008).
98. C. Beard, K. Hochedlinger, K. Plath, A. Wutz, R. Jaenisch, Efficient method to generate single-copy transgenic mice by site-specific integration in embryonic stem cells. Genesis 44, 23-28 (2006).
99. B. Panning, J. Dausman, R. Jaenisch, X chromosome inactivation is mediated by Xist RNA stabilization. Cell 90, 907-916 (1997).
100. Q. L. Ying, A. G. Smith, Defined conditions for neural commitment and differentiation. Methods Enzymol 365, 327-341 (2003).
101. M. Cremer et al., Multicolor 3D fluorescence in situ hybridization for imaging interphase chromosomes. Methods Mol Biol 463, 205-239 (2008).
102. F. Kraus et al., Quantitative 3D structured illumination microscopy of nuclear structures. Nat Protoc 12, 1011-1028 (2017).
103. Y. Markaki, D. Smeets, M. Cremer, L. Schermelleh, Fluorescence in situ hybridization applications for super-resolution 3D structured illumination microscopy. Methods Mol Biol 950, 43-64 (2013).
104. J. Demmerle et al., Strategic and practical guidelines for successful structured illumination microscopy. Nat Protoc 12, 988-1010 (2017).

105. J. Ollion, J. Cochennec, F. Loll, C. Escude, T. Boudier, TANGO: a generic tool for high-throughput 3D image analysis for studying nuclear organization. Bioinformatics 29, 1840-1841 (2013).
106. E. H. Finn, G. Pegoraro, S. Shachar, T. Misteli, Comparative analysis of 2D and 3D distance measurements to study spatial genome organization. Methods 123, 47-55 (2017).
107. J. Y. Tinevez et al., TrackMate: An open and extensible platform for single-particle tracking. Methods 115, 80-90 (2017).
108. M. Dundr, T. Misteli, Measuring dynamics of nuclear proteins by photobleaching. Curr Protoc Cell Biol Chapter 13, Unit 13 15 (2003).
109. S. Lee, D. Cook, M. Lawrence, plyranges: a grammar of genomic data transformation. Genome Biol 20, 4 (2019).
110. M. I. Love, W. Huber, S. Anders, Moderated estimation of fold change and dispersion for RNA-seq data with DESeq2. Genome Biol 15, 550 (2014).
111. S. M. Gartler, L. Goldstein, S. E. Tyler-Freer, R. S. Hansen, The timing of XIST replication: dominance of the domain. Hum Mol Genet 8, 1085-1089 (1999).
112. Bernd A. Berg and Robert C. Harris, From data to probability densities without histograms. Computer Physics Communications 179, 443-448, (2008).
113. Joshua C. Chang, Pak-Wing Fok, and Tom Chou, Bayesian uncertainty quantification for bond energies and mobilities using path integral analysis. Biophysical Journal 109, 966-974, (2015).
114. Joshua C. Chang, Van M. Savage, and Tom Chou, A path-integral approach to bayesian inference for inverse problems using the semiclassical approximation. Journal of Statistical Physics 157, 582-602, (2014).
115. Ramses van Zon and Jeremy Schofield, Constructing smooth potentials of mean force, radial distribution functions, and probability densities from sampled data. Journal of Chemical Physics 132, 154110, (2010).
116. Jose Braga, James G. McNally, and Maria Carmo-Fonseca, A Reaction-Diffusion Model to Study RNA Motion by Quantitative Fluorescence Recovery after Photobleaching. Biophysical Journal 92, 2694-2703, (2007).
117. James G. McNally, Quantitative frap in analysis of molecular binding dynamics in vivo. In Fluorescent Proteins, Methods in Cell Biology 85, 329-351, (2008).
118. Minchul Kang, Charles A. Day, Emmanuele DiBenedetto, and Anne K. Kenworthy, A quantitative approach to analyze binding diffusion kinetics by confocal frap. Biophysical Journal 99, 2737-2747, (2010).
119. C. A. Brackley and D. Marenduzzo. Bridging-induced microphase separation: photobleaching experiments, chromatin domains and the need for active reactions. Briefings in Functional Genomics 19, 111-118, (2020).
120. A. J. Wollman et al., Transcription factor clusters regulate genes in eukaryotic cells. Elife 6, (2017).
121. K. Clauss et al., DNA residence time is a regulatory factor of transcription repression. Nucleic Acids Res 45, 11121-11130 (2017).
122. J. Liu, C. A. Shively, R. D. Mitra, Quantitative analysis of transcription factor binding and expression using calling cards reporter arrays. Nucleic Acids Res 48, e50 (2020).
123. P. Mier et al., Disentangling the complexity of low complexity proteins. Brief Bioinform, 21, 458-472 (2020).
124. Brian D. Hendrich, Robert M. Plenge, and Huntington F. Willard, Identification and characterization of the human XIST gene promoter: implications for models of X chromosome inactivation. Nucleic Acids Research 25, 2661-2671, (1997).
125. Carolina Eliscovich, Adina R. Buxbaum, Zachary B. Katz, and Robert H. Singer. mRNA on the Move: The Road to Its Biological Destiny. Journal of Biological Chemistry 288, 20361-20368, (2013)

Example 2: Xist Nucleates Local Protein Gradients to Propagate Silencing Across the X Chromosome The lncRNA Xist forms ~50 diffraction-limited foci to transcriptionally silence one X-chromosome. How this small number of RNA foci and interacting proteins regulate a much larger number of X-linked genes is unknown. We show that Xist foci are locally confined, contain ~2 RNA molecules, and nucleate supra-molecular complexes (SMCs) that include many copies of the critical silencing protein SPEN. Aggregation and exchange of SMC proteins generate local protein gradients that extend silencing across broad, proximal chromatin regions. Partitioning of numerous SPEN molecules into SMCs is mediated by their intrinsically disordered regions and essential for transcriptional repression. Polycomb deposition via SMCs is required for chromatin compaction, which gradually densifies SMCs and repositions all genes into the SMC-cluster, enabling progressive gene silencing. Our findings introduce a mechanism for functional nuclear compartmentalization whereby crowding of transcriptional and architectural regulators enables the silencing of many target genes by few RNA molecules. We discovered that Xist foci are locally confined and that they induce the de novo formation of local protein compartments that encompass Xist-interactors at concentrations exceeding those of the RNA. We refer to these compartments as supra-molecular-complexes (SMCs). SMCs are dynamic structures formed by transient protein interactions around a slowly exchanging Xist core. The rapid binding and dissociation of most Xist-interacting proteins in SMCs creates local protein concentration gradients. We show that the intrinsically disordered regions of SPEN are essential for its integration into SMCs and for gene silencing. Thus, contrary to the prevailing model, Xist does not act in a ribonucleoprotein complex at each target gene. Instead, it seeds ~50 dynamic protein compartments that mediate gene silencing on the entire chromosome. Our study also explains how different silencing pathways cooperate to achieve robust chromosome-wide silencing in a progressive manner. SMCs initially predominantly form at chromatin regions in spatial proximity to the Xist locus. Polycomb-mediated chromatin reconfiguration and compaction gradually repositions genes more densely under the SMC cluster, allowing SPEN-mediated silencing to spread to all genes.

In summary, our work uncovers a new mechanism of repressive nuclear compartment formation in which RNA-induced protein crowding enables a limited number of locally confined seeding RNA molecules to expand silencing to a much larger number of target genes.

A. Results

1. Progressive Gene Silencing During XCI is Associated with Chromatin Compaction.

To explore how Xist orchestrates the formation of the Xi, we differentiated female mouse embryonic stem cells (ESCs) to epiblast-like cells (EpiLCs), which leads to the induction of Xist expression and initiation of XCI (FIGS. 19A and 26A). Gene silencing occurs predominantly during the transition from day 2 (D2) to D4 as shown by the detection of nascent transcripts of the rapidly silencing X-linked gene Rlim and the two more slowly silencing genes AtrX and Mecp2 (FIGS. 19B, 19C, and 26B). Single cell (sc) RNA-seq analyses extended this result to all X-linked genes (FIGS. 19D and 26C). These data confirm that Xist coating and gene silencing are stepwise processes (Chaumeil et al., 2006) and establish the D2 to D4 transition as a critical window for dissecting the relationship between Xist, its interacting proteins and gradual gene silencing. Henceforth, we refer to the D2 X chromosome as the "pre-Xi" and the D4 X chromosome as the "Xi".

Although architectural differences between the active X chromosome (Xa) and Xi are well known (Darrow et al., 2016; Giorgetti et al., 2016; Teller et al., 2011; Wang et al., 2019), it remains unclear when they arise during XCI. Volume and sphericity measurements upon X-painting show that the pre-Xi is similar to the Xa and that the Xi at D4 is as compact and spherical as in somatic cells (FIGS. 19E and 19F) (Teller et al., 2011). We also assessed the conformation of seven loci on the X through DNA FISH, which revealed a moderate change of the higher-order configuration in the pre-Xi compared to the Xa and a dramatic difference between the Xa and Xi (FIGS. 19G-I and 26D). Thus, gene silencing is associated with major changes in higher-order chromatin structure and both processes need to be considered to understand the mechanism through which Xist foci form the Xi.

2. 50 Xist Foci Containing ~2 Transcripts Each Induce XCI

As the number of Xist foci during the initiation of XCI is unknown, we first quantified them during the D2 to D4 transition. To this end, we generated a female mouse ESC line that allows for the detection of Xist in living cells by super-resolution three-dimensional Structured Illumination Microscopy (3D-SIM). Specifically, we exploited the MS2 RNA-MS2 Coat Protein (MCP) interaction (Bertrand et al., 1998) and tagged the endogenous Xist RNA on one of the two X-chromosomes with 24 MS2-repeats. We then expressed MCP-GFP to label Xist with GFP and confirmed intact gene silencing to demonstrate the functionality of the $Xist^{MS2-GFP}$ allele (FIGS. 19J, 19K, 26G, and 26H).

Quantitative 3D-SIM analysis of $Xist^{MS2-GFP}$ showed that the Xist territory consists of, on average, 74 diffraction-limited foci on the pre-Xi and 60 on the Xi (FIG. 19L), which we corroborated by RNA FISH (FIGS. 26H and 26I). We also found that the doubling of the X chromosome with DNA replication is accompanied by the doubling of Xist foci from ~50 in G1 to ~100 in G2 and that the number of foci correlates with chromosome length (FIGS. 19M and 27A-D). Thus, the variability in the number of Xist foci is largely due to differences in cell cycle across the cell populations. Taken together, these data reveal that XCI is induced by only ~50 Xist foci and that the pre-Xi to Xi transition occurs without a dramatic change in their number.

We next investigated if the amount of the RNA in each focus changes during the pre-Xi to Xi transition. We found that Xist foci maintain their integrated density and volume, consistent with the constitutive transcription of the Xist locus (FIGS. 19N, 26I, S2E and S2F). To estimate the number of Xist molecules per focus, we transiently expressed nanocages consisting of 60 GFP molecules ($cage^{60GFP}$) (Hsia et al., 2016) as internal fluorescence standards in $Xist^{MS2-GFP}$ cells. We confirmed similar intensity profiles of $cage^{60GFP}$ in the nucleus and cytoplasm (FIGS. 27G and 27H). Quantitative 3D-SIM analyses showed that the amount of fluorescence of one $Xist^{MS2-GFP}$ focus on the pre-Xi and Xi corresponds to that of one $cage^{60GFP}$ (FIGS. 19O, 27I and 27J). Since ~30 MCP-GFP molecules bind to 24 MS2-repeats (Wu et al., 2012), we infer that each focus contains ~2 Xist molecules. This result is consistent with measured levels of Xist RNA in single differentiating ESCs (Pacini et al., 2021) and estimated numbers of Xist molecules in differentiated cells (Sunwoo et al., 2015). Thus, only ~100 Xist molecules orchestrate the initiation and maintenance of XCI.

3. Xist Foci are Locally Confined and Form at Open Chromatin Regions

Hence, how the limited number of Xist foci can simultaneously silence the ~1000 X-linked genes remains a puzzle. One possibility is that the Xist foci regulate target genes via rapid diffusion and transient contacts. To investigate the mobility of the foci during the initiation of XCI, we developed conditions for live-cell 3D-SIM of $Xist^{MS2-GFP}$ at D2 and D4 and applied single-particle tracking of individual foci for at least 2 min. We found that Xist foci exhibit restricted motion without fission or fusion (FIGS. 20A and 20B). In 90% of cases, the displacement of each Xist focus over time was less than 200 nm and foci movement was characterized by diffusion in a local confining potential (FIGS. 20C-E). The confined motion of Xist foci is highly correlated with the motion of chromatin loci (Chen et al., 2013; Nozaki et al., 2017). We therefore conclude that Xist foci are tethered to chromatin with high affinity, constraining their movement to the local Brownian motion of chromatin. Thus, XCI is initiated through ~50 sites at which Xist molecules are locally confined.

To investigate if the 'wiggling' of Xist foci around their centers occurs within a specific chromatin environment, we introduced a histone H2B-Halo transgene into $Xist^{MS2-GFP}$ ESCs and performed live-cell 3D-SIM (FIG. 20F). H2B signals were segmented into intensity levels that correspond to chromatin density classes, with class 1 representing DNA-free interchromatin channels (IC) and classes 2 to 7 capturing increasing chromatin densities (Smeets et al., 2014) (FIG. 20G). Xist foci covered predominantly classes 1 to 3 (FIG. 27K). Over time, the chromatin densities underlying the footprint of Xist foci never surpassed class 3 and the centroids remained within chromatin class 2, consistent with the linearly and incrementally increasing chromatin density (FIGS. 20H and 27L). Thus, Xist foci are spatially confined to the periphery of chromatin domains and stably maintain their positions relative to chromatin.

In agreement with these observations, RNA antisense purification (RAP) of Xist followed by DNA sequencing of associated chromatin (Engreitz et al., 2013) showed that Xist localizes to gene-rich, open chromatin regions of the A-compartment (FIG. 20I). We identified 65 and 63 highly overlapping peaks of Xist enrichment on the pre-Xi and Xi, respectively (FIGS. 20J and 27M), similar to the number of foci detected by 3D-SIM. These peaks cover broad genomic regions of 1-5 megabases (FIG. 27N), suggesting that Xist foci are not localizing to the same genomic regions in individual cells. Xist peaks in the Xi are broader than those in the pre-Xi despite the overall similar localization patterns (Pearson's correlation r=0.83) (FIGS. 20I, 20J and 27N), consistent with chromatin contacts of Xist foci changing over time due to chromatin compaction.

4. Xist Nucleates Supra-Molecular Complexes

To explore how Xist effector proteins accumulate relative to ~50 locally confined Xist foci, we set out to quantify, at sub-diffraction resolution, their spatial relationship to Xist and to each other. We initially focused on SPEN, PCGF5, CELF1 and CIZ1, four proteins that bind to distinct repeat sequences of Xist and have different roles in XCI (FIG. 21A) (Loda and Heard, 2019; Wutz et al., 2002). SPEN binds the A-repeat of Xist and activates HDAC3 on chromatin to induce gene silencing (Chu et al., 2015; Dossin et al., 2020; McHugh et al., 2015; Moindrot et al., 2015; Monfort et al., 2015). The non-canonical PRC1 subunit PCGF5 is recruited to the Xi via the B-repeat and supports the silencing of some X-linked genes (Almeida et al., 2017; Bousard et al., 2019; Nesterova et al., 2019; Pintacuda et al., 2017). CELF1 and CIZ1 bind to the E-repeat and restrict Xist to the Xi (Pandya-Jones et al., 2020; Ridings-Figueroa et al., 2017; Sunwoo et al., 2017; Yue et al., 2017).

To interrogate the localization of these representative Xist-interactors, we introduced Halo-tagged transgenes into Xist$^{MS2\text{-}GFP}$ cells. This allowed us to image an antibody-stained and a stably expressed Halo-fusion protein together with Xist by multispectral 3D-SIM (FIGS. 21B, 28A and 28B). We found that the proteins form diffraction-limited assemblies in proximity to Xist foci in both the pre-Xi and Xi that are larger than other nuclear accumulations (FIG. 28B and FIG. 28A). This result indicated that Xist induces the de novo formation of unique protein complexes.

To quantitatively define the protein assemblies surrounding Xist foci, we extracted the nucleus-wide spatial coordinates of thousands of diffraction-limited protein foci (FIGS. 38C-E). We paired protein foci to Xist foci and measured nearest-neighbor distances between pairs of different interactors associated with the same Xist focus (FIG. 21C). We also measured nearest pairwise distances of protein foci located in the remainder of the nucleus. For all pairs, protein foci are on average within ~150-200 nm of each other when associated with Xist, both on the pre-Xi and Xi, but they are separated by >350 nm in the rest of the nucleus (FIG. 21D). Thus, Xist foci locally concentrate effector proteins more than elsewhere in the nucleus. We also found that the density of SPEN, CELF1, PCGF5, and CIZ1 protein particles, respectively, is significantly higher in the pre-Xi and Xi than in the nucleus, consistent with their decreased nearest and average distances in the X-territory (FIGS. 21E, 29A and 29B). Furthermore, the concentration of protein assemblies increases from the pre-Xi to the Xi, along with the observed chromatin compaction.

Hence, large multi-protein assemblies that are not typically found outside the Xi form around Xist foci. In this way, Xist recruitment increases the concentration of proteins within the forming Xi. We refer to the Xist-nucleated proteinaceous nanostructures as Xist-associated SMCs. We also observed their formation when XCI is ectopically induced on an autosome (FIG. 28F) consistent with SMCs being a fundamental feature of the XCI process.

5. SMCs Contain a Wide Spectrum of Xist-Interacting Proteins

Figure 29C:
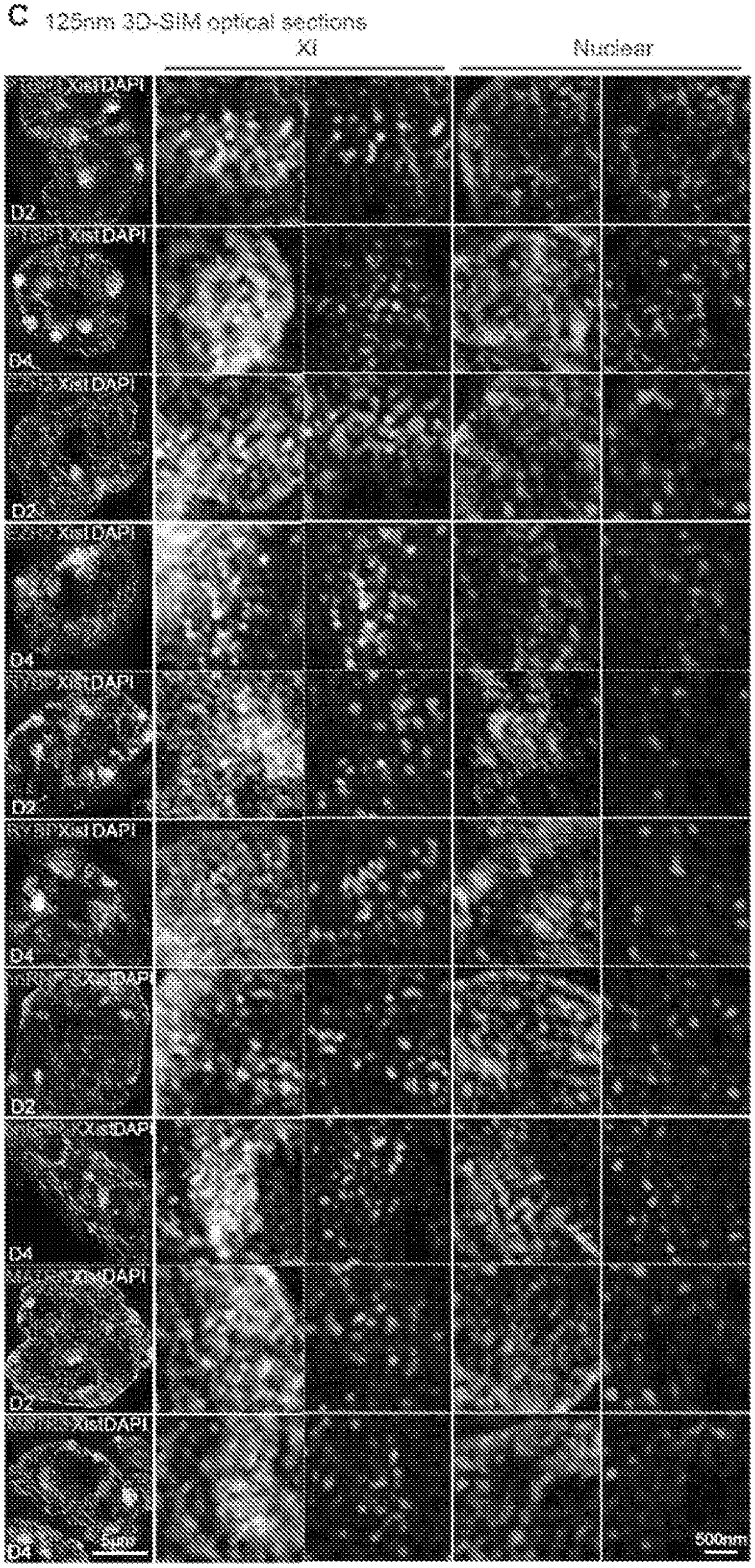

To explore whether integration into SMCs is the main mechanism of protein recruitment in the Xi, we probed the distribution of additional XCI effectors (FIG. 29C), including the PRC1 subunit RYBP (Tavares et al., 2012); the EZH2 subunit of PRC2 (Plath et al., 2003; Silva et al., 2003); hnRNP-K, which binds the Xist B-repeat to recruit PCGF5 (Pintacuda et al., 2017); PTBP1 and MATR3, which regulate Xist localization with CELF1 (Pandya-Jones et al., 2020). For each examined protein, we found that a protein particle associates with Xist foci in a near 1:1 ratio. Nearest neighbor measurements showed that these protein accumulations localize within a 200 nm zone from the centroid of Xist and that they are significantly more proximal to Xist than randomized protein populations (FIG. 21F, 29D and Table S1). These data corroborate the de novo formation of a multi-protein macromolecular cloud around Xist foci at the onset of XCI (FIG. 21G).

Next, we investigated the concentrations of each protein within SMCs compared to concentrations in other accumulations in the nucleus (FIGS. 21H and 29E). Integrated density and particle volume measurements showed that the levels of CIZ1, CELF1, SPEN, PCGF5, EZH2 and RYBP in SMCs significantly exceed those in nuclear assemblies. Moreover, their accumulation in SMCs changes slightly across the pre-Xi to Xi transition, with PCGF5, EZH2 and RYBP levels following nuclear changes, CELF1 levels decreasing, and SPEN levels dramatically increasing. Thus, gene silencing is accompanied by an increase of SPEN molecules in SMCs. MATR3, PTBP1 and hnRNP-K exhibit baseline concentrations in SMCs, suggesting that their recruitment, rather than increased accumulation is essential in XCI.

6. Estimation of SPEN Molecules in SMCs

To estimate number of protein molecules incorporated into SMCs we focused on the critical silencing factor SPEN. We exploited our cage$^{60GFP}$-standard approach and a cell line in which endogenously encoded SPEN is GFP-tagged and Xist can be induced with doxycycline (dox) (Dossin et al., 2020) (FIG. 21I). Compared to developmentally induced XCI, dox-induction results in a larger number of Xist foci, yet yields similar levels of SPEN per SMC. Moreover, before plateauing, SPEN-SMC levels increase between 6 and 18 hrs of dox-addition as seen for the pre-Xi to Xi transition (FIGS. 29F and 29G). Comparing the intensity of the SPEN-GFP signal in SMCs to that of cage$^{60GFP}$, we infer that there are up to 35 SPEN molecules per SMC (FIG. 21J). This finding suggests that each SMC may consist of 100s to 1000s of protein molecules and that many effector proteins likely are significantly enriched relative to the number of RNA molecules (FIG. 21G).

7. Binding to Xist Alters the Kinetic Behavior of Interacting Proteins

Figure 30D:
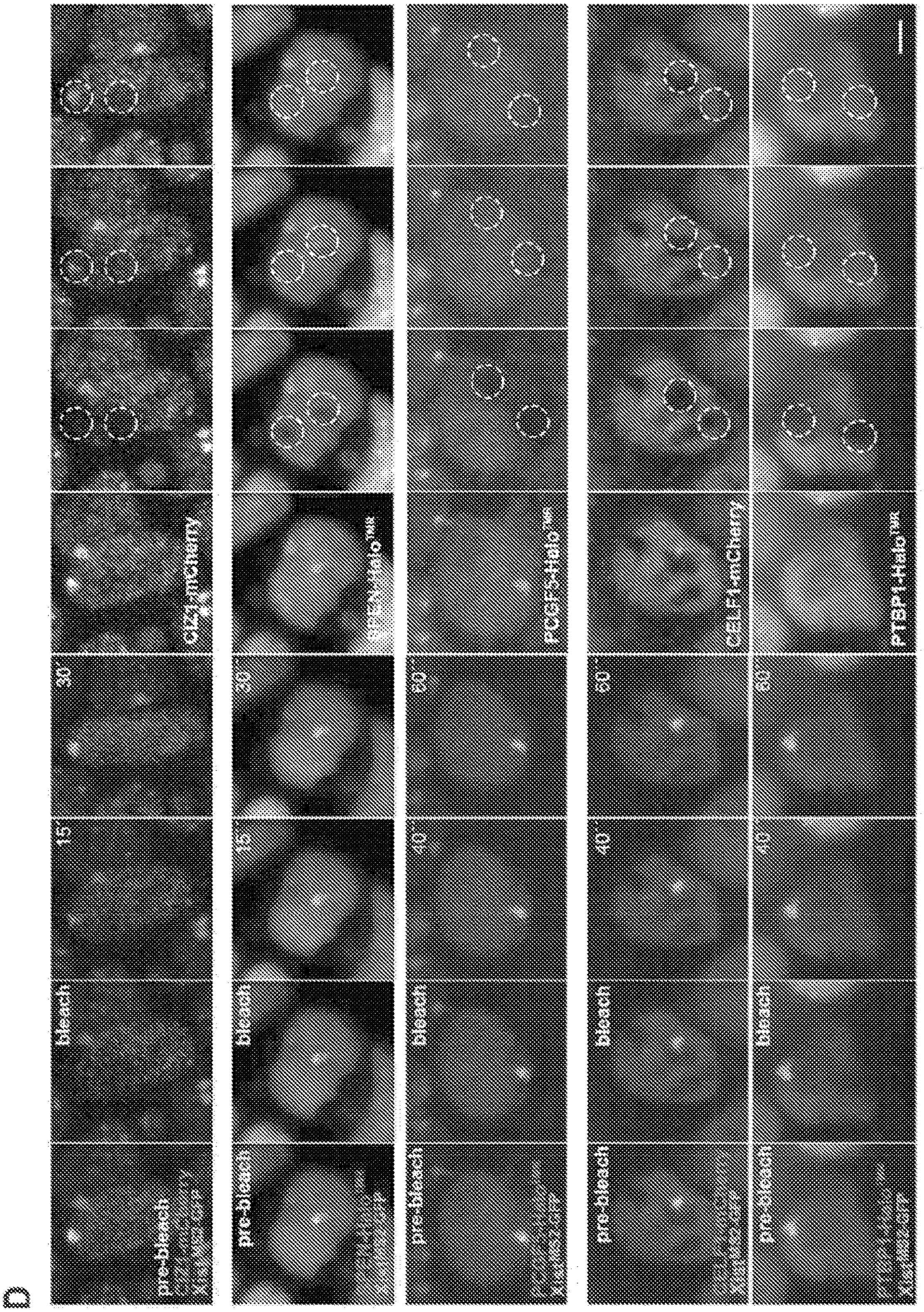

To explore the kinetic behavior of different SMC protein components, we introduced Halo or mCherry-tagged SPEN, PCGF5, CIZ1, CELF1 or PTBP1 fusions into Xist$^{MS2\text{-}GFP}$ ESCs. We then performed Fluorescence Recovery After Photobleaching (FRAP) over the Xist$^{MS2\text{-}GFP}$-demarcated Xi-territory and other same-size nuclear regions. We also examined Xist RNA dynamics upon confirming that no recovery of the Xist$^{MS2\text{-}GFP}$ signals occurred in the absence of transcription (FIGS. 30A-C). We observed a slow exchange of photobleached Xist$^{MS2\text{-}GFP}$ (FIG. 22A), comparable to that of ectopically expressed Xist (Ng et al., 2011). A single-exponential kinetic model provided the best fit to the measured FRAP curve. We inferred a slow dissociation rate (0.05/min) and an average Xist lifetime in the Xi of ~22 min. This result is consistent with a single type of high-affinity interaction between Xist and chromatin (FIGS. 22B and 22C). Similar to Xist, CIZ1 has a ~19 min recovery time in the Xi, which is much longer than that of all other interrogated proteins (FIGS. 22D-G, 30D and 30E). The tight kinetic and spatial relationship between Xist and CIZ1 (FIGS. 21F and 22G) suggests that CIZ1 and Xist molecules form a relatively stable core within an SMC.

Kinetic modelling of the SPEN, PCGF5, CELF1 and PTBP1 FRAP curves yielded faster exchange rates than CIZ1 and Xist and two effective types of binding sites (FIGS. 22F, 22G and 30D-F). Using two-exponential fits, we inferred parameters for the short-lived (n) and long-lived (t) bound fractions within and outside of the Xi. For each protein, the rapid binding events occurred within seconds while slow dissociation requires several minutes (FIGS. 22G and 30G). SPEN was the most dynamic among the examined proteins.

Recruitment by Xist extended the binding rates for these proteins compared to the nucleus, indicating that the Xi forms a unique nuclear compartment within which proteins exhibit distinct kinetic behaviors (FIG. 22G). The kinetic assays indicate that Xist effector proteins with short residence times transiently bind to the slowly exchanging Xist-CIZ1 core. Thus, SMCs are rapidly exchanging dynamic complexes that form local, high affinity concentration platforms. Accordingly, examination of the SPEN and PCGF5 populations in the Xi but outside SMCs (referred to as the Xi-fraction) revealed higher protein concentrations than in nuclear assemblies (FIGS. 30H-K). Therefore, recruitment to SMCs leads to enrichment of constituent proteins across extended local neighborhoods in the X-territory (FIG. 22H).

8. Crowding of SPEN in SMCs is IDR-Dependent

The formation of SMCs is consistent with a requirement for extensive protein-protein interactions (FIG. 21G). We explored this hypothesis by functionally dissecting SPEN. SPEN contains intrinsically disordered regions (IDRs), which typically mediate weak, multivalent interactions (Banani et al., 2017; Cerase et al., 2019; Mittag and Forman-Kay, 2007; Uversky, 2015). We homozygously deleted the IDRs within the endogenous SPEN alleles in female ESCs in which SPEN is tagged with GFP (Dossin et al., 2020) and showed that ΔIDR SPEN expression did not disrupt the formation of the Xist cloud (FIGS. 23A, 23B, 31A and 31B). Deletion of the IDRs does not interfere with the binding of the protein to Xist but eliminates the increased SPEN levels in SMCs to the point that ΔIDR SPEN levels in the pre-Xi and Xi are close to those of the wildtype (WT) protein within nuclear accumulations (FIGS. 23B, 23C, 31C and 31D). We conclude that the accumulation of many SPEN molecules in SMCs is driven exclusively by their IDRs.

We also found that the IDR-mediated accumulation of SPEN into SMCs requires binding to Xist through its RNA-binding (RRM) domains (FIGS. 31C-E). Furthermore, FRAP experiments showed that the deletion of the IDRs or RRMs abolishes the characteristic Xi-immobile fraction of SPEN and dramatically alters residence times, with ΔIDR-SPEN exhibiting very long unbinding times in both the Xi and nuclear fractions, possibly due to the tight binding to the RNA through the RRMs (FIGS. 31F-H). Therefore, the IDRs of SPEN are also critical for creating a dynamic protein assembly (FIG. 23K).

9. IDR-Mediated Crowding of SPEN in SMCs is Required for XCI

The silencing of virtually all X-linked genes is dependent on the SPOC domain of SPEN (Dossin et al., 2020), raising the question of whether the IDR-dependent crowding of SPEN in the Xi is required for the SPOC domain to exert its function. We interrogated the nascent transcription state of five X-linked genes by RNA FISH and observed a striking silencing defect when the IDR-mediated crowding was ablated, which was similar to the lack of silencing observed in ΔSPOC ESCs (Dossin et al., 2020) (FIGS. 23D and 23E).

To explore if the loss of gene silencing in the absence of the IDRs extends to the entire X chromosome, we performed two RNA-seq experiments. First, we used scRNA-seq before and 24 hours after Xist induction in ΔSPOC, ΔIDR, and WT SPEN expressing cells. Although X-linked gene repression was observed in WT cells, both ΔIDR and ΔSPOC SPEN expressing cells displayed a dramatic X chromosome-wide loss of gene silencing, affecting both rapidly and slowly silencing genes (FIGS. 23F and 23G). Second, we tested the effect of the IDR deletion using a rescue approach. We constitutively expressed Halo-tagged ΔIDR or full-length (FL) SPEN in ESCs in which the endogenously encoded SPEN is fused to the AID degron tag and can be depleted by addition of auxin (Dossin et al., 2020) (FIGS. 5H and 5I). Bulk RNA-seq showed that FL but not ΔIDR SPEN can rescue X-linked gene silencing (FIG. 5J). Interestingly, when only the SPOC domain is tightly tethered to Xist (Dossin et al., 2020), X-linked genes are inefficiently silenced (FIGS. 31I-K) consistent with a dynamic SPEN protein being required for XCI.

In summary, our findings demonstrate that the concentration of SPEN and its rapid kinetic behavior in SMCs, both mediated by the IDRs, are required for the protein to exert its silencing function through the SPOC domain (FIG. 23K). This finding is consistent with reports that catalytic rates of IDR-containing DNA modifying enzymes increase with crowding (Kuznetsova et al., 2014; Zimmerman and Pheiffer, 1983).

10. The B-Repeat is Critical for Xi Compaction During Initiation of XCI

Non-canonical PRC1 is recruited to the Xi by the B-repeat of Xist via hnRNP-K (Pintacuda et al., 2017), induces the recruitment of canonical PRC1, PRC2 and accumulation of downstream histone marks (Brockdorff, 2017), and is, in addition to SPEN, needed for the silencing of specific genes (Bousard et al., 2019; Brockdorff, 2017; Colognori et al., 2019; da Rocha et al., 2014; Nesterova et al., 2019; Zylicz et al., 2019). Yet, PRC1 spreads into genes only after silencing has occurred (Zylicz et al., 2019), raising the question of how it contributes to XCI. Since PRC1 is critical for chromatin compaction in various developmental contexts (Boyle et al., 2020; Francis et al., 2004; Grau et al., 2011; Illingworth, 2019), we explored whether the B-repeat is required for the structural reorganization of the Xi.

Figure 32D:
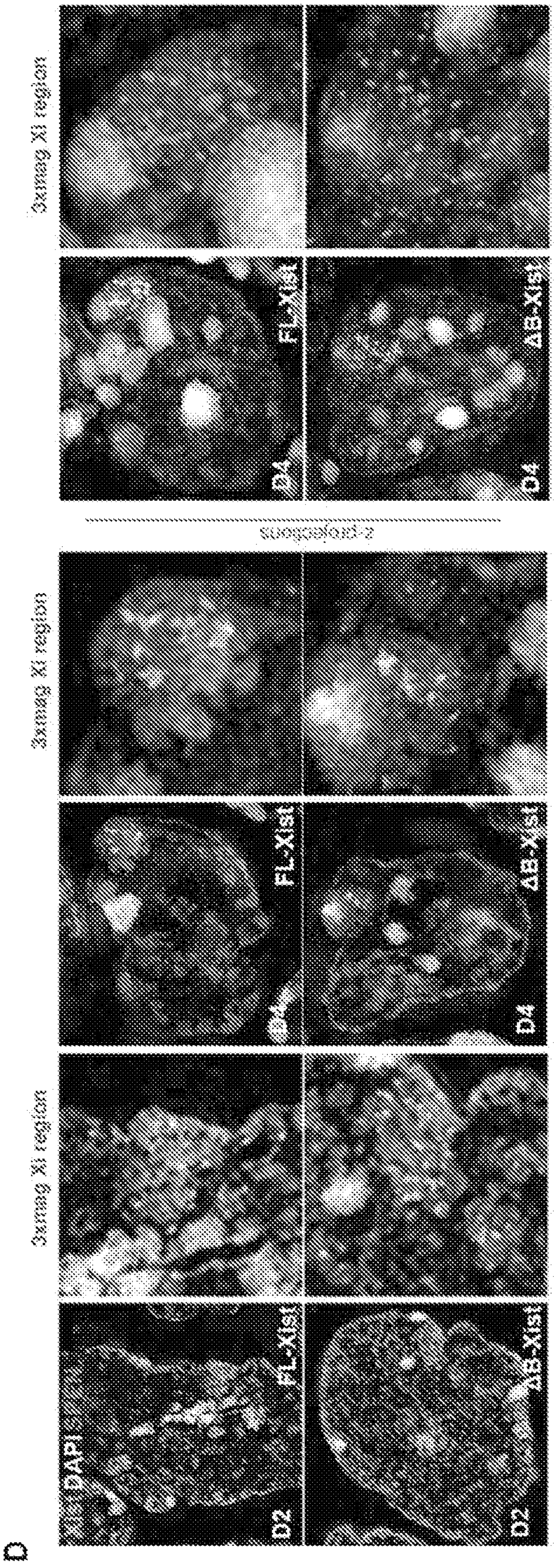

We perturbed PRC1 recruitment to the X by heterozygously deleting the B-repeat (ΔB-Xist) in female ESCs derived from a 129× castaneous (cas) cross and compared the compaction the $Xi^{cas}$ formed by FL-Xist to the $Xi^{129}$ induced by ΔB-Xist. The $Xi^{129}$ could be distinguished via an MS2-tag inserted into the $Xist^{129}$ allele (FIGS. 24A and 24B). We found that deletion of the B-repeat results in less compacted pre-Xi and Xi territories, larger distances between Xist foci and an expansion of the Xist-territory (FIGS. 24B-C and 32A-C). Consistent with this result, the density of SPEN-decorated SMCs is far lower in the ΔB-Xi than in the WT-Xi although the concentrations of SPEN in their respective SMCs are similar (FIGS. 32D and 32E). Together, these findings uncover a role of the B-repeat, and in turn of PRC1 and its downstream effectors, in driving the compaction of the X chromosome and densification of SMCs during XCI initiation.

11. Compaction is Linked to Silencing Dynamics

To explore how X-linked gene silencing dynamics are altered in the absence of compaction, we performed scRNA-seq at D2 and D4. In the absence of the B-repeat, silencing is only moderately perturbed on the pre-Xi and a more pronounced silencing defect is seen for the Xi (FIG. 24E). By analyzing genes according to their silencing kinetics (Barros de Andrade et al., 2019), we found that rapidly and slowly silencing genes are affected in ΔB-Xist cells and that the silencing defect is strongest for the late silencing gene sets (FIGS. 24F-H). These results extend to cells lacking SMCHD1 that controls the compartmentalization of the Xi and is recruited to the Xi by PRC1 (Jansz et al., 2018; Wang et al., 2019) (FIG. 32E). We conclude that compaction by PRC1 and SMCHD1 and the further clustering of the Xist-SMCs allows SPEN to act on all genes.

12. Xist-SMCs Progressively Re-Configure and Silence the Xi

We next explored how genes with different silencing kinetics, i.e. rapidly (early) and slowly (late) silencing genes, localize relative to Xist foci. To determine these spatial relationships, we applied multiple distance metrics to 20 simultaneously detected early or late genes distributed across the entire X chromosome, their nascent transcripts and Xist by RNA and/or DNA FISH and 3D-SIM (FIGS. 25A-D).

We first monitored the distribution of early and late gene loci on the Xa relative to the Xist transcription locus by exploiting the detection of Tsix RNA as a proxy for the X-inactivation center (Xic) where the Xist gene is located (Plath et al., 2002). This analysis showed that early genes are closer to the Xist locus than late genes (FIGS. 25C and 25E). We also found that early genes are closer to individual Xist foci or to the center of the entire cluster of Xist foci than late genes, which is more pronounced on the pre-Xi (FIGS. 25F and 31G). Thus, genomic regions containing early genes are spatially more proximal to the Xist locus at the onset of XCI and more likely to be populated by the Xist cluster. Intriguingly, regardless of early or late silencing kinetics, the nearest distance of active and silenced gene loci to Xist foci does not significantly differ, but genes that are not yet silenced are more likely to be more distal to the center of the Xist cluster (FIGS. 25G and 32H). This finding is consistent with late genes being further away from the Xist cluster in the pre-Xi.

Chromosomal compaction significantly decreases the distances of both early and late genes to Xist foci in the pre-Xi to Xi transition, with a higher impact on late genes (FIG. 25F). Accordingly, we uncovered a more dramatic repositioning of late genes (FIG. 25H). The result of the conformational change is that early and late genes congregate and move closer to the center of the Xist cluster (FIGS. 25C and 32G). Consequently, the same number of Xist foci can progressively silence more genes. The progressive gene silencing during the XCI process can therefore be explained by the spatial organization and reconfiguration of the X chromosome and the spatial relationship of genes to the Xist cluster.

Finally, we explored how loss of compaction affects the organization of genes relative to Xist in cells expressing ΔB-Xist. We found all genes on the ΔB-Xi, regardless of their silencing kinetics, at larger distances from the centroid of the Xist cluster and to each other, and that the overall distances between early and late genes are enlarged compared to WT-Xi (FIG. 25I-L). However, nearest neighbor measurements between Xist foci and early or late genes revealed no significant difference for the ΔB and WT Xi, suggesting that Xist foci localize similarly to target regions (FIG. 25M). These findings indicate that the lack in compaction affects the reorganization of genes, which results in poor clustering of SMCs and inefficient silencing, particularly of late genes.

B. Discussion

1. SMCs are the Functional Units of Xist-Mediated XCI

XCI is a powerful model system for interrogating how a limited number of lncRNA molecules can establish a functional nuclear compartment. Since its discovery, it has been thought that Xist progressively spreads on chromatin to associate with all target genes. This view was refined by the observation that Xist first localizes to sites in close spatial proximity to its transcription locus and then spreads chromosome-wide (Engreitz et al., 2013). With the discovery of Xist foci, it was proposed that the RNA and its interacting proteins sample the chromosome through a "hit-and-run" model (Sunwoo et al., 2015). Our study now shows that Xist foci are instead stably bound to chromatin and that they induce the de novo formation of SMCs. Each Xist-SMC accumulates ~35 copies of the ~500KDa protein SPEN. A comparison with other protein levels in SMCs suggests that other Xist effectors likely concentrate to much higher levels in SMCs.

Our results suggest that different binding environments in SMCs allow for both topological retention of proteins as well as their rapid exchange. We find that IDRs are critical for both the accumulation and the dynamics of intra-SMC SPEN and that supra-molecular aggregation in SMCs is necessary for the catalytic domain of SPEN to exert its silencing function. Intriguingly, many Xist-interacting proteins contain IDRs and have the propensity to self-aggregate (Cerase et al., 2019; Pandya-Jones et al., 2020). Whether the IDRs of SPEN are involved solely in homotypic interactions and how IDRs of other Xist-interactors contribute to the formation and function of SMCs remains an open question. Interestingly, the binding to Xist is required for the IDR-dependent integration of SPEN into SMCs and may impart additional specificity to the protein interactions within the Xi. RNA binding may induce the folding of the unstructured IDRs and enable 'entry' into SMCs, consistent with observations for other IDR-containing proteins (Uversky, 2015).

We suggest that the formation of SMCs induces a phase transition in the Xi, as SMCs surrounding stably bound Xist molecules create a sharp increase in protein density at the boundary of the Xi. Whether SMCs themselves exhibit features of liquid-liquid phase separation and whether the progressive coalescence of chromatin regions induces polymer-polymer phase separation (Frank and Rippe, 2020) remains to be determined.

2. A SMC-Based Model of XCI

The overall synthesis of our work is a fundamentally new model for how Xist establishes the Xi compartment and orchestrates gradual transcriptional silencing (FIG. 25N). Through expression, diffusion, sequestration, and degradation (see section "Expression-diffusion-degradation model for Xist confinement" in Methods), two Xist transcripts become localized and tightly bound to chromatin, initially seeding SMCs at 50 regions that are proximal to the Xist locus and enriched for rapidly silencing genes. By seeding high local concentrations of transiently binding effector proteins in SMCs, Xist induces gradients of silencing proteins, most importantly of SPEN, that can act at genomic locations on the X without their direct association with Xist. This process initiates silencing of early genes on the pre-Xi.

The high concentration of PRC1, SCMHD1 and likely other architectural regulators brought about by SMCs progressively induces higher-order chromatin changes and compaction. Compaction promotes the introduction of more DNA regions, particularly those including late silencing genes, and the overall densification of genes under the Xist-SMC cluster. This process increases the concentration of SPEN in the vicinity of more genes, expanding silencing across the entire X. A constant number of SMCs thereby gains access to an increasing number of genes. However, the presence of an SMC per se is not sufficient to induce effective silencing as genomic regions that are poorly crowded by SMCs silence less efficiently.

By showing that SMC formation and chromatin compaction are interdependent mechanisms, our model fills the knowledge gap of how different repressive pathways cooperate in XCI. The iterative process of establishing SMCs, modifying chromosome architecture and inducing silencing, explains why Xist can induce XCI robustly in each cell, even though the precise location of SMCs and the dynamics of gene silencing and compaction may vary between individual cells.

3. Implications Beyond Xist

Phase separation has recently emerged as a much-debated mechanism in the field of gene regulation (McSwiggen et al., 2019). Yet, the functional role of condensates in gene regulation remains largely undefined. Macromolecular crowding as the mode of heterochromatin formation, described here, expands transcriptional control beyond the seeding molecule. This mechanism may be particularly important for gene regulatory RNAs, typically expressed at low numbers relative to their targets (Cabili et al., 2015; Derrien et al., 2012). Intriguingly, other lncRNAs have also been found to induce spreading of Polycomb complexes (Schertzer et al., 2019), suggesting that a common mechanism in the organization of an efficient repressive nuclear compartment may involve enzymes that induce transcriptional repression together with regulators of chromatin architecture.

4. Limitations of the Study

In this study, we applied super-resolution imaging in combination with kinetic modeling, genomic approaches and functional perturbations to uncover fundamental principles of RNA-seeded nuclear compartmentalization. While the multi-spectral quantitative super-resolution imaging allowed us to explore the spatial relationships of RNA, DNA and protein in individual cells, it is subject to physical limitations. With the resolution of 3D-SIM, we can resolve the distribution of XCI effectors down to few hundreds of kb along the genome. This does not allow us to examine if these effectors are enriched at specific genes which would require even higher resolution (Xie and Liu, 2021). Furthermore, there is a limited number of individual fluorophores that can be employed and thus we are not able to detect several SMC proteins simultaneously with Xist, genes, and gene transcripts. Therefore, we are not able to pinpoint the distributions of various proteins, such as PCGF5 and SPEN, at specific genomic loci and to directly determine what changes trigger the switch from the active to a repressed state. Additionally, fixation, permeabilization, and heat-denaturation applied in FISH or immunodetection experiments solubilize a considerable amount of protein. This suggests that we may be underestimating the protein levels in SMCs. Finally, although a sharp boundary needs to be determined in segmentation-based image analysis, as employed in our study, SMCs likely do not have a defined structure, as kinetic modeling suggests that fast-exchanging proteins result in more graded, distributed structures. Despite these limitations, super-resolution microscopy was critical for disentangling the processes of gene silencing and chromatin reconfiguration and allowed us to distinguish Xist from its protein interactors as functionally distinct entities in the Xi space.

C. STAR Methods

1. Cell Culture

Female mouse polymorphic 129S4/SvJae/castaneus F1 2-1 ESCs (Panning et al., 1997) and its engineered derivatives were grown on 0.5% gelatin-coated flasks seeded with irradiated DR4 feeders (obtained from day 14.5 embryos with appropriate animal protocols in place). Cultures were maintained in mouse ESC medium containing knockout medium DMEM (Life Technologies), 15% FBS (Omega), 2 mM L-glutamine (Life Technologies), 1×NEAA (Life Technologies), 0.1 mM β-Mercaptoethanol (Sigma), 1× Penicillin/Streptomycin (Life Technologies), and 1000 U/ml mouse LIF (homemade) in 5% CO2, 37° C. incubators.

For all EpiLC differentiation experiments, cells were adjusted for 3 passages to feeder-free conditions in the presence of 1000 U/ml LIF and two inhibitors, CHIR99021 (3 μM) and PD0325901 (0.4 μM) (2i+LIF). Epiblast-like (EpiLC) differentiation was performed as described in (Hayashi and Saitou, 2013). Briefly, cells were maintained for 3 passages in serum-free, 2i+LIF N2B27 media containing 1×N2 supplement and 1×B27 supplement (Thermo Fischer), 2 mM L-glutamine (Life Technologies), 1×NEAA (Life Technologies), 0.1 mM β-Mercaptoethanol (Sigma), 0.5× Penicillin/Streptomycin (Life Technologies) prior to EpiLC differentiation. To induce differentiation, cells were dissociated and seeded at a density of $2\times10^5$ cells/ml in N2B27 media containing 20 ng/ml Activin A and 12 ng/ml bFGF on geltrex-coated flasks or coverslips. For experiments extending beyond day 4 of differentiation, we applied a protocol previously described in (Ying and Smith, 2003). Briefly, at day 4 of differentiation, EpiLCs were dissociated with accutase and seeded on geltrex-coated coverslips at a density of $5\times10^5$ cells/cm$^2$. Cells were then grown in N2B27 media supplemented with EGF and FGF (10 ng/ml each), on geltrex-coated coverslips for 4 more days (d8 of differentiation). At this developmental stage, cells have lost Tsix expression as observed in FIG. 19B. Media was exchanged daily.

TX1072, female polymorphic B16/castaneus mouse ESCs lines, carrying a tetO-promoter driving the endogenous Xist allele on the B16 X chromosome ($B6^{tetOXist}Cas^{WTXist}$) and a homozygous insertion of the GFP or Halo tag in the endogenous Spen loci or an endogenous SPOC deletion (ΔSPOC-SPEN-GFP) (Dossin et al., 2020), as well as the ΔIDR-SPEN-GFP and the Rosa26 knockins derivative cell lines generated in this study, were grown on gelatin-coated flasks in feeder-free conditions (2i+LIF) and EpiLC differentiation was performed as described for the F1 2-1 ESCs. When induction of XCI was performed from the tetO-Xist, 0.5 μg/ml doxycycline were added to ESC media without 2i+LIF for 24 hrs. Similarly, male tetO-Xist ESCs were grown on gelatin-coated flasks in feeder-free conditions and induction of Xist expression was performed with addition of 0.5 μg/ml doxycycline in ESC media for 18 to 24 hrs.

For auxin-mediated depletion experiments of TX1072 ESCs expressing SPEN-AID-GFP and Rosa26 rescue knockins, auxin was added to ESC 2i+LIF media at 500 μM for 12 hrs. Following, cells were dissociated by trypsinization and seeded in ESC media without 2i+LIF including 500 μM auxin and 0.5 μg/ml doxycycline for 24 hrs.

C127 cells were purchased from ATCC and human fibroblasts containing abnormal X-chromosomes (GM3827, GM00735, GM06960, GM07213) were obtained from Coriell. These cell lines were cultured in DMEM (Life Technologies), 15% FBS (Omega), 2 mM L-glutamine (Life Technologies) and 1× Penicillin/Streptomycin (Life Technologies).

D. Method Details

1. Plasmid Construction for Engineered Cell Lines

Plasmids containing the 24×MS2 repeats (#31865) and MS2-Coat-Protein-GFP (MCP-GFP) coding sequence (#27121) were obtained from Addgene. The pBglII5k plasmid was used for targeting the 24×MS2 repeats into Xist (Jonkers et al., 2008) and contains homology arms for insertion into exon 7 of Xist, downstream of the E-repeat sequence, and a floxed neomycin resistance cassette. The 24×MS2 repeats were excised from plasmid #31865 by restriction digest with BglII and BamHI and inserted into the pBglII5k plasmid by Infusion cloning yielding the pBglII5k-24×MS2 plasmid (which replaces the 16×MS2 repeat array originally contained in the pBglII5k plasmid). The coding region for MCP-GFP was amplified by PCR and introduced under control of a tetracycline-inducible promoter (tetO) into the pBS31 plasmid (pgkATGfrt) (Beard et al., 2006) by infusion cloning yielding pBS31-MCP-GFP. A reverse tetracycline TransActivator (rtTA3) cassette containing the PGK promoter and a BGH polyA element was amplified by PCR from the MXS_PGK::rtTA3-bGHpA plasmid (#62446, Addgene) and introduced into the unique AscI site of pBS31-MCP-GFP, downstream of the tetO-MCP-GFP-polyA insert, by Infusion cloning, resulting in the pBS31-MCP-GFP-rtTA3 plasmid. For deletion of the B-repeat of Xist the p13-5-Xist-Bdel plasmid was constructed from PCR-amplified 5' and 3' homology regions obtained from the PCV-Xist-PA plasmid and a loxP-flanked hygroTK cassette that replaces the B-repeat sequence (chrX: 103480156-103480430, mm10) that were inserted into a PBS-KS (+) plasmid.

2. Plasmid Construction to Generate Transgenic Lines

For the integration of transgenes expressing various mCherry or Halo protein fusions under the control of the endogenous Rosa26 promoter in $Xist^{MS2\text{-}GFP}$ ESCs, we employed a parent plasmid harboring homology arms for targeting the Rosa26 locus and a loxP-flanked puromycin cassette for antibiotic selection (R26-SA-EGFP-puro). A splice-acceptor (SA) sequence and a splice-donor (SD) coding sequence were synthesized by Genewiz and inserted into the R26-SA-EGFP-puro, after MluI/MfeI restriction digest to remove the GFP, by Infusion reaction. The resulting pYM215-R26-SA/SD-puro plasmid was used as the parent plasmid for insertion of all protein fusions in three-piece infusion reactions. The coding sequence for CIZ1 was amplified from donor plasmid pBS32-MCP-CIZ1. Coding sequences for histone H2B and mCherry were amplified from a H2B-mCherry plasmid (Addgene, #20972) and the Halo cDNA was obtained from plasmid Halo-EasyFusion (Addgene, #112852). The coding sequences for PTBP1, PCGF5, and CELF1 were synthesized (Genewiz).

To generate the Spen-ΔRRM or ΔIDR-Halo plasmids introduced in $Xist^{MS2\text{-}GFP}$ ESCs or TX1072 ESCs, the full-length Spen Entry Clone (Sp22) was modified using Polymerase Incomplete Primer Extension-based mutagenesis with primers designed to delete amino acids 639-3460 or 1-591, respectively. Sp22 and the Spen-ΔIDR or Spen-ΔRRM entry clones, respectively, were inserted into the PyPP-CAG-Halo-V5-IRES-Puro destination vector using Gateway LR Recombination, generating PyPP-CAG-Halo-full-length-Spen-V5, PyPP-CAG-Halo-Spen-ΔIDR-V5 and PyPP-CAG-Halo-Spen-ΔRRM-V5, respectively, also containing an IRES-puromycin resistance cassette for selection. These plasmids enable constitutive expression of Spen variants with an N-terminal Halo tag and a C-terminal V5 tag and contain a polyoma episomal origin of replication for efficient propagation in mammalian cell culture.

For integration of the full length (FL-) and ΔIDR-SPEN-Halo transgenes into the SPEN-AID-GFP female ESC lines the previously described plasmid pDF46 for targeting into the Rosa26 locus was used (Dossin et al., 2020). Halo was amplified from plasmid Halo-EasyFusion (Addgene, #112852) and inserted upstream the SPEN coding sequence of pFD46 by Infusion cloning resulting in the plasmid pYM300. Similarly, the FL-SPEN coding sequence was excised from pFD46 by restriction digest and Infusion cloning was performed to insert Halo-ΔIDR-SPEN amplified from plasmid PyPP-CAG-Halo-Spen-ΔIDR-V5, resulting in plasmid pYM301. For the integration of FL-SPEN-Halo into the Xist-$FL^{cas}$Xist-$ΔB^{129}$ female ESCs and 36.11 cells, a male ESC line carrying an autosomal tetO-Xist transgene (on chromosome 11) (Wutz and Jaenisch, 2000) the same strategy was employed. All plasmids were verified by restriction digests and sequencing.

3. Targeting and Cell Line Generation

For targeting, F1 2-1 female ESC lines were grown on DR4 feeders. All targetings were performed by electroporation using the GenePulserII (Biorad). Approximately $2\times10^7$ cells and 50 μg of DNA were resuspended in 400 μl PBS in 4 mm diameter cuvettes and pulsed twice for 0.2 msec at 800V. To target the Rosa26 locus with plasmids pYM300 or pYM301 and pFD82, pFD83 in TX1072 ESCs expressing SPEN-AID-GFP, female F1 2-1 $Xist^{129ΔB/CasWT}$ ESCs and male ESCs carrying an autosomal tetO-Xist transgene (36.11) the 3D Nucleofector (Lonza) was used with program CG-104 and 100 μl cuvettes according to the manufacturer's instructions. Antibiotics were added to the growth media 24-36 hours after electroporation. Puromycin was used at 1.5 μg/ml, hygromycin at 130 μg/ml and G418 at 400 μg/ml. The culture medium containing the respective antibiotics was exchanged every 2 to 3 days. Once adequate colony growth was observed (1-2 weeks), 100-200 colonies were picked under a stereoscope, dissociated by trypsinization and seeded in 96-well plate replicates. One replicate plate was used for genomic DNA extraction and subsequent genotyping PCR. All positive clones used in this study were screened to ensure they maintain two X chromosomes in the undifferentiated state indicated by the presence of two Tsix transcripts in RNA FISH experiments and that gene silencing by Xist and normal Xist distribution across the X-territory upon induction of differentiation as applicable (FIGS. 19K and 26G, left).

4. Integration of 24×MS2 Repeats into the Xist Locus

The pBglII5k-24×MS2 plasmid was electroporated into the F1 2-1 ESC line after linearization with XhoI. The cell culture was exposed to neomycin selection 36 hrs post-electroporation. Colonies were picked and expanded for screening by genotyping PCR and RNA FISH with Xist and MS2 probes was performed on EpiLCs at day 4 as shown in FIG. 26G. We confirmed that the 24×MS2-repeat unit was introduced into the 129 allele (FIG. 26G, right). This observation comes in line with the known skewing of XCI in 129/Cas female cells, where ~80% of cells inactivate the 129 allele. The loxP-flanked neomycin resistance cassette was removed from targeted clones by transient expression of Cre-recombinase. Subsequently, a FRT-recombination site-containing a landing pad (FRT-neo plasmid) (Beard et al., 2006) was targeted into the Col1A locus (on chromosome 11) in F1 $2\text{-}1^{24\times MS2\text{-}Xist}$ ESCs. The MCP-GFP-rtTA3 expression cassette was then inserted into the FRT site by electroporation of a FlpO-recombinase-encoding plasmid and the pBS31-MCP-GFP-rtTA3 plasmid. The resulting ESC line was denoted as $Xist^{MS2\text{-}GFP}$.

5. Engineering Strategy to Delete the IDRs of SPEN

CRISPR/Cas9-based genome editing was used for the deletion of the IDRs of SPEN with two guide RNAs targeting intronic sequences flanking the IDR-encoding exons, which were synthesized by Synthego. Targeting was performed in the TX1072-SPEN-GFP cell line (Dossin et al., 2020). Cells were targeted using recombinant Cas9 protein (Synthego) and gRNAs with the 4D Nucleofector (Lonza). $\sim2.5\times10^5$ cells/ml were resuspended in 20 μl Lonza solution and electroporated with 1.8 μl of gRNA1 (5'-GAUGGCC-UAGAACUACAGGGUGG-3' (SEQ ID NO:1)), 1.8 μl gRNA2 (5'-CCUGUGUUAACACUUAGAGCAGC-3' (SEQ ID NO:2)) and 2.4 μl Cas9 using program CG-104. gRNA sequences are given in Table S2. Nucleofected cells were serially diluted and plated onto 10 cm dishes. Once adequate colony growth was observed (1-2 weeks), 100 colonies were picked under a stereoscope, dissociated by trypsinization, and seeded in 96-well plate replicates. One replicate plate was used for genomic DNA extraction and subsequent genotyping PCR. Genotyping PCR was performed as shown in FIG. 31A. Positive clones were selected based on an expected 605 bp band and sequenced to verify deletion. Biallelic expression was confirmed using RT-PCR with oligo-dT primers and sequencing as shown in FIG. 31B, scoring for SNPs in exon 5 (rs27580268) and exon 7 (rs223335536).

6. Engineering Strategy to Delete the B-Repeat of Xist

F1 2-1 ESC line previously targeted with an 12×MS2 tag in the large final Xist exon on the 129 allele (Jonkers et al., 2008) or male V6.5 ESCs expressing Xist under a tetO promoter (Engreitz et al., 2013) were electroporated with a linearized plasmid harboring homology arms for targeting into the B-repeat region of XIST and replacing it with a loxP-flanked hygroTK cassette for antibiotic selection. The loxP-flanked hygroTK resistance cassette was removed from targeted clones by transient expression of the Cre-recombinase and ganciclovir treatment. Genotyping and confirmation of deletion of the B-repeat in both cell lines and targeting on the 129 allele in F1 2-1 ESCs were performed by Southern blotting (not shown).

7. Expression of Cage$^{60GFP}$ in ESCs

The gene encoding ct-60 (cage$^{60GFP}$) was amplified by PCR from plasmid I3-01-ct60GFP (Hsia et al., 2016). The fragment was introduced under control of the CACGS promoter into the pBS32 plasmid by Infusion reaction yielding pBS32-cage$^{60GFP}$ and positive clones were confirmed by restriction digests and sequencing. The pBS32 plasmid was derived from the pBS31 plasmid upon replacement of the tetO promoter with a CAGGS promoter. To visualize both Xist$^{MS2-GFP}$ and cage$^{60GFP}$, Xist$^{MS2-GFP}$ ESCs were differentiated into EpiLCs to induce Xist expression and doxycycline was added at 0.5 μg/ml for 2 hrs to induce MCP-GFP expression. Expression of the cage$^{60GFP}$ was achieved by transient transfection of the pBS32-cage$^{60GFP}$ plasmid into differentiating cells by Lipofectamine3000 24 hours prior to imaging, according to the manufacturer's instructions.

8. Halo Labelling

For FRAP experiments of Halo-fused proteins, 5 μM of TMR Halo ligand was added to the culture medium for 30 min following a 30 min incubation in media without added ligand to wash-off unbound ligand. For fixed and live-cell 3D-SIM imaging, 1 μM JF549 or JF646 Halo ligands were introduced to the media for 15 min, washed-off twice with PBS and exchanged with fresh medium which was incubated for another 15 min. Live-cell imaging or fixation was done as described in the corresponding sections.

9. Immunofluorescence Staining

Immunodetection was performed as described in (Kraus et al., 2017). In brief, cells were grown on geltrex-coated high precision coverslips at the desired differentiation state. Coverslips were then transferred to new multi-well plates, washed three times with PBS and fixed with 2% formaldehyde dissolved in PBS for 10 min, followed by two washes with PBST (1×PBS, 0.05% Tween 20). Samples were then quenched for 10 min with 20 mM glycine in PBS. Following samples were washed with PBS and permeabilized with 0.5% Triton X-100 dissolved in PBS for 10 min and washed once with PBST. Samples were then blocked for 1 hr in blocking buffer (PBST, 2% BSA, 0.5% Fish skin gelatin) and incubated with primary antibodies diluted in blocking buffer for 1 hr in a humidified chamber at RT. Samples where then washed three times with PBST followed by incubation with secondary antibodies for 45 min and another round of PBST washes. Samples were then washed once with PBS, post-fixed with 4% formaldehyde dissolved in PBS for 10 min, followed by two washes with PBST. Chromatin counterstaining was performed using DAPI dissolved in PBST at a concentration of 2 μg/ml for 5 min. Samples were then washed four times with PBS, mounted on slides with Vectashield and sealed with Covergrip. For combined Halo ligand and antibody detection, cells were labelled with the Halo ligands as described in the Halo labeling section, fixed and processed by immunostaining. For the 4-color 3D-SIM imaging where we detect combinations of proteins together with Xist$^{MS2-GFP}$ (FIGS. 21D and 28A) we used CIZ1-Halo and CELF1 antibody staining, SPEN-Halo and CIZ1 antibody staining, PCGF5-Halo and CIZ1/CELF1 antibody staining. Halo transgenes were detected with the Halo ligand JF549 and primary antibodies with secondary antibodies conjugated to AlexaFluor647. In FIGS. 21H and 29C we used endogenous Halo-tagged SPEN (Dossin et al., 2020) and Halo transgenes for detection of CIZ1, PCGF5 and PTBP1 labelled by the Halo ligand JF549 and antibody stainings with primary and secondary antibodies conjugated to CF568 dye for CELF1, RYBP, EZH2 and hnRNP-K. In FIGS. 31C and 32D we used Halo transgenes FL-/ΔIDR-/ΔRRM-SPEN expressed in Xist$^{MS2-GFP}$ or F1 2-1 Xist$^{129\Delta B/CasWT}$ EpiLCs labelled by the Halo ligand JF549. In FIG. 21F, RYBP and CIZ1 are detected with antibodies and secondaries conjugated to CF568, while SPEN is stably integrated into the Rosa26 locus (plasmid YM301) and detected with the JF549 Halo ligand. In FIG. 5C, we detect the endogenous WT-SPEN-GFP or ΔIDR-SPEN-GFP with anti-GFP antibodies. We compared the distribution of the CIZ1-Halo fusion protein and the endogenous (antibody-stained) CIZ1 protein and show the same trend (FIG. 21B) similarly to the distribution of endogenously Halo- or GFP-tagged SPEN proteins to Halo tagged transgenes (FIGS. 21H, 23C and 31E).

10. Antibodies and Dilutions

Endogenous CELF1 was detected with monoclonal rabbit anti-CUG-BP1 antibody ab129115 (1/800; Abcam); hnRNP-K with polyclonal rabbit antibody A300-678A (1/800); MATR3 with polyclonal rabbit antibody IHC-00081 (1/200, Bethyl); RYBP (DEDAF) with polyclonal rabbit antibody AB3637 (1/1000; Sigma); Ezh2 with monoclonal rabbit antibody #5246 (1/500; Cell Signaling Technology); CIZ1 with a polyclonal rabbit antibody NB100-74624 (1/800; Novus Biologicals), and histone H3 phospho-Serine 10 with the polyclonal rabbit anti-histone H3-phospho-Serine10 #39253 (1/1000; Active Motif). GFP with a polyclonal rabbit antibody ab6556 (1/500, Abcam). Two secondary antibodies were used, including high cross-absorbed donkey anti-rabbit IgG CF568 antibody SAB4600076 (1/400; Sigma) and high cross-absorbed goat anti-rabbit IgG Alexa Fluor 647 antibody A21245 (1/400; Life Technologies).

11. FISH Probe Synthesis

Probes for DNA and RNA FISH experiments were labelled by Nick Translation (NT) as previously described (Cremer et al., 2008). Briefly, 1 μg of DNA was labelled in a 50 μl NT reaction for 8 hrs using 1.3-2.5 μl fluorescently-labelled dUTPs, 1 μl of DNA Polymerase (Thermo Fisher Scientific) and 2 μl of DNAse I (Sigma-Aldrich) from a stock which was freshly prepared by a 1:200 dilution in ice-cold H2O. NT reactions were purified using magnetic beads, probes were then resuspended in Nuclease-free H2O and ethanol-precipitated together with Salmon sperm and Cot1 DNA at −80C ON. After precipitation and washes with ethanol series (70-100%), probes were resuspended in deionized formamide with shaking at 37 C ON. Probes were then adjusted in hybridization buffer (50% formamide, 2×SSC, 10% dextran sulfate) and stored at −20 C. To create mouse Xist probes, we used a full-length mouse Xist cDNA plasmid (p15A-31-17.9 kb Xist). Human XIST probes were created from a full-length XIST cDNA construct. For assessing X-linked gene silencing, Atrx probes were synthesized using BAC RP23-265D6, Rlim probes using fosmid WI1-2704K12 and Mecp2 probes using fosmid WI-894A5. For the chromosome barcoding experiment, we used BACs RP23-53H15, RP23-83J1, RP23-451D5, RP24-81K23, RP24-374B8, RP23-401G5, RP23-104K18. To create an intronic probe against the first intron of Xist, the corresponding region was amplified from the Xist-encoding BAC RP23-223G18 and was labelled by NT. To create MS2 probes the corresponding region was amplified from plasmid #31865 (Addgene) and labelled by NT. For multispectral chromosome barcoding experiments, individual BAC s were labelled separately, pooled in a 1:1 ratio and used at 0.1 μg/cm$^2$. DNA from flow sorted mouse X-chromosomes was a gift from Irina Solovei and labelled using the Bioprimer kit according to the manufacturer's instructions. NT products were labelled with Atto488-dUTP, Alexa Fluor 568-dUTP, Cy3-dUTP, Cy5-dUTP, Texas Red-dUTP and chromosome paints were labelled with Atto448-dUTPs or Cy3-dUTPs. Probes used in this study include: FIG. 19B: Xist-Atto488, Rlim-AlexaFluor568, Atrx-Cy5; FIG. 19E: mmX-Atto488, Xist-Alexa568; FIG. 19H: Color-coded as green-Atto488, yellow-Cy3, red-Texas Red, magenta-Cy5; FIG. 23B: Xist-AlexaFluore568; FIG. 23D: Xist-Atto488, Rlim-, AtrX-AlexaFluor568; FIG. 24B: mmX-Atto488, MS2-AlexaFluor568, Xist-Cy5; FIG. 25B: Genes-Atto550, Transcript-Alexa647N; FIG. 25C, 25I: Early genes-Atto550, Late-genes-Alexa647N; FIG. 26B: Xist-Atto488, Mecp2-Cy3; FIG. 26G: MS2-Atto488, Xist-Cy3, Atrx-Cy5; FIG. 26H: Xist-Atto488; FIG. 27A: Xist-Atto488; FIG. 27C: XIST-Atto488; FIG. 27E: Xist-Atto488, Xist Intron1-Cy3; FIGS. 30A and 30B: Xist-Atto488; FIGS. 31B and 31D: Xist-Atto488. All BACs and fosmids used in this study were purchased from CHORI-BACPAC.

12. Oligo FISH Probe Design and Synthesis

We selected 20 early (half time [0-0.4] days) and 20 very late (half time [1-1.6] days) silencing genes from published silencing kinetics data (Barros de Andrade et al., 2019) that are longer than 10 kb and have high expression levels in ESCs. To ensure the assessment of genes across the length of the chromosome, we selected no more than five genes per early or late silencing group from each 10 Mb region of the X chromosome.

The resulting early silencing genes were: ENSMUSG00000025862, ENSMUSG00000055780, ENSMUSG00000036022, ENSMUSG00000023092, ENSMUSG00000000838, ENSMUSG00000016382, ENSMUSG00000025246, ENSMUSG00000025059, ENSMUSG00000035232, ENSMUSG00000050332, ENSMUSG00000079487, ENSMUSG00000034055, ENSMUSG00000056537, ENSMUSG00000046449, ENSMUSG00000031333, ENSMUSG00000031232, ENSMUSG00000025531, ENSMUSG00000025271, ENSMUSG00000041649, ENSMUSG00000025289.

The late silencing genes were: ENSMUSG00000031161, ENSMUSG00000040363, ENSMUSG00000031012, ENSMUSG00000031060, ENSMUSG00000001173, ENSMUSG00000063785, ENSMUSG00000025630, ENSMUSG00000031351, ENSMUSG00000002015, ENSMUSG00000031328, ENSMUSG00000031197, ENSMUSG00000006678, ENSMUSG00000035150, ENSMUSG00000034480, ENSMUSG00000041229, ENSMUSG00000045180, ENSMUSG00000046873, ENSMUSG00000067194, ENSMUSG00000079316, ENSMUSG00000031352.

We note that the first 40 Mb of the chromosome are poor in early-silencing genes that provide high expression levels (RPKMs) for sufficient detection by oligonucleotide FISH. Custom fluorescent oligonucleotide probe pools (MyTags) targeting either genes or their corresponding transcripts were designed and synthesized by Daicel Arbor Biosciences. To detect nascent gene transcripts, ~500 45 bp oligonucleotide probes targeting gene introns downstream from the transcriptional start site of the gene were synthesized spanning 31 to 68 kb. To detect genes, ~500 45 bp anti-sense oligonucleotide probes targeting upstream from the transcriptional start site were synthesized, spanning between 31 to 61 kb. Probe sequences are given in Table S2.

13. RNA/DNA and Immuno-RNA FISH

RNA and DNA FISH experiments were conducted as previously described (Markaki et al., 2013). Briefly, cells were grown on geltrex-coated high precision coverslips at the desired differentiation state. Coverslips were then transferred to new multi-well plates, washed three times with PBS and fixed with 3% formaldehyde dissolved in PBS for 10 min, followed by two washes with PBS. Samples were then quenched for 10 min with 20 mM glycine in PBS. Following, samples were washed with PBS and permeabilized with 0.5% Triton X-100 dissolved in PBS for 15 min, washed twice with PBST, equilibrated in 2×SSC for 10 min and incubated for 30 min to 2 hrs with 50% formamide/2× SSC. Probes were denatured at 76 C for 7 min and kept on ice. To hybridize the specimens, probes were spotted on slides and coverslips were placed on the probes and sealed with rubber cement. All probes were used at 0.1 μg/cm$^2$ and oligonucleotide probes were used at 10 μmol/cm$^2$. For DNA FISH, a denaturation step was performed for 2 min at 76 C. Samples were then hybridized in a humidified chamber at 37 C ON. After demounting coverslips, unbound probes were washed-off with three 20 min washes with 2×SSCT (2×SSC, 0.5% Tween 20) under mild shaking, followed by three 5 min washes with 4×SSCT. For DNA FISH samples were washed with three additional 5 min washes with 0.1×SSC. Following, samples were post-fixed and chromatin was counterstained with DAPI as described in the Immunofluorescence staining section. For sequential RNA and DNA FISH experiments with X chromosome paints (mmX paints) or oligonucleotide probes and Xist probes, RNA FISH was performed first, samples were post-fixed and DNA FISH followed. For the detection of SPEN proteins fused to GFP together with Xist RNA, detected by FISH probes, immunodetection was performed first, samples were post-fixed and RNA FISH followed.

14. Confocal Laser Scanning Microscopy

Confocal and improved confocal (Airyscan detector) laser scanning microscopy was performed on the LSM880 platform equipped with 100×/1.46NA or 63×/1.4 NA plan Apochromat oil objectives and 405/488 diode and 594 Helium-Neon lasers (Carl Zeiss Microscopy, Thornwood, NY). To optimize imaging and reduce photobleaching, the regions of interest in each case were marked at the appropriate magnifications were used. The pixel size and z-optical sectioning were set to meet the Nyquist sampling criterion in each case. Airyscan raw data were reconstructed using the ZEN Black (v2.3) software.

For the detection of genomic regions across the X chromosome with spectral barcoding, cells were seeded on gridded coverslips and DNA FISH was performed first. 5-color optical z-stacks of 0.35 μm were acquired on a confocal Zeiss LSM880 system. Grid coordinates were recorded and spatial coordinates of the acquired positions were recorded on the ZEN Black software and saved. Following samples were equilibrated with 50% formamide in 2×SSC pH 7.2 solution for 3 hours at 37° C. followed by RNA FISH with Cy3-labelled Xist probes. Specimens were returned to the microscope stage and saved spatial coordinates were revisited to acquire the Xist RNA signal and discriminate between the Xi and Xa in downstream analyses. Although hybridization of RNA usually precedes DNA FISH, we have found that Xist RNA is remarkably stable during the sequential process. Since the sequential hybridization for this experiment was only necessary for the scoring of the Xi, without the need for harsh probe strip-off steps, RNA FISH was performed last.

15. Detection of Cell Cycle Stages

To discriminate between different cell cycle stages, we used a combination of EdU pulse labelling, to detect S-phase cells, and anti-histone H3-phospho-Serine10 (Active Motif, #39253), to detect G2/M phase cells, while G1 cells remained marker-free. EdU and click-iT labeling were performed according to the manufacturer's instructions. A 10 mM EdU stock solution was diluted 1:1000 in growth media and cells were pulsed for 20 minutes prior to fixation. RNA FISH with Xist RNA probes was performed in the 488 channel and detection of EdU by click-iT reaction with CF dye Azide 568 (Biotium, #92082) were combined with immunodetection of phospho-histone H3 Serine 10 and secondary antibodies conjugated to CF568, where RNA FISH was performed first (Markaki et al., 2013). For the assessment of Xist foci features and number throughout the cell cycle in EpiLCs (at day 4 of differentiation), we used the $Xist^{MS2-GFP}$ cell line and detected $Xist^{MS2-GFP}$ signals after addition of 0.5 μg/ml doxycycline for 2 hrs.

16. Super-Resolution Microscopy

3D-Structured Illumination Microscopy (3D-SIM) was performed on a DeltaVision OMX-SR system (Cytiva, Marlborough, MA, USA) equipped with a 60×/1.42 NA Plan Apo oil immersion objective (Olympus, Tokyo, Japan), sCMOS cameras (PCO, Kelheim, Germany) and 405, 488, 642 nm diode lasers and a 568 nm DPSS laser. Image stacks were acquired on the OMX AcquireSR software package 4.4.9934 with a z-steps of 125 nm and with 15 raw images per plane (five phases, three angles). Raw data were computationally reconstructed with the soft-WoRx 7.0.0 software package (Cytiva, Marlborough, MA, USA) using a Wiener filter set at 0.001 to 0.002 (up to 0.006 for DAPI) and optical transfer functions (OTFs) measured specifically for each channel using immersion oil with different refractive indices (RIs) as described in (Demmerle et al., 2017; Kraus et al., 2017). Images from different channels were registered using alignment parameters obtained from a calibration slide of 100 nm gold grid holes and a second calibration for axial alignment using 100 nm diameter Tetraspeck beads according to established procedures (Demmerle et al., 2017).

17. Live-Cell Imaging

Wide-field and confocal scanning microscopy (for FRAP experiments) or 3D-SIM live-cell imaging (4D-SIM) were performed at 37° C. (for 3D-SIM in conjunction with an objective heater), with 5% $CO_2$, controlled humidity and 10% $O_2$, having equilibrated the system and immersion oils for at least five hours prior to acquisitions. This equilibration was particularly important for obtaining artifact-free 3D-SIM datasets and minimize stage drift. Cells were differentiated in geltrex-coated chambers fitted with a high precision glass (ibidi) with daily exchange of media. To induce MCP-GFP expression, doxycycline was added to the cells two hours prior to acquisitions at a concentration of 1 μg/ml for 2 hrs prior to imaging. Imaging was performed in media containing no phenol red and supplemented with ProlongLive Antifade reagent (Thermo Fisher). For live-cell 3D-SIM imaging, typically 1 μm to 2 μm stacks of 125 nm z-sections were acquired in 1- or 2-color 3D-SIM imaging to obtain 240-500 raw images per frame in 5-8 second intervals depending on exposure times and z-depth. Photobleaching over time was corrected by using histogram matching on the BleachCorrection plugin in ImageJ/Fiji.

18. FRAP Experiments

FRAP experiments with z-sectioning for $Xist^{MS2-GFP}$ and CIZ1-mCherry were performed on an LSM880 equipped with an Airyscan on a Plan-Apochromat 63×1.4NA oil immersion objective, an image size of 67.5 μm×67.5 μm with a pixel size of 0.085 μm. Z-optical stacks of 0.5 μm were obtained through a 15 μm z-depth. Bleaching was performed in ROIs demarcating the Xist territory or corresponding nuclear (control) regions at full laser power and 4 iterations with a pixel dwell time of 4.04 μsec. The first post-bleach frame was acquired immediately after bleaching. Time series were acquired every 1.3 minutes up to 10 frames and every 2 minutes thereafter for a total of 30 minutes with an Argon ion 488 nm laser or a DPSS 561 nm laser set to 1% laser power.

Single-plane FRAP experiments for all other proteins were performed on the OMX-SR platform in widefield mode and an image size of 512×512 pixels with a pixel size of 0.08 μm. In these experiments we employed transgenic cells lines carrying mCherry-tagged CIZ1 and CELF1 and carrying Halo-tagged FL-/ΔIDR-/ΔRMM-SPEN, PCGF5 and PTBP1, respectively (FIGS. 22F, 30D and 31E). Images were acquired for $Xist^{MS2-GFP}$ in the 488 nm channel (95 MHz—6% amplitude, 20 msec) and for all mCherry- or Halo-fused-TMR proteins in the 568 nm channel (272 MHz, 6% amplitude, 50-100 ms exposure). Bleaching in ROIs demarcating the Xist territory or corresponding nuclear (control) regions was performed by using the 568 nm laser line in the Ring-TIRF/PK photokinetics module with a bleach spot of 1 μm for one iteration for 0.1 seconds.

19. RNA-Antisense Purification (RAP)-Seq

F1 2-1 female mouse ESCs were seeded on geltrex-coated plates and differentiated for 2 or 4 days. $5\times10^6$ cells were collected per condition after dissociation by accutase and RAP-seq was performed (Engreitz et al., 2013). Briefly, harvested cells were incubated for 45 minutes with 2 mM DSG in PBS at RT, crosslinked with 3% formaldehyde for 10 min and quenched with 500 mM glycine. Following, cells were pelleted at 1,500×g for 5 min and flash frozen. Pellets were resuspended in 10 ml nuclear extraction buffer LB1 containing 50 mM HEPES-KOH (pH 7.5), 140 mM NaCl, 1 mM EDTA, 10% (vol/vol) glycerol, 0.5% (vol/vol) NP-40/Igepal CA-630 and 0.25% (vol/vol) Triton X-100 and incubated for 10 min with rotation at 4 C, then pelleted at 2000×g for 5 min and the same procedure was followed with buffer LB2, containing 10 mM Tris-HCL (pH 8.0), 200 mM NaCl, 1 mM EDTA and 0.5 mM EGTA (Mohammed et al., 2016). For cell lysis, nuclei were resuspended in 300 μl buffer LB3 containing 10 mM Tris-HCl (pH 8.0), 100 mM NaCl, 1 mM EDTA, 0.5 mM EGTA, 0.1% (wt/vol) sodium deoxycholate and 0.5% (vol/vol) N-lauroylsarcosine and sonicated on ice using a Misonix S-400 sonicator with microtip for 2 min with 1 sec pulses intermitted by 3 sec pauses. Chromatin was then digested using TURBO DNase at a concentration of 0.1-0.4 U/μl at 37 C for 15 min. For each pulldown library, an input library was also generated. The RNA pulldown was performed using 50 pmol of 90 nt long biotinylated oligonucleotide probes for every $5\times10^6$ cells and 1 mg of Streptavidin C1 beads. DNA was eluted by RNase H digestion, and the crosslinks were reversed by proteinase K digestion of the eluted DNA at 60° C. The DNA libraries were prepared using NEB Next Ultra End Rpair/dA-Tailing Module (NEB) and TruSeq DNA adapters (Illumina) were ligated using Quick Ligase (NEB). Libraries were amplified by KAPA HiFi Polymerase, pooled and sequenced on the Illlumina HiSeq 6000 platform to generate 50 bp pair-end reads. Probe sequences are given in Table S2.

20. Single Cell RNA-Seq scRNA-seq was performed in the female Cas/129 F1 2-1 $Xist^{129WT/CasWT}$ and the $Xist^{129\Delta B/CasWT}$ ESC lines at days 2 and days 4 of EpiLC differentiation. For the $B6^{tetOXist}Cas^{WTXist}$ ESC lines expressing SPEN-GFP or ΔSPOC-SPEN-GFP (Dossin et al., 2020) and ΔIDR-SPEN-GFP generated in this study, scRNA-seq was performed without (Oh) or with (24 hr) of 0.5 μg/ml doxycycline to induce tetO-Xist expression.

Cells were dissociated with accutase for 5 minutes, washed 3 times with DPBS and resuspended in PBS containing 0.04% BSA. Cell concentration was adjusted between 800 to 1200 cells/μl and cell suspension was kept on ice before loading on the 10× Genomics Chromium instrument. scRNA-seq libraries were generated using the Chromium single cell 3' reagent kit V3.1. Individual libraries were designed to target up to 10,000 cells. Libraries were generated following manufacturer's instructions and library fragment size distribution was determined by BioAnalyzer. Libraries were pooled and sequenced on the Illumina Novaseq 6000 platform to generate 100 bp pair-end reads.

21. Bulk RNA-Seq

Bulk mRNA-seq libraries were generated from $B6^{tetOXist}Cas^{WTXist}$ homozygously expressing WT-SPEN-AID-GFP (Dossin et al., 2020) and auxin degraded WT-SPEN-AID-GFP with no Rosa26 knockin rescue, full length (FL)-SPEN Rosa26 knockin rescue, or ΔIDR-SPEN Rosa26 knockin rescue at 0 h and 24 h dox treatment. Cells grown and treated as described above were washed with DPBS and collected into TRI reagent. Lysates were processed immediately or snap-frozen in liquid nitrogen and stored at −80C for up to 3 days. All conditions were collected from three biological replicates where samples for each replicate were processed at the same time. RNA was isolated using the Zymo Research RNA miniprep isolation kit according to manufacturer's instructions. RNA-seq libraries were prepared using the TrueSeq Stranded mRNA Library Prep Kit according to manufacturer's instructions. Libraries were pooled and sequenced on the Illumina Novaseq 6000 platform to generate 100 bp pair-end reads.

22. CLAP-Seq

CLAP-seq libraries were generated from TX1072 ESC lines expressing the FL-, ΔIDR- or ΔRRM-Halo-SPEN at day 4 of differentiation with the addition of 0.5 μg/ml doxycycline for the last 24 hrs to induce tetO-Xist expression. For each pulldown library, an input library was also generated. ~$50\times10^6$ cells were collected for each replicate. Cells grown on gelatin-coated 150 $cm^2$ culture dishes were washed three times with ice-cold PBS and UV-cross-linked on ice using 0.25 Jcm-2 (UV2.5 k) of UV at 254 nm in a Spectrolinker UV Crosslinker. Cells were then collected through scraping on ice and centrifuged at 1,500×g for 5 min, washed once with PBS and pelleted by centrifugation in aliquots of $5\times10^6$ cells. Pellets were snap frozen in liquid nitrogen for storage at −80 C. CLAP-seq using the HaloLink Resin to pulldown the Halo-tagged proteins was performed as previously described (Quinodoz et al., 2020). In brief, each pellet was lysed for 10 min in 1 ml Lysis buffer containing 50 mM HEPES, pH 7.4, 100 mM NaCl, 1% NP-40, 0.1% SDS, 0.5% Sodium Deoxycholate, 1× Protease Inhibitor Cocktail (Promega), 200U of Murine RNase Inhibitor, 20U Turbo DNase and 1× Manganese/Calcium Mix (0.5 mM CaCl2, 2.5 mM MnCl2) at 37 C. Lysates were pelleted at 800×g for 8 min at 4 C, the supernatant was removed and pellets were resuspended in 1 ml Lysis buffer and sonicated for 30 sec with 0.7 sec pulses intermitted by 2.3 sec pauses. After removal a 10 min incubation at 37 C, samples were pelleted at 15,000×g for 2 min and the resulting supernatant was collected and stored on ice. The HaloLink Resin was washed three times in Wash buffer (1×PBS, 0.1% Triton) and blocked for 20 min in Blocking buffer (50 mM HEPES, pH 7.5, 10 μg/ml Random 9-mer, 100 μg/ml BSA). Following the HaloLink Resin was incubated with the supernatant for 3-16 hrs under rotation at 4 C. After incubation, three washes in Wash buffer were performed at RT and three additional washes at 90 C for 2 min with the following buffers: NLS buffer (50 mM HEPES pH 7.5, 2% NLS, 10 mM EDTA, 0.1% NP-40, 10 mM DTT), High Salt Buffer (50 mM HEPES pH 7.5, 10 mM EDTA, 0.1% NP-40, 1M NaCl), 8M Urea Buffer (50 mM HEPES pH 7.5, 10 mM EDTA, 0.1% NP-40, 8 M Urea) and Tween buffer (50 mM HEPES pH 7.5, 0.1% Tween 20, 10 mM EDTA). The HaloLink Resin was then equilibrated by washing three times with Elution buffer (50 mM HEPES pH 7.5, 0.5 mM EDTA, 0.1% NP-40) at 30 C and elution was performed by resuspension in 100 μl of NLS buffer containing 10% Proteinase K and shaking at 50° C. for 30 minutes. Successful elution of the Halo-fused proteins was tested by Western blotting. After elution RNA overhangs were repaired by treatment with FastAP and T4 Polynucleotide Kinase with no ATP at 37° C. for 15 min and 1 hr, respectively. The RNA was then reverse transcribed and cDNA was synthesized using Suprescript III according to the manufacturer's instructions. Following the DNA was amplified by PCR using illumina sequencing adaptors libraries, pooled and sequenced on the Illlumina HiSeq 6000 platform to generate 100 bp pair-end reads.

E. Quantification and Statistical Analysis

1. Quantitative 3D-SIM Analyses

For image segmentation and image objects (particles) determination, 32-bit raw datasets were imported into ImageJ/Fiji (Schindelin et al., 2012) and converted to 16-bit tiff composite stacks. The segmentation of Xist and protein particles (foci) was performed as previously described in (Kraus et al., 2017) using the TANGO suite (Ollion et al., 2013). Specifically, raw datasets without filtering or subtraction of signals were imported into the segmentation pipeline. Image segmentation pipelines, adjustment of thresholds and creation of seeds were performed using high-throughput batch-processing and without manual intervention. Resulting masks of segmented particles were inspected by overlays over the raw data to ensure that the majority of signals were contained in the area to be analyzed. Nuclear masks were created using the DAPI channel as the segmentation volume. For each channel, a duplicate was generated and filtered with a 3D Gaussian filter with standard deviation of 1 (σ=1) and a Tophat filter with a radius of two pixels in xy and a one-pixel radius in z. The filtered image was segmented using the 3D Suite's Watershed method. Seed threshold and image threshold for watershed were calculated by equations Mean+StdDev*2*seed multiplier and (Mean+StdDev*2*seed multiplier)/image multiplier (Signal-to-Noise Ratio, SNR), respectively, where seed multiplier and image multiplier were determined and inspected manually to ensure the inclusion of all the regions of interest (ROIs) and the removal of background noise. Object features and distance measurements were performed using the 3D ImageJ Suite's "Measure 3D", "Quantif 3D" and "Distance" option plugins for ImageJ/Fiji.

For the assessment of the cage$^{60GFP}$ versus Xist signals, Xist$^{MS2\text{-}GFP}$ cells expressing the cage$^{60GFP}$ plasmid were typically imaged in the same Field of View (FOV) as cells with the Xist$^{MS2\text{-}GFP}$ signal, allowing us to obtain data that could be directly compared. When cells expressed both entities, since the cages are located in the cytosol in the majority of cells, nuclear masks from the DAPI channel were created and Xist$^{MS2\text{-}GFP}$ signals were measured inside the masked regions, whereas the signal from the GFP-expressing cages was measured outside the nuclear masks. For the comparison of intensities of cages expressed in the cytosol or in the nucleus same masking procedure was applied. The variability of the integrated density of fluorescent cages imaged under 3D-SIM conditions was compared to that obtained by a similar analysis in the original publication (Hsia et al., 2016) and found that results are within the same range. The number of Xist foci is typically lower when detecting the RNA via MCP-GFP compared to detection by RNA FISH using probes that cover the entire spliced transcript. The labelling with FISH probes captures the entire RNA molecule in contrast to MCP-GFP, which detects a region in the last large exon of Xist downstream to the E-repeat sequence. Therefore, RNA FISH-based detection results in slightly larger and possibly more complex Xist structure. Moreover, the different average number of Xist foci between cells at D2, D4, D8 of differentiation or in C127 cells, defined across the cell population without discriminating cell cycle stage (FIGS. 19L, 26I, and 27B), is likely a reflection of different populations of cells across the different cell states.

For the comparison of the integrated densities of SPEN-GFP and cage$^{60GFP}$, cells expressing the cage$^{60GFP}$ plasmid and cells expressing SPEN-GFP after addition of 0.5 μg/ml doxycycline, to induce expression of the tetO-Bglmcherry-Xist, were imaged under the same settings and processed datasets with the same threshold to define seeds and objects (particles). We found that the increase in Xist-associated SPEN accumulation over time observed from the D2 to D4 transition also occurs with doxycycline induction at similar levels between 6 and 18 hrs of Xist induction. Moreover, the levels of SPEN in SMCs are the same upon tetO-Xist induction at 18 hrs as for WT-Xist at D4 of differentiation (not shown).

To extract global nuclear protein particle features (in and outside the Xi) such as mean intensity, integrated density (amount of fluorescence per defined particle volume) and volume, masks of the protein signals of interest were created by filtering raw data with a 3D Gaussian blur followed by automatic thresholding to include all signals and exclude nucleoli. ROIs within a 4 μm radius of Xist centroids were selected for features extraction to limit computation time to ~1 hour per nucleus. Nearest neighbor centroid distances and all distances between ROIs within each channel and across different channels were extracted using the 3D ImageJ Suite for minimal distance and average distance analysis, respectively. Distance averaging was performed in Python. Assignment of Xist-associated signals was based on a proximity threshold to Xist centroids with a radius of 250 nm. Signals 500 nm away from Xist centroids, resulting in a 'rim' around the Xi due to the scattering of many Xist foci throughout the Xi, were defined as the nuclear fraction. To test the specificity of the tight spatial association of Xist and its associated protein particles in the Xi we performed randomized controls (FIG. 29D). We first determined the Xi territory by generating voxel arrays corresponding to a 350 nm radius from Xist foci centroids. The overlapping (double-called) voxels were removed. We then generated random positions equal to Xist-associated protein particles within the Xi masks of each nucleus using Python's numpy.random.choice function. We found a statistically significant difference between the nearest-neighbor Xist-associated protein particle to Xist compared to the randomized positions. The comparison of protein features, such as integrated density of fluorescence and volume, was performed by measurements acquired in the same laser line (568 nm) for all proteins detected either with the Halo ligand JF549 or primary and secondary antibodies conjugated to CF568 dye. For each experiment, ROIs with integrated density and volume values below the 10th percentile or above the 90th percentile of the dataset were removed as outliers.

For the oligo-FISH analysis, signal centroid from 3D-SIM data were extracted as described above using the 3D ImageJ Suite. Signal coordinates were imported into Python using Pandas and separated by cell and signal type (late, early, DNA, RNA, Xist) into NumPy arrays. We detected on average ~10-30 foci for each gene pool per X chromosome. Numbers in the higher range can likely be explained by the detection of some genomic regions as doublets after DNA replication or the segmentation of extended structures. Xist cluster centroids were calculated for each nucleus using the corresponding Xist array and centroid formula:

$$G_{x,y,z} = \left(\frac{x_1 + x_2 + x_3 + \ldots + x_n}{n}, \frac{y_1 + y_2 + y_3 + \ldots + y_n}{n}, \frac{z_1 + z_2 + z_3 + \ldots + z_n}{n}\right)$$

Distance to Xist centroid were then calculated using the spatial coordinates of each gene centroid to Xist centroid for the corresponding nucleus using the distance formula. Gene transcriptional activity was determined by pairing DNA signals to RNA signals in each nucleus. Nearest neighbor (NN) of DNA to RNA was determined by calculating the distance between DNA and RNA centroids. DNA centroids with a NN RNA closer than 350 nm were paired and labeled as "active gene" while those with a farther NN were labelled as "silent gene".

2. X-Territory Volume and Sphericity Measurements

Confocal optical stacks were imported to ImageJ/Fiji and converted to 16-bit tiffs. Raw data were processed using the "Smooth" function and an automatic threshold, using either the Yen or Otsu method, was set to create 3D masks for the X chromosome territories. Assignment of the Xi was based on RNA FISH signals from the Xist channel. Masks were imported into 3D Suite and the volume and sphericity measurements of the X chromosomes (Xa and Xi) were extracted. Sphericity is defined as the length of the object over its width, with a maximum value of one.

3. Extraction of X Chromosome Configurations

Confocal optical stacks from sequential rounds were imported into Fiji/ImageJ and superimposed and alignment of the two sequential rounds was performed with the affine transformation of the StackReg plugin based on the DAPI channel. Data were smoothed with a 3D Gaussian blur with a standard deviation of 1 (σ=1) and background removal was performed using the "Subtract Background" plugin with a rolling ball radius of 10 pixels. Xa and Xi (scored by the presence of Xist RNA) were identified and saved as separate stacks. Subsequently, each probe signal centroid was extracted using the “3D Object Counter” plugin. The 3D Object Counter generated a list of coordinates of probe signals for each channel. To assign signals to multi-spectral barcodes consisting of two labels, a nearest neighbor search between the two corresponding channels was applied based on all spatial coordinates in each channel. Once pairs of signals were assigned to the multi-spectral barcodes the coordinates obtained in the shortest wavelength were used. In cases where two adjacent signals were detected per probe, potentially due to the presence of transcripts or DNA replication, only one of the signals was used. The coordinates of individual barcodes for the Xa and Xi at days 2 and 4 of EpiLC differentiation were reoriented in 3D space to compute spatial statistics across all cells. To obtain configurations of chromosomal backbones, for each set of probe coordinates, principal component analysis (PCA) was performed in the x and y axes using MATLAB. The z axis was unused as the segmentation resolution in that axis is significantly lower, contributing to large variations in the z coordinate (Finn et al., 2017) and confounding the reorientation method used which is highly sensitive to anisotropic error. The principal component is assumed to be the “backbone” of the chromosome: the expected orientation of a chromosome if initially stretched out along that component’s direction before entropically relaxing into an equilibrium configuration. Each set of probes are rotated in order to align its corresponding principal components with the y-axis and translated such that the probes’ centroid is aligned with the coordinate origin. Probes of the same loci were then statistically compared to locate their local spatial centroid and 95% confidence interval for Xa day 2, Xi day 2, Xa day 4, and Xi day 4 separately. Ellipsoids encompassing the 95% confidence interval were plotted around each loci centroid. In order to quantify the relative compaction between Xa and Xi from day 2 to day 4, the pairwise distances of 3D coordinates (x,y,z) between each barcode location were measured and averaged over all cells. Averages of Xa distances were subtracted from those of Xi at day 2 and the same was done for day 4 in order to measure the absolute change between chromosomes. A heatmap of this change was plotted where large negative numbers indicate a higher compaction.

4. Single-Particle Tracking (SPT) of Xist Foci

Individual Xist particles from live-cell 3D-SIM data were extracted by using TrackMate (Tinevez et al., 2017), an ImageJ plugin. DoG Detector with a 0.2 μm diameter was used to define the particles and the Simple LAP Tracker with 0.25 max linking distance, 0.3 gap-closing max distance and 2 gap-closing max frame gap were used to track the particles and generate trajectories. Trajectories that were not possible to track for over 10 consecutive frames were not used. Over 850 trajectories from 30 cells were analyzed and approximately 50% of all Xist granules without manual intervention were possible to track per nucleus for an average of 2 min. To characterize the motion of Xist foci, the data extracted from the software were fed into downstream confinement analyses described in Methods S1 File (see section on “Xist foci position trajectories and effective confining potentials”).

5. 4D-SIM Image Registration

Two types of motion are captured simultaneously in 4D-SIM microscopy: a) the developmental motion of the cell and the nucleus, and b) the individual motion of Xist foci within the nucleus. To specifically extract (b) from live-cell 3D-SIM images we implemented the following processing pipeline using Python: 1) A set of Xist foci were tracked using TrackMate and spatial coordinates were extracted and imported into Python using PyTrackmate 2) For each timestep t, the individual displacement vectors $x_{i,t}$ of each Xist focus were calculated using NumPy and Pandas. 3) For each time-step, individual displacement vectors were averaged to obtain $X_t$, an approximation of the developmental motion in that time-step. 4) This developmental motion was then subtracted from the displacement vector of each Xist focus to arrive at an approximation to granule i’s motion, $x_{i,t}-X_t$.

6. H2B Density Classification and Xist Localization

Histone H2B-Halo$^{JF646}$ intensities were extracted on ImageJ/Fiji plugin using the “getValue” macro command, that iterates over every pixel in the image to get the intensity value of each pixel, generating a list of all the pixel intensities and their corresponding coordinates. The list of intensities was imported to Python. Then, seven intensity/density classes of equal variance were determined. The 3D Suite was used to create Xist masks, while Xist trajectories were extracted from TrackMate to obtain spatial coordinates (centroids) from each time point. The matrices were paired within the radius of one pixel and chromatin density classes were measured under the masks. Radial distances were measured at all pixels within the respective 100, 250, 500 nm radius of the Xist centroid and the maximal intensity value within that range was defined. Averaged values were then plotted in a line graph as a function of time. To extract the nearest neighbors (NN) in chromatin density maps, neighboring intensities for each H2B pixel were determined as the average intensity of all adjacent pixels and stored in an array. A strip plot was used to plot the averaged intensity values where each value was assigned to one of the 7 classes based on the class of the origin pixel (FIG. 27L).

7. FRAP Data Analysis

FRAP time series were imported into Fiji and converted to 16-bit tiffs. Datasets from Xist and CIZ1 derived from z-stacking were projected for each timepoint. To correct for drift, images were registered using the Correct3DDrift plugin and datasets that could not be registered were discarded. To measure FRAP recoveries data were normalized for fluorescence decay as described (Dundr and Misteli, 2003). In brief, ~2 μm user-defined ROIs were created to define and measure the bleached region ($I_t$), a randomly selected unbleached nuclear region ($T_t$), and a randomly selected region outside the cell ($B_t$) for each timepoint. A relative intensity for each timepoint was calculated using the equation: $I_{rel}=(T_0-B_0)\times(I_{(t)}-B_{(t)})/(T_{(t)}-B_{(t)})\times(I_0-B_0)$ where $T_0$ and $I_0$ are derived from the average intensity of the region of interest during prebleach. To derive the FRAP recovery, $I_{rel}$ was measured through time. For compiling figures, FRAP time series were bleach-corrected using the BleachCorrect ImageJ/Fiji plugin. To infer dissociation rates and residence times, FRAP curves for Xist and all proteins were fit to single or double exponential models derived from mass-action kinetics. Squared errors were minimized to obtain best-fit detachment rates, binding site densities, and freely diffusing fractions described in the Methods S1 file (“Mass-action binding and dissociation model of FRAP dynamics”).

8. Image Data Statistical Analysis and Visualization

Data analysis and visualization were performed using Python and executed in Google Colaboratory. All violin plots, boxplots, bar plots and point-plots were generated using Seaborn and Matplotlib. NumPy and SciPy were used for mathematical computation and Pandas for data analysis. Unless stated otherwise, all graphs show the median as the central point or the central line, and bars on point plots represent the standard deviation. Point plots of protein integrated density and volume in FIGS. 21H, 28B, 30J, 30K and 31D show the percentage of the maximum absolute value in each group. Statistical differences between two groups were analyzed by the two-sided Wilcoxon's or Mann-Whitney rank-sum test (scipy.stats.mannwhitneyu). The Kruskal-Wallis H-test was used for statistical comparisons between multiple groups (scipy.stats.kruskal). Statistical significance was defined as a p-value less than 0.05.

9. RAP-Seq Data Analysis

RAP-seq reads were trimmed using trim_galore (v0.4.1) with default parameters to remove the standard Illumina adaptor sequences. Bowtie2 (v2.2.9) was used to align reads to the mouse genome (mm9) with the default parameters. Reads with mapping quality less than 30 were removed using samtools (v1.2). Picard MarkDuplicates (v2.1.0) was used to remove PCR duplicates. Bedtools intersect (v2.26.0) was used to count reads in sliding windows (100 Kb every 25 Kb) along the X chromosome. Xist localization across the X-chromosome was defined by calculating the Xist enrichment scores (pulldown/input) in the sliding windows. Unmappable regions were masked.

MACS2 (Zhang et al., 2008) was used to call broadPeaks in D2 and D4 Xist pulldown data, using the input as control. Peaks within 50 kb were merged. To identify overlapping Xist peaks between D2 and D4, the respective X-linked peak sets were intersected using bedtools intersect. The most significant peaks were selected with a log 10(qvalue)>13 cutoff. The R package makeVennDiagram with connectedPeaks=min was used to make the Venn Diagram from the two peak ranges.

To plot the average Xist enrichment around the summits of Xist peaks, Xist peak summits defined for D2 were used and filtered for summit scores>100 on the X chromosome. The RAP-seq enrichment scores for 2500 kb up and downstream of these D2 summits were extracted from the D2 and D4 data using normalizeToMatrix function in the R package EnrichedHeatmap.

10. Hi-C Compartments

To compare Hi-C compartmentalization and Xist enrichment, Hi-C PC1 values were downloaded from GSE99991 (Wang et al., 2018). Analysis was performed in R (v3.6.0). PC1 values from undifferentiated ESCs were correlated with Xist enrichment at D2 and PC1 values at differentiation D4 with Xist enrichment at D4. In addition, Xist enrichment at D2 and D4 were correlated. Datasets were intersected with plyranges (v1.4.4) (Lee et al., 2019). Plots were made with ggplot2 (v3.3.2) and pearson's correlation coefficients and p-values (two-sided t-test, r≠0) were calculated with the function stat_cor in the R package ggpubr (v0.4.0).

11. SNP Calling

Single nucleotide polymorphisms (SNPs) were identified to distinguish the *Mus castaneous* (Cas) genome from the 12954/SvJae (129) and C57BL/6J (B16) strains of *Mus musculus*. Parental genome sequencing data were downloaded from publicly available databases (Cas genome sequence (EMBL-EBI: ERP000042); 129 genome sequence (SRA: SRX037820). In order to identify distinguishing SNPs, we first aligned WGS reads of each strain to the mm10 genome with bowtie2 (v2.3.5.1), filtered multimapped reads (mapq<10) with samtools (v1.7), and removed duplicates with GATK (v4.1.4.1) MarkDuplicates. For allelic analysis in cas/129 hybrid cells, we jointly called SNPs with the aligned Cas data and the aligned 129 data and filtered out low quality SNPs with bcftools (v1.8). For allelic analysis in cas/B16 hybrid cells, we called SNPs with the aligned Cas data alone and filtered out low quality SNPs with bcftools. SNPs were required to have a minimum depth of 5, with at least 90% of the reads supporting the alternate allele, a minimum of 3 reads supporting the alternate allele and no more than 2 reads supporting the reference allele. Indels and complex SNPs were not included. To filter the cas/129 SNPs, SNP that were present in both strains were excluded: When a SNP is present in one strain, the other strain must have fewer than 10% of reads supporting the alternate allele, at least 2 reads supporting the reference allele, and fewer than 2 reads supporting the alternate allele. The resulting cas/129 and cas/B16 variant call files (VCFs) were used in subsequent allelic analysis.

12. Single Cell RNA-Seq Data Analysis

Cellranger count (v5.0.1) was used to align and process the scRNA-seq reads to the mm10 genome with the option [--include-introns]. Seurat (v3.9.9.9024) in R (v3.6.1) to filter out low quality cells based on number of unique feature counts or a percent mitochondrial reads (<7%). As the feature counts per cell is partially a function of read depth per cell, the threshold used was based on the number of features in the bulk of the cells, and ranged between 1500 and 2000. Vartrix (v1.1.14) was used to identify and count reads with informative SNPs (allelic reads) with the options [--scoring-method coverage -umi]. Either the cas/129 VCF or the cas/B16 VCF described above were used, as appropriate for the strain. All subsequent analyses were done in R. Allelic reads from chrX were summarized across genes to generate Xi allelic ratios (Xi/(Xi+Xa) reads) for each gene. Lowly expressed genes were filtered out, by requiring a minimum of 10 cells in each library to have at least one allelic read of that gene. Xi allelic ratios for each gene were calculated per cell, requiring a minimum of 3 allelic reads to get an Xi ratio for a given gene in a cell.

For scRNA-seq data of the female F1 2-1 $Xist^{129WT/CasWT}$ or $Xist^{129\Delta B/CasWT}$ EpiLCs, cells with biallelic or undetectable Xist expression ($<3$ allelic reads), and XO cells, were excluded, and the Xi was determined based on monoallelic Xist expression. Xi allelic ratios between $WT^{129}$ XCI and $\Delta B^{129}$ XCI were compared using a one-sided welch t test (p<0.05) with the R function t.test, where each cell is a replicate.

For the scRNA-seq data of TX1072 ($B6^{tetOXist}Cas^{WTXist}$) ESC lines expressing WT-SPEN-GFP, ΔIDR-SPEN-GFP, and ΔSPOC-SPEN-GFP at 0 h and 24 h of dox treatment, where Xist is induced by doxycycline from the B16 allele. XO cells were excluded. All cells were assumed to inactivate the Bl6 X chromosome. The Xi ratios between 0 and 24 hours dox induction of Xist for the respective cell line were compared using a one-sided welch t-test (p<0.05) with the R function t.test, where each cell is a replicate.

The mean Xi allelic ratios per gene were found for each set of cells, and plotted with ggplot2. Statistical tests comparing distributions were performed with the function stat_compare_means in the R package ggpubr. The Wilcoxon rank sum test was used for pairwise comparisons, while the Kruskal-Wallis test was used to compare multiple groups.

13. Bulk RNA-Seq Data Analysis

Reads were aligned to the mm10 genome with STAR (v2.7.1a), filtered multimapped reads (mapq<10) with samtools (v1.7) and allelic ratios were found using GATK (v4.1.4.1) ASEReadCounter and the Cas/Bl6 VCF described above. Allelic reads were assigned to genes using bedtools intersect with all genes from the gencode mm10 annotation file (gencode.vM24.annotation.gtf). All subsequent analyses were done in R. Due to the tetO Xist promoter on the Bl6 allele, the Bl6 X chromosome was inactivated in all cells. Allelic reads were summed across genes and the allelic ratios (Xi/(Xi+Xa) reads) were found. Genes with fewer than 10 reads with informative SNPs (allelic reads) were filtered out from each sample. Xi ratios between 0 h and 24 h dox were compared with a one-sided welch t-test ($p<0.05$) with the R function t.test, with 3 replicates per condition. The mean Xi allelic ratios per gene were found for each condition, and plotted with ggplot2. Statistical tests comparing distributions were performed with the function stat_compare_means in the R package ggpubr. The Wilcoxon rank sum test was used for pairwise comparisons, while the Kruskal-Wallis test was used to compare multiple groups.

X-Linked Gene Silencing Dynamics

The silencing half-times of genes during XCI were downloaded from (Barros de Andrade et al., 2019) and analyzed in R. X-linked genes with a half-time range of 0-0.4 days were classified as early-silencing genes, of 0.4-1 days as late-silencing genes, of 1-2 days as very late silencing genes, and >2 days as escapee genes.

14. CLAP-Seq Data Analysis

CLAP-seq libraries of FL, ΔIDR and ΔRRM SPEN were aligned to the mm10 genome with STAR (v2.7.1a), filtered multimapped reads (mapq<10) with samtools (v1.7), duplicate reads were removed with GATK (v4.1.4.1) MarkDuplicates. RPKM values were calculated for each sample in 100 bp bins smoothed across 300 bp with deeptools, only counting the forward strand in order to avoid double counting fragments, (v3.5.0) with the options [--normalizeUsing RPKM --binSize 100-samFlagInclude 64 --skipNAs]. Enrichment was calculated in R by dividing SPEN pulldown RPKM over input RPKM in each bin. The R package ggplot2 was used to plot the enrichment scores.

15. Xist-Tethered SPOC Silencing

To identify genes that were repressed by SPOC tethered to Xist in the absence of SPEN, we used previously published allele-specific RNA-seq count data from GSE131784 of $B6^{tetOXist}Cas^{WTXist}$ ESC lines expressing SPEN-AID-GFP where depletion of SPEN was rescued through tethering of BglG-GFP-SPOC or BglG-GFP (as a control) to tetO-Xist-Bgl stem-loop RNA via BglG (Dossin et al., 2020).

SPOC silencing values for each gene were calculated as described (Dossin et al., 2020). Briefly, we filtered out genes that were skewed or not silenced under control conditions. We then calculated a silencing index under normal conditions ($silencing\_index_{DOX}=1-(allelic\_ratio_{DOX}/allelic\_ratio_{control})$) and after degrading SPEN and expressing SPOC tethered to Xist ($silencing\_index_{SPOC}=1-(allelic\_ratio_{SPOC}/allelic\_ratio_{control})$). To quantify the silencing defect in cells expressing only Xist-tethered SPOC, we calculated the silencing defect ($silencing\_defect=1-(silencing\_index_{SPOC}/silencing\_index_{DOX})$). We calculated the silencing defects for the control BglG-GFP rescue identically. The silencing defect per gene was found for each condition and plotted with ggplot2. Statistical tests comparing distributions were performed with the function stat_compare_means in the R package ggpubr. The Wilcoxon rank sum test was used for pairwise comparisons, while the Kruskal-Wallis test was used to compare multiple groups.

16. SMCHD1 Sensitivity

To identify genes with a silencing defect as a result of the knockout of Smchd1, we downloaded RNA-seq allelic counts from GSE99991 and classified genes as SMCHD1-sensitive or -insensitive following the previously analysis pipeline (Wang et al). All analysis was performed in R. Briefly, the Xi allelic ratio (Xi/(Xi+Xa) reads) was determined per X-linked gene. Genes with fewer than 13 reads with informative SNPs (allelic reads), a skewed allelic ratio, or that escape X inactivation were filtered out. SMCHD1-sensitive genes were defined as having Xi allelic ratio in SMCHD1 knockout neural progenitor cells (NPCs) of 3-fold greater than Xi allelic ratio in WT NPCs. The silencing half-time from (kinetics paper ref) was plotted for SMCHD1-sensitive and -insensitive genes with the R package ggplot2, and distributions were compared with a Wilcoxon rank sum test using the function stat_compare_means from the R package ggpubr.

F. References

The following references, to the extent that they provide exemplary procedural or other details supplementary to those set forth herein, are specifically incorporated herein by reference.

1. Almeida, M., Pintacuda, G., Masui, O., Koseki, Y., Gdula, M., Cerase, A., Brown, D., Mould, A., Innocent, C., Nakayama, M., et al. (2017). PCGF3/5-PRC1 initiates Polycomb recruitment in X chromosome inactivation. Science 356, 1081-1084.
2. Banani, S. F., Lee, H. O., Hyman, A. A., and Rosen, M. K. (2017). Biomolecular condensates: organizers of cellular biochemistry. Nat Rev Mol Cell Biol 18, 285-298.
3. Barros de Andrade, E. S. L., Jonkers, I., Syx, L., Dunkel, I., Chaumeil, J., Picard, C., Foret, B., Chen, C. J., Lis, J. T., Heard, E., et al. (2019). Kinetics of Xist-induced gene silencing can be predicted from combinations of epigenetic and genomic features. Genome Res 29, 1087-1099.
4. Beard, C., Hochedlinger, K., Plath, K., Wutz, A., and Jaenisch, R. (2006). Efficient method to generate single-copy transgenic mice by site-specific integration in embryonic stem cells. Genesis 44, 23-28.
5. Berg, B. A., and Harris, R. C. (2008). From data to probability densities without histograms. Computer Physics Communications 179, 443-448.
6. Bertrand, E., Chartrand, P., Schaefer, M., Shenoy, S. M., Singer, R. H., and Long, R. M. (1998). Localization of ASH1 mRNA particles in living yeast. Molecular cell 2, 437-445.
7. Blelloch, R. H., Hochedlinger, K., Yamada, Y., Brennan, C., Kim, M., Mintz, B., Chin, L., and Jaenisch, R. (2004). Nuclear cloning of embryonal carcinoma cells. Proc Natl Acad Sci USA 101, 13985-13990.
8. Blewitt, M. E., Gendrel, A. V., Pang, Z., Sparrow, D. B., Whitelaw, N., Craig, J. M., Apedaile, A., Hilton, D. J., Dunwoodie, S. L., Brockdorff, N., et al. (2008). SmcHD1, containing a structural-maintenance-of-chromosomes hinge domain, has a critical role in X inactivation. Nat Genet 40, 663-669.
9. Bousard, A., Raposo, A. C., Zylicz, J. J., Picard, C., Pires, V. B., Qi, Y., Gil, C., Syx, L., Chang, H. Y., Heard, E., et al. (2019). The role of Xist-mediated Polycomb recruitment in the initiation of X-chromosome inactivation. EMBO Rep 20, e48019.
10. Boyle, S., Flyamer, I. M., Williamson, I., Sengupta, D., Bickmore, W. A., and Illingworth, R. S. (2020). A central role for canonical PRC1 in shaping the 3D nuclear landscape. Genes Dev 34, 931-949.
11. Brackley, C. A., and Marenduzzo, D. (2020). Bridging-induced microphase separation: photobleaching experiments, chromatin domains and the need for active reactions. Brief Funct Genomics 19, 111-118.
12. Braga, J., McNally, J. G., and Carmo-Fonseca, M. (2007). A reaction-diffusion model to study RNA motion by quantitative fluorescence recovery after photobleaching. Biophys J 92, 2694-2703.
13. Brockdorff, N. (2017). Polycomb complexes in X chromosome inactivation. Philos Trans R Soc Lond B Biol Sci 372.

14. Brockdorff, N., Bowness, J. S., and Wei, G. (2020). Progress toward understanding chromosome silencing by Xist RNA. Genes & development 34, 733-744.
15. Cabili, M. N., Dunagin, M. C., McClanahan, P. D., Biaesch, A., Padovan-Merhar, O., Regev, A., Rinn, J. L., and Raj, A. (2015). Localization and abundance analysis of human lncRNAs at single-cell and single-molecule resolution. Genome Biol 16, 20.
16. Cerase, A., Armaos, A., Neumayer, C., Avner, P., Guttman, M., and Tartaglia, G. G. (2019). Phase separation drives X-chromosome inactivation: a hypothesis. Nat Struct Mol Biol 26, 331-334.
17. Cerase, A., Smeets, D., Tang, Y. A., Gdula, M., Kraus, F., Spivakov, M., Moindrot, B., Leleu, M., Tattermusch, A., Demmerle, J., et al. (2014). Spatial separation of Xist RNA and polycomb proteins revealed by superresolution microscopy. Proc Natl Acad Sci USA 111, 2235-2240.
18. Chang, J. C., Fok, P. W., and Chou, T. (2015). Bayesian Uncertainty Quantification for Bond Energies and Mobilities Using Path Integral Analysis. Biophys J 109, 966-974.
19. Chang, J. C., Savage, V. M., and Chou, T. (2014). A path-integral approach to bayesian inference for inverse problems using the semiclassical approximation. Journal of Statistical Physics 109, 966-974.
20. Chaumeil, J., Le Baccon, P., Wutz, A., and Heard, E. (2006). A novel role for Xist RNA in the formation of a repressive nuclear compartment into which genes are recruited when silenced. Genes Dev 20, 2223-2237.
21. Chen, B., Gilbert, L. A., Cimini, B. A., Schnitzbauer, J., Zhang, W., Li, G. W., Park, J., Blackburn, E. H., Weissman, J. S., Qi, L. S., et al. (2013). Dynamic imaging of genomic loci in living human cells by an optimized CRISPR/Cas system. Cell 155, 1479-1491.
22. Chu, C., Zhang, Q. C., da Rocha, S. T., Flynn, R. A., Bharadwaj, M., Calabrese, J. M., Magnuson, T., Heard, E., and Chang, H. Y. (2015). Systematic discovery of Xist RNA binding proteins. Cell 161, 404-416.
23. Clemson, C. M., McNeil, J. A., Willard, H. F., and Lawrence, J. B. (1996). XIST RNA paints the inactive X chromosome at interphase: evidence for a novel RNA involved in nuclear/chromosome structure. J Cell Biol 132, 259-275.
24. Colognori, D., Sunwoo, H., Kriz, A. J., Wang, C. Y., and Lee, J. T. (2019). Xist Deletional Analysis Reveals an Interdependency between Xist RNA and Polycomb Complexes for Spreading along the Inactive X. Mol Cell 74, 101-117 e110.
25. Cremer, M., Grasser, F., Lanctot, C., Muller, S., Neusser, M., Zinner, R., Solovei, I., and Cremer, T. (2008). Multicolor 3D fluorescence in situ hybridization for imaging interphase chromosomes. Methods Mol Biol 463, 205-239.
26. da Rocha, S. T., Boeva, V., Escamilla-Del-Arenal, M., Ancelin, K., Granier, C., Matias, N. R., Sanulli, S., Chow, J., Schulz, E., Picard, C., et al. (2014). Jarid2 Is Implicated in the Initial Xist-Induced Targeting of PRC2 to the Inactive X Chromosome. Mol Cell 53, 301-316.
27. Danecek, P., Bonfield, J. K., Liddle, J., Marshall, J., Ohan, V., Pollard, M. O., Whitwham, A., Keane, T., McCarthy, S. A., Davies, R. M., et al. (2021). Twelve years of SAMtools and BCFtools. Gigascience 10.
28. Darrow, E. M., Huntley, M. H., Dudchenko, O., Stamenova, E. K., Durand, N. C., Sun, Z., Huang, S. C., Sanborn, A. L., Machol, I., Shamim, M., et al. (2016). Deletion of DXZ4 on the human inactive X chromosome alters higher-order genome architecture. Proc Natl Acad Sci USA 113, E4504-4512.
29. Demmerle, J., Innocent, C., North, A. J., Ball, G., Muller, M., Miron, E., Matsuda, A., Dobbie, I. M., Markaki, Y., and Schermelleh, L. (2017). Strategic and practical guidelines for successful structured illumination microscopy. Nat Protoc 12, 988-1010.
30. Derrien, T., Johnson, R., Bussotti, G., Tanzer, A., Djebali, S., Tilgner, H., Guernec, G., Martin, D., Merkel, A., Knowles, D. G., et al. (2012). The GENCODE v7 catalog of human long noncoding RNAs: analysis of their gene structure, evolution, and expression. Genome Res 22, 1775-1789.
31. Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.
32. Dossin, F., Pinheiro, I., Zylicz, J. J., Roensch, J., Collombet, S., Le Saux, A., Chelmicki, T., Attia, M., Kapoor, V., Zhan, Y., et al. (2020). SPEN integrates transcriptional and epigenetic control of X-inactivation. Nature 578, 455-460.
33. Dundr, M., and Misteli, T. (2003). Measuring dynamics of nuclear proteins by photobleaching. Curr Protoc Cell Biol Chapter 13, Unit 13 15.
34. Eliscovich, C., Buxbaum, A. R., Katz, Z. B., and Singer, R. H. (2013). mRNA on the move: the road to its biological destiny. J Biol Chem 288, 20361-20368.
35. Engreitz, J. M., Ollikainen, N., and Guttman, M. (2016). Long non-coding RNAs: spatial amplifiers that control nuclear structure and gene expression. Nat Rev Mol Cell Biol 17, 756-770.
36. Engreitz, J. M., Pandya-Jones, A., McDonel, P., Shishkin, A., Sirokman, K., Surka, C., Kadri, S., Xing, J., Goren, A., Lander, E. S., et al. (2013). The Xist lncRNA exploits three-dimensional genome architecture to spread across the X chromosome. Science 341, 1237973.
37. Finn, E. H., Pegoraro, G., Shachar, S., and Misteli, T. (2017). Comparative analysis of 2D and 3D distance measurements to study spatial genome organization. Methods 123, 47-55.
38. Francis, N. J., Kingston, R. E., and Woodcock, C. L. (2004). Chromatin compaction by a polycomb group protein complex. Science 306, 1574-1577.
39. Frank, L., and Rippe, K. (2020). Repetitive RNAs as Regulators of Chromatin-Associated Subcompartment Formation by Phase Separation. J Mol Biol 432, 4270-4286.
40. Fusco, D., Accornero, N., Lavoie, B., Shenoy, S. M., Blanchard, J. M., Singer, R. H., and Bertrand, E. (2003). Single mRNA molecules demonstrate probabilistic movement in living mammalian cells. Curr Biol 13, 161-167.
41. Galupa, R., and Heard, E. (2018). X-Chromosome Inactivation: A Crossroads Between Chromosome Architecture and Gene Regulation. Annu Rev Genet 52, 535-566.
42. Giorgetti, L., Lajoie, B. R., Carter, A. C., Attia, M., Zhan, Y., Xu, J., Chen, C. J., Kaplan, N., Chang, H. Y., Heard, E., et al. (2016). Structural organization of the inactive X chromosome in the mouse. Nature 535, 575-579.
43. Grau, D. J., Chapman, B. A., Garlick, J. D., Borowsky, M., Francis, N. J., and Kingston, R. E. (2011). Compaction of chromatin by diverse Polycomb group proteins requires localized regions of high charge. Genes Dev 25, 2210-2221.

44. Gu, B., Posfai, E., and Rossant, J. (2018a). Efficient generation of targeted large insertions by microinjection into two-cell-stage mouse embryos. Nat Biotechnol 36, 632-637.
45. Gu, Z., Eils, R., Schlesner, M., and Ishaque, N. (2018b). EnrichedHeatmap: an R/Bioconductor package for comprehensive visualization of genomic signal associations. BMC Genomics.
46. Harris, C. R., Millman, K. J., van der Walt, S. J., Gommers, R., Virtanen, P., Cournapeau, D., Wieser, E., Taylor, J., Berg, S., Smith, N. J., et al. (2020). Array programming with NumPy. Nature 585, 357-362.
47. Hayashi, K., and Saitou, M. (2013). Generation of eggs from mouse embryonic stem cells and induced pluripotent stem cells. Nat Protoc 8, 1513-1524.
48. Hendrich, B. D., Plenge, R. M., and Willard, H. F. (1997). Identification and characterization of the human XIST gene promoter: implications for models of X chromosome inactivation. Nucleic Acids Res 25, 2661-2671.
49. Hsia, Y., Bale, J. B., Gonen, S., Shi, D., Sheffler, W., Fong, K. K., Nattermann, U., Xu, C., Huang, P. S., Ravichandran, R., et al. (2016). Design of a hyperstable 60-subunit protein dodecahedron. [corrected]. Nature 535, 136-139.
50. Hunter, J. D. (2007). Matplotlib: A 2D Graphics Environment. Computing in Science & Engineering 9, 90-95.
51. Illingworth, R. S. (2019). Chromatin folding and nuclear architecture: PRC1 function in 3D. Curr Opin Genet Dev 55, 82-90.
52. Jansz, N., Nesterova, T., Keniry, A., Iminitoff, M., Hickey, P. F., Pintacuda, G., Masui, O., Kobelke, S., Geoghegan, N., Breslin, K. A., et al. (2018). Smchd1 Targeting to the Inactive X Is Dependent on the Xist-HnrnpK-PRC1 Pathway. Cell Rep 25, 1912-1923 e1919.
53. Jegu, T., Aeby, E., and Lee, J. T. (2017). The X chromosome in space. Nat Rev Genet 18, 377-389.
54. Jonkers, I., Monkhorst, K., Rentmeester, E., Grootegoed, J. A., Grosveld, F., and Gribnau, J. (2008). Xist RNA is confined to the nuclear territory of the silenced X chromosome throughout the cell cycle. Mol Cell Biol 28, 5583-5594.
55. Kang, M., Day, C. A., DiBenedetto, E., and Kenworthy, A. K. (2010). A quantitative approach to analyze binding diffusion kinetics by confocal FRAP. Biophys J 99, 2737-2747.
56. Kranz, A., Fu, J., Duerschke, K., Weidlich, S., Naumann, R., Stewart, A. F., and Anastassiadis, K. (2010). An improved Flp deleter mouse in C57Bl/6 based on Flpo recombinase. Genesis 48, 512-520.
57. Kraus, F., Miron, E., Demmerle, J., Chitiashvili, T., Budco, A., Alle, Q., Matsuda, A., Leonhardt, H., Schermelleh, L., and Markaki, Y. (2017). Quantitative 3D structured illumination microscopy of nuclear structures. Nat Protoc 12, 1011-1028.
58. Kuznetsova, I. M., Turoverov, K. K., and Uversky, V. N. (2014). What macromolecular crowding can do to a protein. Int J Mol Sci 15, 23090-23140.
59. Langmead, B., Trapnell, C., Pop, M., and Salzberg, S. L. (2009). Ultrafast and memory-efficient alignment of short DNA sequences to the human genome. Genome Biol 10, R25.
60. Lee, S., Cook, D., and Lawrence, M. (2019). plyranges: a grammar of genomic data transformation. Genome Biol 20, 4.
61. Loda, A., and Heard, E. (2019). Xist RNA in action: Past, present, and future. PLoS Genet 15, e1008333.
62. Markaki, Y., Smeets, D., Cremer, M., and Schermelleh, L. (2013). Fluorescence in situ hybridization applications for super-resolution 3D structured illumination microscopy. Methods in molecular biology (Clifton, NJ 950, 43-64.
63. Markaki, Y., Smeets, D., Fiedler, S., Schmid, V. J., Schermelleh, L., Cremer, T., and Cremer, M. (2012). The potential of 3D-FISH and super-resolution structured illumination microscopy for studies of 3D nuclear architecture: 3D structured illumination microscopy of defined chromosomal structures visualized by 3D (immuno)-FISH opens new perspectives for studies of nuclear architecture. Bioessays 34, 412-426.
64. Marks, H., Kerstens, H. H., Barakat, T. S., Splinter, E., Dirks, R. A., van Mierlo, G., Joshi, O., Wang, S. Y., Babak, T., Albers, C. A., et al. (2015). Dynamics of gene silencing during X inactivation using allele-specific RNA-seq. Genome Biol 16, 149.
65. McHugh, C. A., Chen, C. K., Chow, A., Surka, C. F., Tran, C., McDonel, P., Pandya-Jones, A., Blanco, M., Burghard, C., Moradian, A., et al. (2015). The Xist lncRNA interacts directly with SHARP to silence transcription through HDAC3. Nature 521, 232-236.
66. McNally, J. G. (2008). Quantitative FRAP in analysis of molecular binding dynamics in vivo. Methods Cell Biol 85, 329-351.
67. McSwiggen, D. T., Mir, M., Darzacq, X., and Tjian, R. (2019). Evaluating phase separation in live cells: diagnosis, caveats, and functional consequences. Genes Dev 33, 1619-1634.
68. Minajigi, A., Froberg, J., Wei, C., Sunwoo, H., Kesner, B., Colognori, D., Lessing, D., Payer, B., Boukhali, M., Haas, W., et al. (2015). Chromosomes. A comprehensive Xist interactome reveals cohesin repulsion and an RNA-directed chromosome conformation. Science 349.
69. Minkovsky, A., Sahakyan, A., Rankin-Gee, E., Bonora, G., Patel, S., and Plath, K. (2014). The Mbd1-Atf7ip-Setdb1 pathway contributes to the maintenance of X chromosome inactivation. Epigenetics Chromatin 7, 12.
70. Mittag, T., and Forman-Kay, J. D. (2007). Atomic-level characterization of disordered protein ensembles. Curr Opin Struct Biol 17, 3-14.
71. Mohammed, H., Taylor, C., Brown, G. D., Papachristou, E. K., Carroll, J. S., and D'Santos, C. S. (2016). Rapid immunoprecipitation mass spectrometry of endogenous proteins (RIME) for analysis of chromatin complexes. Nat Protoc 11, 316-326.
72. Moindrot, B., Cerase, A., Coker, H., Masui, O., Grijzenhout, A., Pintacuda, G., Schermelleh, L., Nesterova, T. B., and Brockdorff, N. (2015). A Pooled shRNA Screen Identifies Rbm15, Spen, and Wtap as Factors Required for Xist RNA-Mediated Silencing. Cell Rep 12, 562-572.
73. Monfort, A., Di Minin, G., Postlmayr, A., Freimann, R., Arieti, F., Thore, S., and Wutz, A. (2015). Identification of Spen as a Crucial Factor for Xist Function through Forward Genetic Screening in Haploid Embryonic Stem Cells. Cell Rep 12, 554-561.
74. Mor, A., Suliman, S., Ben-Yishay, R., Yunger, S., Brody, Y., and Shav-Tal, Y. (2010). Dynamics of single mRNP nucleocytoplasmic transport and export through the nuclear pore in living cells. Nat Cell Biol 12, 543-552.
75. Nam, H. S., and Benezra, R. (2009). High levels of Id1 expression define B1 type adult neural stem cells. Cell Stem Cell 5, 515-526.
76. Nesterova, T. B., Wei, G., Coker, H., Pintacuda, G., Bowness, J. S., Zhang, T., Almeida, M., Bloechl, B., Moindrot, B., Carter, E. J., et al. (2019). Systematic allelic analysis defines the interplay of key pathways in X chromosome inactivation. Nat Commun 10, 3129.
77. Ng, K., Daigle, N., Bancaud, A., Ohhata, T., Humphreys, P., Walker, R., Ellenberg, J., and Wutz, A. (2011). A system for imaging the regulatory noncoding Xist RNA in living mouse embryonic stem cells. Mol Biol Cell 22, 2634-2645.
78. Nozaki, T., Imai, R., Tanbo, M., Nagashima, R., Tamura, S., Tani, T., Joti, Y., Tomita, M., Hibino, K., Kanemaki, M. T., et al. (2017). Dynamic Organization of Chromatin Domains Revealed by Super-Resolution Live-Cell Imaging. Mol Cell 67, 282-293 e287.
79. Ollion, J., Cochennec, J., Loll, F., Escude, C., and Boudier, T. (2013). TANGO: a generic tool for high-throughput 3D image analysis for studying nuclear organization. Bioinformatics 29, 1840-1841.
80. Pacini, G., Dunkel, I., Mages, N., Mutzel, V., Timmermann, B., Marsico, A., and Schulz, E. G. (2021). Integrated analysis of Xist upregulation and X-chromosome inactivation with single-cell and single-allele resolution. Nat Commun 12, 3638.
81. Pandya-Jones, A., Markaki, Y., Serizay, J., Chitiashvili, T., Mancia Leon, W. R., Damianov, A., Chronis, C., Papp, B., Chen, C. K., McKee, R., et al. (2020). A protein assembly mediates Xist localization and gene silencing. Nature.
82. Panning, B., Dausman, J., and Jaenisch, R. (1997). X chromosome inactivation is mediated by Xist RNA stabilization. Cell 90, 907-916.
83. Pintacuda, G., Wei, G., Roustan, C., Kirmizitas, B. A., Solcan, N., Cerase, A., Castello, A., Mohammed, S., Moindrot, B., Nesterova, T. B., et al. (2017). hnRNPK Recruits PCGF3/5-PRC1 to the Xist RNA B-Repeat to Establish Polycomb-Mediated Chromosomal Silencing. Mol Cell 68, 955-969 e910.
84. Plath, K., Fang, J., Mlynarczyk-Evans, S. K., Cao, R., Worringer, K. A., Wang, H., de la Cruz, C. C., Otte, A. P., Panning, B., and Zhang, Y. (2003). Role of histone H3 lysine 27 methylation in X inactivation. Science 300, 131-135.
85. Plath, K., Mlynarczyk-Evans, S., Nusinow, D. A., and Panning, B. (2002). Xist RNA and the mechanism of X chromosome inactivation. Annu Rev Genet 36, 233-278.
86. Quinlan, A. R., and Hall, I. M. (2010). BEDTools: a flexible suite of utilities for comparing genomic features. Bioinformatics 26, 841-842.
87. Quinodoz, S. A., Bhat, P., Ollikainen, N., Jachowicz, J. W., Banerjee, A. K., Chovanec, P., Blanco, M. R., Chow, A., Markaki, Y., Plath, K., et al. (2020). RNA promotes the formation of spatial compartments in the nucleus. bioRxiv, 2020.2008.2025.267435.
88. R Core Team (2021). R: A language and environment for statistical computing. R Foundation for Statistical Computing, Vienna, Austria.
89. Ramirez, F., Ryan, D. P., Gruning, B., Bhardwaj, V., Kilpert, F., Richter, A. S., Heyne, S., Dundar, F., and Manke, T. (2016). deepTools2: a next generation web server for deep-sequencing data analysis. Nucleic Acids Res 44, W160-165.
90. Ridings-Figueroa, R., Stewart, E. R., Nesterova, T. B., Coker, H., Pintacuda, G., Godwin, J., Wilson, R., Haslam, A., Lilley, F., Ruigrok, R., et al. (2017). The nuclear matrix protein CIZ1 facilitates localization of Xist RNA to the inactive X-chromosome territory. Genes Dev 31, 876-888.
91. Rinn, J. L., and Chang, H. Y. (2012). Genome regulation by long noncoding RNAs. Annu Rev Biochem 81, 145-166.
92. RStudio Team (2020). RStudio: Integrated Development for R. RStudio, PBC, Boston, MA.
93. Rueden, C. T., Schindelin, J., Hiner, M. C., DeZonia, B. E., Walter, A. E., Arena, E. T., and Eliceiri, K. W. (2017). ImageJ2: ImageJ for the next generation of scientific image data. BMC Bioinformatics 18, 529.
94. Schertzer, M. D., Braceros, K. C. A., Starmer, J., Cherney, R. E., Lee, D. M., Salazar, G., Justice, M., Bischoff, S. R., Cowley, D. O., Ariel, P., et al. (2019). lncRNA-Induced Spread of Polycomb Controlled by Genome Architecture, RNA Abundance, and CpG Island DNA. Mol Cell 75, 523-537 e510.
95. Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat Methods 9, 676-682.
96. Silva, J., Mak, W., Zvetkova, I., Appanah, R., Nesterova, T. B., Webster, Z., Peters, A. H., Jenuwein, T., Otte, A. P., and Brockdorff, N. (2003). Establishment of histone h3 methylation on the inactive X chromosome requires transient recruitment of Eed-Enx1 polycomb group complexes. Dev Cell 4, 481-495.
97. Simon, M. D., Pinter, S. F., Fang, R., Sarma, K., Rutenberg-Schoenberg, M., Bowman, S. K., Kesner, B. A., Maier, V. K., Kingston, R. E., and Lee, J. T. (2013). High-resolution Xist binding maps reveal two-step spreading during X-chromosome inactivation. Nature 504, 465-469.
98. Sladitschek, H. L., and Neveu, P. A. (2015). MXS-Chaining: A Highly Efficient Cloning Platform for Imaging and Flow Cytometry Approaches in Mammalian Systems. PLoS One 10, e0124958.
99. Smeets, D., Markaki, Y., Schmid, V. J., Kraus, F., Tattermusch, A., Cerase, A., Sterr, M., Fiedler, S., Demmerle, J., Popken, J., et al. (2014). Three-dimensional super-resolution microscopy of the inactive X chromosome territory reveals a collapse of its active nuclear compartment harboring distinct Xist RNA foci. Epigenetics & chromatin 7, 8.
100. Statello, L., Guo, C. J., Chen, L. L., and Huarte, M. (2021). Gene regulation by long non-coding RNAs and its biological functions. Nat Rev Mol Cell Biol 22, 96-118.
101. Sunwoo, H., Colognori, D., Froberg, J. E., Jeon, Y., and Lee, J. T. (2017). Repeat E anchors Xist RNA to the inactive X chromosomal compartment through CDKN1A-interacting protein (CIZ1). Proc Natl Acad Sci USA 114, 10654-10659.
102. Sunwoo, H., Wu, J. Y., and Lee, J. T. (2015). The Xist RNA-PRC2 complex at 20-nm resolution reveals a low Xist stoichiometry and suggests a hit-and-run mechanism in mouse cells. Proc Natl Acad Sci USA 112, E4216-4225.
103. Tavares, L., Dimitrova, E., Oxley, D., Webster, J., Poot, R., Demmers, J., Berstarosti, K., Taylor, S., Ura, H., Koide, H., et al. (2012). RYBP-PRC1 complexes mediate H2A ubiquitylation at polycomb target sites independently of PRC2 and H3K27me3. Cell 148, 664-678.
104. Teller, K., Illner, D., Thamm, S., Casas-Delucchi, C. S., Versteeg, R., Indemans, M., Cremer, T., and Cremer, M. (2011). A top-down analysis of Xa- and Xi-territories reveals differences of higher order structure at >1=20 Mb genomic length scales. Nucleus 2, 465-477.
105. The pandas development team (2020). pandas-dev/pandas: Pandas. Zenodo.
106. Tinevez, J. Y., Perry, N., Schindelin, J., Hoopes, G. M., Reynolds, G. D., Laplantine, E., Bednarek, S. Y., Shorte, S. L., and Eliceiri, K. W. (2017). TrackMate: An open and extensible platform for single-particle tracking. Methods 115, 80-90.

107. Uversky, V. N. (2015). The multifaceted roles of intrinsic disorder in protein complexes. FEBS Lett 589, 2498-2506.
108. Van der Auwera, G. A., and O'Connor, B. D. (2020). Genomics in the Cloud: Using Docker, GATK, and WDL in Terra (1st Edition). O'Reilly Media.
109. van Rossum, G., and Drake, F. L. (2009). Python 3 Reference Manual. Scotts Valley, CA.
110. van Zon, R., and Schofield, J. (2010). Constructing smooth potentials of mean force, radial distribution functions and probability densities from sampled data. Journal of Chemical Physics 132, 154110.
111. Virtanen, P., Gommers, R., Oliphant, T. E., Haberland, M., Reddy, T., Cournapeau, D., Burovski, E., Peterson, P., Weckesser, W., Bright, J., et al. (2020). SciPy 1.0: fundamental algorithms for scientific computing in Python. Nat Methods 17, 261-272.
112. Wang, C. Y., Colognori, D., Sunwoo, H., Wang, D., and Lee, J. T. (2019). PRC1 collaborates with SMCHD1 to fold the X-chromosome and spread Xist RNA between chromosome compartments. Nat Commun 10, 2950.
113. Wang, C. Y., Jegu, T., Chu, H. P., Oh, H. J., and Lee, J. T. (2018). SMCHD1 Merges Chromosome Compartments and Assists Formation of Super-Structures on the Inactive X. Cell 174, 406-421 e425.
114. Waskom, M. L. (2021). seaborn: statistical data visualization. Journal of Open Source Software 6, 3021.
115. Wickham et al. (2019). Welcome to the tidyverse. Journal of Open Source Software 4 (43).
116. Wu, B., Chao, J. A., and Singer, R. H. (2012). Fluorescence fluctuation spectroscopy enables quantitative imaging of single mRNAs in living cells. Biophys J 102, 2936-2944.
117. Wutz, A. (2011). Gene silencing in X-chromosome inactivation: advances in understanding facultative heterochromatin formation. Nat Rev Genet 12, 542-553.
118. Wutz, A., and Jaenisch, R. (2000). A shift from reversible to irreversible X inactivation is triggered during ES cell differentiation. Mol Cell 5, 695-705.
119. Wutz, A., Rasmussen, T. P., and Jaenisch, R. (2002). Chromosomal silencing and localization are mediated by different domains of Xist RNA. Nat Genet 30, 167-174.
120. Xie, L., and Liu, Z. (2021). Single-cell imaging of genome organization and dynamics. Mol Syst Biol 17, e9653.
121. Ying, Q. L., and Smith, A. G. (2003). Defined conditions for neural commitment and differentiation. Methods Enzymol 365, 327-341.
122. Yue, M., Ogawa, A., Yamada, N., Charles Richard, J. L., Barski, A., and Ogawa, Y. (2017). Xist RNA repeat E is essential for ASH2L recruitment to the inactive X and regulates histone modifications and escape gene expression. PLoS Genet 13, e1006890.
123. Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome Biol 9, R137.
124. Zhu, L. J., Gazin, C., Lawson, N. D., Pages, H., Lin, S. M., Lapointe, D. S., and Green, M. R. (2010). ChIPpeakAnno: a Bioconductor package to annotate ChIP-seq and ChIP-chip data. BMC Bioinformatics 11, 237.
125. Zimmerman, S. B., and Pheiffer, B. H. (1983). Macromolecular crowding allows blunt-end ligation by DNA ligases from rat liver or *Escherichia coli*. Proc Natl Acad Sci USA 80, 5852-5856.
126. Zylicz, J. J., Bousard, A., Zumer, K., Dossin, F., Mohammad, E., da Rocha, S. T., Schwalb, B., Syx, L., Dingli, F., Loew, D., et al. (2019). The Implication of Early Chromatin Changes in X Chromosome Inactivation. Cell 176, 182-197 e123.

Example 3: Reactivation of Genes on the X-Chromosome

Mammalian genomes encode many thousands of long ncRNAs (lncRNAs) that enrich within the chromatin-associated fraction of the nucleus. Many of these lncRNAs display cell- and developmental state-restricted expression. Recent work has also revealed that chromatin-associated lncRNAs exploit and shape 3-dimensional genome organization to regulate gene expression. The lncRNA Xist is a remarkable model for gene regulation by a chromatin-associated, developmentally-regulated lncRNA. Xist is encoded on the X-chromosome and is expressed on one of the two X-chromosomes in female mammalian cells, which it coats in cis to initiate silencing of almost all genes on that chromosome. This process forms the inactive X-chromosome (Xi). X chromosome inactivation (XCI) is a key female developmental process that compensates for X-linked genes dosage imbalance between sexes. It is a formidable example of concerted gene regulation and a paradigm for epigenetic processes.

Importantly, the mosaicism in X-linked gene expression that results from the developmental silencing of one X chromosome impacts greatly on human health. Rett Syndrome, for example, is causally linked to mutations in the X-linked gene MECP2. In this disease state, the Xi serves as a reservoir for a functional, but transcriptionally silent, gene copy that could replace the expression of the disease allele expressed from the active X chromosome. Animal studies have shown that reactivating or delivering this functional MECP2 gene copy—even after disease symptoms emerge—can lead to complete reversion of neurological defects. However, the major gap in applying this strategy in patients has been the lack of knowledge regarding how Xist inactivates the X chromosome and the mechanisms that would lead to reactivation.

FIG. 33 shows that a reporter gene on the Xi reactivates when inhibition of both PTBP1 and DNA methylation is combined. More experiments are being done now to define the role of the Xi-compartment in the maintenance of silencing in differentiated cells. This work will establish methods that result in the deconstruction of the higher order protein condensate in the Xi to induce the reactivation of X-linked genes and treat X-linked human disorders in females.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A method for re-activating an inactive X-chromosome in a cell, wherein the inactive X-chromosome is associated with Xist-mediated gene silencing, the method comprising contacting the cell with a polypyrimidine tract-binding protein 1 (PTBP1) inhibitor and a DNA demethylating agent, wherein the PTBP1 inhibitor is a nucleic acid inhibitor that is complimentary to an mRNA encoded by PTBP1, and wherein the nucleic acid inhibitor is a small interfering RNA (siRNA), a double stranded RNA (dsRNA), a short hairpin RNA (shRNA), or an antisense oligonucleotide.

2. The method of claim 1, wherein the DNA demethylating agent comprises 5-aza-2'-deoxycytidine (decitabine) or 5-azacytidine (azacitidine).

3. The method of claim 1, wherein the PTBP1 inhibitor is an siRNA.

4. The method of claim 1, wherein the PTBP1 inhibitor is an antisense oligonucleotide.

5. A method for treating Rett syndrome or an X-linked disorder in a subject, wherein the subject has an inactive X-chromosome which is associated with Xist-mediated gene silencing, the method comprising administering a polypyrimidine tract-binding protein 1 (PTBP1) inhibitor and a DNA demethylating agent to the subject, wherein the PTBP1 inhibitor is a nucleic acid inhibitor that is complimentary to an mRNA encoded by PTBP1, and wherein the nucleic acid inhibitor is a small interfering RNA (siRNA), a double stranded RNA (dsRNA), a short hairpin RNA (shRNA), or an antisense oligonucleotide.

6. The method of claim 5, wherein the DNA demethylating agent comprises 5-aza-2'-deoxycytidine (decitabine) or 5-azacytidine (azacitidine).

7. The method of claim 5, wherein the PTBP1 inhibitor is an siRNA.

8. The method of claim 5, wherein the PTBP1 inhibitor is an antisense oligonucleotide.

9. The method of claim 5, wherein the X-linked disorder is Fragile X syndrome, ataxia syndrome, Duchenne muscular dystrophy, Becker muscular dystrophy, hypophosphatasia rickets, alport syndrome, ornithine transcarbamylase deficiency, fabry disease, or Emery-Dreifuss muscular dystrophy.

10. The method of claim 5, wherein the PTBP1 inhibitor and the DNA demethylating agent are administered intravenously, intramuscularly, intraperitoneally, subcutaneously, or a combination thereof.

* * * * *

SEQUENCE LISTING

```
<160> NUMBER OF SEQ ID NOS: 3

<210> SEQ ID NO 1
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 1

gauggccuag aacuacaggg ugg                                          23


<210> SEQ ID NO 2
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 2

ccuguguuaa cacuuagagc agc                                          23


<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3

taagattaag aagtacccca                                              20
```